US012797455B2

(12) United States Patent
Osorio Arguello et al.

(10) Patent No.: US 12,797,455 B2
(45) Date of Patent: Nov. 17, 2026

(54) IMMUNOGENIC AND VACCINE COMPOSITIONS AGAINST SWINE DYSENTERY

(71) Applicant: HIPRA SCIENTIFIC, S.L.U., Amer (ES)

(72) Inventors: Jesús María Osorio Arguello, Amer (ES); Jaume Piñol Ribas, Valldoreix (ES); Luis González González, Amer (ES); Jordi Montané Giralt, Amer (ES); Marta Sitjà Arnau, Amer (ES); Enrique Querol Murillo, Barcelona (ES)

(73) Assignee: HIPRA SCIENTIFIC, S.L.U., Amer (ES)

( * ) Notice: Subject to any disclaimer, the term of this patent is extended or adjusted under 35 U.S.C. 154(b) by 660 days.

(21) Appl. No.: 18/259,633

(22) PCT Filed: Dec. 28, 2021

(86) PCT No.: PCT/EP2021/087718
§ 371 (c)(1),
(2) Date: Jun. 28, 2023

(87) PCT Pub. No.: WO2022/144353
PCT Pub. Date: Jul. 7, 2022

(65) Prior Publication Data
US 2024/0108708 A1 Apr. 4, 2024

(30) Foreign Application Priority Data
Dec. 29, 2020 (EP) .................................... 20383166

(51) Int. Cl.
*A61K 39/02* (2006.01)
*A61K 39/00* (2006.01)
*A61P 31/04* (2006.01)

(52) U.S. Cl.
CPC .......... *A61K 39/0225* (2013.01); *A61P 31/04* (2018.01); *A61K 2039/521* (2013.01); *A61K 2039/70* (2013.01)

(58) Field of Classification Search
None
See application file for complete search history.

(56) References Cited

U.S. PATENT DOCUMENTS

2015/0246107 A1 9/2015 Nagy et al.

FOREIGN PATENT DOCUMENTS

WO 2014207202 A1 12/2014
WO 2017118581 A1 7/2017
WO 2019081583 A1 5/2019

OTHER PUBLICATIONS

Tom La et al., "Evidence that the 36kb plasmid of contributes to virulence," Veterinary Microbiology, Feb. 24, 2011, pp. 150-155, vol. 153, No. 1.
Tom La et al., "Absence of a set of plasmid-encoded genes is predictive of reduced pathogenic potential in Brachyspira hyodysenteriae," Veterinary Research, Dec. 16, 2014, vol. 45, No. 1.
Matthew I. Bellgard et al., "Genome Sequence of the Pathogenic Intestinal Spirochete *Brachyspira hyodysenteriae* Reveals Adaptations to Its Lifestyle in the Porcine Large Intestine," PLOS ONE, Mar. 1, 2009, pp. e4641-e4641, vol. 4, No. 3.
Rafael Diego et al., "Serpulina hyodysenteriae challenge of fattening pigs vaccinated with an adjuvanted bivalent bacterin against swine dysentery", Vaccine, Jan. 1, 1995, pp. 663-667, vol. 13, No. 7.
Leroy D. Olson, "Exacerbated onset of dysentery in swine vaccinated with inactivated adjuvanted serpulina hyodysenteriae," American Journal of Veterinary Research, Jan. 1994, pp. 67-71, vol. 55, No. 1.
Stephen F. Altschul et al., "Basic Local Alignment Search Tool," J. Mol. Biol., May 1990, pp. 403-410, vol. 215.
Eric R. Burrough et al., "Comparative virulence of clinical *Brachyspira* spp. isolates in inoculated pigs," J Vet Diagn Invest., Sep. 2012, pp. 1025-1034., vol. 24, No. 6.
Christian F. Hansen et al., "A high dietary concentration of inulin is necessary to reduce the incidence of swine dysentery in pigs experimentally challenged with Brachyspira hyodysenteriae," Br J Nutr., Jun. 2011, pp. 1506-1513, vol. 106.
Remington's Pharmaceutical Sciences by E.W. Martin, 21st Edition, 15 2005.
"Handbook of Pharmaceutical Excipients", Rowe C. R.; Paul J. S.; Marian E.Q., sixth Edition 2009.
Ben Langmead et al., "Fast gapped-read alignment with Bowtie 2," Nature Methods, Apr. 2012, pp. 357-359, vol. 9, No. 4.
Heng Li et al., "The Sequence Alignment/Map format and SAMtools," Bioinformatics, Jun. 2008, pp. 2,078-2,079, vol. 25, No. 16.

(Continued)

*Primary Examiner* — Brian Gangle
(74) *Attorney, Agent, or Firm* — Pilloff Passino & Cosenza LLP; Rachel Pilloff; Sean Passino

(57) ABSTRACT

The invention relates to an immunogenic or vaccine composition comprising an inactivated bacterium from the species *Brachyspira hyodysenteriae*, to a method for producing said composition and to the medical use of this composition for inducing an immune response against a bacterium from the species *Brachyspira hyodysenteriae* or for protecting against an infection caused by a bacterium from the species *Brachyspira hyodysenteriae*. Further, the invention relates to a method for selecting a bacterium from the species *Brachyspira hyodysenteriae* useful for manufacturing a vaccine against swine dysentery.

18 Claims, 4 Drawing Sheets

Specification includes a Sequence Listing.

(56) References Cited

OTHER PUBLICATIONS

Daniel C. Koboldt et al., VarScan 2: Somatic mutation and copy number alteration discovery in cancer by exome sequencing, Genome Research, Mar. 2012, pp. 568-576.
Daniel R. Zerbino et al., Velvet: Algorithms for de novo short read assembly using de Bruijn graphs, Genome Research, 2009, 821-829.
Anton Bankevich et al., SPAdes: A New Genome Assembly Algorithm and Its Applications to Single-Cell Sequencing, Journal of Computational biology, May 2012, pp. 455-477, vol. 19, No. 5.
International Search Report and Written Opinion for PCT/EP2021/087718, mailed Apr. 28, 2022.

SEQUENCE LISTING

```
<160> NUMBER OF SEQ ID NOS: 123

<210> SEQ ID NO 1
<211> LENGTH: 864
<212> TYPE: DNA
<213> ORGANISM: Brachysprira hyodysenteriae

<400> SEQUENCE: 1

atgaaaggaa tcgtattagc aggcggaagc ggaacaagac tttatccaat gacaaatgtt      60

atatcaaaac agcttttgcc aatatacgat aaaccaatgg tatattatcc attatcagtt     120

ttaatgcttt caaaaattaa agatatactt gtaatatcta cagaaaatga tacaccgctt     180

tttaaaaaat tattaaaaga cggaagtcaa tggggatgca atattgaata tgctgtgcaa     240

aaagcaccta atggacttgc agaagcattt ataataggag aaagttttat aggaaaagat     300

aatgtttcta tgatattagg tgataatata ttttttggac aaagcttttc ttctgtatta     360

gaaaaaagtg ctaagataga taatggggct gttatatttg cttatcaagt aaaagatcct     420

gaacgtttcg gtatagttga aatagataaa gattataatg ctttatctat agaagaaaaa     480

cctaaaaatc caaagtctaa ttatgctgtt acaggtcttt atttttatga taatgatgta     540

gttaatattt caaaaaatat taagccttct gcaagagggg agcttgaaat aacagatgtt     600

aataaagtat atttagaaaa taaaaaactt aaagttgaag tactaggacg cggatttgct     660

tggcttgata ccggtacaag agatagtctt attcaggctt ctcaatttgt gtctgctgta     720

gaaaatattg aaggtatgca gatagcttgt ttagaagaaa tagcttataa taataaatgg     780

attgatgctt caaaaataga agagactgca tcaaaattga aaaactcaga atatggtaaa     840

tacttaatta atttaattaa atag                                            864

<210> SEQ ID NO 2
<211> LENGTH: 1071
<212> TYPE: DNA
<213> ORGANISM: Brachysprira hyodysenteriae

<400> SEQUENCE: 2

atgagaaatt ttaataatat tttagttact ggtggatgcg gttttatagg atcaaacttt      60

ataagataca tattagaaaa atctgattat aaaggcaata ttataaatat agatgcctta     120

acttatgcag gaaacagaga aaatttaata gatatagaaa aaaaatataa agatagatat     180

ttctttgaaa aagttaatat ttgtgatgat aaaaaaataa atgaaatatt ttcaaaatat     240

aatcctgatt gtatagtgca ttttgctgca gaaagtcatg ttgaccgttc aatatacgga     300

ccaaaagatt ttcttgaaac taatataatg ggaactttta ttttattaga agctgctcgt     360

aaattatggg aaaataataa agaaaataaa ctatttcatc atataagtac agacgaagtt     420

tacggatctt taggtgaaac aggttatttt tatgaaacta ctccttatga tcctagaagt     480

ccttactcat catcaaaagc ttcaagtgat catattgtaa aagcatatta tcatacttat     540

aatctgcctg ttacaatatc taattgcagc aacaattatg gcccttatca attccctgaa     600
```

aaattaatac ctttaatgat ttctaatata gtagaagaaa aagatcttcc tgtttatgga 660
gatggaaaaa atataagaga ttggatattt gttgaagatc ataataatgc agtaattgat 720
ataatacata aaggcagggt aggagagacc tacaatatcg gcggagaaaa cgagattact 780
aatattgata tggtaaatat tttatgtgag aaattatctg ctaaaatgaa taaagaaaaa 840
gattattata aaaaattaat caaatttgta aaagacagag ccggtcatga cagaagatat 900
gctataaact gcgataaaat aaaaaaagaa ttaggatggg aaagaaaata cgatttcaat 960
accgccattg atataactat agattggtat ttaaataaca aacaatggat agataatatt 1020
aaaagcggag aatataaaaa atggattgag ttaaactact cgtctaaata a 1071

<210> SEQ ID NO 3
<211> LENGTH: 579
<212> TYPE: DNA
<213> ORGANISM: Brachysprira hyodysenteriae

<400> SEQUENCE: 3
atgcctttta catttaaaaa acttgatata aacggacttt ttatagcaga acctcgtatc 60
tttggagatt caagaggtta tttcctagaa acatattctg agaaagattt ttttgaagct 120
ggaatcaaag aaaaatttgt acaagataat caatctaaat caacaaaaaa tgtattaaga 180
ggacttcatt atcagaaaaa atattgtcag gctaaattgg ttagagtatt agaaggtgaa 240
gtatttgatg ttgcagtaga tttgagaaat gattctccaa cttttggaaa atattatggg 300
gtattattaa cagaagaaaa taaaaagcag ttctttattc ctaaaggttt tgcacatgga 360
tttattgttc taagcgaatc agctgttttt gcttataaat gttctgactt ttatcaccct 420
gaagaagagg gtggtataat atataatgat aaaaatatta atatagattg gacttgcgat 480
actaaagatg tattagtatc tgataaagat ttaaaattac cagagtttga caaaaataaa 540
aaatattttt cattagatgg aaattggatt ggagaataa 579

<210> SEQ ID NO 4
<211> LENGTH: 861
<212> TYPE: DNA
<213> ORGANISM: Brachysprira hyodysenteriae

<400> SEQUENCE: 4
atgatttggg taattggtaa aaatggaatg cttgctcaag atatactcaa agcattcaat 60
aaaaataata tagaatatac ttcaacagct tctaatatag atattactaa tattgatata 120
cttaataact ttataaaaga taaaaatatt aaaacaataa taaattgttc tgcatataca 180
aaagtagatt tagcagaaga tgaaaaagat atttgctata aagttaatgg agaaggtgta 240
aaaaatataa cagaaatagc ttctaatata aatgcagatt taattcattt ttctactgat 300
tatgtatttg atggagaaaa taacaaacca tacaatgaag aagataaaac taatccaata 360
aatatttacg gcaaaagtaa attagagggt gaaaaatatg ctttatttta taataaagca 420
atagttatta gagtatcttg gctatatgga atttatggaa aaaattttgt atatactatg 480
attaatttga tgaatagtaa agaaagcata aaagtagtta atgatcaatt tggatctcct 540
acatatacag aagatgttgc tatggtaata tatgatatta taaaaaataa caattttgat 600
tacggacttt atcattatac taatgaaggt aatatatcat ggtatgattt tgctaaaact 660
atatataata aaggaaaaga gtataatatt ataaataatg attgcaaagt aaatccatgt 720
actacagaag aatatccaac caaagctaaa agacctaaat acagtgtttt atctgtagaa 780
aaaataaaaa gatatgttaa aatatataat tatgaagata gcttaaatag tttttttaac 840
atatatcaaa aaaataaata a 861

<210> SEQ ID NO 5
<211> LENGTH: 1872
<212> TYPE: DNA
<213> ORGANISM: Brachysprira hyodysenteriae

<400> SEQUENCE: 5
atgaatgata aatatgttat atgttcaatt acaacaggat ttacagatca actcataaat 60
tttgctacag caatatatat tagagaaaaa tataaaaaaa atgtaaaatt agatatatca 120
tggttttctg tttatgaaaa tacagattat ttgggaatag aaaaacgtaa cctggaagta 180
ctaaatatat ttaatgactt taattttgaa atagctacaa aaaaagaaat agatatagct 240
ttaaagtcta tttttataga tggtagatat gaaaatatag ataaaatatt aaaatccaat 300
aaacatatat atgttggacc atatgttgga catactttat tttactatgg acatattaat 360
atttcttctt ttttcaatct tgacaaatat tttattaatt tattaaatga aaaacataaa 420
aacatattaa atgacatgtc atcttttgaa agtgttacta tacatataag acgaggagat 480
tatatgtatg cgttaaaaat agatggaaga aagaataatg cttctttaga ctatatatat 540
acatcaataa aatatttaaa taatacttta gaaaataaaa atataaaatt ttatatattt 600
tctaataata aaaaatatat aaaaaataat ttaataccaa tttttcaaaa taataatatt 660
aattttgaaa ttatagaaga taatcctgaa tatatagatt tttatttaat gactaaatgt 720
aagcatataa tatcttcatt aggaaaattt gcaaaagtag cttttaaatt tataaaaaat 780
gaaaataaaa tatttataga tacagacaat atttataatt tgaaaaaaga atatttctat 840
aaaaatattt gtgaaaaata ctgcaacata atttatgaag aatataataa tataaaaaca 900
tatatatcaa aaaataatat gatatatata ctagacttaa ttgaaaaaaa taatataaag 960
aatatatgtc aaataggctt gctagacggt ttagaaactc atactctatt aaaatattca 1020
gcagacaata ataactgttt taatttatta tgttttgaaa ataatgaaag agatatagtt 1080
ggaatagaat taaaaaattt aacagaaaat gaaaaaaaac tatttacatt atatatagaa 1140
cagtctcctt tagatataga taattctttt aatataaaaa atatagattt tatctttttt 1200
acaaaagaaa attctaatcc tctagtattc atttatttaa tatacttatt tccatttatg 1260
aaagaagaaa tcataatagt atttaatgat attataagtg gtaaatatta ttctggaagt 1320
tattgtatat ttaatatgtt taatggagaa aaaaatcaat tttataattt taatacaaat 1380
aaatatgaca atatcggata tataaaaata aagaaacaag aattattaaa tataataaaa 1440
aaaatatctg ttatagaata tgatggttat ataaataaat tttttatgaa taaattaata 1500
gataacagaa atgattatta taattatttt gatttagata tgtcatacat taggttaaat 1560
aatttaaagc aatatatgaa ggataaattt gatatagaat attcaaatta tataatctct 1620
aacatagaaa ataatattat taattatgaa aaacaatatt ataaaaacca aaaaaaataat 1680 ttttattctc aaaatcaaat acatatttct aaaatagaaa atataataga taaacataat 1740
aaattaatta atagtatatc ttggtggata cctataaaaa aattaagaga aaatttcaaa 1800
aataaattta taagaccaga ccagaccaga ccagaccaga ccagaccaga ccagaccaga 1860
cctaatatgt aa 1872

<210> SEQ ID NO 6
<211> LENGTH: 981

<212> TYPE: DNA
<213> ORGANISM: Brachysprira hyodysenteriae

<400> SEQUENCE: 6
atgaaaagat tagccgtatt tgcaggatat gataaagaca atataattga tgattatgtt 60
gtatattata ttaaagaatt aaaaaaaata tctgatataa tctatgtatc agattgcaat 120
atgtcagata atgaattaaa aaaaattaat gattactgca tacatatcat aaatggaagg 180
catgaagaat atgatttcgg atcatataaa agaggatatc tatatgccaa agaaaataat 240
atgcttcaaa attatgatta tttaatactt tgtaatgatt cttgctatgg acctttattt 300
gatttggaaa acataataaa taaaatgaat gattataatt ttggaggcat atctattagt 360
aaagatttaa aaatagcaaa tcataattat ataactagct tttttatata cataaacaaa 420
aacatattta ataaagattt ctttaataat tttatttatg atataaaaaa agaagaagat 480
aaaatggata tcataaaaaa atatgaattt ggactttcaa aactaatgct tgataataat 540
atagaattaa aaggcttatt taatgataat ggagaattta acagaccata ctttaatcca 600
ttagctctaa tagaagaagg atatcctttt ttaaaaaaac atgtactaga aaaaaaagta 660
actgttcctt taaatataga tgaactaaca aatattataa aaataataaa aaataattac 720
gatataaaat taatagttaa tcatttaaat agagttgctg ataaagaaca aattaaatat 780
ttatttcaaa aatataaacc atataaaaaa acatttattc atgaaaaaat tttctcctta 840
tttaccagat attcaccatc aggtaaatat caaacagtat ataatttttt taattttcta 900
actatatcaa tagacaaacc aattaaagat tcatacatag aaactgacta taaagatttt 960 aatttttat tagaaatata a 981

<210> SEQ ID NO 7
<211> LENGTH: 1218
<212> TYPE: DNA
<213> ORGANISM: Brachysprira hyodysenteriae

<400> SEQUENCE: 7
atgataagtt atttaaataa aaggtataaa atgaataaat gtgaatgcag tcaatgcaaa 60
aatagagaat atgatatatc agaatatttg gttcttgaag atgacttgaa aattttagat 120
aatgaaagac cactaggaat atcaggacat ttaagggtta aagatgaagc tatgagttta 180
gctgaatgca ttgattcatg catagacttt ttagatgaac ttataataac ttataacaca 240
tcttcagata acacagaaga aatattaaaa aactacgaaa aaaaatatcc tgaaaaaatt 300
aaactatttc attataaacc taatattata agatacaata aagatgagta taatacaaaa 360
tattcacaaa tacactattt agataattat tacaattatg gactaattaa aataaaatac 420
aaatattatg ttaaaataga tgctgatcaa atttatttca cagataaatt attaaaatta 480
agagaattat taatattaga tataaatcaa ataaaattaa gcaataatat aaataaatta 540
ttattaataa ataaaatagc ttggtgcata cctatcaaaa aattacgaaa taaatttaga 600
acatattgta ttagaaagta tttcaataaa gataaaaatt atatttataa tggtgatgaa 660
aatatattat cattagatga ttttatttta ttatctagga aaagacattc agataaaaat 720
atcagttatg atcttgcagg attcaatcta atattacata ataataaatt atatttagat 780
acatattggc ctatgaatgg cggacgtttt gatcatgtgc tgtatcaagc atcttattct 840
aataaatatt ttatgaatga aatatttgaa gtaaatcaaa ctcctcataa tagaataatt 900
ttagggatgt tttgggtaca ttttggaaat attaaacata attttcaata tgatgattct 960
ttttatttac tagaatataa tgatataaaa aattctaaag tagaaaattt ttctcataaa 1020
atgaaaaata ttgataatga tgataaaata gaaaaatata taagagataa tacttttata 1080
aaatattttg atgaggataa aaaatacctt aataatgttt tttataataa atacttgaca 1140
aaaccacttg actatgctat aaaaaacaat gatgaattag taaatttata tggaaaaact 1200
attattactg taaaatga 1218

<210> SEQ ID NO 8
<211> LENGTH: 795
<212> TYPE: DNA
<213> ORGANISM: Brachysprira hyodysenteriae

<400> SEQUENCE: 8
atgtctagca atataataga tacaatagct tggtggattc ctattaaatc cattagaata 60
aaatttagaa atgcaacaaa gaaaaagttc aataatttta tttttaacaa aatagatttt 120
aactacgtta atacaaataa tatagaactt atactcaata aatataatga aatatttgtc 180
ccattaatat taagtaacga aaaaaaatac aaaaaaaata gaaatagcga gttaataaat 240
aaatatttaa ctggtttaaa aggtgttgaa ataggaggaa gcgctggagc tgattttggt 300
atagacgcta tacaagttaa tattgtcgat gccaatcagg aacacaataa ttattatcaa 360
caaacaaata ttttaggttc gggatataat caaagaactg atatcatatc atgtggtgat 420
gtattaccat ttcaagataa ttcaatagac tttgtattct caagtcatgt actagaacat 480
ttctatgacc ctataaaagc tttaaaagaa tggtacagag ttataaaaaa agacggatat 540
atagctatga tagtacctca taaagaaaga acattcgata aagatagaga tagaacaact 600
ttaaatgaat taatagaaag acataataag gttaaaaatt ataaatacaa tgtggatgaa 660
agaggaatgc atttttctgt ttggataaca gaagatatac tagaattatg caaatattta 720
aatatgaatg taattgaata tctagatgta gatgatgctg taggtaatgg atttgctatt 780
atcataaaaa aataa 795

<210> SEQ ID NO 9
<211> LENGTH: 623
<212> TYPE: PRT
<213> ORGANISM: Brachysprira hyodysenteriae

<400> SEQUENCE: 9

Met Asn Asp Lys Tyr Val Ile Cys Ser Ile Thr Thr Gly Phe Thr Asp
1 5 10 15

Gln Leu Ile Asn Phe Ala Thr Ala Ile Tyr Ile Arg Glu Lys Tyr Lys
20 25 30

Lys Asn Val Lys Leu Asp Ile Ser Trp Phe Ser Val Tyr Glu Asn Thr
35 40 45

Asp Tyr Leu Gly Ile Glu Lys Arg Asn Leu Glu Val Leu Asn Ile Phe
50 55 60

Asn Asp Phe Asn Phe Glu Ile Ala Thr Lys Lys Glu Ile Asp Ile Ala
65 70 75 80

Leu Lys Ser Ile Phe Ile Asp Gly Arg Tyr Glu Asn Ile Asp Lys Ile
85 90 95

Leu Lys Ser Asn Lys His Ile Tyr Val Gly Pro Tyr Val Gly His Thr
100 105 110

Leu Phe Tyr Tyr Gly His Ile Asn Ile Ser Ser Phe Phe Asn Leu Asp
115 120 125

Lys Tyr Phe Ile Asn Leu Leu Asn Glu Lys His Lys Asn Ile Leu Asn

```
    130                 135                 140

Asp Met Ser Ser Phe Glu Ser Val Thr Ile His Ile Arg Arg Gly Asp
145                 150                 155                 160

Tyr Met Tyr Ala Leu Lys Ile Asp Gly Arg Lys Asn Asn Ala Ser Leu
                165                 170                 175

Asp Tyr Ile Tyr Thr Ser Ile Lys Tyr Leu Asn Asn Thr Leu Glu Asn
            180                 185                 190

Lys Asn Ile Lys Phe Tyr Ile Phe Ser Asn Asn Lys Lys Tyr Ile Lys
        195                 200                 205

Asn Asn Leu Ile Pro Ile Phe Gln Asn Asn Asn Ile Asn Phe Glu Ile
    210                 215                 220

Ile Glu Asp Asn Pro Glu Tyr Ile Asp Phe Tyr Leu Met Thr Lys Cys
225                 230                 235                 240

Lys His Ile Ile Ser Ser Leu Gly Lys Phe Ala Lys Val Ala Phe Lys
                245                 250                 255

Phe Ile Lys Asn Glu Asn Lys Ile Phe Ile Asp Thr Asp Asn Ile Tyr
            260                 265                 270

Asn Leu Lys Lys Glu Tyr Phe Tyr Lys Asn Ile Cys Glu Lys Tyr Cys
        275                 280                 285

Asn Ile Ile Tyr Glu Glu Tyr Asn Asn Ile Lys Thr Tyr Ile Ser Lys
    290                 295                 300

Asn Asn Met Ile Tyr Ile Leu Asp Leu Ile Glu Lys Asn Asn Ile Lys
305                 310                 315                 320

Asn Ile Cys Gln Ile Gly Leu Leu Asp Gly Leu Glu Thr His Thr Leu
                325                 330                 335

Leu Lys Tyr Ser Ala Asp Asn Asn Asn Cys Phe Asn Leu Leu Cys Phe
            340                 345                 350

Glu Asn Asn Glu Arg Asp Ile Val Gly Ile Glu Leu Lys Asn Leu Thr
        355                 360                 365

Glu Asn Glu Lys Lys Leu Phe Thr Leu Tyr Ile Glu Gln Ser Pro Leu
    370                 375                 380

Asp Ile Asp Asn Ser Phe Asn Ile Lys Asn Ile Asp Phe Ile Phe Phe
385                 390                 395                 400

Thr Lys Glu Asn Ser Asn Pro Leu Val Phe Ile Tyr Leu Ile Tyr Leu
                405                 410                 415

Phe Pro Phe Met Lys Glu Glu Ile Ile Ile Val Phe Asn Asp Ile Ile
            420                 425                 430

Ser Gly Lys Tyr Tyr Ser Gly Ser Tyr Cys Ile Phe Asn Met Phe Asn
        435                 440                 445

Gly Glu Lys Asn Gln Phe Tyr Asn Phe Asn Thr Asn Lys Tyr Asp Asn
    450                 455                 460

Ile Gly Tyr Ile Lys Ile Lys Lys Gln Glu Leu Leu Asn Ile Ile Lys
465                 470                 475                 480

Lys Ile Ser Val Ile Glu Tyr Asp Gly Tyr Ile Asn Lys Phe Phe Met
                485                 490                 495

Asn Lys Leu Ile Asp Asn Arg Asn Asp Tyr Tyr Asn Tyr Phe Asp Leu
            500                 505                 510

Asp Met Ser Tyr Ile Arg Leu Asn Asn Leu Lys Gln Tyr Met Lys Asp
        515                 520                 525

Lys Phe Asp Ile Glu Tyr Ser Asn Tyr Ile Ile Ser Asn Ile Glu Asn
    530                 535                 540

Asn Ile Ile Asn Tyr Glu Lys Gln Tyr Tyr Lys Asn Gln Lys Asn Asn
545                 550                 555                 560
```

Phe Tyr Ser Gln Asn Gln Ile His Ile Ser Lys Ile Glu Asn Ile Ile
565 570 575

Asp Lys His Asn Lys Leu Ile Asn Ser Ile Ser Trp Trp Ile Pro Ile
580 585 590

Lys Lys Leu Arg Glu Asn Phe Lys Asn Lys Phe Ile Arg Pro Asp Gln
595 600 605

Thr Arg Pro Asp Gln Thr Arg Pro Asp Gln Thr Arg Pro Asn Met
610 615 620

<210> SEQ ID NO 10
<211> LENGTH: 405
<212> TYPE: PRT
<213> ORGANISM: Brachysprira hyodysenteriae

<400> SEQUENCE: 10

Met Ile Ser Tyr Leu Asn Lys Arg Tyr Lys Met Asn Lys Cys Glu Cys
1 5 10 15

Ser Gln Cys Lys Asn Arg Glu Tyr Asp Ile Ser Glu Tyr Leu Val Leu
20 25 30

Glu Asp Asp Leu Lys Ile Leu Asp Asn Glu Arg Pro Leu Gly Ile Ser
35 40 45

Gly His Leu Arg Val Lys Asp Glu Ala Met Ser Leu Ala Glu Cys Ile
50 55 60

Asp Ser Cys Ile Asp Phe Leu Asp Glu Leu Ile Ile Thr Tyr Asn Thr
65 70 75 80

Ser Ser Asp Asn Thr Glu Glu Ile Leu Lys Asn Tyr Glu Lys Lys Tyr
85 90 95

Pro Glu Lys Ile Lys Leu Phe His Tyr Lys Pro Asn Ile Ile Arg Tyr
100 105 110

Asn Lys Asp Glu Tyr Asn Thr Lys Tyr Ser Gln Ile His Tyr Leu Asp
115 120 125

Asn Tyr Tyr Asn Tyr Gly Leu Ile Lys Ile Lys Tyr Lys Tyr Tyr Val
130 135 140

Lys Ile Asp Ala Asp Gln Ile Tyr Phe Thr Asp Lys Leu Leu Lys Leu
145 150 155 160

Arg Glu Leu Leu Ile Leu Asp Ile Asn Gln Ile Lys Leu Ser Asn Asn
165 170 175

Ile Asn Lys Leu Leu Leu Ile Asn Lys Ile Ala Trp Cys Ile Pro Ile
180 185 190

Lys Lys Leu Arg Asn Lys Phe Arg Thr Tyr Cys Ile Arg Lys Tyr Phe
195 200 205

Asn Lys Asp Lys Asn Tyr Ile Tyr Asn Gly Asp Glu Asn Ile Leu Ser
210 215 220

Leu Asp Asp Phe Ile Leu Leu Ser Arg Lys Arg His Ser Asp Lys Asn
225 230 235 240

Ile Ser Tyr Asp Leu Ala Gly Phe Asn Leu Ile Leu His Asn Asn Lys
245 250 255

Leu Tyr Leu Asp Thr Tyr Trp Pro Met Asn Gly Gly Arg Phe Asp His
260 265 270

Val Leu Tyr Gln Ala Ser Tyr Ser Asn Lys Tyr Phe Met Asn Glu Ile
275 280 285

Phe Glu Val Asn Gln Thr Pro His Asn Arg Ile Ile Leu Gly Met Phe
290 295 300

Trp Val His Phe Gly Asn Ile Lys His Asn Phe Gln Tyr Asp Asp Ser

```
305                 310                 315                 320

Phe Tyr Leu Leu Glu Tyr Asn Asp Ile Lys Asn Ser Lys Val Glu Asn
                325                 330                 335

Phe Ser His Lys Met Lys Asn Ile Asp Asn Asp Asp Lys Ile Glu Lys
            340                 345                 350

Tyr Ile Arg Asp Asn Thr Phe Ile Lys Tyr Phe Asp Glu Asp Lys Lys
        355                 360                 365

Tyr Leu Asn Asn Val Phe Tyr Asn Lys Tyr Leu Thr Lys Pro Leu Asp
    370                 375                 380

Tyr Ala Ile Lys Asn Asn Asp Glu Leu Val Asn Leu Tyr Gly Lys Thr
385                 390                 395                 400

Ile Ile Thr Val Lys
                405


<210> SEQ ID NO 11
<211> LENGTH: 287
<212> TYPE: PRT
<213> ORGANISM: Brachysprira hyodysenteriae

<400> SEQUENCE: 11

Met Lys Gly Ile Val Leu Ala Gly Gly Ser Gly Thr Arg Leu Tyr Pro
1               5                   10                  15

Met Thr Asn Val Ile Ser Lys Gln Leu Leu Pro Ile Tyr Asp Lys Pro
            20                  25                  30

Met Val Tyr Tyr Pro Leu Ser Val Leu Met Leu Ser Lys Ile Lys Asp
        35                  40                  45

Ile Leu Val Ile Ser Thr Glu Asn Asp Thr Pro Leu Phe Lys Lys Leu
    50                  55                  60

Leu Lys Asp Gly Ser Gln Trp Gly Cys Asn Ile Glu Tyr Ala Val Gln
65                  70                  75                  80

Lys Ala Pro Asn Gly Leu Ala Glu Ala Phe Ile Ile Gly Glu Ser Phe
                85                  90                  95

Ile Gly Lys Asp Asn Val Ser Met Ile Leu Gly Asp Asn Ile Phe Phe
            100                 105                 110

Gly Gln Ser Phe Ser Ser Val Leu Glu Lys Ser Ala Lys Ile Asp Asn
        115                 120                 125

Gly Ala Val Ile Phe Ala Tyr Gln Val Lys Asp Pro Glu Arg Phe Gly
    130                 135                 140

Ile Val Glu Ile Asp Lys Asp Tyr Asn Ala Leu Ser Ile Glu Glu Lys
145                 150                 155                 160

Pro Lys Asn Pro Lys Ser Asn Tyr Ala Val Thr Gly Leu Tyr Phe Tyr
                165                 170                 175

Asp Asn Asp Val Val Asn Ile Ser Lys Asn Ile Lys Pro Ser Ala Arg
            180                 185                 190

Gly Glu Leu Glu Ile Thr Asp Val Asn Lys Val Tyr Leu Glu Asn Lys
        195                 200                 205

Lys Leu Lys Val Glu Val Leu Gly Arg Gly Phe Ala Trp Leu Asp Thr
    210                 215                 220

Gly Thr Arg Asp Ser Leu Ile Gln Ala Ser Gln Phe Val Ser Ala Val
225                 230                 235                 240

Glu Asn Ile Glu Gly Met Gln Ile Ala Cys Leu Glu Glu Ile Ala Tyr
                245                 250                 255

Asn Asn Lys Trp Ile Asp Ala Ser Lys Ile Glu Glu Thr Ala Ser Lys
            260                 265                 270
```

Leu Lys Asn Ser Glu Tyr Gly Lys Tyr Leu Ile Asn Leu Ile Lys
275 280 285

<210> SEQ ID NO 12
<211> LENGTH: 356
<212> TYPE: PRT
<213> ORGANISM: Brachysprira hyodysenteriae

<400> SEQUENCE: 12

Met Arg Asn Phe Asn Asn Ile Leu Val Thr Gly Gly Cys Gly Phe Ile
1 5 10 15

Gly Ser Asn Phe Ile Arg Tyr Ile Leu Glu Lys Ser Asp Tyr Lys Gly
20 25 30

Asn Ile Ile Asn Ile Asp Ala Leu Thr Tyr Ala Gly Asn Arg Glu Asn
35 40 45

Leu Ile Asp Ile Glu Lys Lys Tyr Lys Asp Arg Tyr Phe Phe Glu Lys
50 55 60

Val Asn Ile Cys Asp Asp Lys Lys Ile Asn Glu Ile Phe Ser Lys Tyr
65 70 75 80

Asn Pro Asp Cys Ile Val His Phe Ala Ala Glu Ser His Val Asp Arg
85 90 95

Ser Ile Tyr Gly Pro Lys Asp Phe Leu Glu Thr Asn Ile Met Gly Thr
100 105 110

Phe Ile Leu Leu Glu Ala Ala Arg Lys Leu Trp Glu Asn Asn Lys Glu
115 120 125

Asn Lys Leu Phe His His Ile Ser Thr Asp Glu Val Tyr Gly Ser Leu
130 135 140

Gly Glu Thr Gly Tyr Phe Tyr Glu Thr Thr Pro Tyr Asp Pro Arg Ser
145 150 155 160

Pro Tyr Ser Ser Ser Lys Ala Ser Ser Asp His Ile Val Lys Ala Tyr
165 170 175

Tyr His Thr Tyr Asn Leu Pro Val Thr Ile Ser Asn Cys Ser Asn Asn
180 185 190

Tyr Gly Pro Tyr Gln Phe Pro Glu Lys Leu Ile Pro Leu Met Ile Ser
195 200 205

Asn Ile Val Glu Glu Lys Asp Leu Pro Val Tyr Gly Asp Gly Lys Asn
210 215 220

Ile Arg Asp Trp Ile Phe Val Glu Asp His Asn Asn Ala Val Ile Asp
225 230 235 240

Ile Ile His Lys Gly Arg Val Gly Glu Thr Tyr Asn Ile Gly Gly Glu
245 250 255

Asn Glu Ile Thr Asn Ile Asp Met Val Asn Ile Leu Cys Glu Lys Leu
260 265 270

Ser Ala Lys Met Asn Lys Glu Lys Asp Tyr Tyr Lys Lys Leu Ile Lys
275 280 285

Phe Val Lys Asp Arg Ala Gly His Asp Arg Arg Tyr Ala Ile Asn Cys
290 295 300

Asp Lys Ile Lys Lys Glu Leu Gly Trp Glu Arg Lys Tyr Asp Phe Asn
305 310 315 320

Thr Ala Ile Asp Ile Thr Ile Asp Trp Tyr Leu Asn Asn Lys Gln Trp
325 330 335

Ile Asp Asn Ile Lys Ser Gly Glu Tyr Lys Lys Trp Ile Glu Leu Asn
340 345 350

Tyr Ser Ser Lys
355

<210> SEQ ID NO 13
<211> LENGTH: 192
<212> TYPE: PRT
<213> ORGANISM: Brachysprira hyodysenteriae

<400> SEQUENCE: 13

```
Met Pro Phe Thr Phe Lys Lys Leu Asp Ile Asn Gly Leu Phe Ile Ala
1               5                   10                  15

Glu Pro Arg Ile Phe Gly Asp Ser Arg Gly Tyr Phe Leu Glu Thr Tyr
            20                  25                  30

Ser Glu Lys Asp Phe Phe Glu Ala Gly Ile Lys Glu Lys Phe Val Gln
        35                  40                  45

Asp Asn Gln Ser Lys Ser Thr Lys Asn Val Leu Arg Gly Leu His Tyr
    50                  55                  60

Gln Lys Lys Tyr Cys Gln Ala Lys Leu Val Arg Val Leu Glu Gly Glu
65                  70                  75                  80

Val Phe Asp Val Ala Val Asp Leu Arg Asn Asp Ser Pro Thr Phe Gly
                85                  90                  95

Lys Tyr Tyr Gly Val Leu Leu Thr Glu Glu Asn Lys Lys Gln Phe Phe
            100                 105                 110

Ile Pro Lys Gly Phe Ala His Gly Phe Ile Val Leu Ser Glu Ser Ala
        115                 120                 125

Val Phe Ala Tyr Lys Cys Ser Asp Phe Tyr His Pro Glu Glu Glu Gly
    130                 135                 140

Gly Ile Ile Tyr Asn Asp Lys Asn Ile Asn Ile Asp Trp Thr Cys Asp
145                 150                 155                 160

Thr Lys Asp Val Leu Val Ser Asp Lys Asp Leu Lys Leu Pro Glu Phe
                165                 170                 175

Asp Lys Asn Lys Lys Tyr Phe Ser Leu Asp Gly Asn Trp Ile Gly Glu
            180                 185                 190
```

<210> SEQ ID NO 14
<211> LENGTH: 286
<212> TYPE: PRT
<213> ORGANISM: Brachysprira hyodysenteriae

<400> SEQUENCE: 14

```
Met Ile Trp Val Ile Gly Lys Asn Gly Met Leu Ala Gln Asp Ile Leu
1               5                   10                  15

Lys Ala Phe Asn Lys Asn Asn Ile Glu Tyr Thr Ser Thr Ala Ser Asn
            20                  25                  30

Ile Asp Ile Thr Asn Ile Asp Ile Leu Asn Asn Phe Ile Lys Asp Lys
        35                  40                  45

Asn Ile Lys Thr Ile Ile Asn Cys Ser Ala Tyr Thr Lys Val Asp Leu
    50                  55                  60

Ala Glu Asp Glu Lys Asp Ile Cys Tyr Lys Val Asn Gly Glu Gly Val
65                  70                  75                  80

Lys Asn Ile Thr Glu Ile Ala Ser Asn Ile Asn Ala Asp Leu Ile His
                85                  90                  95

Phe Ser Thr Asp Tyr Val Phe Asp Gly Glu Asn Asn Lys Pro Tyr Asn
            100                 105                 110

Glu Glu Asp Lys Thr Asn Pro Ile Asn Ile Tyr Gly Lys Ser Lys Leu
        115                 120                 125

Glu Gly Glu Lys Tyr Ala Leu Phe Tyr Asn Lys Ala Ile Val Ile Arg
    130                 135                 140
```

Val Ser Trp Leu Tyr Gly Ile Tyr Gly Lys Asn Phe Val Tyr Thr Met
145 150 155 160

Ile Asn Leu Met Asn Ser Lys Glu Ser Ile Lys Val Val Asn Asp Gln
165 170 175

Phe Gly Ser Pro Thr Tyr Thr Glu Asp Val Ala Met Val Ile Tyr Asp
180 185 190

Ile Ile Lys Asn Asn Asn Phe Asp Tyr Gly Leu Tyr His Tyr Thr Asn
195 200 205

Glu Gly Asn Ile Ser Trp Tyr Asp Phe Ala Lys Thr Ile Tyr Asn Lys
210 215 220

Gly Lys Glu Tyr Asn Ile Ile Asn Asn Asp Cys Lys Val Asn Pro Cys
225 230 235 240

Thr Thr Glu Glu Tyr Pro Thr Lys Ala Lys Arg Pro Lys Tyr Ser Val
245 250 255

Leu Ser Val Glu Lys Ile Lys Arg Tyr Val Lys Ile Tyr Asn Tyr Glu
260 265 270

Asp Ser Leu Asn Ser Phe Phe Asn Ile Tyr Gln Lys Asn Lys
275 280 285

<210> SEQ ID NO 15
<211> LENGTH: 326
<212> TYPE: PRT
<213> ORGANISM: Brachysprira hyodysenteriae

<400> SEQUENCE: 15

Met Lys Arg Leu Ala Val Phe Ala Gly Tyr Asp Lys Asp Asn Ile Ile
1 5 10 15

Asp Asp Tyr Val Val Tyr Tyr Ile Lys Glu Leu Lys Lys Ile Ser Asp
20 25 30

Ile Ile Tyr Val Ser Asp Cys Asn Met Ser Asp Asn Glu Leu Lys Lys
35 40 45

Ile Asn Asp Tyr Cys Ile His Ile Ile Asn Gly Arg His Glu Glu Tyr
50 55 60

Asp Phe Gly Ser Tyr Lys Arg Gly Tyr Leu Tyr Ala Lys Glu Asn Asn
65 70 75 80

Met Leu Gln Asn Tyr Asp Tyr Leu Ile Leu Cys Asn Asp Ser Cys Tyr
85 90 95

Gly Pro Leu Phe Asp Leu Glu Asn Ile Ile Asn Lys Met Asn Asp Tyr
100 105 110

Asn Phe Gly Gly Ile Ser Ile Ser Lys Asp Leu Lys Ile Ala Asn His
115 120 125

Asn Tyr Ile Thr Ser Phe Phe Ile Tyr Ile Asn Lys Asn Ile Phe Asn
130 135 140

Lys Asp Phe Phe Asn Asn Phe Ile Tyr Asp Ile Lys Lys Glu Glu Asp
145 150 155 160

Lys Met Asp Ile Ile Lys Lys Tyr Glu Phe Gly Leu Ser Lys Leu Met
165 170 175

Leu Asp Asn Asn Ile Glu Leu Lys Gly Leu Phe Asn Asp Asn Gly Glu
180 185 190

Phe Asn Arg Pro Tyr Phe Asn Pro Leu Ala Leu Ile Glu Glu Gly Tyr
195 200 205

Pro Phe Leu Lys Lys His Val Leu Glu Lys Lys Val Thr Val Pro Leu
210 215 220

Asn Ile Asp Glu Leu Thr Asn Ile Ile Lys Ile Ile Lys Asn Asn Tyr

```
225                 230                 235                 240

Asp Ile Lys Leu Ile Val Asn His Leu Asn Arg Val Ala Asp Lys Glu
                245                 250                 255

Gln Ile Lys Tyr Leu Phe Gln Lys Tyr Lys Pro Tyr Lys Lys Thr Phe
            260                 265                 270

Ile His Glu Lys Ile Phe Ser Leu Phe Thr Arg Tyr Ser Pro Ser Gly
        275                 280                 285

Lys Tyr Gln Thr Val Tyr Asn Phe Phe Asn Phe Leu Thr Ile Ser Ile
    290                 295                 300

Asp Lys Pro Ile Lys Asp Ser Tyr Ile Glu Thr Asp Tyr Lys Asp Phe
305                 310                 315                 320

Asn Phe Leu Leu Glu Ile
                325


<210> SEQ ID NO 16
<211> LENGTH: 264
<212> TYPE: PRT
<213> ORGANISM: Brachysprira hyodysenteriae

<400> SEQUENCE: 16

Met Ser Ser Asn Ile Ile Asp Thr Ile Ala Trp Trp Ile Pro Ile Lys
1               5                   10                  15

Ser Ile Arg Ile Lys Phe Arg Asn Ala Thr Lys Lys Lys Phe Asn Asn
            20                  25                  30

Phe Ile Phe Asn Lys Ile Asp Phe Asn Tyr Val Asn Thr Asn Asn Ile
        35                  40                  45

Glu Leu Ile Leu Asn Lys Tyr Asn Glu Ile Phe Val Pro Leu Ile Leu
    50                  55                  60

Ser Asn Glu Lys Lys Tyr Lys Lys Asn Arg Asn Ser Glu Leu Ile Asn
65                  70                  75                  80

Lys Tyr Leu Thr Gly Leu Lys Gly Val Glu Ile Gly Gly Ser Ala Gly
                85                  90                  95

Ala Asp Phe Gly Ile Asp Ala Ile Gln Val Asn Ile Val Asp Ala Asn
            100                 105                 110

Gln Glu His Asn Asn Tyr Tyr Gln Gln Thr Asn Ile Leu Gly Ser Gly
        115                 120                 125

Tyr Asn Gln Arg Thr Asp Ile Ile Ser Cys Gly Asp Val Leu Pro Phe
    130                 135                 140

Gln Asp Asn Ser Ile Asp Phe Val Phe Ser Ser His Val Leu Glu His
145                 150                 155                 160

Phe Tyr Asp Pro Ile Lys Ala Leu Lys Glu Trp Tyr Arg Val Ile Lys
                165                 170                 175

Lys Asp Gly Tyr Ile Ala Met Ile Val Pro His Lys Glu Arg Thr Phe
            180                 185                 190

Asp Lys Asp Arg Asp Arg Thr Thr Leu Asn Glu Leu Ile Glu Arg His
        195                 200                 205

Asn Lys Val Lys Asn Tyr Lys Tyr Asn Val Asp Glu Arg Gly Met His
    210                 215                 220

Phe Ser Val Trp Ile Thr Glu Asp Ile Leu Glu Leu Cys Lys Tyr Leu
225                 230                 235                 240

Asn Met Asn Val Ile Glu Tyr Leu Asp Val Asp Asp Ala Val Gly Asn
                245                 250                 255

Gly Phe Ala Ile Ile Ile Lys Lys
            260
```

<210> SEQ ID NO 17
<211> LENGTH: 1818
<212> TYPE: DNA
<213> ORGANISM: Brachysprira hyodysenteriae

<400> SEQUENCE: 17
atgaatgata aatatgttat atgttcaatt acaacaggat ttacagatca actcataaat 60
tttgctacag caatatatat tagagaaaaa tataaaaaaa atgtaaaatt agatatatca 120
tggttttctg tttatgaaaa tacagattat ttgggaatag aaaaacgtaa cctggaagta 180
ctaaatatat ttaatgactt taattttgaa atagctacaa aaaaagaaat agatatagct 240
ttaaagtcta tttttataga tggtagatat gaaaatatag ataaaatatt aaaatccaat 300
aaacatatat atgttggaca tactttattt tactatggac atattaatat ttcttctttt 360
ttcaatcttg acaaatattt tattaattta ttaaatgaaa aacataaaaa catattaaat 420
tacatgtcat cttttgaaag tgttgctata catataagac gaggagatta tatgtatgcg 480
ttaaaaatag atggaagaaa gaataatgct tctttagact atatatatac atcaataaaa 540
tatttaaata atactttaga aaataaaaat ataaaatttt atatattttc taataataaa 600
aaatatataa aaaataattt aataccaatt tttcaaaata ataatattaa ttttgaaatt 660
atagaagata atcctgaata tatagatttt tatttaatga ctaaatgtaa gcatataata 720
tcttcattag gaaaatttgc aaaagtagct tttaaattta taaaaaatga aaataaaata 780
tttatagata cagacaatat ttataatttg aaaaaagaat atttctataa aaatatttgt 840
gaaaaatact gcaacataat ttatgaagaa tataataata taaaaacata tatatcaaaa 900
aataatatga tatatatact agacttaatt gaaaaaaata atataaagaa tatatgtcaa 960
ataggcttgc tagacggttt agaaactcat actctattaa aatattcagc agacaataat 1020
aactgtttta atttattatg ttttgaaaat aatgaaagag atatagttgg aatagaatta 1080
aaaaatttaa cagaaaatga aaaaaaacta tttacattat atatagaaca gtctccttta 1140
gatatagata attcttttaa tataaaaaat atagatttta tctttttttac aaaagaaaat 1200
tctaatcctc tagtattcat ttatttaata tacttatttc catttatgaa agaagaaatc 1260
ataatagtat ttaatgatat tataagtggt aaatattatt ctggaagtta ttgtatattt 1320
aatatgttta atggagaaaa aaatcaattt tataatttta atacaaataa atatgacaat 1380
atcggatata taaaaataaa gaaacaagaa ttattaaata taataaaaaa aatatctgtt 1440
atagaatatg atggttatat aaataaattt tttatgaata aattaataga taacagaaat 1500
gattattata attattttga tttagatatg tcatacatta ggttaaataa tttaaagcaa 1560
tatatgaagg ataaatttga tatagaatat tcaaattata taatctctaa catagaaaat 1620
aatattatta attatgaaaa acaatattat aaaaaccaaa aaaataattt ttattctcaa 1680
aatcaaatac atatttctaa aatagaaaat ataatagata aacataataa attaattaat 1740
agtatatctt ggtggatacc tataaaagaa ttaagagaaa atttcaaaaa taaatttata 1800
agaccagacc agacctaa 1818

<210> SEQ ID NO 18
<211> LENGTH: 1902
<212> TYPE: DNA
<213> ORGANISM: Brachysprira hyodysenteriae

<400> SEQUENCE: 18
atgaatgata aatatgttat atgttcaatt acaacaggat ttacagatca actcataaat 60

```
tttgctacag caatatatat tagagaaaaa tataaaaaaa atgtaaaatt agatatatca    120
tggttttctg tttatgaaaa tacagattat ttgggaatag aaaaacgtaa cctggaagta    180
ctaaatatat ttaatgactt taattttgaa atagctacaa aaaaagaaat agatatagct    240
ttaaagtcta tttttataga tggtagatat gaaaatatag ataaaatatt aaaatccaat    300
aaacatatat atgttggacc atatgttgga catactttat tttactatgg acatattaat    360
atttcttctt ttttcaatct tgacaaatat tttattaatt tattaaatga aaaacataaa    420
aacatattaa atgacatgtc atcttttgaa agtgttgcta tacatataag acgaggagat    480
tatatgtatg cgttaaaaat agatggaaga aagaataatg cttctttaga ctatatatat    540
acatcaataa aatatttaaa taatacttta gaaaataaaa atataaaatt ttatatattt    600
tctaataata aaaaatatat aaaaaataat ttaataccaa tttttcaaaa taataatatt    660
aattttgaaa ttatagaaga taatcctgaa tatatagatt tttatttaat gactaaatgt    720
aagcatataa tatcttcatt aggaaaattt gcaaaagtag cttttaaatt tataaaaaat    780
gaaaataaaa tatttataga tacagacaat atttataatt tgaaaaaaga atatttctat    840
aaaaatattt gtgaaaaata ctgcaacata atttatgaag aatataataa tataaaaaca    900
tatatatcaa aaaataatat gatatatata ctagacttaa ttgaaaaaaa taatataaag    960
aatatatgtc aaataggctt gctagacggt ttagaaactc atactctatt aaaatattca   1020
gcagacaata ataactgttt taatttatta tgttttgaaa ataatgaaag agatatagtt   1080
ggaatagaat taaaaaattt aacagaaaat gaaaaaaaac tatttacatt atatatagaa   1140
cagtctcctt tagatataga taattctttt aatataaaaa atatagattt tatctttttt   1200
acaaaagaaa attctaatcc tctagtattc atttatttaa tatacttatt tccatttatg   1260
aaagaagaaa tcataatagt atttaatgat attataagtg ataaatatta ttctggaagt   1320
tattgtatat ttaatatgtt taatggagaa aaaaatcaat tttataattt taatacaaat   1380
gaatatgaca atatcggata tataaaaata aagaaacaag aattattaaa tataataaaa   1440
aaaatatctg ttatagaata tgatggttat ataaataaat tttttatgaa taaattaata   1500
gataacagaa atgattatta taattatttt gatttagata tgtcatacat taggttaaat   1560
aatttaaagc aatatatgaa ggataaattt gatatagaat attcaaatta tataatctct   1620
aacatagaaa ataatattat taattatgaa aaacaatatt ataaaaacca aaaaaataat   1680
ttttattcca aaaatcaaat acatatttct aaaatagaaa atataataga taaacataat   1740
aaattaatta atagtatatc ttggtggata cctataaaaa aattaagaga aaatttcaaa   1800
aataaattta taagaccaga ccagaccaga ccagaccaga ccagaccaga ccagaccaga   1860
ccagaccaga ccagaccaga ccagaccaga cctaatatgt aa                      1902
```

<210> SEQ ID NO 19
<211> LENGTH: 1860
<212> TYPE: DNA
<213> ORGANISM: Brachysprira hyodysenteriae

<400> SEQUENCE: 19

```
atgaatgata aatatgttat atgttcaatt acaacaggat ttacagatca actcataaat     60
tttgctacag caatatatat tagagaaaaa tataaaaaaa atgtaaaatt agatatatca    120
tggttttctg tttatgaaaa tacagattat ttgggaatag aaaaacgtaa tctggaagta    180
ctaaatatat ttaatgactt taattttgaa atagctacaa aaaaagaaat agatatagct    240
```

ttaaagtcta tttttataga tggtagatat gaaaatatag ataaaatatt aaaatccaat 300
aaacatatat atgttggacc atatgttgga catactttat tttactatgg acatattaat 360
atttcttctt ttttcaatct tgacaaatat tttattaatt tattaaatga aaaacataaa 420
aacatattaa atgacatgtc atcttttgaa agtgttgcta tacatataag acgaggagat 480
tatatgtatg cgttaaaaat agatggaaga aagaataatg cttctttaga ctatatatat 540
acatcaataa aatatttaaa taatacttta gaaaataaaa atataaaatt ttatatattt 600
tctaataata aaaaatatat aaaaaataat ttaataccaa tttttcaaaa taataatatt 660
aattttgaaa ttatagaaga taatcctgaa tatatagatt tttatttaat gactaaatgt 720
aagcatataa tatcttcatt aggaaaattt gcaaaagtag cttttaaatt tataaaaaat 780
gaaaataaaa tatttataga tacagacaat atttataatt tgaaaaaaga atatttctat 840
aaaaatattt gtgaaaaata ctgcaacata atttatgaag aatataataa tataaaaaca 900
tatatatcaa aaaataatat gatatatata ctagacttaa ttgaaaaaaa taatataaag 960
aatatatgtc aaataggctt gctagacggt ttagaaactc atactctatt aaaatattca 1020
gcagacaata ataactgttt taatttatta tgttttgaaa ataatgaaag agatatagtt 1080
ggaatagaat taaaaaattt aacagaaaat gaaaaaaaac tatttacatt atatatagaa 1140
cagtctcctt tagatataga taattctttt aatataaaaa atatagattt tatctttttt 1200
acaaaagaaa attctaatcc tctagtattc atttatttaa tatacttatt tccatttatg 1260
aaagaagaaa tcataatagt atttaatgat attataagtg ataaatatta ttctggaagt 1320
tattgtatat ttaatatgtt taatggagaa aaaaatcaat tttataattt taatacaaat 1380
aaatatgaca atatcggata tataaaaata aagaaacaag aattattaaa tataataaaa 1440
aaaatatctg ttatagaata tgatggttat ataaataaat tttttatgaa taaattaata 1500
gataacagaa atgattatta taattatttt gatttagata tgtcatacat taggttaaat 1560
aatttaaagc aatatatgaa ggataaattt gatatagaat attcaaatta tataatcttt 1620
aacatagaaa ataatattat taattatgaa aaacaatatt ataaaaacca aaaaaataat 1680
ttttattcca aaaatcaaat acatatttct aaaatagaaa atataataga taaacataat 1740
aaattaatta atagtatatc ttggtggata cctataaaaa aattaagaga aaatttcaaa 1800
aataaattta taagaccaga ccagaccaga ccagaccaga ccagaccaga ccagacctaa 1860

<210> SEQ ID NO 20
<211> LENGTH: 1935
<212> TYPE: DNA
<213> ORGANISM: Brachysprira hyodysenteriae

<400> SEQUENCE: 20
atgaatgata aatatgttat atgttcaatt acaacaggat ttacagatca actcataaat 60
tttgctacag caatatatat tagagaaaaa tataaaaaaa atgtaaaatt agatatatca 120
tggttttctg tttatgaaaa tacagattat ttgggaatag aaaaacgtaa cctggaagta 180
ctaaatatat ttaatgactt taattttgaa atagctacaa aaaaagaaat agatatagct 240
ttaaagtcta tttttataga tggtagatat gaaaatatag ataaaatatt aaaatccaat 300
aaacatatat atgttggacc atatgttgga catactttat tttactatgg acatattaat 360
atttcttctt ttttcaatct tgacaaatat tttattaatt tattaaatga aaaacataaa 420
aacatattaa atgacatgtc atcttttgaa agtgttgcta tacatataag acgaggagat 480
tatatgtatg cgttaaaaat agatggaaga aagaataatg cttctttaga ctatatatat 540

```
acatcaataa aatatttaaa taatacttta gaaaataaaa atataaaatt ttatatattt    600
tctaataata aaaaatatat aaaaaataat ttaataccaa tttttcaaaa taataatatt    660
aattttgaaa ttatagaaga taatcctgaa tatatagatt tttatttaat gactaaatgt    720
aagcatataa tatcttcatt aggaaaattt gcaaaagtag cttttaaatt tataaaaaat    780
gaaaataaaa tatttataga tacagacaat atttataatt tgaaaaaaga atatttctat    840
aaaaatattt gtgaaaaata ctgcaacata atttatgaag aatataataa tataaaaaca    900
tatatatcaa aaaataatat gatatatata ctagacttaa ttgaaaaaaa taatataaag    960
aatatatgtc aaataggctt gctagacggt ttagaaactc atactctatt aaaatattca   1020
gcagacaata ataactgttt taatttatta tgttttgaaa ataatgaaag agatatagtt   1080
ggaatagaat taaaaaattt aacagaaaat gaaaaaaaac tatttacatt atatatagaa   1140
cagtctcctt tagatataga taattctttt aatataaaaa atatagattt tatctttttt   1200
acaaaagaaa attctaatcc tctagtattc atttatttaa tatacttatt tccatttatg   1260
aaagaagaaa tcataatagt atttaatgat attataagtg gtaaatatta ttctggaagt   1320
tattgtatat ttaatatgtt taatggagaa aaaaatcaat tttataattt taatacaaat   1380
aaatatgaca atatcggata tataaaaata aagaaacaag aattattaaa tataataaaa   1440
aaaatatctg ttatagaata tgatggttat ataaataaat tttttatgaa taaattaata   1500
gataacagaa atgattatta taattatttt gatttagata tgtcatacat taggttaaat   1560
aatttaaagc aatatatgaa ggataaattt gatatagaat attcaaatta tataatctct   1620
aacatagaaa ataatattat taattatgaa aaacaatatt ataaaaacca aaaaaataat   1680
ttttattctc aaaatcaaat acatatttct aaaatagaaa atataataga taaacataat   1740
aaattaatta atagtatatc ttggtggata cctataaaaa aattaagaga aaatttcaaa   1800
aataaattta taagaccaga ccagaccaga ccagaccaga ccagaccaga ccagaccaga   1860
ccagacctaa tatgtaaaga atacatatat aatatactat attacaaaat aaataaatta   1920
caatatataa attaa                                                    1935
```

<210> SEQ ID NO 21
<211> LENGTH: 1860
<212> TYPE: DNA
<213> ORGANISM: Brachysprira hyodysenteriae

<400> SEQUENCE: 21

```
atgaatgata aatatgttat atgttcaatt acaacaggat ttacagatca actcataaat     60
tttgctacag caatatatat tagagaaaaa tataaaaaaa atgtaaaatt agatatatca    120
tggttttctg tttatgaaaa tacagattat ttgggaatag aaaaacgtaa cctggaagta    180
ctaaatatat ttaatgactt taattttgaa atagctacaa aaaaagaaat agatatagct    240
ttaaagtcta tttttataga tggtagatat gaaaatatag ataaaatatt aaaatccaat    300
aaacatatat atgttggacc atatgttgga catactttat tttactatgg acatattaat    360
atttcttctt ttttcaatct tgacaaatat tttattaatt tattaaatga aaaacataaa    420
aacatattaa atgacatgtc atcttttgaa agtgttacta tacatataag acgaggagat    480
tatatgtatg cgttaaaaat agatggaaga aagaataatg cttctttaga ctatatatat    540
acatcaataa aatatttaaa taatacttta gaaaataaaa atataaaatt ttatatattt    600
tctaataata aaaaatatat aaaaaataat ttaataccaa tttttcaaaa taataatatt    660
```

```
aattttgaaa ttatagaaga taatcctgaa tatatagatt tttatttaat gactaaatgt    720

aagcatataa tatcttcatt aggaaaattt gcaaaagtag cttttaaatt tataaaaaat    780

gaaaataaaa tatttataga tacagacaat atttataatt tgaaaaaaga atatttctat    840

aaaaatattt gtgaaaaata ctgcaacata atttatgaag aatataataa tataaaaaca    900

tatatatcaa aaaataatat gatatatata ctagacttaa ttgaaaaaaa taatataaag    960

aatatatgtc aaataggctt gctagacggt ttagaaactc atactctatt aaaatattca   1020

gcagacaata ataactgttt taatttatta tgttttgaaa ataatgaaag agatatagtt   1080

ggaatagaat taaaaaattt aacagaaaat gaaaaaaaac tatttacatt atatatagaa   1140

cagtctcctt tagatataga taattctttt aatataaaaa atatagattt tatctttttt   1200

acaaaagaaa attctaatcc tctagtattc atttatttaa tatacttatt tccatttatg   1260

aaagaagaaa tcataatagt atttaatgat attataagtg gtaaatatta ttctggaagt   1320

tattgtatat ttaatatgtt taatggagaa aaaaatcaat tttataattt taatacaaat   1380

aaatatgaca atatcggata tataaaaata aagaaacaag aattattaaa tataataaaa   1440

aaaatatctg ttatagaata tgatggttat ataaataaat tttttatgaa taaattaata   1500

gataacagaa atgattatta taattatttt gatttagata tgtcatacat taggttaaat   1560

aatttaaagc aatatatgaa ggataaattt gatatagaat attcaaatta tataatctct   1620

aacatagaaa ataatattat taattatgaa aaacaatatt ataaaaacca aaaaaataat   1680

ttttattctc aaaatcaaat acatatttct aaaatagaaa atataataga taaacataat   1740

aaattaatta atagtatatc ttggtggata cctataaaaa aattaagaga aaatttcaaa   1800

aataaattta taagaccaga ccagaccaga ccagaccaga ccagaccaga ccagacctaa   1860
```

<210> SEQ ID NO 22
<211> LENGTH: 1860
<212> TYPE: DNA
<213> ORGANISM: Brachysprira hyodysenteriae

<400> SEQUENCE: 22

```
atgaatgata aatatgttat atgttcaatt acaacaggat ttacagatca actcataaat     60

tttgctacag caatatatat tagagaaaaa tataaaaaaa atgtaaaatt agatatatca    120

tggttttctg tttatgaaaa tacagattat ttgggaatag aaaaacgtaa cctggaagta    180

ctaaatatat ttaatgactt taattttgaa atagctacaa aaaaagaaat agatatagct    240

ttaaagtcta tttttataga tggtagatat gaaaatatag ataaaatatt aaaatccaat    300

aaacatatat atgttggacc atatgttgga catactttat tttactatgg acatattaat    360

atttcttctt ttttcaatct tgacaaatat tttattaatt tattaaatga aaaacataaa    420

aacatattaa attacatgtc atcttttgaa agtgttgcta tacatataag acgaggagat    480

tatatgtatg cgttaaaaat agatggaaga aagaataatg cttctttaga ctatatatat    540

acatcaataa aatatttaaa taatacttta gaaaataaaa atataaaatt tttatatattt    600

tctaataata aaaaatatat aaaaaataat ttaataccaa tttttcaaaa taataatatt    660

aattttgaaa ttatagaaga taatcctgaa tatatagatt tttatttaat gactaaatgt    720

aagcatataa tatcttcatt aggaaaattt gcaaaagtag cttttaaatt tataaaaaat    780

gaaaataaaa tatttataga tacagacaat atttataatt tgaaaaaaga atatttctat    840

aaaaatattt gtgaaaaata ctgcaacata atttatgaag aatataataa tataaaaaca    900

tatatatcaa aaaataatat gatatatata ctagacttaa ttgaaaaaaa taatataaag    960
```

aatatatgtc aaataggctt gctagacggt ttagaaactc atactctatt aaaatattca 1020
gcagacaata ataactgttt taatttatta tgttttgaaa ataatgaaag agatatagtt 1080
ggaatagaat taaaaaattt aacagaaaat gaaaaaaaac tatttacatt atatatagaa 1140
cagtctcctt tagatataga taattctttt aatataaaaa atatagattt tatctttttt 1200
acaaaagaaa attctaatcc tctagtattc atttatttaa tatacttatt tccatttatg 1260
aaagaagaaa tcataatagt atttaatgat attataagtg gtaaatatta ttctggaagt 1320
tattgtatat ttaatatgtt taatggagaa aaaaatcaat tttataattt taatacaaat 1380
aaatatgaca atatcggata tataaaaata aagaaacaag aattattaaa tataataaaa 1440
aaaatatctg ttatagaata tgatggttat ataaataaat tttttatgaa taaattaata 1500
gataacagaa atgattatta taattatttt gatttagata tgtcatacat taggttaaat 1560
aatttaaagc aatatatgaa ggataaattt gatatagaat attcaaatta tataatctct 1620
aacatagaaa ataatattat taattatgaa aaacaatatt ataaaaacca aaaaaataat 1680
ttttattctc aaaatcaaat acatatttct aaaatagaaa atataataga taaacataat 1740
aaattaatta atagtatatc ttggtggata cctataaaag aattaagaga aaatttcaaa 1800
aataaattta taagaccaga ccagaccaga ccagaccaga ccagaccaga ccagacctaa 1860

<210> SEQ ID NO 23
<211> LENGTH: 1860
<212> TYPE: DNA
<213> ORGANISM: Brachysprira hyodysenteriae

<400> SEQUENCE: 23
atgaatgata aatatgttat atgttcaatt acaacaggat ttacagatca actcataaat 60
tttgctacag caatatatat tagagaaaaa tataaaaaaa atgtaaaatt agatatatca 120
tggttttctg tttatgaaaa tacagattat ttgggaatag aaaaacgtaa cctggaagta 180
ctaaatatat ttaatgactt taattttgaa atagctacaa aaaaagaaat agatatagct 240
ttaaagtcta tttttataga tggtagatat gaaaatatag ataaaatatt aaaatccaat 300
aaacatatat atgttggacc atatgttgga catactttat tttactatgg acatattaat 360
atttcttctt ttttcaatct tgacaaatat tttattaatt tattaaatga aaaacataaa 420
aacatattaa attacatgtc atcttttgaa agtgttgcta tacatataag acgaggagat 480
tatatgtatg cgttaaaaat agatggaaga aagaataatg cttctttaga ctatatatat 540
acatcaataa aatatttaaa taatacttta gaaaataaaa atataaaatt ttatatattt 600
tctaataata aaaaatatat aaaaaataat ttaataccaa tttttcaaaa taataatatt 660
aattttgaaa ttatagaaga taatcctgaa tatatagatt tttatttaat gactaaatgt 720
aagcatataa tatcttcatt aggaaaattt gcaaaagtag cttttaaatt tataaaaaat 780
gaaaataaaa tatttataga tacagacaat atttataatt tgaaaaaaga atatttctat 840
aaaaatattt gtgaaaaata ctgcaacata atttatgaag aatataataa tataaaaaca 900
tatatatcaa aaaataatat gatatatata ctagacttaa ttgaaaaaaa taatataaag 960
aatatatgtc aaataggctt gctagacggt ttagaaactc atactctatt aaaatattca 1020
gcagacaata ataactgttt taatttatta tgttttgaaa ataatgaaag agatatagtt 1080
ggaatagaat taaaaaattt aacagaaaat gaaaaaaaac tatttacatt atatatagaa 1140
cagtctcctt tagatataga taattctttt aatataaaaa atatagattt tatctttttt 1200
acaaaagaaa attctaatcc tctagtattc atttatttaa tatacttatt tccatttatg 1260
aaagaagaaa tcataatagt atttaatgat attataagtg gtaaatatta ttctggaagt 1320
tattgtatat ttaatatgtt taatggagaa aaaaatcaat tttataattt taatacaaat 1380
aaatatgaca atatcggata tataaaaata aagaaacaag aattattaaa tataataaaa 1440
aaaatatctg ttatagaata tgatggttat ataaataaat tttttatgaa taaattaata 1500
gataacagaa atgattatta taattatttt gatttagata tgtcatacat taggttaaat 1560
aatttaaagc aatatatgaa ggataaattt gatatagaat attcaaatta tataatctct 1620
aacatagaaa ataatattat taattatgaa aaacaatatt ataaaaacca aaaaaaataat 1680 ttttattctc aaaatcaaat acatatttct aaaatagaaa atataataga taaacataat 1740
aaattaatta atagtatatc ttggtggata cctataaaaa aattaagaga aaatttcaaa 1800
aataaattta taagaccaga ccagaccaga ccagaccaga ccagaccaga ccagacctaa 1860

<210> SEQ ID NO 24
<211> LENGTH: 1860
<212> TYPE: DNA
<213> ORGANISM: Brachysprira hyodysenteriae

<400> SEQUENCE: 24
atgaatgata aatatgttat atgttcaatt acaacaggat ttacagatca actcataaat 60
tttgctacag caatatatat tagagaaaaa tataaaaaaa atgtaaaatt agatatatca 120
tggttttctg tttatgaaaa tacagattat ttgggaatag aaaaacgtaa cctggaagta 180
ctaaatatat ttaatgactt taattttgaa atagctacaa aaaaagaaat agatatagct 240
ttaaagtcta tttttataga tggtagatat gaaaatatag ataaaatatt aaaatccaat 300
aaacatatat atgttggacc atatgttgga catactttat tttactatgg acatattaat 360
atttcttctt ttttcaatct tgacaaatat tttattaatt tattaaatga aaaacataaa 420
aacatattaa attacatgtc atcttttgaa agtgttgcta tacatataag acgaggagat 480
tatatgtatg cgttaaaaat agatggaaga aagaataatg cttctttaga ctatatatat 540
acatcaataa aatatttaaa taatacttta gaaaataaaa atataaaatt ttatatattt 600
tctaataata aaaaatatat aaaaaataat ttaataccaa tttttcaaaa taataatatt 660
aattttgaaa ttatagaaga taatcctgaa tatatagatt tttatttaat gactaaatgt 720
aagcatataa tatcttcatt aggaaaattt gcaaaagtag cttttaaatt tataaaaaat 780
gaaaataaaa tatttataga tacagacaat atttataatt tgaaaaaaga atatttctat 840
aaaaatattt gtgaaaaata ctgcaacata atttatgaag aatataataa tataaaaaca 900
tatatatcaa aaaataatat gatatatata ctagacttaa ttgaaaaaaa taatataaag 960
aatatatgtc aaataggctt gctagacggt ttagaaactc atactctatt aaaatattca 1020
gcagacaata ataactgttt taatttatta tgttttgaaa ataatgaaag agatataatt 1080
ggaatagaat taaaaaattt aacagaaaat gaaaaaaaac tatttacatt atatatagaa 1140
cagtctcctt tagatataga taattctttt aatataaaaa atatagattt tatctttttt 1200
acaaaagaaa attctaatcc tctagtattc atttatttaa tatacttatt tccatttatg 1260
aaagaagaaa tcataatagt atttaatgat attataagtg gtaaatatta ttctggaagt 1320
tattgtatat ttaatatgtt taatggagaa aaaaatcaat tttataattt taatacaaat 1380
aaatatgaca atatcggata tataaaaata aagaaacaag aattattaaa tataataaaa 1440
aaaatatctg ttatagaata tgatggttat ataaataaat tttttatgaa taaattaata 1500
gataacagaa atgattatta taattatttt gatttagata tgtcatacat taggttaaat 1560
aatttaaagc aatatatgaa ggataaattt gatatagaat attcaaatta tataatctct 1620
aacatagaaa ataatattat taattatgaa aaacaatatt ataaaaacca aaaaaataat 1680
ttttattctc aaaatcaaat acatatttct aaaatagaaa atataataga taaacataat 1740
aaattaatta atagtatatc ttggtggata cctataaaaa aattaagaga aaatttcaaa 1800
aataaattta taagaccaga ccagaccaga ccagaccaga ccagaccaga ccagacctaa 1860

<210> SEQ ID NO 25
<211> LENGTH: 1857
<212> TYPE: DNA
<213> ORGANISM: Brachysprira hyodysenteriae

<400> SEQUENCE: 25
atgaatgata aatatgttat atgttcaatt acaacaggat ttacagatca actcataaat 60
tttgctacag caatatatat tagagaaaaa tataaaaaaa atgtaaaatt agatatatca 120
tggttttctg tttatgaaaa tacagattat ttgggaatag aaaaacgtaa cctggaagta 180
ctaaatatat ttaatgactt taattttgaa atagctacaa aaaaagaaat agatatagct 240
ttaaagtcta tttttataga tggtagatat gaaaatatag ataaaatatt aaaatccaat 300
aaacatatat atgttggacc atatgttgga catactttat tttactatgg acatattaat 360
atttcttctt ttttcaatct tgacaaatat tttattaatt tattaaatga aaaacataaa 420
aacatattaa attacatgtc atcttttgaa agtgttgcta tacatataag acgaggagat 480
tatatgtatg cgttaaaaat agatggaaga aagaataatg cttctttaga ctatatatat 540
acatcaataa aatatttaaa taatacttta gaaaataaaa atataaaatt ttatatattt 600
tctaataata aaaaatatat aaaaaataat ttaataccaa tttttcaaaa taataatatt 660
aattttgaaa ttatagaaga taatcctgaa tatatagatt tttatttaat gactaaatgt 720
aagcatataa tatcttcatt aggaaaattt gcaaaagtag cttttaaatt tataaaaaat 780
gaaaataaaa tatttataga tacagacaat atttataatt tgaaaaaaga atatttctat 840
aaaaatattt gtgaaaaata ctgcaacata atttatgaag aatataataa tataaaaaca 900
tatatatcaa aaaataatat gatatatata ctagacttaa ttgaaaaaaa taatataaag 960
aatatatgtc aaataggctt gctagacggt ttagaaactc atactctatt aaaatattca 1020
gcagacaata ataactgttt taatttatta tgttttgaaa ataatgaaag agatatagtt 1080
ggaatagaat taaaaaattt aacagaaaat gaaaaaaaac tatttacatt atatatagaa 1140
cagtctcctt tagatataga taattctttt aatataaaaa atatagattt tatctttttt 1200
acaaaagaaa attctaatcc tctagtattc atttatttaa tatacttatt tccatttatg 1260
aaagaagaaa tcataatagt atttaatgat attataagtg gtaaatatta ttctggaagt 1320
tattgtatat ttaatatgtt taatggagaa aaaaatcaat tttataattt taatacaaat 1380
aaatatgaca atatcggata tataaaaata aagaaacaag aattattaaa tataataaaa 1440
aaaatatctg ttatagaata tgatggttat ataaataaat tttttatgaa taaattaata 1500
gataacagaa atgattatta taattatttt gatttagata tgtcatacat taggttaaat 1560
aatttaaagc aatatatgaa ggataaattt gatatagaat attcaaatta tataatctct 1620
aacatagaaa ataatattat taattatgaa aaacaatatt ataaaaacca aaaaaataat 1680
ttttattctc aaaatcaaat acatatttct aaaatagaaa atataataga taaacataat 1740
aaattaatta atagtatatc ttggtggata cctataaaag aattaagaga aaatttcaaa 1800
aataaattta taagaccaga ccagaccaga ccagaccaga ccagacctaa tatgtaa 1857

<210> SEQ ID NO 26
<211> LENGTH: 1802
<212> TYPE: DNA
<213> ORGANISM: Brachysprira hyodysenteriae

<400> SEQUENCE: 26
caatatatat tagagaaaaa tataaaaaaa atgtaaaatt agatatatca tggttttctg 60
tttatgaaaa tacagattat ttgggaatag aaaaacgtaa cctggaagta ctaaatatat 120
ttaatgactt taattttgaa atagctacaa aaaaagaaat agatatagct ttaaagtcta 180
tttttataga tggtagatat gaaaatatag ataaaatatt aaaatccaat aaacatatat 240
atgttggacc atatgttgga catactttat tttactatgg acatattaat atttcttctt 300
ttttcaatct tgacaaatat tttattaatt tattaaataa aaaacataaa aacatattaa 360
atgacatgtc atcttttgaa agtgttgcta tacatataag acgaggagat tatatgtatg 420
cgttaaaaat agatggaaga aagaataatg cttctttaga ctatatatat acatcaataa 480
aatatttaaa taatacttta gaaaataaaa atataaaatt ttatatattt tctaataata 540
aaaaatatat aaaaaataat ttaataccaa tttttcaaaa taataatatt aattttgaaa 600
ttatagaaga taatcctgaa tatatagatt tttatttaat gactaaatgt aagcatataa 660
tatcttcatt aggaaaattt gcaaaagtag cttttaaatt tataaaaaat gaaaataaaa 720
tatttataga tacagacaat atttataatt tgaaaaaaga atatttctat aaaaatattt 780
gtgaaaaata ctgcaacata atttatgaag aatataataa tataaaaaca tatatatcaa 840
aaaataatat gatatatata ctagacttaa ttgaaaaaaa taatataaag aatatatgtc 900
aaataggctt gctagacggt ttagaaactc atactctatt aaaatattca gcatacaata 960
ataactgttt taatttatta tgttttgaaa ataatgaaag agatatagtt ggaatagaat 1020
taaaaaattt aacagaaaat gaaaaaaaac tatttacatt atatatagaa cagtctcctt 1080
tagatataga taattctttt aatataaaaa atatagattt tatctttttt acaaaagaaa 1140
attctaatcc tctagtattc atttatttaa tatacttatt tccatttatg aaagaagaaa 1200
tcataatagt atttaatgat attataagtg gtaaatatta ttctggaagt tattgtatat 1260
ttaatatgtt taatggagaa aaaaatcaat tttataattt taatacaaat aaatatgaca 1320
atatcggata tataaaaata aagaaacaag aattattaaa tataataaaa aaaatatctg 1380
ttatagaata tgatggttat ataaataaat tttttatgaa taaattaata gataacagaa 1440
atgattatta taattatttt gatttagata tgtcatacat taggttaaat aatttaaagc 1500
aatatatgaa ggataaattt gatatagaat attcaaatta tataatctct aacatagaaa 1560
ataatattat taattatgaa aaacaatatt ataaaaacca aaaaaataat ttttattctc 1620
aaaatcaaat acatatttct aaaatagaaa atataataga taaacataat aaattaatta 1680
atagtatatc ttggtggata cctataaaaa aattaagaga aaatttcaaa aataaattta 1740
taagaccaga ccagaccaga ccagaccaga ccagaccaga ccagaccaga cctaatatgt 1800
aa 1802

<210> SEQ ID NO 27
<211> LENGTH: 1845
<212> TYPE: DNA
<213> ORGANISM: Brachysprira hyodysenteriae

<400> SEQUENCE: 27

```
atgaatgata aatatgttat atgttcaatt acaacaggat ttacagatca actcataaat     60
tttgctacag caatatatat tagagaaaaa tataaaaaaa atgtaaaatt agatatatca    120
tggttttctg tttatgaaaa tacagattat ttgggaatag aaaaacgtaa cctggaagta    180
ctaaatatat ttaatgactt taattttgaa atagctacaa aaaaagaaat agatatagct    240
ttaaagtcta tttttataga tggtagatat gaaaatatag ataaaatatt aaaatccaat    300
aaacatatat atgttggacc atatgttgga catactttat tttactatgg acatattaat    360
atttcttctt ttttcaatct tgacaaatat tttattaatt tattaaatga aaaacataaa    420
aacatattaa attacatgtc atcttttgaa agtgttgcta tacatataag acgaggagat    480
tatatgtatg cgttaaaaat agatggaaga aagaataatg cttctttaga ctatatatat    540
acatcaataa aatatttaaa taatacttta gaaaataaaa atataaaatt ttatatattt    600
tctaataata aaaaatatat aaaaaataat ttaataccaa tttttcaaaa taataatatt    660
aattttgaaa ttatagaaga taatcctgaa tatatagatt tttatttaat gactaaatgt    720
aagcatataa tatcttcatt aggaaaattt gcaaaagtag cttttaaatt tataaaaaat    780
gaaaataaaa tatttataga tacagacaat atttataatt tgaaaaaaga atatttctat    840
aaaaatattt gtgaaaaata ctgcaacata atttatgaag aatataataa tataaaaaca    900
tatatatcaa aaaataatat gatatatata ctagacttaa ttgaaaaaaa taatataaag    960
aatatatgtc aaataggctt gctagacggt ttagaaactc atactctatt aaaatattca   1020
gcagacaata ataactgttt taatttatta tgttttgaaa ataatgaaag agatatagtt   1080
ggaatagaat taaaaaattt aacagaaaat gaaaaaaaac tatttacatt atatatagaa   1140
cagtctcctt tagatataga taattctttt aatataaaaa atatagattt tatctttttt   1200
acaaaagaaa attctaatcc tctagtattc atttatttaa tatacttatt tccatttatg   1260
aaagaagaaa tcataatagt atttaatgat attataagtg gtaaatatta ttctggaagt   1320
tattgtatat ttaatatgtt taatggagaa aaaaatcaat tttataattt taatacaaat   1380
aaatatgaca atatcggata tataaaaata aagaaacaag aattattaaa tataataaaa   1440
aaaatatctg ttatagaata tgatggttat ataaataaat tttttatgaa taaattaata   1500
gataacagaa atgattatta taattatttt gatttagata tgtcatacat taggttaaat   1560
aatttaaagc aatatatgaa ggataaattt gatatagaat attcaaatta tataatctct   1620
aacatagaaa ataatattat taattatgaa aaacaatatt ataaaaacca aaaaaaataat  1680
ttttattctc aaaatcaaat acatatttct aaaatagaaa atataataga taaacataat   1740
aaattaatta atagtatatc ttggtggata cctataaaaa aattaagaga aaatttcaaa   1800
aataaattta taagaccaga ccagaccaga ccagaccaga cctaa                    1845
```

<210> SEQ ID NO 28
<211> LENGTH: 1887
<212> TYPE: DNA
<213> ORGANISM: Brachysprira hyodysenteriae

<400> SEQUENCE: 28

```
atgaatgata aatatgttat atgttcaatt acaacaggat ttacagatca actcataaat     60
tttgctacag caatatatat tagagaaaaa tataaaaaaa atgtaaaatt agatatatca    120
tggttttctg tttatgaaaa tacagattat ttgggaatag aaaaacgtaa cctggaagta    180
```

```
ctaaatatat ttaatgactt taattttgaa atagctacaa aaaaagaaat agatatagct    240

ttaaagtcta tttttataga tggtagatat gaaaatatag ataaaatatt aaaatccaat    300

aaacatatat atgttggacc atatgttgga catactttat tttactatgg acatattaat    360

atttcttctt ttttcaatct tgacaaatat tttattaatt tattaaatga aaaacataaa    420

aacatattaa atgacatgtc atcttttgaa agtgttacta tacatataag acgaggagat    480

tatatgtatg cgttaaaaat agatggaaga aagaataatg cttctttaga ctatatatat    540

acatcaataa aatatttaaa taatacttta gaaaataaaa atataaaatt ttatatattt    600

tctaataata aaaaatatat aaaaaataat ttaataccaa tttttcaaaa taataatatt    660

aattttgaaa ttatagaaga taatcctgaa tatatagatt tttatttaat gactaaatgt    720

aagcatataa tatcttcatt aggaaaattt gcaaaagtag cttttaaatt tataaaaaat    780

gaaaataaaa tatttataga tacagacaat atttataatt tgaaaaaaga atatttctat    840

aaaaatattt gtgaaaaata ctgcaacata atttatgaag aatataataa tataaaaaca    900

tatatatcaa aaaataatat gatatatata ctagacttaa ttgaaaaaaa taatataaag    960

aatatatgtc aaataggctt gctagacggt ttagaaactc atactctatt aaaatattca   1020

gcagacaata ataactgttt taatttatta tgttttgaaa ataatgaaag agatatagtt   1080

ggaatagaat taaaaaattt aacagaaaat gaaaaaaaac tatttacatt atatatagaa   1140

cagtctcctt tagatataga taattctttt aatataaaaa atatagattt tatctttttt   1200

acaaaagaaa attctaatcc tctagtattc atttatttaa tatacttatt tccatttatg   1260

aaagaagaaa tcataatagt atttaatgat attataagtg gtaaatatta ttctggaagt   1320

tattgtatat ttaatatgtt taatggagaa aaaaatcaat tttataattt taatacaaat   1380

aaatatgaca atatcggata tataaaaata aagaaacaag aattattaaa tataataaaa   1440

aaaatatctg ttatagaata tgatggttat ataaataaat tttttatgaa taaattaata   1500

gataacagaa atgattatta taattatttt gatttagata tgtcatacat taggttaaat   1560

aatttaaagc aatatatgaa ggataaattt gatatagaat attcaaatta tataatctct   1620

aacatagaaa ataatattat taattatgaa aaacaatatt ataaaaacca aaaaaaataat   1680

ttttattctc aaaatcaaat acatatttct aaaatagaaa atataataga taaacataat   1740

aaattaatta atagtatatc ttggtggata cctataaaaa aattaagaga aaatttcaaa   1800

aataaattta taagaccaga ccagaccaga ccagaccaga ccagaccaga ccagaccaga   1860

ccagaccaga ccagacctaa tatgtaa                                       1887
```

```
<210> SEQ ID NO 29
<211> LENGTH: 1872
<212> TYPE: DNA
<213> ORGANISM: Brachysprira hyodysenteriae

<400> SEQUENCE: 29

atgaatgata aatatgttat atgttcaatt acaacaggat ttacagatca actcataaat     60

tttgctacag caatatatat tagagaaaaa tataaaaaaa atgtaaaatt agatatatca    120

tggttttctg tttatgaaaa tacagattat ttgggaatag aaaaacgtaa cctggaagta    180

ctaaatatat ttaatgactt taattttgaa atagctacaa aaaaagaaat agatatagct    240

ttaaagtcta tttttataga tggtagatat gaaaatatag ataaaatatt aaaatccaat    300

aaacatatat atgttggacc atatgttgga catactttat tttactatgg acatattaat    360

atttcttctt ttttcaatct tgacaaatat tttattaatt tattaaatga aaaacataaa    420
```

aacatattaa attacatgtc atcttttgaa agtgttgcta tacatataag acgaggagat 480
tatatgtatg cgttaaaaat agatggaaga aagaataatg cttctttaga ctatatatat 540
acatcaataa aatatttaaa taatacttta gaaaataaaa atataaaatt ttatatattt 600
tctaataata aaaaatatat aaaaaataat ttaataccaa tttttcaaaa taataatatt 660
aattttgaaa ttatagaaga taatcctgaa tatatagatt tttatttaat gactaaatgt 720
aagcatataa tatcttcatt aggaaaattt gcaaaagtag cttttaaatt tataaaaaat 780
gaaaataaaa tatttataga tacagacaat atttataatt tgaaaaaaga atatttctat 840
aaaaatattt gtgaaaaata ctgcaacata atttatgaag aatataataa tataaaaaca 900
tatatatcaa aaaataatat gatatatata ctagacttaa ttgaaaaaaa taatataaag 960
aatatatgtc aaataggctt gctagacggt ttagaaactc atactctatt aaaatattca 1020
gcagacaata ataactgttt taatttatta tgttttgaaa ataatgaaag agatatagtt 1080
ggaatagaat taaaaaattt aacagaaaat gaaaaaaaac tatttacatt atatatagaa 1140
cagtctcctt tagatataga taattctttt aatataaaaa atatagattt tatctttttt 1200
acaaaagaaa attctaatcc tctagtattc atttatttaa tatacttatt tccatttatg 1260
aaagaagaaa tcataatagt atttaatgat attataagtg gtaaatatta ttctggaagt 1320
tattgtatat ttaatatgtt taatggagaa aaaaatcaat tttataattt taatacaaat 1380
aaatatgaca atatcggata tataaaaata aagaaacaag aattattaaa tataataaaa 1440
aaaatatctg ttatagaata tgatggttat ataaataaat tttttatgaa taaattaata 1500
gataacagaa atgattatta taattatttt gatttagata tgtcatacat taggttaaat 1560
aatttaaagc aatatatgaa ggataaattt gatatagaat attcaaatta tataatctct 1620
aacatagaaa ataatattat taattatgaa aaacaatatt ataaaaacca aaaaaataat 1680
ttttattctc aaaatcaaat acatatttct aaaatagaaa atataataga taaacataat 1740
aaattaatta atagtatatc ttggtggata cctataaaag aattaagaga aaatttcaaa 1800
aataaattta taagaccaga ccagaccaga ccagaccaga ccagaccaga ccagaccaga 1860
cctaatatgt aa 1872

<210> SEQ ID NO 30
<211> LENGTH: 1875
<212> TYPE: DNA
<213> ORGANISM: Brachysprira hyodysenteriae

<400> SEQUENCE: 30
atgaatgata aatatgttat atgttcaatt acaacaggat ttacagatca actcataaat 60
tttgctacag caatatatat tagagaaaaa tataaaaaaa atgtaaaatt agatatatca 120
tggttttctg tttatgaaaa tacagattat ttgggaatag aaaaacgtaa cctggaagta 180
ctaaatatat ttaatgactt taattttgaa atagctacaa aaaaagaaat agatatagct 240
ttaaagtcta tttttataga tggtagatat gaaaatatag ataaaatatt aaaatccaat 300
aaacatatat atgttggacc atatgttgga catactttat tttactatgg acatattaat 360
atttcttctt ttttcaatct tgacaaatat tttattaatt tattaaatga aaaacataaa 420
aacatattaa attacatgtc atcttttgaa agtgttgcta tacatataag acgaggagat 480
tatatgtatg cgttaaaaat agatggaaga aagaataatg cttctttaga ctatatatat 540
acatcaataa aatatttaaa taatacttta gaaaataaaa atataaaatt ttatatattt 600

```
tctaataata aaaaatatat aaaaaataat ttaataccaa tttttcaaaa taataatatt    660

aattttgaaa ttatagaaga taatcctgaa tatatagatt tttatttaat gactaaatgt    720

aagcatataa tatcttcatt aggaaaattt gcaaaagtag cttttaaatt tataaaaaat    780

gaaaataaaa tatttataga tacagacaat atttataatt tgaaaaaaga atatttctat    840

aaaaatattt gtgaaaaata ctgcaacata atttatgaag aatataataa tataaaaaca    900

tatatatcaa aaaataatat gatatatata ctagacttaa ttgaaaaaaa taatataaag    960

aatatatgtc aaataggctt gctagacggt ttagaaactc atactctatt aaaatattca   1020

gcagacaata ataactgttt taatttatta tgttttgaaa ataatgaaag agatatagtt   1080

ggaatagaat taaaaaattt aacagaaaat gaaaaaaaac tatttacatt atatatagaa   1140

cagtctcctt tagatataga taattctttt aatataaaaa atatagattt tatctttttt   1200

acaaaagaaa attctaatcc tctagtattc atttatttaa tatacttatt tccatttatg   1260

aaagaagaaa tcataatagt atttaatgat attataagtg gtaaatatta ttctggaagt   1320

tattgtatat ttaatatgtt taatggagaa aaaaatcaat tttataattt taatacaaat   1380

aaatatgaca atatcggata tataaaaata aagaaacaag aattattaaa tataataaaa   1440

aaaatatctg ttatagaata tgatggttat ataaataaat tttttatgaa taaattaata   1500

gataacagaa atgattatta taattatttt gatttagata tgtcatacat taggttaaat   1560

aatttaaagc aatatatgaa ggataaattt gatatagaat attcaaatta tataatctct   1620

aacatagaaa ataatattat taattatgaa aaacaatatt ataaaaacca aaaaaataat   1680

ttttattctc aaaatcaaat acatatttct aaaatagaaa atataataga taaacataat   1740

aaattaatta atagtatatc ttggtggata cctataaaaa aattaagaga aaatttcaaa   1800

aataaattta taagaccaga ccagaccaga ccagaccaga ccagaccaga ccagaccaga   1860

ccagaccaga cctaa                                                    1875
```

<210> SEQ ID NO 31
<211> LENGTH: 1947
<212> TYPE: DNA
<213> ORGANISM: Brachysprira hyodysenteriae
<220> FEATURE:
<221> NAME/KEY: misc_feature
<222> LOCATION: (1858)..(1899)
<223> OTHER INFORMATION: n is a, c, g, or t

<400> SEQUENCE: 31

```
atgaatgata aatatgttat atgttcaatt acaacaggat ttacagatca actcataaat     60

tttgctacag caatatatat tagagaaaaa tataaaaaaa atgtaaaatt agatatatca    120

tggttttctg tttatgaaaa tacagattat ttgggaatag aaaaacgtaa cctggaagta    180

ctaaatatat ttaatgactt taattttgaa atagctacaa aaaaagaaat agatatagct    240

ttaaagtcta tttttataga tggtagatat gaaaatatag ataaaatatt aaaatccaat    300

aaacatatat atgttggacc atatgttgga catactttat tttactatgg acatattaat    360

atttcttctt ttttcaatct tgacaaatat tttattaatt tattaaatga aaaacataaa    420

aacatattaa atgacatgtc atctttttgaa agtgttacta tacatataag acgaggagat    480

tatatgtatg cgttaaaaat agatggaaga aagaataatg cttctttaga ctatatatat    540

acatcaataa aatatttaaa taatacttta gaaaataaaa atataaaatt ttatatattt    600

tctaataata aaaaatatat aaaaaataat ttaataccaa tttttcaaaa taataatatt    660

aattttgaaa ttatagaaga taatcctgaa tatatagatt tttatttaat gactaaatgt    720
```

aagcatataa tatcttcatt aggaaaattt gcaaaagtag cttttaaatt tataaaaaat 780
gaaaataaaa tatttataga tacagacaat atttataatt tgaaaaaaga atatttctat 840
aaaaatattt gtgaaaaata ctgcaacata atttatgaag aatataataa tataaaaaca 900
tatatatcaa aaaataatat gatatatata ctagacttaa ttgaaaaaaa taatataaag 960
aatatatgtc aaataggctt gctagacggt ttagaaactc atactctatt aaaatattca 1020
gcagacaata ataactgttt taatttatta tgttttgaaa ataatgaaag agatatagtt 1080
ggaatagaat taaaaaattt aacagaaaat gaaaaaaaac tatttacatt atatatagaa 1140
cagtctcctt tagatataga taattctttt aatataaaaa atatagattt tatctttttt 1200
acaaaagaaa attctaatcc tctagtattc atttatttaa tatacttatt tccatttatg 1260
aaagaagaaa tcataatagt atttaatgat attataagtg gtaaatatta ttctggaagt 1320
tattgtatat ttaatatgtt taatggagaa aaaaatcaat tttataattt taatacaaat 1380
aaatatgaca atatcggata tataaaaata aagaaacaag aattattaaa tataataaaa 1440
aaaatatctg ttatagaata tgatggttat ataaataaat tttttatgaa taaattaata 1500
gataacagaa atgattatta taattatttt gatttagata tgtcatacat taggttaaat 1560
aatttaaagc aatatatgaa ggataaattt gatatagaat attcaaatta tataatctct 1620
aacatagaaa ataatattat taattatgaa aaacaatatt ataaaaacca aaaaaataat 1680
ttttattctc aaaatcaaat acatatttct aaaatagaaa atataataga taaacataat 1740
aaattaatta atagtatatc ttggtggata cctataaaaa aattaagaga aaatttcaaa 1800
aataaattta taagaccaga ccagaccaga ccagaccaga ccagaccaga ccagaccnnn 1860
nnnnnnnnnn nnnnnnnnnn nnnnnnnnnn nnnnnnnnna gaccagacca gaccagacca 1920
gaccagacca gaccagacca gacctaa 1947

<210> SEQ ID NO 32
<211> LENGTH: 864
<212> TYPE: DNA
<213> ORGANISM: Brachysprira hyodysenteriae

<400> SEQUENCE: 32
atgaaaggaa tcgtattagc aggcggaagc ggaacaagac tttatccaat gacaaatgtt 60
atatcaaaac agcttttgcc aatatacgat aaaccaatgg tatattatcc attatcagtt 120
ttaatgcttt caaaaattaa agatatactt gtaatatcta cagaaaatga tacaccgctt 180
tttaaaaaat tattaaaaga cggaagtcaa tggggatgca atattgaata tgctgtgcaa 240
aaagcaccta atggacttgc agaagcattt ataataggag aaagttttat aggaaaagat 300
aatgtttcta tgatattagg tgataaatata ttttttggac aaagcttttc ttctgtatta 360
gaaaaaagtg ctaagataga taatggggct gttatatttg cttatcaagt aaaagatcct 420
gaacgtttcg gtatagttga aatagataaa gactataatg ctttatctat agaagaaaaa 480
cctaaaaatc caaagtctaa ttatgctgtt acaggtcttt atttttatga taatgatgta 540
gttaatattt caaaaaatat taagccttct gcaagagggg agcttgaaat aacagatgtt 600
aataaagtat atttagaaaa caaaaaactt aaagttgaag tactaggacg cggatttgct 660
tggcttgata ccggtacaag agatagtctt cttcaggctt ctcaatttgt gtctgctgta 720
gaaaatattg aaggtatgca aatagcttgt ttagaagaaa tagcttataa taataaatgg 780
attgatgctt caataataga agagactgca tcaaaattga aaaactcaga atatggtaaa 840
tacttgatta atttaataaa atag 864

<210> SEQ ID NO 33
<211> LENGTH: 864
<212> TYPE: DNA
<213> ORGANISM: Brachysprira hyodysenteriae

<400> SEQUENCE: 33
atgaaaggaa tcgtattagc aggcggaagc ggaacaagac tttatccaat gacaaatgtt 60
atatcaaaac agcttttgcc aatatacgat aaaccaatgg tatattatcc attatcagtt 120
ttaatgcttt caaaaattaa agatatactt gtaatatcta cagaaaatga tacaccgctt 180
tttaaaaaat tattaaaaga cggaagtcaa tggggatgca atattgaata tgctgtgcaa 240
aaagcaccta atggacttgc agaagcattt ataataggag aaagttttat aggaaaagat 300
aatgtttcta tgatattagg tgataatata ttttttggac aaagcttttc ttctgtatta 360
gaaaaaagtg ctaagatata taatggggct gttatatttg cttatcaagt aaaagatcct 420
gaacgtttcg gtatagttga aatagataaa gattataatg ctttatctat agaagaaaaa 480
cctaaaaatc caaagtctaa ttatgctgtt acaggtcttt atttttatga taatgatgta 540
gttaatattt caaaaaatat taagccttct gcaagagggg agcttgaaat aacagatgtt 600
aataaagtat atttagaaaa caaaaaactt aaagttgaag tactaggacg cggatttgct 660
tggcttgata ccggtacaag agatagtctt cttcaggctt ctcaatttgt atctgctgta 720
gaaaatatcg aaggtatgca gatagcttgt ttagaagaaa tagcttataa taataaatgg 780
attgatgctt caaaaataga agagactgca tcaaaattga aaaactcaga atatggtaaa 840
tacttgatta atttaataaa ataa 864

<210> SEQ ID NO 34
<211> LENGTH: 864
<212> TYPE: DNA
<213> ORGANISM: Brachysprira hyodysenteriae

<400> SEQUENCE: 34
atgaaaggaa tcgtattagc aggcggaagc ggaacaagac tttatccaat gacaaatgtt 60
atatcaaaac agcttttgcc aatatacgat aaaccaatgg tatattatcc attatcagtt 120
ttaatgcttt caaaaattaa agatatactt gtaatatcta cagaaaatga tacaccgctt 180
tttaaaaaat tattaaaaga cggaagtcaa tggggatgca atattgaata tgctgtgcaa 240
aaagcaccta atggacttgc agaagcattt ataataggag aaagttttat aggaaaagat 300
aatgtttcta tgatattagg tgataatata ttttttggac aaagcttttc ttctgtatta 360
gaaaaaagtg ctaagataga taatggggct gttatatttg cttatcaagt aaaagatcct 420
gaacgtttcg gtatagttga aatagataaa gattataatg ctttatctat agaagaaaaa 480
cctaaaaatc caaagtctaa ttatgctgtt acaggtcttt atttttatga taatgatgta 540
gttaatattt caaaaaatat taagccttct gcaagagggg agcttgaaat aacagatgtt 600
aataaagtat atttagaaaa caaaaaactt aaagttgaag tactaggacg cggatttgct 660
tggcttgata ccggtacaag agatagtctt cttcaggctt ctcaatttgt atctgctgta 720
gaaaatatcg aaggtatgca gatagcttgt ttagaagaaa tagcttataa taataaatgg 780
attgatgctt caaaaataga agagactgca tcaaaattga aaaactcaga atatggtaaa 840
tacttgatta atttaataaa ataa 864

<210> SEQ ID NO 35
<211> LENGTH: 864
<212> TYPE: DNA
<213> ORGANISM: Brachysprira hyodysenteriae

<400> SEQUENCE: 35

```
atgaaaggaa tcgtattagc aggcggaagc ggaacaagac tttatccaat gacaaatgtt     60
atatcaaaac agcttttgcc aatatacgat aaaccaatgg tatattatcc attatcagtt    120
ttaatgcttt caaaaattaa agatatactt gtaatatcta cagaaaatga tacaccgctt    180
tttaaaaaat tattaaaaga cggaaggcaa tggggatgca atattgaata tgctgtgcaa    240
aaagcaccta atggacttgc agaagcattt ataataggag aaagttttat aggaaaagat    300
aatgtttcta tgatattagg tgataatata ttttttggac aaagcttttc ttctgtatta    360
gaaaaaagtg ctaagataga taatggggct gttatatttg cttatcaagt aaaagatcct    420
gaacgtttcg gtatagttga aatagataaa gattataatg ctttatctat agaagaaaaa    480
cctaaaaatc caaagtctaa ttatgctgtt acaggtcttt atttttatga taatgatgta    540
gttaatattt caaaaaatat taagccttct gcaagagggg agcttgaaat aacagatgtt    600
aataaagtat atttagaaaa caaaaaactt aaagttgaag tactaggacg cggatttgct    660
tggcttgata ccggtacaag agatagtctt cttcaggctt ctcaatttgt atctgctgta    720
gaaaatatcg aaggtatgca gatagcttgt ttagaagaaa tagcttataa taataaatgg    780
attgatgctt caaaaataga agagactgca tcaaaattga aaaactcaga atatggtaaa    840
tacttgatta atttaataaa ataa                                           864
```

<210> SEQ ID NO 36
<211> LENGTH: 864
<212> TYPE: DNA
<213> ORGANISM: Brachysprira hyodysenteriae

<400> SEQUENCE: 36

```
atgaaaggaa tcgtattagc aggcggaagc ggaacaagac tttatccgat gacaaatgtt     60
atatcaaaac agcttttgcc aatatacgat aaaccgatgg tatattatcc attatcagtt    120
ttaatgcttt caaaaattaa agatatactt gtaatatcta cagaaaatga tacaccgctt    180
tttaaaaaat tattaaaaga cggaagtcaa tggggatgca atattgaata tgctgtgcaa    240
aaagcaccta atggacttgc agaagcattt ataataggag aaagttttat aggaaaagat    300
aatgtttcta tgatattagg tgataatata ttttttggac aaagcttttc ttctgtatta    360
gaaaaaagtg ctaagataga taatggggct gttatatttg cttatcaagt aaaagatcct    420
gaacgtttcg gtatagttga aatagataaa gactataatg ctttatctat agaagaaaaa    480
cctaaaaatc caaagtctaa ttatgctgtt acaggtcttt atttttatga taatgatgta    540
gttaatattt caaaaaatat taagccttct gcaagagggg agcttgaaat aacagatgtt    600
aataaagtat atttagaaaa caaaaaactt aaagttgaag tactaggacg cggatttgct    660
tggcttgata ccggtacaag agatagtctt cttcaggctt ctcaatttgt atctgctgta    720
gaaaatatcg aaggtatgca gatagcttgt ttagaagaaa tagcttataa taataaatgg    780
attgatgctt caaaaataga agagactgca tcaaaattga aaaactcaga atatggtaaa    840
tacttaatta atttaattaa atag                                           864
```

<210> SEQ ID NO 37
<211> LENGTH: 864
<212> TYPE: DNA

<213> ORGANISM: Brachysprira hyodysenteriae

<400> SEQUENCE: 37
atgaaaggaa tcgtattagc aggcggaagc ggaacaagac tttatccaat gacaaatgtt 60
atatcaaaac agcttttgcc aatatacgat aaaccaatgg tatattatcc attatcagtt 120
ttaatgcttt caaaaattaa agatatactt gtaatatcta cagaaaatga tacaccgctt 180
tttaaaaaat tattaaaaga cggaaggcaa tggggatgca atattgaata tgctgtgcaa 240
aaagcaccta atggacttgc agaagcattt ataataggag aaagttttat aggaaaagat 300
aatgtttcta tgatattagg tgataaatata tttttggac aaagcttttc ttctgtatta 360
gaaaaaagtg ctaagataga taatggggct gttatatttg cttatcaagt aaaagatcct 420
gaacgtttcg gtatagttga aatagataaa gactataatg ctttatctat agaagaaaaa 480
cctaaaaatc caaagtctaa ttatgctgtt acaggtcttt atttttatga taatgatgta 540
gttaatattt caaaaaatat taagccttct gcaagagggg agcttgaaat aacagatgtt 600
aataaagtat atttagaaaa caaaaaactt aaagttgaag tactaggacg cggatttgct 660
tggcttgata ccggtacaag agatagtctt cttcaggctt ctcaatttgt atctgctgta 720
gaaaatatcg aaggtatgca gatagcttgt ttagaagaaa tagcttataa taataaatgg 780
attgatgctt caaaaataga agagactgca tcaaaattga aaaactcaga atatggtaaa 840
tacttaatta atttaattaa atag 864

<210> SEQ ID NO 38
<211> LENGTH: 864
<212> TYPE: DNA
<213> ORGANISM: Brachysprira hyodysenteriae

<400> SEQUENCE: 38
atgaaaggaa tcgtattagc aggcggaagc ggaacaagac tttatccaat gacaaatgtt 60
atatcaaaac agcttttgcc aatatacgat aaaccaatgg tatattatcc attatcagtt 120
ttaatgcttt caaaaattaa agatatactt gtaatatcta cagaaaatga tacaccgctt 180
tttaaaaaat tattaaaaga cggaagtcaa tggggatgca atattgaata tgctgtgcaa 240
aaagcaccta atggacttgc agaagcattt ataataggag aaagttttat aggaaaagat 300
aatgtttcta tgatattagg tgataaatata tttttggac aaagcttttc ttctgtatta 360
gaaaaaagtg ctaagataga taatggggct gttatatttg cttatcaagt aaaagatcct 420
gaacgtttcg gtatagttga aatagataaa gattataatg ctttatctat agaagaaaaa 480
cctaaaaatc caaagtctaa ttatgctgtt acaggtcttt atttttatga taatgatgta 540
gttaatattt caaaaaatat taagccttct gcaagagggg agcttgaaat aacagatgtt 600
aataaagtat atttagaaaa caaaaaactt aaagttgaag tactaggacg cggatttgct 660
tggcttgata ccggtacaag agatagtctt cttcaggctt ctcaatttgt atctgctgta 720
gaaaatatcg aaggtatgca gatagcttgt ttagaagaaa tagcttataa taataaatgg 780
attgatgctt caaaaataga agagactgca tcaaaattga aaaactcaga atatggtaaa 840
tacttaatta atttaattaa atag 864

<210> SEQ ID NO 39
<211> LENGTH: 864
<212> TYPE: DNA
<213> ORGANISM: Brachysprira hyodysenteriae

<400> SEQUENCE: 39
atgaaaggaa tcgtattagc aggcggaagc ggaacaagac tttatccaat gacaaatgtt 60
atatcaaaac agcttttgcc aatatacgat aaaccaatgg tatattatcc attatcagtt 120
ttaatgcttt caaaaattaa agatatactt gtaatatcta cagaaaatga tacaccgctt 180
tttaaaaaat tattaaaaga cggaagtcaa tggggatgca atattgaata tgctgtgcaa 240
aaagcaccta atggacttgc agaagcattt ataataggag aaagttttat aggaaaagat 300
aatgtttcta tgatattagg tgataatata ttttttggac aaagcttttc ttctgtatta 360
gaaaaaagtg ctaagataga taatggggct gttatatttg cttatcaagt aaaagatcct 420
gaacgtttcg gtatagttga aatagataaa gactataatg ctttatctat agaagaaaaa 480
cctaaaaatc caaagtctaa ttatgctgtt acaggtcttt atttttatga taatgatgta 540
gttaatattt caaaaaatat taagccttct gcaagagggg agcttgaaat aacagatgtt 600
aataaagtat atttagaaaa caaaaaactt aaagttgaag tactaggacg cggatttgct 660
tggcttgata ccggtacaag agatagtctt cttcaggctt ctcaatttgt atctgctgta 720
gaaaatatcg aaggtatgca gatagcttgt ttagaagaaa tagcttataa taataaatgg 780
attgatgctt caaaaataga agagactgca tcaaaattga aaaactcaga atatggtaaa 840
tacttaatta atttaattaa atag 864

<210> SEQ ID NO 40
<211> LENGTH: 864
<212> TYPE: DNA
<213> ORGANISM: Brachysprira hyodysenteriae

<400> SEQUENCE: 40
atgaaaggaa tcgtattagc aggcggaagc ggaacaagac tttatccaat gacaaatgtt 60
atatcaaaac agcttttgcc aatatacgat aaaccaatgg tatattatcc attatcagtt 120
ttaatgcttt caaaaattaa agatatactt gtaatatcta cagaaaatga tacaccgctt 180
tttaaaaaat tattaaaaga cggaagtcaa tggggatgca atattgaata tgctgtgcaa 240
aaagcaccta atggacttgc agaagcattt ataataggag aaagttttat aggaaaagat 300
aatgtttcta tgatattagg tgataatata ttttttggac aaagcttttc ttctgtatta 360
gaaaaaagtg ctaagatata taatggggct gttatatttg cttatcaagt aaaagatcct 420
gaacgtttcg gtatagttga aatagataaa gactataatg ctttatctat agaagaaaaa 480
cctaaaaatc caaagtctaa ttatgctgtt acaggtcttt atttttatga taatgatgta 540
gttaatattt caaaaaatat taagccttct gcaagagggg agcttgaaat aacagatgtt 600
aataaagtat atttagaaaa caaaaaactt aaagttgaag tactaggacg cggatttgct 660
tggcttgata ccggtacaag agatagtctt cttcaggctt ctcaatttgt atctgctgta 720
gaaaatatcg aaggtatgca gatagcttgt ttagaagaaa tagcttataa taataaatgg 780
attgatgctt caaaaataga agagactgca tcaaaattga aaaactcaga atatggtaaa 840
tacttaatta atttaattaa atag 864

<210> SEQ ID NO 41
<211> LENGTH: 864
<212> TYPE: DNA
<213> ORGANISM: Brachysprira hyodysenteriae

<400> SEQUENCE: 41
atgaaaggaa tcgtattagc aggcggaagc ggaacaagac tttatccaat gacaaatgtt 60
atatcaaaac agcttttgcc aatatacgat aaaccaatgg tatattatcc attatcagtt 120
ttaatgcttt caaaaattaa agatatactt gtaatatcta cagaaaatga tacaccgctt 180
tttaaaaaat tattaaaaga tggaagtcaa tggggatgca atattgaata tgctgtgcaa 240
aaagcaccta atggacttgc agaagcattt ataataggag aaagttttat aggaaaagat 300
aatgtttcta tgatattagg tgataatata ttttttggac aaagcttttc ttctgtatta 360
gaaaaaagtg ctaagataga taatggggct gttatatttg cttatcaagt aaaagatcct 420
gaacgtttcg gtatagttga aatagataaa gactataatg ctttatctat agaagaaaaa 480
cctaaaaatc caaagtctaa ttatgctgtt acaggtcttt atttttatga taatgatgta 540
gttaatattt caaaaaatat taagccttct gcaagagggg agcttgaaat aacagatgtt 600
aataaagtat atttagaaaa caaaaaactt aaagttgaag tactaggacg cggatttgct 660
tggcttgata ccggtacaag agatagtctt cttcaggctt ctcaatttgt atctgctgta 720
gaaaatatcg aaggtatgca gatagcttgt ttagaagaaa tagcttataa taataaatgg 780
attgatgctt caaaaataga agagactgca tcaaaattga aaaactcaga atatggtaaa 840
tacttaatta atttaattaa atag 864

<210> SEQ ID NO 42
<211> LENGTH: 864
<212> TYPE: DNA
<213> ORGANISM: Brachysprira hyodysenteriae

<400> SEQUENCE: 42
atgaaaggaa tcgtattagc aggcggaagc ggaacaagac tttatccaat gacaaatgtt 60
atatcaaaac agcttttgcc aatatacgat aaaccaatgg tatattatcc attatcagtt 120
ttaatgcttt caaaaattaa agatatactt gtaatatcta cagaaaatga tacaccgctt 180
tttaaaaaat tattaaaaga tggaagtcaa tggggatgca atattgaata tgctgtacaa 240
aaagcaccta atggacttgc agaagcattt ataataggag aaagttttat aggaaaagat 300
aatgtttcta tgatattagg tgataatata ttttttggac aaagcttttc ttctgtatta 360
gaaaaaagtg ctaagataga taatggggct gttatatttg cttatcaagt aaaagatcct 420
gaacgtttcg gtatagttga aatagataaa gactataatg ctttatctat agaagaaaaa 480
cctaaaaatc caaagtctaa ttatgctgtt acaggtcttt atttttatga taatgatgta 540
gttaatattt caaaaaatat taagccttct gcaagagggg agcttgaaat aacagatgtt 600
aataaagtat atttagaaaa caaaaaactt aaagttgaag tactaggacg cggatttgct 660
tggcttgata ccggtacaag agatagtctt cttcaggctt ctcaatttgt atctgctgta 720
gaaaatatcg aaggtatgca gatagcttgt ttagaagaaa tagcttataa taataaatgg 780
attgatgctt caaaaataga agagactgca tcaaaattga aaaactcaga atatggtaaa 840
tacttaatta atttaattaa atag 864

<210> SEQ ID NO 43
<211> LENGTH: 864
<212> TYPE: DNA
<213> ORGANISM: Brachysprira hyodysenteriae

<400> SEQUENCE: 43
atgaaaggaa tcgtattagc aggcggaagc ggaacaagac tttatccaat gacaaatgtt 60
atatcaaaac agcttttgcc aatatacgat aaaccaatgg tatattatcc attatcagtt 120
ttaatgcttt caaaaattaa agatatactt gtaatatcta cagaaaatga tacaccgctt 180
tttaaaaaat tattaaaaga cggaagtcaa tggggatgca atattgaata tgctgtacaa 240
aaagcaccta atggacttgc agaagcattt ataataggag aaagttttat aggaaaagat 300
aatgtttcta tgatattagg tgataatata ttttttggac aaagcttttc ttctgtatta 360
gaaaaaagtg ctaagataga taatggggct gttatatttg cttatcaagt aaaagatcct 420
gaacgtttcg gtatagttga aatagataaa gactataatg ctttatctat agaagaaaaa 480
cctaaaaatc caaagtctaa ttatgctgtt acaggtcttt atttttatga taatgatgta 540
gttaatattt caaaaaatat taagccttct gcaagagggg agcttgaaat aacagatgtt 600
aataaagtat atttagaaaa caaaaaactt aaagttgaag tactaggacg cggatttgct 660
tggcttgata ccggtacaag agatagtctt cttcaggctt ctcaatttgt atctgctgta 720
gaaaatatcg aaggtatgca gatagcttgt ttagaagaaa tagcttataa taataaatgg 780
attgatgctt caaaaataga agagactgca tcaaaattga aaaactcaga atatggtaaa 840
tacttaatta atttaattaa atag 864

<210> SEQ ID NO 44
<211> LENGTH: 864
<212> TYPE: DNA
<213> ORGANISM: Brachysprira hyodysenteriae

<400> SEQUENCE: 44
atgaaaggaa tcgtattagc aggcggaagc ggaacaagac tttatccaat gacaaatgtt 60
atatcaaaac agcttttgcc aatatacgat aaaccaatgg tatattatcc attatcagtt 120
ttaatgcttt caaaaattaa agatatactt gtaatatcta cagaaaatga tacaccgctt 180
tttaaaaaat tattaaaaga cggaagtcaa tggggatgca atattgaata tgctgtgcaa 240
aaagcaccta atggacttgc agaagcattt ataataggag aaagttttat aggaaaagat 300
aatgtttcta tgacattagg tgataatata ttttttggac aaagcttttc ttctgtatta 360
gaaaaaagtg ctaagataga taatggggct gttatatttg cttatcaagt aaaagatcct 420
gaacgtttcg gtatagttga aatagataaa gattataatg ctttatctat agaagaaaaa 480
cctaaaaatc caaagtctaa ttatgctgtt acaggtcttt atttttatga taatgatgta 540
gttaatattt caaaaaatat taagccttct gcaagagggg agcttgaaat aacagatgtt 600
aataaagtat atttagaaaa caaaaaactt aaagttgaag tactaggacg cggatttgct 660
tggcttgata ccggtacaag agatagtctt cttcaggctt ctcaatttgt atctgctgta 720
gaaaatatcg aaggtatgca gatagcttgt ttagaagaaa tagcttataa taataaatgg 780
attgatgctt caaaaataga agagactgca tcaaaattga aaaactcaga atatggtaaa 840
tacttgatta atttaataaa ataa 864

<210> SEQ ID NO 45
<211> LENGTH: 1071
<212> TYPE: DNA
<213> ORGANISM: Brachysprira hyodysenteriae

<400> SEQUENCE: 45
atgagaaatt ttaataatat tttagttaca ggcggatgcg gttttattgg aacaaatttt 60
ataagatata tattgcaaaa aactgaatat aaaggcaata ttataaatat agatgcctta 120
acttatgcag gaaacagaga aaatttaata gatatagaaa aaaaatataa agatagatat 180
ttctttgaaa aagttaatat ttgtgatgac aaaaaagtaa atgaaatatt ttcacaatat 240
aatcctgatt gtatagtaca ttttgcagca gaaagtcatg ttgaccgttc aatatacgga 300
ccaaaagatt ttcttgaaac aaatataatg gggactttta ttttattaga agctgctcgt 360
aaattatggg aaaacaataa agaaaataaa ctattccatc atataagcac agacgaagtt 420
tacggatctt taggtgaaac aggttatttt tatgaaacta caccttatga tcctagaagt 480
ccttactcat catcaaaagc ttcaagcgat catattgtaa aagcatatta tcatacttat 540
aatctgcctg ttacaatatc taattgcagc aacaattacg gtccttatca attccctgaa 600
aaattaatac ctttaatgat ttctaatata gtagaagaaa aagatcttcc tgtttatggt 660
gatggaaaaa atataagaga ttggatattt gttgaagatc ataataatgc agtaattgat 720
ataatacata aaggcagagt aggagagact tacaatatcg gcggagaaaa tgagattact 780
aatattgata tggtaaatat tttatgtgag aaattatctg ctaaaatgaa taaagaaaaa 840
gattattata aaaaattaat caaatttgta aaagacagat ccggtcatga cagaagatat 900
gctataaact gcgataaaat aaaaaaagaa ttaggatggg aaagaaaata cgatttcaat 960
acagccattg atataactat agattggtat ttaaataaca aacaatggat agataatatt 1020
aaaagcggag aatataaaaa atggattgag ttaaactact cgtctaaata a 1071

<210> SEQ ID NO 46
<211> LENGTH: 1071
<212> TYPE: DNA
<213> ORGANISM: Brachysprira hyodysenteriae

<400> SEQUENCE: 46
atgagaaatt ttaataatat tttagttact ggcggatgcg gttttatagg atcaaacttt 60
ataagataca tattagaaaa atctgattat aaaggcaata ttataaatat agatgcctta 120
acttatgcag gaaacagaga aaatttaata gatatagaaa aaaaatataa agatagatat 180
ttctttgaaa aagttaatat ttgtgatgat aaaaaaaataa atgaaatatt ttcaaaatat 240
aatcctgatt gtatagtgca ttttgctgca gaaagtcatg ttgaccgttc aatatacgga 300
ccaaaagatt ttcttgaaac taatataatg ggaactttta ttttattaga agctgctcgt 360
aaattatggg aaaataataa agaaaataaa ctattccatc atataagcac agacgaagtt 420
tacggatctt taggtgaaac aggttatttt tatgaaacta ctccttatga tcctagaagt 480
ccttactcat catcaaaagc ttcaagcgat catattgtaa aagcatatta tcatacttat 540
aatctgcctg ttacaatatc taattgcagc aacaattatg gcccttatca attccctgaa 600
aaattaatac ctttaatgat ttctaatata gtagaagaaa aagatcttcc tgtttatgga 660
gatggaaaaa atataagaga ttggatattt gttgaagatc ataataatgc agtaattgat 720
ataatacata aaggcagggt aggagagacc tacaatatcg gcggagaaaa cgagattact 780
aatattgata tggtaaatat tttatgtgag aaattatctg ctaaaatgaa taaagaaaaa 840
gattattata aaaaattaat caaatttgta aaagacagag ctgggcatga cagaagatat 900
gctataaact gcgataaaat aaaaaaagaa ttaggatggg aaagaaaata cgatttcaat 960
acagccattg atattactat agattggtat ttaaataaca aacaatggat agataatatt 1020
aaaagcggag aatataaaaa atggattgag ttaaactact cgtctaaata a 1071

<210> SEQ ID NO 47
<211> LENGTH: 1071
<212> TYPE: DNA
<213> ORGANISM: Brachysprira hyodysenteriae

<400> SEQUENCE: 47

```
atgagaaatt ttaataatat tttagttact ggcggatgcg gttttatagg atcaaacttt     60
ataagataca tattagaaaa atctgattat aaaggcaata ttataaatat agatgcctta    120
acttatgcag gaaacagaga aaatttaata gatatagaaa aaaaatataa agatagatat    180
ttctttgaaa aagttaatat ttgtgatgat aaaaaaataa atgaaatatt ttcaaaatat    240
aatcctgatt gtatagtgca ttttgctgca gaaagtcatg ttgaccgttc aatatacgga    300
ccaaaagatt ttcttgaaac taatataatg ggaactttta ttttattaga agctgctcgt    360
aaattatggg aaaataataa agaaaataaa ctattccatc atataagcac agacgaagtt    420
tacggatctt taggtgaaac aggttatttt tatgaaacta ctccttatga tcctagaagt    480
ccttactcat catcaaaagc ttcaagcgat catattgtaa aagcatatta tcatacttat    540
aatctgcctg ttacaatatc taattgcagc aacaattatg gcccttatca attccctgaa    600
aaattaatac ctttaatgat ttctaatata gtagaagaaa aagatcttcc tgtttatgga    660
gatggaaaaa atataagaga ttggatattt gttgaagatc ataataatgc agtaattgat    720
ataatacata aaggcagggt aggagagact tacaatattg gcggagaaaa cgagattact    780
aatattgata tggtaaatat tttatgtgag aaattatctg ctaaaatgaa taaagaaaaa    840
gattattata aaaaattaat caaatttgta aaagacagag ccggtcatga cagaagatat    900
gctataaact gcgataaaat aaaaaaagaa ttaggatggg aaagaaaata cgatttcaat    960
accgccattg atataactat agattggtat ttaaataaca aacaatggat agataatatt   1020
aaaagcggag aatataaaaa atggattgag ttaaactact cgtctaaata a            1071
```

<210> SEQ ID NO 48
<211> LENGTH: 1071
<212> TYPE: DNA
<213> ORGANISM: Brachysprira hyodysenteriae

<400> SEQUENCE: 48

```
atgagaaatt ttaataatat tttagttact ggtggatgcg gttttatagg atcaaacttt     60
ataagataca tattagaaaa atctgattat aaaggcaata ttataaatat agatgcctta    120
acttatgcag gaaacagaga aaatttaata gatatagaaa aaaaatataa agatagatat    180
ttctttgaaa aagttaatat ttgtgatgat aaaaaaataa atgaaatatt ttcaaaatat    240
aatcctgatt gtatagtgca ttttgctgca gaaagtcatg ttgaccgttc aatatacgga    300
ccaaaagatt ttcttgaaac taatataatg ggaactttta ttttattaga agctgctcgt    360
aaattatggg aaaataataa agaaaataaa ctattccatc atataagcac agacgaagtt    420
tacggatctt taggtgaaac aggttatttt tatgaaacta ctccttatga tcctagaagt    480
ccttactcat catcaaaagc ttcaagcgat catattgtaa aagcatatta tcatacttat    540
aatctgcctg ttacaatatc taattgcagc aacaattatg gcccttatca attccctgaa    600
aaattaatac ctttaatgat ttctaatata gtagaagaaa aagatcttcc tgtttatgga    660
gatggaaaaa atataagaga ttggatattt gttgaagatc ataataatgc agtaattgat    720
ataatacata aaggcagggt aggagagact tacaatattg gcggagaaaa cgagattact    780
aatattgata tggtaaatat tttatgtgag aaattatctg ctaaaatgaa taaagaaaaa    840
gattattata aaaaattaat caaatttgta aaagacagag ccggtcatga cagaagatat    900
gctataaact gcgataaaat aaaaaaagaa ttaggatggg aaagaaaata cgatttcaat    960
acagccattg atataactat agattggtat ttaaataaca aacaatggat agataatatt   1020
```

aaaagcggag aatataaaaa atggattgag ttaaactact catctaaata a 1071

<210> SEQ ID NO 49
<211> LENGTH: 1071
<212> TYPE: DNA
<213> ORGANISM: Brachysprira hyodysenteriae

<400> SEQUENCE: 49
atgagaaatt ttaataatat tttagttact ggcggatgcg gttttatagg atcaaacttt 60
ataagataca tattagaaaa atctgattat aaaggcaata ttataaatat agatgcctta 120
acttatgcag gaaacagaga aaatttaata gatatagaaa aaaaatataa agatagatat 180
ttctttgaaa aagttaatat ttgtgatgat aaaaaaataa atgaaatatt ttcaaaatat 240
aatcctgatt gtatagtgca ttttgctgca gaaagtcatg ttgaccgttc aatatacgga 300
ccaaaagatt ttcttgaaac taatataatg ggaactttta ttttattaga agctgctcgt 360
aaattatggg aaaataataa agaaaataaa ctattccatc atataagcac agacgaagtt 420
tacggatctt taggtgaaac aggttatttt tatgaaacta ctccttatga tcctagaagt 480
ccttactcat catcaaaagc ttcaagcgat catattgtaa aagcatatta tcatacttat 540
aatctgcctg ttacaatatc taattgcagc aacaattatg gcccttatca attccctgaa 600
aaattaatac ctttaatgat ttctaatata gtagaagaaa aagatcttcc tgtttatgga 660
gatggaaaaa atataagaga ttggatattt gttgaagatc ataataatgc agtaattgat 720
ataatacata aaggcagggt aggagagact tacaatattg gcggagaaaa cgagattact 780
aatattgata tggtaaatat tttatgtgag aaattatctg ctaaaatgaa taaagaaaaa 840
gattattata aaaaattaat caaatttgta aaagacagag ccggtcatga cagaagatat 900
gctataaact gcgataaaat aaaaaaagaa ttaggatggg aaagaaaata cgatttcaat 960
acagccattg atataactat agattggtat ttaaataaca aacaatggat agataatatt 1020
aaaagcggag aatataaaaa atggattgag ttaaactact catctaaata a 1071

<210> SEQ ID NO 50
<211> LENGTH: 1071
<212> TYPE: DNA
<213> ORGANISM: Brachysprira hyodysenteriae

<400> SEQUENCE: 50
atgagaaatt ttaataatat tttagttact ggcggatgcg gttttatagg atcaaacttt 60
ataagataca tattagaaaa atctgattat aaaggcaata ttataaatat agatgcctta 120
acttatgcag gaaacagaga aaatttaata tatatagaaa aaaaatataa agatagatat 180
ttctttgaaa aagttaatat ttgtgatgat aaaaaaataa atgaaatatt ttcaaaatat 240
aatcctgatt gtatagtgca ttttgctgca gaaagtcatg ttgaccgttc aatatacgga 300
ccaaaagatt ttcttgaaac taatataatg ggaactttta ttttattaga agctgctcgt 360
aaattatggg aaaataataa agaaaataaa ctattccatc atataagcac agacgaagtt 420
tacggatctt taggtgaaac aggttatttt tatgaaacta ctccttatga tcctagaagt 480
ccttactcat catcaaaagc ttcaagcgat catattgtaa aagcatatta tcatacttat 540
aatctgcctg ttacaatatc taattgcagc aacaattatg gcccttatca attccctgaa 600
aaattaatac ctttaatgat ttctaatata gtagaagaaa aagatcttcc tgtttatgga 660
gatggaaaaa atataagaga ttggatattt gttgaagatc ataataatgc agtaattgat 720
ataatacata aaggcagggt aggagagact tacaatattg gcggagaaaa cgagattact 780
aatattgata tggtaaatat tttatgtgag aaattatctg ctaaaatgaa taaagaaaaa 840
gattattata aaaaattaat caaatttgta aaagacagag ccggtcatga cagaagatat 900
gctataaact gcgataaaat aaaaaaagaa ttaggatggg aaagaaaata cgatttcaat 960
acagccattg atataactat agattggtat ttaaataaca aacaatggat agataatatt 1020
aaaagcggag aatataaaaa atggattgag ttaaactact catctaaata a 1071

<210> SEQ ID NO 51
<211> LENGTH: 1071
<212> TYPE: DNA
<213> ORGANISM: Brachysprira hyodysenteriae

<400> SEQUENCE: 51
atgagaaatt ttaataatat tttagttact ggcggatgcg gttttatagg ctcaaacttt 60
ataagataca tattagaaaa atctgattat aaaggcaata ttataaatat agatgcctta 120
acttatgcag gaaacagaga aaatttaata gatatagaaa aaaaatataa agatagatat 180
ttctttgaaa aagttaatat ttgtgatgat aaaaaaataa atgaaatatt ttcaaaatat 240
aatcctgatt gtatagtgca ttttgctgca gaaagtcatg ttgaccgttc aatatacgga 300
ccaaaagatt ttcttgaaac taatataatg ggaactttta ttttattaga agctgctcgt 360
aaattatggg aaaataataa agaaaataaa ctattccatc atataagcac agacgaagtt 420
tacggatctt taggtgaaac aggttatttt tatgaaacta ctccttatga tcctagaagt 480
ccttactcat catcaaaagc ttcaagtgat catattgtaa aagcatatta tcatacttat 540
aatctgcctg ttacaatatc taattgcagc aacaattatg gcccttatca attccctgaa 600
aaattaatac ctttaatgat ttctaatata gtagaagaaa aagatcttcc tgtttatgga 660
gatggaaaaa atataagaga ttggatattt gttgaagatc ataataatgc agtaattgat 720
ataatacata aaggcagggt aggagagacc tacaatatcg gcggagaaaa cgagattact 780
aatattgata tggtaaatat tttatgtgag aaattatctg ctaaaatgaa taaagaaaaa 840
gattattata aaaaattaat caaatttgta aaagacagag ccggtcatga cagaagatat 900
gctataaact gcgataaaat aaaaaaagaa ttaggatggg aaagaaaata cgatttcaat 960
acaggcattg atattactat agattggtat ttaaataaca aacaatggat agataatatt 1020
aaaagcggag aatataaaaa atggattgag ttaaactact catctaaata a 1071

<210> SEQ ID NO 52
<211> LENGTH: 1071
<212> TYPE: DNA
<213> ORGANISM: Brachysprira hyodysenteriae

<400> SEQUENCE: 52
atgagaaatt ttaataatat tttagttact ggcggatgcg gttttatagg atcaaacttt 60
ataagataca tattagaaaa atctgattat aaaggcaata ttataaatat agatgcctta 120
acttatgcag gaaacagaga aaatttaata gatatagaaa aaaaatataa agatagatat 180
ttctttgaaa aagttaatat ttgtgatgat aaaaaaataa atgaaatatt ttcaaaatat 240
aatcctgatt gtatagtgca ttttgctgca gaaagtcatg ttgaccgttc aatatacgga 300
ccaaaagatt ttcttgaaac taatataatg ggaactttta ttttattaga agctgctcgt 360
aaattatggg aaaataataa agaaaataaa ctatttcatc atataagtac agacgaagtt 420
tacggatctt taggtgaaac aggttatttt tatgaaacta ctccttatga tcctagaagt 480

```
ccttactcat catcaaaagc ttcaagtgat catattgtaa aagcatatta tcatacttat    540

aatctgcctg ttacaatatc taattgcagc aacaattatg gcccttatca attccctgaa    600

aaattaatac ctttaatgat ttctaatata gtagaagaaa aagatcttcc tgtttatgga    660

gatggaaaaa atataagaga ttggatattt gttgaagatc ataataatgc agtaattgat    720

ataatacata aaggcagggt aggagagacc tacaatatcg gcggagaaaa cgagattact    780

aatattgata tggtaaatat tttatgtgag aaattatctg ctaaaatgaa taaagaaaaa    840

gattattata aaaaattaat caaatttgta aaagacagag ccggtcatga cagaagatat    900

gctataaact gcgataaaat aaaaaaagaa ttaggatggg aaagaaaata cgatttcaat    960

acagccattg atataactat agattggtat ttaaataaca aacaatggat agataatatt   1020

aaaagcggag aatataaaaa atggattgag ttaaactact cgtctaaata a            1071
```

<210> SEQ ID NO 53
<211> LENGTH: 1071
<212> TYPE: DNA
<213> ORGANISM: Brachysprira hyodysenteriae

<400> SEQUENCE: 53

```
atgagaaatt ttaataatat tttagttact ggcggatgcg gttttatagg ctcaaacttt     60

ataagataca tattagaaaa atctgattat aaaggcaata ttataaatat agatgcctta    120

acttatgcag gaaacagaga aaatttaata gatatagaaa aaaaatataa agatagatat    180

ttctttgaaa aagttaatat ttgtgatgat aaaaaaataa atgaaatatt ttcaaaatat    240

aatcctgatt gtatagtgca ttttgctgca gaaagtcatg ttgaccgttc aatatacgga    300

ccaaaagatt ttcttgaaac taatataatg ggaactttta ttttattaga agctgctcgt    360

aaattatggg aaaataataa agaaaataaa ctatttcatc atataagtac agacgaagtt    420

tacggatctt taggtgaaac aggttatttt tatgaaacta ctccttatga tcctagaagt    480

ccttactcat catcaaaagc ttcaagtgat catattgtaa aagcatatta tcatacttat    540

aatctgcctg ttacaatatc taattgcagc aacaattatg gcccttatca attccctgaa    600

aaattaatac ctttaatgat ttctaatata gtagaagaaa aagatcttcc tgtttatgga    660

gatggaaaaa atataagaga ttggatattt gttgaagatc ataataatgc agtaattgat    720

ataatacata aaggcagggt aggagagacc tacaatatcg gcggagaaaa cgagattact    780

aatattgata tggtaaatat tttatgtgag aaattatctg ctaaaatgaa taaagaaaaa    840

gattattata aaaaattaat caaatttgta aaagacagat ccggtcatga cagaagatat    900

gctataaact gcgataaaat aaaaaaagaa ttaggatggg aaagaaaata cgatttcaat    960

acagccattg atataactat agattggtat ttaaataaca aacaatggat agataatatt   1020

aaaagcggag aatataaaaa atggattgag ttaaactact cgtctaaata a            1071
```

<210> SEQ ID NO 54
<211> LENGTH: 1071
<212> TYPE: DNA
<213> ORGANISM: Brachysprira hyodysenteriae

<400> SEQUENCE: 54

```
atgagaaatt ttaataatat tttagttact ggcggatgcg gttttatagg atcaaacttt     60

ataagataca tattagaaaa atctgattat aaaggcaata ttataaatat agatgcctta    120

acttatgcag gaaacagaga aaatttaata gatatagaaa aaaaatataa agatagatat    180

ttctttgaaa aagttaatat ttgtgatgat aaaaaaataa atgaaatatt ttcaaaatat    240
```

aatcctgatt gtatagtgca ttttgctgca gaaagtcatg ttgaccgttc aatatacgga 300
ccaaaagatt ttcttgaaac taatataatg ggaactttta ttttattaga agctgctcgt 360
aaattatggg aaaataataa agaaaataaa ctatttcatc atataagtac agacgaagtt 420
tacggatctt taggtgaaac aggttatttt tatgaaacta ctccttatga tcctagaagt 480
ccttactcat catcaaaagc ttcaagtgat catattgtaa aagcatatta tcatacttat 540
aatctgcctg ttacaatatc taattgcagc aacaattatg gcccttatca attccctgaa 600
aaattaatac ctttaatgat ttctaatata gtagaagaaa aagatcttcc tgtttatgga 660
gatggaaaaa atataagaga ttggatattt gttgaagatc ataataatgc agtaattgat 720
ataatacata aaggcagggt aggagagacc tacaatatcg gcggagaaaa cgagattact 780
aatattgata tggtaaatat tttatgtgag aaattatctg ctaaaatgaa taaagaaaaa 840
gattattata aaaaattaat caaatttgta aaagacagat ccggtcatga cagaagatat 900
gctataaact gcgataaaat aaaaaaagaa ttaggatggg aaagaaaata cgatttcaat 960
acagccattg atataactat agattggtat ttaaataaca aacaatggat agataatatt 1020
aaaagcggag aatataaaaa atggattgag ttaaactact cgtctaaata a 1071

<210> SEQ ID NO 55
<211> LENGTH: 579
<212> TYPE: DNA
<213> ORGANISM: Brachysprira hyodysenteriae

<400> SEQUENCE: 55
atgcctttta catttaaaaa acttgatata aacggacttt ttatagcaga acctcgtatc 60
tttggagatt caagaggtta tttcctagaa acatattctg agaaagattt ttttgaagct 120
ggaatcaaag aaaaatttgt acaagataat caatctaaat caacaaaaaa tgtattaaga 180
ggacttcatt atcagaaaaa atattgtcag gctaaattgg ttagagtatt agaaggtgaa 240
gtatttgatg ttgcagtaga tttgagaaat gattctccaa cttttggaaa atattatggg 300
gtattattaa cagaagaaaa taaaaagcag ttctttattc ctaaaggttt tgcacatgga 360
tttattgttt taagcgaatc agctgttttt gcttataaat gttctgactt ttatcaccct 420
gaagaagagg gtggtataat atataatgat aaaaatatta atatagattg gacttgcgat 480
actaaagatg tattagtatc tgataaagat ttaaaattac tagagtttga caaaaataaa 540
aaatattttt cattagatgg aaattggatt ggtgaataa 579

<210> SEQ ID NO 56
<211> LENGTH: 579
<212> TYPE: DNA
<213> ORGANISM: Brachysprira hyodysenteriae

<400> SEQUENCE: 56
atgcctttta catttaaaaa acttgatata aacggacttt ttatagcaga acctcgtatc 60
tttggagatt caagaggtta tttcctagaa acatattctg agaaagattt ttttgaagct 120
ggaatcaaag aaaaatttgt acaagataat caatctaaat caacaaaaaa tgtattaaga 180
ggacttcatt atcagaaaaa atattgtcag gctaaattgg ttagagtatt agaaggtgaa 240
gtatttgatg ttgcagtaga tttgagaaat gattctccaa cttttggaaa atattatggg 300
gtattattaa cagaagaaaa taaaaagcag ttctttattc ctaaaggttt tgcacatgga 360
tttattgttt taagcgaatc agctgttttt gcttataaat gttctgactt ttatcaccct 420
gaagaagagg gtggtataat atataatgat aaaaatatta atatagattg gacttgcgat 480
actaaagatg tattagtatc tgataaagat ttaaaattac cagagtttga caaaaataaa 540
aaatattttt cattagatgg aaattggatt ggtgaataa 579

<210> SEQ ID NO 57
<211> LENGTH: 579
<212> TYPE: DNA
<213> ORGANISM: Brachysprira hyodysenteriae

<400> SEQUENCE: 57
atgcctttta catttaaaaa acttgatata aacggacttt ttatagcaga acctcgtatc 60
tttggagatt caagaggtta tttcctagaa acatattctg agaaagattt ttttgaagct 120
ggaatcaaag aaaaatttgt acaagataat caatctaaat caacaaaaaa tgtattaaga 180
ggacttcatt atcagaaaaa atattgtcag gctaaattgg ttagagtatt agaaggtaaa 240
gtatttgatg ttgcagtaga tttgagaaat gattctccaa cttttggaaa atattatggt 300
gttttattaa cagaagaaaa taaaaagcag ttctttattc ctaaaggttt tgcacatgga 360
tttattgttc taagcgaatc agctgttttt gcttataaat gttctgactt ttatcaccct 420
gaagaagagg gtggtataat atataatgat aaaaatatta atatagattg gacttgcgat 480
actaaagatg tattagtatc tgataaagat ttaaaattac cagagtttga caaaaataaa 540
aaatattttt cattagatgg aaattggatt ggagaataa 579

<210> SEQ ID NO 58
<211> LENGTH: 579
<212> TYPE: DNA
<213> ORGANISM: Brachysprira hyodysenteriae

<400> SEQUENCE: 58
atgcctttta catttaaaaa acttgatata aacggacttt ttatagcaga acctcgtatc 60
tttggagatt caagaggtta tttcctagaa acatattctg agaaagattt ttttgaagct 120
ggaatcaaag aaaaatttgt acaagataat caatctaaat caacaaaaaa tgtattaaga 180
ggacttcatt atcagaaaaa atattgtcag gctaaattgg ttagagtatt agaaggtgaa 240
gtatttgatg ttgcagtaga tttgagaaat gattctccaa cttttggaaa atattatggt 300
gttttattaa cagaagaaaa taaaaagcag ttctttattc ctaaaggttt tgcacatgga 360
tttattgttc taagcgaatc agctgttttt gcttataaat gttctgactt ttatcaccct 420
gaagaagagg gtggtataat atataatgat aaaaatatta atatagattg gacttgcgat 480
actaaagatg tattagtatc tgataaagat ttaaaattac cagagtttga caaaaataaa 540
aaatattttt cattagatgg aaattggatt ggagaataa 579

<210> SEQ ID NO 59
<211> LENGTH: 579
<212> TYPE: DNA
<213> ORGANISM: Brachysprira hyodysenteriae

<400> SEQUENCE: 59
atgcctttta catttaaaaa acttgatata aacggacttt ttatagcaga acctcgtatc 60
tttggagatt caagaggtta tttcctagaa acatattctg agaaagattt ttttgaagct 120
ggaatcaaag aaaaatttgt acaagataat caatctaaat caacaaaaaa tgtattaaga 180
ggacttcatt atcagaaaaa atattgtcag gctaaattgg ttagagtatt agaaggtgaa 240
gtatttgatg ttgcagtaga tttgagaaat gattctccaa cttttggaaa atattatggg 300
gtattattaa cagaagaaaa taaaaagcag ttctttattc ctaaaggttt tgcacatgga 360
tttattgttc taagcgaatc agctgttttt gcttataaat gttctgactt ttatcaccct 420
gaagaagagg gtggtataat atataatgat aaaaatatta atatagattg gacttgcgat 480
actaaagatg tattagtatc tgataaagat ttaaaattac ctgagtttga caaaaataaa 540
aaatattttt cattagatgg aaattggatt ggtgaataa 579

<210> SEQ ID NO 60
<211> LENGTH: 579
<212> TYPE: DNA
<213> ORGANISM: Brachysprira hyodysenteriae

<400> SEQUENCE: 60
atgcctttta catttaaaaa acttgatata aacggacttt ttatagcaga acctcgtatc 60
tttggagatt caagaggtta tttcctagaa acatattctg agaaagattt ttttgaagct 120
ggaatcaaag aaaaatttgt acaagataat caatctaaat caacaaaaaa tgtattaaga 180
ggacttcatt atcagaaaaa atattgtcag gctaaattgg ttagagtatt agaaggtgaa 240
gtatttgatg ttgcagtaga tttgagaaat gattctccaa cttttggaaa atattatggg 300
gtattattaa cagaagaaaa taaaaagcag ttctttattc ctaaaggttt tgcacatgga 360
tttattgttt taagcgaatc agctgttttt acttataaat gttctgactt ttatcaccct 420
gaagaagagg gtggtataat atataatgat aaaaatatta atatagattg gacttgcgat 480
actaaagatg tattagtatc tgataaagat ttaaaattac cagagtttga caaaaataaa 540
aaatattttt cattagatgg aaattggatt ggagaataa 579

<210> SEQ ID NO 61
<211> LENGTH: 579
<212> TYPE: DNA
<213> ORGANISM: Brachysprira hyodysenteriae

<400> SEQUENCE: 61
atgcctttta catttaaaaa acttgatata aacggacttt ttatagcaga acctcgtatc 60
tttggagatt caagaggtta tttcctagaa acatattctg agaaagattt ttttgaagct 120
ggaatcaaag aaaaatttgt acaagataat caatctaaat caacaaaaaa tgtattaaga 180
ggacttcatt atcagaaaaa atattgtcag gctaaattgg ttagagtatt agaaggtgaa 240
gtatttgatg ttgcagtaga tttgagaaat gattctccaa cttttggaaa atattatggg 300
gtattattaa cagaagaaaa taaaaagcag ttctttattc ctaaaggttt tgcacatgga 360
tttattgttt taagcgaatc agctgttttt acttataaat gttctgactt ttatcaccct 420
gaagaagagg gtggtataat atataatgat aaaaatatta atatagattg gacttgcgat 480
actaaagatg tattagtatc tgataaagat ttaaaattac cagagtttga caaaaataaa 540
aaatattttt cattagatgg aaattggatt ggagaataa 579

<210> SEQ ID NO 62
<211> LENGTH: 861
<212> TYPE: DNA
<213> ORGANISM: Brachysprira hyodysenteriae

<400> SEQUENCE: 62
atgatttggg taattggtaa aaatggaatg cttgctcaag atatactcaa agcattcaat 60
aaaaataata tagaatatac ttcaacagct tctaatatag atattactaa tattgatata 120
cttaataact ttataaaaga taaaaatatt aaaacaataa taaattgttc tgcatataca 180
aaagtagatt tagcagaaga tgaaaaagat atttgctata aagttaatgg agaaggtgta 240
aaaaatataa cagaaatagc ttctaatata aatgcagatt taattcattt ttctactgat 300
tatgtatttg atggagaaaa taacaaacca tacaatgaag aagataaaac taatccaata 360
aatatttacg gcaaaagtaa attagagggt gaaaaatatg ctttatttta taataaagca 420
atagttatta gagtatcttg gctatatgga atttatggaa aaaattttgt atatactatg 480
attaatttga tgaatagtaa agaaagcata aaagtagtta atgatcaatt tggatctcct 540
acatatacag aagatgttgc tatggtaata tatgatatta taaaaaataa caattttgat 600
tatggacttt atcattatac taatgaaggt aatatatcat ggtatgattt tgctaaaact 660
atatataata aaggaaaaga gtataaatatt ataaataatg attgcaaagt aaatccatgt 720
actacagaag aatatccaac caaagctaaa agacctaaat acagtgtttt atctgtagaa 780
aaaataaaaa gatatgttaa aatatataat tatgaagata gcttaaatag tttttttaac 840
atatatcaaa aaaataaata a 861

<210> SEQ ID NO 63
<211> LENGTH: 861
<212> TYPE: DNA
<213> ORGANISM: Brachysprira hyodysenteriae

<400> SEQUENCE: 63
atgatttgga taattggtaa aaatggaatg cttgctcaag atatactcca agtattcaat 60
aaaaataata tagaatatac ttcaacagct tctaatatag atattactaa tattgatata 120
cttaataact ttataaaaga taaaaatatt aaaacaataa taaattgttc tgcatataca 180
aaagtagatt tagcagaaga tgaaaaagat atttgctata aagttaatgg agaaggtgta 240
aaaaatataa cagaaatagc ttctaatata aatgcagatt taattcattt ttctactgat 300
tatgtatttg atggagaaaa taacaaacca tacaatgaag aagataaaac taatccaata 360
aatatttacg gcaaaagtaa attagagggt gaaaaatatg ctttatccta taataaatca 420
atagttatta gagtatcttg gctatatggt atttatggta aaaattttgt atatactatg 480
attaatttga tgaatagtaa agaaagcata aaagtagtta atgatcaatt tggatctcct 540
acatatacag aagatgttgc tatggtaata tatgatatta taaaaaataa caatttttat 600
tacggacttt atcattatac taatgaaggt gatatatcat ggtatgattt tgctaaaact 660
atatataata aaggaaaaga gtataaatatt ataaataatg attgcaaagt aaatccatgt 720
actacagaag aatatccaac caaagctaaa agacctaaat acagtgtttt atctgtagaa 780
aaaataaaaa gatatgttaa aatatataat tatgaagata gcttaaatag tttttttaac 840
atatatcaaa aaaataaata a 861

<210> SEQ ID NO 64
<211> LENGTH: 861
<212> TYPE: DNA
<213> ORGANISM: Brachysprira hyodysenteriae

<400> SEQUENCE: 64
atgatttgga taattggtaa aaatggaatg cttgctcaag atatactcca agtattcaat 60
aaaaataata tagaatatac ttcaacagct tctaatatag atattactaa tattgatata 120
cttaataact ttataaaaga taaaaatatt aaaacaataa taaattgttc tgcatataca 180
aaagtagatt tagcagaaga tgaaaaagat atttgctata aagttaatgg agaaggtgta 240
aaaaatataa cagaaatagc ttctaatata aatgcagatt taattcattt ttctactgat 300
tatgtatttg atggagaaaa taacaaacca tacaatgaag aagataaaac taatccaata 360
aatatttacg gcaaaagtaa attagagggt gaaaaatatg ctttatccta taataaatca 420
atagttatta gagtatcttg gctatatggt atttatggta aaaattttgt atatactatg 480
attaatttga tgaatagtaa agaaagcata aaagtagtta atgatcaatt tggatctcct 540
acatatacag aagatgttgc tatggtaata tatgatatta taaaaaataa caattttgat 600
tacggacttt atcattatac taatgaaggt gatatatcat ggtatgattt tgctaaaact 660
atatataata aaggaaaaga gtataatatt ataaataatg attgcaaagt aaatccatgt 720
actacagaag aatatccaac caaagctaaa agacctaaat acagtgtttt atctgtagaa 780
aaaataaaaa gatatgttaa aatatataat tatgaagata gcttaaatag tttttttaac 840
atatatcaaa aaaataaata a 861

<210> SEQ ID NO 65
<211> LENGTH: 882
<212> TYPE: DNA
<213> ORGANISM: Brachysprira hyodysenteriae

<400> SEQUENCE: 65
atgatttggg taattggtaa aaatggaatg cttgctcaag atatactcaa agcattcaat 60
aaaaataata tagaatatac ttcaacagct tctaatatag atattactaa tattgatata 120
cttaataact ttataaaaga taaaaatatt aaaacaataa taaattgttc tgcatataca 180
aaagtagatt tagcagaaga tgaaaaagat atttgctata aagttaatgg agaaggtgta 240
aaaaatataa cagaaatagc ttctaatata aatgcagatt taattcattt ttctactgat 300
tatgtatttg atggagaaaa taacaaacca tacaatgaag aagataaaac taatccaata 360
aatatttacg gcaaaagtaa attagagggt gaaaaatatg ctttatttta taataaagca 420
atagttatta gagtatcttg gctatatgga atttatggaa aaaattttgt atatactatg 480
attaatttga tgaatagtaa agaaagcata aaagtagtta atgatcaatt tggatctcct 540
acatatacag aagatgttgc tatggtaata tatgatatta taaaaaataa caattttgat 600
tacggacttt atcattatac taatgaaggt aatatatcat ggtatgattt tgctaaaact 660
atatataata aaggaaaaga gtataatatt ataaataatg attgcaaagt aaatccatgt 720
actacagaag aatatccaac caaagctaaa agacctaaat acagtgtttt atctgtagaa 780
aaaataaaaa gatatgttaa aatatataat tatgaagata gcttaaatag ttttttaaca 840
tatatcaaaa aaataaataa tttttggagt ttattagtat ga 882

<210> SEQ ID NO 66
<211> LENGTH: 861
<212> TYPE: DNA
<213> ORGANISM: Brachysprira hyodysenteriae

<400> SEQUENCE: 66
atgatttgga taattggtaa aaatggaatg cttgctcaag atatactcca agtattcaat 60
aaaaataata tagaatatac ttcaacagct tctaatatag atattactaa tattgatata 120
cttaataact ttataaaaga taaaaatatt aaaacaataa taaattgttc tgcatataca 180
aaagtagatt tagcagaaga tgaaaaagat atttgctata aagttaatgg agaaggtgta 240
aaaaatataa cagaaatagc ttctaatata aatgcagatt taattcattt ttctactgat 300
tatgtatttg atggagaaaa taacaaacca tacaatgaag aagataaaac taatccaata 360
aatatttacg gcaaaagtaa attagagggt gaaaaatatg ctttatttta taataaagca 420
atagttatta gagtatcttg gctatatgga atttatggaa aaaattttgt atatactatg 480
attaatttga tgaatagtaa agaaagcata aaagtagtta atgatcaatt tggatctcct 540
acatatacag aagatgttgc tatggtaata tatgatatta taaaaaataa caattttgat 600
tacggacttt atcattatac taatgaaggt aatatatcat ggtatgattt tgctaaaact 660
atatataata aaggaaaaga gtataatatt ataaataatg attgcaaagt aaatccatgt 720
actacagaag aatatccaac caaagctaaa agacctaaat acagtgtttt atctgtagaa 780
aaaataaaaa gatatgttaa aatatataat tatgaagata gcttaaatag tttttttaac 840
atatatcaaa aaaataaata a 861

<210> SEQ ID NO 67
<211> LENGTH: 861
<212> TYPE: DNA
<213> ORGANISM: Brachysprira hyodysenteriae

<400> SEQUENCE: 67
atgatttggg taattggtaa aaatggaatg cttgctcaag atatactcaa agcattcaat 60
aaaaataata tagaatatac ttcaacagct tctaatatag atattactaa tgttgatata 120
cttaataact ttataaaaga taaaaatatt aaaacaataa taaattgttc tgcatataca 180
aaagtagatt tagcagaaga tgaaaaagat atttgctata aagttaatgg agaaggtgta 240
aaaaatataa cagaaatagc ttctaatata aatgcagatt taattcattt ttctactgat 300
tatgtatttg atggagaaaa taacaaacca tacaatgaag aagataaaac taatccaata 360
aatatttacg gcaaaagtaa attagagggt gaaaaatatg ctttatttta taataaagca 420
atagttatta gagtatcttg gctatatgga atttatggaa aaaattttgt atatactatg 480
attaatttga tgaatagtaa agaaagcata aaagtagtta atgatcaatt tggatctcct 540
acatatacag aagatgttgc tatggtaata tatgatatta taaaaaataa caattttgat 600
tacggacttt atcattatac taatgaaggt aatatatcat ggtatgattt tgctaaaact 660
atatataata aaggaaaaga gtataatatt ataaataatg attgcaaagt aaatccatgt 720
actacagaag aatatccaac caaagctaaa agacctaaat acagtgtttt atctgtagaa 780
aaaataaaaa gatatgttaa aatatataat tatgaagata gcttaaatag tttttttaac 840
atatatcaaa aaaataaata a 861

<210> SEQ ID NO 68
<211> LENGTH: 861
<212> TYPE: DNA
<213> ORGANISM: Brachysprira hyodysenteriae

<400> SEQUENCE: 68
atgatttggg taattggtaa aaatggaatg cttgctcaag atatactcaa agcattcaat 60
aaaaataata tagaatatac ttcaacagct tctaatatag atattactaa tattgatata 120
cttaataact ttataaaaga tcaaaatatt aaaacaataa taaattgttc tgcatataca 180
aaagtagatt tagcagaaga tgaaaaagat atttgctata aagttaatgg agaaggtgta 240
aaaaatataa cagaaatagc ttctaatata aatgcagatt taattcattt ttctactgat 300
tatgtatttg atggagaaaa taacaaacca tacaatgaag aagataaaac taatccaata 360
aatatttacg gcaaaagtaa attagagggt gaaaaatatg ctttatttta taataaagca 420
atagttatta gagtatcttg gctatatgga atttatggaa aaaattttgt atatactatg 480
attaatttga tgaatagtaa agaaagcata aaagtagtta atgatcaatt tggatctcct 540
acatatacag aagatgttgc tatggtaata tatgatatta taaaaaataa caattttgat 600
tacggacttt atcattatac taatgaaggt aatatatcat ggtatgattt tgctaaaact 660
atatataata aaggaaaaga gtataatatt ataaataatg attgcaaagt aaatccatgt 720
actacagaag aatatccaac caaagctaaa agacctaaat acagtgtttt atctgtagaa 780
aaaataaaaa gatatgttaa aatatataat tatgaagata gcttaaatag ttttttttaac 840 atatatcaaa aaaataaata a 861

<210> SEQ ID NO 69
<211> LENGTH: 981
<212> TYPE: DNA
<213> ORGANISM: Brachysprira hyodysenteriae

<400> SEQUENCE: 69
atgaaaagat tagccgtatt tgcaggatat gataaagaca atataattga tgattatgtt 60
gtatattata ttaaagaatt aaaaaaaata gctgatataa tctatgtatc agattgcaac 120
atgtcagata atgaattaaa aaaaattaat gactactgca tacatatcat aaatggaagg 180
catgaagaat atgatttcgg atcatataaa agaggatatc tatatgccaa agaaaataat 240
atacttcaaa attatgatta tttaatactt tgtaatgatt cttgctatgg acctttattt 300
gatttggaaa acataataaa taaaatgaat aattatgatt ttggaggtat atctattagt 360
aaagatttaa aaatagcaaa tcataattac ataactagct tttttatata cataaataaa 420
aacatattta ataaagattt ctttaatgat tttattttta atataaaaaa agaagaagat 480
aaaatggata tcataaaaaa atatgagttc ggactttcaa aactaatgct tgataataat 540
atagaattaa aaggcttatt taatgataat ggagagttta acagaccata ttttaatcca 600
ttagccctaa tagaagaagg atatcctttt ttaaaaaaac atgtactaga aaaaaaaata 660
actgttcctt taaatataaa tgaactaaca aatattataa aaataataaa aaataattac 720
gatataaaat taatagttaa tcatttaaac agagttgctg ataaagaaca aattaaatat 780
ttatttcaaa aatataagcc atataaaaaa atatttattc atgaaaaaat tttctcctta 840
tttaccagat attcaccatc aggtaaatat caaaccgtat ataaattttt taattttcta 900
actatatcaa tagataaacc aattaaagat tcatacatag aaactgacta taaagatttt 960
aatttcttat tagaaatata a 981

<210> SEQ ID NO 70
<211> LENGTH: 981
<212> TYPE: DNA
<213> ORGANISM: Brachysprira hyodysenteriae

<400> SEQUENCE: 70
atgaaaagat tagccgtatt tgcaggatat gataaagaca atataattga tgattatgtt 60
gtatattata ttaaagaatt aaaaaaaata tctgatataa tctatgtatc agattgcaat 120
atgtcagata atgaattaaa aaaaattaat gattactgca tacatatcat aaatggaagg 180
catgaagaat atgatttcgg atcatataaa agaggatatc tatatgccaa agaaaataat 240
atacttcaaa attatgatta tttaatactt tgtaatgatt cttgctatgg acctttattt 300
gatttggaaa acataataaa taaaatgaat gattatgatt ttggaggcat atctattagt 360
aaagatttaa aaatagcaaa tcataattat ataactagct tttttatata cataaacaaa 420
aacatattta ataaagattt ctttaatgat tttatttatg atataaaaaa agaagaagat 480
aaaatggata tcataaaaaa atatgaattt ggactttcaa aactaatgct tgataataat 540
atagaattaa aaggcttatt taatgataat ggagaattta acagaccata ctttaatcca 600
ttagctctaa tagaagaagg atatcctttt ttaaaaaaac atgtactaga aaaaaaagta 660
actgttcctt taaatataga tgaactaaca aatattataa aaataataaa aaataattac 720
gatataaaat taatagttaa tcatttaaat agagttgctg ataaagaaca aattaaatat 780
ttatttcaaa aatataaacc atataaaaaa acatttattc atgaaaaaat tttctcctta 840
tttaccagat attcaccatc aggtaaatat caaacagtat ataatttttt taattttcta 900
actatatcaa tagacaaacc aattaaagat tcatacatag aaactgacta taaagatttt 960
aattttttat tagaaatata a 981

<210> SEQ ID NO 71
<211> LENGTH: 981
<212> TYPE: DNA
<213> ORGANISM: Brachysprira hyodysenteriae

<400> SEQUENCE: 71
atgaaaagat tagccgtatt tgcaggatat gacaaagaca atataattga tgattatgtt 60
gtatattata ttaaagaatt aaaaaaaata tctgatataa tctatgtatc agattgcaat 120
atgtcagata atgaattaaa aaaaattaat gattactgca tacatatcat aaatggaagg 180
catgaagaat atgatttcgg atcatataaa agaggatatc tatatgccaa agaaaataat 240
atacttcaaa attatgatta tttaatactt tgtaatgatt cttgctatgg acctttattt 300
gatttggaaa acataataaa taaaatgaat gattatgatt ttggaggcat atctattagt 360
aaagatttaa aaatagcaaa tcataattat ataactagct tttttatata cataaacaaa 420
aacatattta ataaagattt ctttaataat tttatttatg atataaaaaa agaagaagat 480
aaaatggata tcataaaaaa atatgaattt ggactttcaa aactaatgct tgataataat 540
atagaattaa aaggcttatt taatgataat ggagaattta acagaccata ctttaatcca 600
ttagctctaa tagaagaagg atatcctttt ttaaaaaaac atgtactaga aaaaaaagta 660
actgttcctt taaatataga tgaactaaca aatattataa aaataataaa aaataattac 720
gatataaaat taatagttaa tcatttaaat agagttgctg ataaagaaca aattaaatat 780
ttatttcaaa aatataaacc atataaaaaa acatttattc atgaaaaaat tttctcctta 840
tttaccagat attcaccatc aggtaaatat caaacagtat ataatttttt taattttcta 900
actatatcaa tagacaaacc aattaaagat tcatacatag aaactgacta taaagatttt 960
aattttttat tagaaatata a 981

<210> SEQ ID NO 72
<211> LENGTH: 981
<212> TYPE: DNA
<213> ORGANISM: Brachysprira hyodysenteriae

<400> SEQUENCE: 72
atgaaaagat tagccgtatt tgcaggatat gataaagaca atataattga tgattatgtt 60
gtatattata ttaaagaatt aaaaaaaata tctgatataa tctatgtatc agattgcaat 120
atgtcagata atgaattaaa aaaaattaat gattactgca tacatatcat aaatggaagg 180
catgaagaat atgatttcgg atcatataaa agaggatatc tatatgccaa agaaaataat 240

```
atacttcaaa attatgatta tttaatactt tgtaatgatt cttgctatgg acctttattt    300

gatttggaaa acataataaa taaaatgaat gattatgatt ttggaggcat atctattagt    360

aaagatttaa aaatagcaaa tcataattat ataactagct tttttatata cataaacaaa    420

aacatattta ataaagattt ctttaatgat tttatttatg atataaaaaa agaagaagat    480

aaaatggata tcataaaaaa atatgaattt ggactttcaa aactaatgct tgataataat    540

atagaattaa aaggcttatt taatgataat ggagaattta acagaccata ctttaatcca    600

ttagctctaa tagaagaagg atatcctttt ttaaaaaaac atgtactaga aaaaaaagta    660

actgttcctt taaatataga tgaactaaca aatattataa aaataataaa aaataattac    720

gatataaaat taatagttaa tcatttaaat agagttgctg ataaagaaca aattaaatat    780

ttatttcaaa aatataaacc atataaaaaa acatttattc atgaaaaaat tttctcctta    840

tttaccagat attcaccatc aggtaaatat caaaccgtat ataaattttt taattttcta    900

actatatcaa tagacaaacc aattaaagat tcatacatag aaactgacta taaagatttt    960

aattttttat tagaaatata a                                              981
```

<210> SEQ ID NO 73
<211> LENGTH: 981
<212> TYPE: DNA
<213> ORGANISM: Brachysprira hyodysenteriae

<400> SEQUENCE: 73

```
atgaaaagat tagccgtatt tgcaggatat gacaaagaca atataattga tgattatgtt     60

gtatattata ttaaagaatt aaaaaaaata tctgatataa tctatgtatc agattgcaat    120

atgtcagata atgaattaaa aaaaattaat gattactgca tacatatcat aaatggaagg    180

catgaagaat atgatttcgg atcatataaa agaggatatc tatatgccaa agaaaataat    240

atacttcaaa attatgatta tttaatactt tgtaatgatt cttgctatgg acctttattt    300

gatttggaaa acataataaa taaaatgaat gattatgatt ttggaggcat atctattagt    360

aaagatttaa aaatagcaaa tcataattat ataactagct tttttatata cataaacaaa    420

aacatattta ataaagattt ctttaatgat tttatttatg atataaaaaa agaagaagat    480

aaaatggata tcataaaaaa atatgaattt ggactttcaa aactaatgct tgataataat    540

atagaattaa aaggcttatt taatgataat ggagaattta acagaccata ctttaatcca    600

ttagctctaa tagaagaagg atatcctttt ttaaaaaaac atgtactaga aaaaaaagta    660

actgttcctt taaatataga tgaactaaca aatattataa aaataataaa aaataattac    720

gatataaaat taatagttaa tcatttaaat agagttgctg ataaagaaca aattaaatat    780

ttatttcaaa aatataaacc atataaaaaa acatttattc atgaaaaaat tttctcctta    840

tttaccagat attcaccatc aggtaaatat caaacagtat ataaattttt taattttcta    900

actatatcaa tagacaaacc aattaaagat tcatacatag aaactgacta taaagatttt    960

aattttttat tagaaatata a                                              981
```

<210> SEQ ID NO 74
<211> LENGTH: 981
<212> TYPE: DNA
<213> ORGANISM: Brachysprira hyodysenteriae

<400> SEQUENCE: 74

```
atgaaaagat tagccgtatt tgcaggatat gacaaagaca atataattga tgattatgtt     60
```

```
gtatattata ttaaagaatt aaaaaaaata tctgatataa tctatgtatc agattgcaat    120

atgtcagata atgaattaaa aaaaattaat gattactgca tacatatcat aaatggaagg    180

catgaagaat atgatttcgg atcatataaa agaggatatc tatatgccaa agaaaataat    240

atacttcaaa attatgatta tttaatactt tgtaatgatt cttgctatgg acctttattt    300

gatttggaaa acataataaa taaaatgaat gattatgatt ttggaggcat atctattagt    360

aaagatttaa aaatagcaaa tcataattat ataactagct tttttatata cataaacaaa    420

aacatattta ataaagattt ctttaatgat tttatttatg atataaaaaa agaagaagat    480

aaaatggata tcataaaaaa atatgaattt ggactttcaa aactaatgct tgataataat    540

atagaattaa aaggcttatt taatgataat ggagaattta acagaccata ctttaatcca    600

ttagctctaa tagaagaagg atatcctttt ttaaaaaaac atgtactaga aaaaaaagta    660

actgttcctt taaatataga tgaactaaca aatattataa aaataataaa aaataattac    720

gatataaaat taatagttaa tcatttaaat agagttgctg ataaagaaca aattaaatat    780

ttatttcaaa aatataaacc atataaaaaa acatttattc atgaaaaaat tttctcctta    840

tttaccagat attcaccatc aggtaaatat caaaccgtat ataaattttt taattttcta    900

actatatcaa tagacaaacc aattaaagat tcatacatag aaactgacta taaagatttt    960

aattttttat tagaaatata a                                              981
```

<210> SEQ ID NO 75
<211> LENGTH: 981
<212> TYPE: DNA
<213> ORGANISM: Brachysprira hyodysenteriae

<400> SEQUENCE: 75

```
atgaaaagat tagccgtatt tgcaggatat gataaagaca atataattga tgattatgtt     60

gtatattata ttaaagaatt aaaaaaaata gctgatataa tctatgtatc agattgcaat    120

atgtcagata atgaattaaa aaaaattaat aattactgca tacatatcat aaatggaagg    180

catgaggaat atgattttgg atcatataaa agaggatatc tatatgccaa agaaaacaat    240

atacttcaaa attatgatta tttaatactt tgtaatgatt cttgctatgg acctttattt    300

gatttggaaa acatagtaaa taaaatgaat gattatgatt tcggaggtat atctattagt    360

aaagatttaa aaatagcaaa tcataattat ataactagct tttttatata cataaacaaa    420

aacatattta ataaagattt ctttaatgat tttatttatg atataaaaaa agaagaagat    480

aaaatggata tcataaaaaa atatgagttt ggactttcaa aactcatgct tgataataat    540

atagaattaa aaggcttatt taatgataat ggagagttta acaggccata ttttaatcca    600

ttagctctaa tagaagaagg atatcctttt ttaaaaaaac atgtactaga aaaaaaagta    660

actgttcctt taaatataga tgaactaaca aatattataa aaataataaa aaataattac    720

gatataaaat taatagttaa tcatttaaat agagttgctg ataaagaaca aattaaatat    780

ttatttcaaa aatataaacc atataaaaaa acatttattc atgaaaaaat tttctcctta    840

tttaccagat attcaccatc aggtaaatat caaacagtat ataatttttt taattttcta    900

actatatcaa tagacaaacc aattaaagat tcatacatag aaactgacta taaagatttt    960

aattttttat tagaaatata a                                              981
```

<210> SEQ ID NO 76
<211> LENGTH: 981
<212> TYPE: DNA
<213> ORGANISM: Brachysprira hyodysenteriae

<400> SEQUENCE: 76

```
atgaaaagat tagccgtatt tgcaggatat gataaagaca atataattga tgattatgtt     60
gtatattata ttaaagaatt aaaaaaaata gctgatataa tctatgtatc agattgcaat    120
atgtcagata atgaattaaa aaaaattaat aattactgca tacatatcat aaatggaagg    180
catgaggaat atgattttgg atcatataaa agaggatatc tatatgccaa agaaaacaat    240
atacttcaaa attatgatta tttaatactt tgtaatgatt cttgctatgg acctttattt    300
gatttggaaa acatagtaaa taaaatgaat gattatgatt tcggaggtat atctattagt    360
aaagatttaa aaatagcaaa tcataattat ataactagct tttttatata cataaacaaa    420
aacatattta ataaagattt ctttaatgat tttatttatg atataaaaaa agaagaagat    480
aaaatggata tcataaaaaa atatgagttt ggactttcaa aactcatgct tgataataat    540
atagaattaa aaggcttatt taatgataat ggagagttta acaggccata ttttaatcca    600
ttagctctaa tagaagaagg atatcctttt ttaaaaaaac atgtactaga aaaaaaagta    660
actgttcctt taaatataga tgaactaaca aatattataa aaataataaa aaataattac    720
gatataaaat taatagttaa tcatttaaat agagttgctg ataaagaaca aattaaatat    780
ttatttcaaa aatataaacc atataaaaaa acatttattc atgaaaaaat tttctcctta    840
tttaccagat attcaccatc aggtaaatat caaacagtat ataaattttt taattttcta    900
actatatcaa tagacaaacc aattaaagat tcatacatag aaactgacta taaagatttt    960
aatttcttat tgaaaatata a                                              981
```

<210> SEQ ID NO 77
<211> LENGTH: 1188
<212> TYPE: DNA
<213> ORGANISM: Brachysprira hyodysenteriae

<400> SEQUENCE: 77

```
atgaatacat gtgaatgcag tcaatgcaaa aatagagaat atgatatatc agaatattta     60
gttcttgaag atgacttgaa aattttagat aatgaaagac cactaggaat atcaggacat    120
ttaagggtta aagatgaagc tatgagttta gccgaatgta ttgattcatg catagacttt    180
ttagatgaac ttataataac ttataacaca tcttcagata acacagaaga aatattaaaa    240
aactacgaaa aaaaatatcc tgaaaaaatt aaactatttc attataaacc taatattatt    300
agatacaata aagatgagta taatacaaaa tattcacaaa tacactattt agataattat    360
tacaattatg gactaattaa aataaaatac aaatattatg ttaaaataga tgctgatcaa    420
atttatttca cagataaatt attaaaatta agagaattat taatattaga tataaatcaa    480
ataaaattaa gcaataatat aaataaatta ttattaataa ataaaatagc ttggtgcata    540
cctatcaaaa aattacgaaa taaatttaga acatattgta ttagaaagta tttcaataaa    600
gataaaaatt atatttataa tggtgatgaa aatatattat cattagatga ttttatttta    660
ttatctagga aaagacattc agataaaaat atcagttatg atcttgcagg attcaatcta    720
atattacata ataataaatt atatttagat acatattggc ctatgaatgg cggacgtttt    780
gatcatgtgc tgtatcaagc atcttattct aataaatatt ttatgaatga aatatttgaa    840
gtaaatcaaa ctcctcataa tagaataatt ttagggatgt tttgggtaca ttttggaaat    900
attaaacata attttcaata tgatgattct ttttatttac tagaatataa tgatataaaa    960
aattctaaag tagaaaattt ttctcataaa atgaaaaata ttgataatga tgataaaata   1020
```

gaaaaatata taagagataa tacttttata aaatattttg atgaggataa aaaatacctt 1080
aataatgttt tttataataa atacttgaca aaaccacttg actatgctat aaaaaacaat 1140
gatgaattag taaatttata tggaaaaact attattactg taaaatga 1188

<210> SEQ ID NO 78
<211> LENGTH: 1218
<212> TYPE: DNA
<213> ORGANISM: Brachysprira hyodysenteriae

<400> SEQUENCE: 78
atgataagtt atttaaataa aaggtataaa atgaataaat gtgaatgcag tcaatgcaaa 60
aatagagaat atgatatatc agaatatttg gttcttgaag atgacttgaa aattttagat 120
aatgaaagac cactaggaat atcaggacat ttaagggtta aagatgaagc tatgagttta 180
gctgaatgca ttgattcatg catagacttt ttagatgaac ttataataac ttataacaca 240
tcttcagata acacagaaga aatattaaaa aactacgaaa aaaaatatcc tgaaaaaatt 300
aaactatttc attataaacc taatattata agatacaata aagatgagta taatacaaaa 360
tattcacaaa tacactattt agataattat tacaattatg gactaattaa aataaaatac 420
aaatattatg ttaaaataga tgctgatcaa atttatttca cagataaatt attaaaatta 480
agagaattat taatattaga tataaatcaa ataaaattaa gcaataatat aaataaatta 540
ttattaataa ataaaatagc ttggtgcata cctatcaaaa aattacgaaa taaatttaga 600
acatattgta ttagaaagta tttcaataaa gataaaaatt atatttataa tggtgatgaa 660
aatatattat cattagatga tttcatttta ttatctagga aaagacattc agataaaaat 720
atcagttatg atcttgcagg attcaatcta atattacata ataataaatt atatttagat 780
atatattggc ctatgaatgg cggacgtttt gatcatgtgc tgtatcaagc atcttattct 840
aataaatatt ttatgaatga aatatttgaa gtaaatcaaa ctcctcataa tagaataatt 900
ttagggatgt tttgggtaca ttttggaaat attaaacata attttcaata tgatgattct 960
ttttatttac tagaatataa tgatataaaa aattctaaag tagaaaattt ttctcataaa 1020
atgaaaaata ttgataatga tgataaaata gaaaaatata taagagataa tacttttata 1080
aaatattttg atgaggataa aaaatacctt aataatgttt tttataataa atacttgaca 1140
aaaccacttg actatgctat aaaaaacaat gatgaattag taaatttata tggaaaaact 1200
attattactg taaaatga 1218

<210> SEQ ID NO 79
<211> LENGTH: 1188
<212> TYPE: DNA
<213> ORGANISM: Brachysprira hyodysenteriae

<400> SEQUENCE: 79
atgaataaat gtgaatgcag tcaatgccaa aatagagaat atgatatatc agaatatttg 60
gttcttgaag atgacttgaa aattttagat aatgaaagac cactaggaat atcaggacat 120
ttaagagtta aagatgaagc tatgagttta gctgaatgca ttgattcatg catagacttt 180
ttagatgaac ttataataac ttataacaca tcttcagata acacagaaga aatattaaaa 240
aactacgaaa aaaaatatcc tgaaaaaatt aaactatttc attataaacc taatattata 300
agatacaata aagatgagta taatacaaaa tattcacaaa tacactattt agataattat 360
tacaattatg gactaattaa aataaaatac aaatattatg ttaaaataga tgctgatcaa 420
atttatttca cagataaatt attaaaatta agagaattat taatattaga tataaatcaa 480

```
ataaaattaa gcaataatat aaataaatta ttattaataa ataaaatagc ttggtgcata    540

cctatcaaaa aattacgaaa taaatttaga acatattgta ttagaaagta tttcaataaa    600

gataaaaatt atatttataa tggtgatgaa aatatattat cattagatga ttttatttta    660

ttatctagga aaagacattc agataaaaat atcagttatg atcttgcagg attcaatcta    720

atattacata ataataaatt atatttagat acatattggc ctatgaatgg cggacgtttt    780

gatcatgtgc tgtatcaagc atcttattct aataaatatt ttatgaatga aatatttgaa    840

gtaaatcaaa ctcctcataa tagaataatt ttagggatgt tttgggtaca ttttggaaat    900

attaaacata attttcaata tgatgattct ttttatttac tagaatataa tgatataaaa    960

aattctaaag tagaaaattt ttctcataaa atgaaaaata ttgataatga tgataaaata   1020

gaaaaatata taagagataa tacttttata aaatattttg atgaggataa aaaatacctt   1080

aataatgttt tttataataa atacttgaca aaaccacttg actatgctat aaaaaacaat   1140

gatgaattag taaatttata tggaaaaact attattactg taaaatga                1188
```

<210> SEQ ID NO 80
<211> LENGTH: 1218
<212> TYPE: DNA
<213> ORGANISM: Brachysprira hyodysenteriae

<400> SEQUENCE: 80

```
atgataagtt atttaaataa aaggtataaa atgaataaat gtgaatgcag tcaatgcaaa     60

aatagagaat atgatatatc agaatatttg gttcttgaag atgacttgaa aattttagat    120

aatgaaagac cactaggaat atcaggacat ttaagagtta aagatgaagc tatgagttta    180

gctgaatgca ttgattcatg catagacttt ttagatgaac ttataataac ttataacaca    240

tcttcagata acacagaaga aatattaaaa aactacgaaa aaaaatatcc tgaaaaaatt    300

aaactatttc attataaacc taatattata agatacaata aagatgagta taatacaaaa    360

tattcacaaa tacactattt agataattat tacaattatg gactaattaa aataaaatac    420

aaatattatg ttaaaataga tgctgatcaa atttatttca cagataaatt attaaaatta    480

agagaattat taatattaga tataaatcaa ataaaattaa gcaataatat aaataaatta    540

ttattaataa ataaaatagc ttggtgcata cctatcaaaa aattacgaaa taaatttaga    600

acatattgta ttagaaagta tttcaataaa gataaaaatt atatttataa tggtgatgaa    660

aatatattat cattagatga ttttatttta ttatctagga aaagacattc agataaaaat    720

atcagttatg atcttgcagg attcaatcta atattacata ataataaatt atatttagat    780

acatattggc ctatgaatgg cggacgtttt gatcatgtgc tgtatcaagc atcttattct    840

aataaatatt ttatgaatga aatatttgaa gtaaatcaaa ctcctcataa tagaataatt    900

ttagggatgt tttgggtaca ttttggaaat attaaacata attttcaata tgatgattct    960

ttttatttac tagaatataa tgatataaaa aattctaaag tagaaaattt ttctcataaa   1020

atgaaaaata ttgataatga tgataaaata gaaaaatata taagagataa tacttttata   1080

aaatattttg atgaggataa aaaatacctt aataatgttt tttataataa atacttgaca   1140

aaaccacttg actatgctat aaaaaacaat gatgaattag taaatttata tggaaaaact   1200

attattactg taaaatga                                                 1218
```

<210> SEQ ID NO 81
<211> LENGTH: 1188
<212> TYPE: DNA

<213> ORGANISM: Brachysprira hyodysenteriae

<400> SEQUENCE: 81
atgaataaat gtgaatgcag tcaatgcaaa aatagagaat atgatatacc agaatatttg 60
gttcttgaag atgacttgaa aattttagat aatgaaagac cactaggaat atcaggacat 120
ttaagggtta aagatgaagc tatgagttta gctgaatgca ttgattcatg catagacttt 180
ttagatgaac ttataataac ttataacaca tcttcagata acacagaaga aatattaaaa 240
aactacgaaa aaaaatatcc tgaaaaaatt aaactatttc attataaacc taatattata 300
agatacaata aagatgagta taatacaaaa tattcacaaa tacactattt agataattat 360
tacaattatg gactaagtaa aataaaatac aaatattatg ttaaaataga tgctgatcaa 420
atttatttca cagataaatt attaaaatta agagaattat taatattaga tataaatcaa 480
ataaaattaa gcaataatat aaataaatta ttattaataa ataaaatagc ttggtgcata 540
cctatcaaaa aattacgaaa taaatttaga acatattgta ttagaaagta tttcaataaa 600
gataaaaatt atatttataa tggtgatgaa aatatattat cattagatga ttttatttta 660
ttatctagga aaagacattc agataaaaat atcagttatg atcttgcagg attcaatcta 720
atattacata ataataaatt atatttagat acatattggc ctatgaatgg cggacgtttt 780
gatcatgtgc tgtatcaagc atcttattct aataaatatt ttatgaatga aatatttgaa 840
gtaaatcaaa ctcctcataa tagaataatt ttagggatgt tttgggtaca ttttggaaat 900
attaaacata attttcaata tgatgattct ttttatttac tagaatataa tgatataaaa 960
aattctaaag tagaaaattt ttctcataaa atgaaaaata ttgataatga tgataaaata 1020
gaaaaatata taagagataa tacttttata aaatatttg atgaggataa aaaatacctt 1080
aataatgttt tttataataa atacttgaca aaaccacttg actatgctat aaaaaacaat 1140
gatgaattag taaatttata tggaaaaact attattactg taaaatga 1188

<210> SEQ ID NO 82
<211> LENGTH: 795
<212> TYPE: DNA
<213> ORGANISM: Brachysprira hyodysenteriae

<400> SEQUENCE: 82
atgtctagca atataataga tacaatagct tggtggattc ctattaaatc cattagaata 60
aaatttagaa atgcaacaaa gaaaaagttc aataatttta tttttaacaa aatagatttt 120
aactacgtta atacaaataa tatagaactt atactcaata aatacaatga aatatttgtc 180
ccattaatat taagtaacga aaaaaaatac aaaaaaaata gaaatagcga gttaataaat 240
aaatatttaa ctggtttaaa aggtgttgaa ataggaggaa gcgctggagc tgattttggt 300
atagacgcta tacaagttaa tattgtcgat gccaatcagg aacacaataa ttattatcaa 360
caaacaaata ttttaggttc gggatataat caaagaactg atatcatatc atgtggtgat 420
gtattaccat ttcaagataa ttcaatagac tttgtattct caagtcatgt actagaacat 480
ttctatgacc ctataaaagc tttaaaagaa tggtacagag ttataaaaaa agacggatat 540
atagctatga tagtacctca taaagaaaga acattcgata aagatagaga tagaacaact 600
ttaaatgaat taatagaaag acataataag gttaaaaatt ataaatacaa tgtggatgaa 660
agaggaatgc atttttctgt ttggataaca gaagatatac tagaattatg caaatattta 720
aatatgaatg taattgaata tctagatgta gatgatgctg taggtaatgg atttgctatt 780
atcataaaaa aataa 795

<210> SEQ ID NO 83
<211> LENGTH: 648
<212> TYPE: PRT
<213> ORGANISM: Brachysprira hyodysenteriae
<220> FEATURE:
<221> NAME/KEY: misc_feature
<222> LOCATION: (620)..(633)
<223> OTHER INFORMATION: Xaa can be any naturally occurring amino acid

<400> SEQUENCE: 83

```
Met Asn Asp Lys Tyr Val Ile Cys Ser Ile Thr Thr Gly Phe Thr Asp
1               5                   10                  15

Gln Leu Ile Asn Phe Ala Thr Ala Ile Tyr Ile Arg Glu Lys Tyr Lys
            20                  25                  30

Lys Asn Val Lys Leu Asp Ile Ser Trp Phe Ser Val Tyr Glu Asn Thr
        35                  40                  45

Asp Tyr Leu Gly Ile Glu Lys Arg Asn Leu Glu Val Leu Asn Ile Phe
    50                  55                  60

Asn Asp Phe Asn Phe Glu Ile Ala Thr Lys Lys Glu Ile Asp Ile Ala
65                  70                  75                  80

Leu Lys Ser Ile Phe Ile Asp Gly Arg Tyr Glu Asn Ile Asp Lys Ile
                85                  90                  95

Leu Lys Ser Asn Lys His Ile Tyr Val Gly Pro Tyr Val Gly His Thr
            100                 105                 110

Leu Phe Tyr Tyr Gly His Ile Asn Ile Ser Ser Phe Phe Asn Leu Asp
        115                 120                 125

Lys Tyr Phe Ile Asn Leu Leu Asn Glu Lys His Lys Asn Ile Leu Asn
    130                 135                 140

Asp Met Ser Ser Phe Glu Ser Val Thr Ile His Ile Arg Arg Gly Asp
145                 150                 155                 160

Tyr Met Tyr Ala Leu Lys Ile Asp Gly Arg Lys Asn Asn Ala Ser Leu
                165                 170                 175

Asp Tyr Ile Tyr Thr Ser Ile Lys Tyr Leu Asn Asn Thr Leu Glu Asn
            180                 185                 190

Lys Asn Ile Lys Phe Tyr Ile Phe Ser Asn Asn Lys Lys Tyr Ile Lys
        195                 200                 205

Asn Asn Leu Ile Pro Ile Phe Gln Asn Asn Asn Ile Asn Phe Glu Ile
    210                 215                 220

Ile Glu Asp Asn Pro Glu Tyr Ile Asp Phe Tyr Leu Met Thr Lys Cys
225                 230                 235                 240

Lys His Ile Ile Ser Ser Leu Gly Lys Phe Ala Lys Val Ala Phe Lys
                245                 250                 255

Phe Ile Lys Asn Glu Asn Lys Ile Phe Ile Asp Thr Asp Asn Ile Tyr
            260                 265                 270

Asn Leu Lys Lys Glu Tyr Phe Tyr Lys Asn Ile Cys Glu Lys Tyr Cys
        275                 280                 285

Asn Ile Ile Tyr Glu Glu Tyr Asn Asn Ile Lys Thr Tyr Ile Ser Lys
    290                 295                 300

Asn Asn Met Ile Tyr Ile Leu Asp Leu Ile Glu Lys Asn Asn Ile Lys
305                 310                 315                 320

Asn Ile Cys Gln Ile Gly Leu Leu Asp Gly Leu Glu Thr His Thr Leu
                325                 330                 335

Leu Lys Tyr Ser Ala Asp Asn Asn Asn Cys Phe Asn Leu Leu Cys Phe
            340                 345                 350
```

Glu Asn Asn Glu Arg Asp Ile Val Gly Ile Glu Leu Lys Asn Leu Thr
355 360 365

Glu Asn Glu Lys Lys Leu Phe Thr Leu Tyr Ile Glu Gln Ser Pro Leu
370 375 380

Asp Ile Asp Asn Ser Phe Asn Ile Lys Asn Ile Asp Phe Ile Phe Phe
385 390 395 400

Thr Lys Glu Asn Ser Asn Pro Leu Val Phe Ile Tyr Leu Ile Tyr Leu
405 410 415

Phe Pro Phe Met Lys Glu Glu Ile Ile Ile Val Phe Asn Asp Ile Ile
420 425 430

Ser Gly Lys Tyr Tyr Ser Gly Ser Tyr Cys Ile Phe Asn Met Phe Asn
435 440 445

Gly Glu Lys Asn Gln Phe Tyr Asn Phe Asn Thr Asn Lys Tyr Asp Asn
450 455 460

Ile Gly Tyr Ile Lys Ile Lys Lys Gln Glu Leu Leu Asn Ile Ile Lys
465 470 475 480

Lys Ile Ser Val Ile Glu Tyr Asp Gly Tyr Ile Asn Lys Phe Phe Met
485 490 495

Asn Lys Leu Ile Asp Asn Arg Asn Asp Tyr Tyr Asn Tyr Phe Asp Leu
500 505 510

Asp Met Ser Tyr Ile Arg Leu Asn Asn Leu Lys Gln Tyr Met Lys Asp
515 520 525

Lys Phe Asp Ile Glu Tyr Ser Asn Tyr Ile Ile Ser Asn Ile Glu Asn
530 535 540

Asn Ile Ile Asn Tyr Glu Lys Gln Tyr Tyr Lys Asn Gln Lys Asn Asn
545 550 555 560

Phe Tyr Ser Gln Asn Gln Ile His Ile Ser Lys Ile Glu Asn Ile Ile
565 570 575

Asp Lys His Asn Lys Leu Ile Asn Ser Ile Ser Trp Trp Ile Pro Ile
580 585 590

Lys Lys Leu Arg Glu Asn Phe Lys Asn Lys Phe Ile Arg Pro Asp Gln
595 600 605

Thr Arg Pro Asp Gln Thr Arg Pro Asp Gln Thr Xaa Xaa Xaa Xaa Xaa
610 615 620

Xaa Xaa Xaa Xaa Xaa Xaa Xaa Xaa Xaa Arg Pro Asp Gln Thr Arg Pro
625 630 635 640

Asp Gln Thr Arg Pro Asp Gln Thr
645

<210> SEQ ID NO 84
<211> LENGTH: 624
<212> TYPE: PRT
<213> ORGANISM: Brachysprira hyodysenteriae

<400> SEQUENCE: 84

Met Asn Asp Lys Tyr Val Ile Cys Ser Ile Thr Thr Gly Phe Thr Asp
1 5 10 15

Gln Leu Ile Asn Phe Ala Thr Ala Ile Tyr Ile Arg Glu Lys Tyr Lys
20 25 30

Lys Asn Val Lys Leu Asp Ile Ser Trp Phe Ser Val Tyr Glu Asn Thr
35 40 45

Asp Tyr Leu Gly Ile Glu Lys Arg Asn Leu Glu Val Leu Asn Ile Phe
50 55 60

Asn Asp Phe Asn Phe Glu Ile Ala Thr Lys Lys Glu Ile Asp Ile Ala
65 70 75 80

```
Leu Lys Ser Ile Phe Ile Asp Gly Arg Tyr Glu Asn Ile Asp Lys Ile
                85                  90                  95

Leu Lys Ser Asn Lys His Ile Tyr Val Gly Pro Tyr Val Gly His Thr
            100                 105                 110

Leu Phe Tyr Tyr Gly His Ile Asn Ile Ser Ser Phe Phe Asn Leu Asp
        115                 120                 125

Lys Tyr Phe Ile Asn Leu Leu Asn Glu Lys His Lys Asn Ile Leu Asn
    130                 135                 140

Tyr Met Ser Ser Phe Glu Ser Val Ala Ile His Ile Arg Arg Gly Asp
145                 150                 155                 160

Tyr Met Tyr Ala Leu Lys Ile Asp Gly Arg Lys Asn Asn Ala Ser Leu
                165                 170                 175

Asp Tyr Ile Tyr Thr Ser Ile Lys Tyr Leu Asn Asn Thr Leu Glu Asn
            180                 185                 190

Lys Asn Ile Lys Phe Tyr Ile Phe Ser Asn Asn Lys Lys Tyr Ile Lys
        195                 200                 205

Asn Asn Leu Ile Pro Ile Phe Gln Asn Asn Asn Ile Asn Phe Glu Ile
    210                 215                 220

Ile Glu Asp Asn Pro Glu Tyr Ile Asp Phe Tyr Leu Met Thr Lys Cys
225                 230                 235                 240

Lys His Ile Ile Ser Ser Leu Gly Lys Phe Ala Lys Val Ala Phe Lys
                245                 250                 255

Phe Ile Lys Asn Glu Asn Lys Ile Phe Ile Asp Thr Asp Asn Ile Tyr
            260                 265                 270

Asn Leu Lys Lys Glu Tyr Phe Tyr Lys Asn Ile Cys Glu Lys Tyr Cys
        275                 280                 285

Asn Ile Ile Tyr Glu Glu Tyr Asn Asn Ile Lys Thr Tyr Ile Ser Lys
    290                 295                 300

Asn Asn Met Ile Tyr Ile Leu Asp Leu Ile Glu Lys Asn Asn Ile Lys
305                 310                 315                 320

Asn Ile Cys Gln Ile Gly Leu Leu Asp Gly Leu Glu Thr His Thr Leu
                325                 330                 335

Leu Lys Tyr Ser Ala Asp Asn Asn Asn Cys Phe Asn Leu Leu Cys Phe
            340                 345                 350

Glu Asn Asn Glu Arg Asp Ile Val Gly Ile Glu Leu Lys Asn Leu Thr
        355                 360                 365

Glu Asn Glu Lys Lys Leu Phe Thr Leu Tyr Ile Glu Gln Ser Pro Leu
    370                 375                 380

Asp Ile Asp Asn Ser Phe Asn Ile Lys Asn Ile Asp Phe Ile Phe Phe
385                 390                 395                 400

Thr Lys Glu Asn Ser Asn Pro Leu Val Phe Ile Tyr Leu Ile Tyr Leu
                405                 410                 415

Phe Pro Phe Met Lys Glu Glu Ile Ile Ile Val Phe Asn Asp Ile Ile
            420                 425                 430

Ser Gly Lys Tyr Tyr Ser Gly Ser Tyr Cys Ile Phe Asn Met Phe Asn
        435                 440                 445

Gly Glu Lys Asn Gln Phe Tyr Asn Phe Asn Thr Asn Lys Tyr Asp Asn
    450                 455                 460

Ile Gly Tyr Ile Lys Ile Lys Lys Gln Glu Leu Leu Asn Ile Ile Lys
465                 470                 475                 480

Lys Ile Ser Val Ile Glu Tyr Asp Gly Tyr Ile Asn Lys Phe Phe Met
                485                 490                 495
```

```
Asn Lys Leu Ile Asp Asn Arg Asn Asp Tyr Tyr Asn Tyr Phe Asp Leu
            500                 505                 510

Asp Met Ser Tyr Ile Arg Leu Asn Asn Leu Lys Gln Tyr Met Lys Asp
        515                 520                 525

Lys Phe Asp Ile Glu Tyr Ser Asn Tyr Ile Ile Ser Asn Ile Glu Asn
    530                 535                 540

Asn Ile Ile Asn Tyr Glu Lys Gln Tyr Tyr Lys Asn Gln Lys Asn Asn
545                 550                 555                 560

Phe Tyr Ser Gln Asn Gln Ile His Ile Ser Lys Ile Glu Asn Ile Ile
                565                 570                 575

Asp Lys His Asn Lys Leu Ile Asn Ser Ile Ser Trp Trp Ile Pro Ile
            580                 585                 590

Lys Lys Leu Arg Glu Asn Phe Lys Asn Lys Phe Ile Arg Pro Asp Gln
        595                 600                 605

Thr Arg Pro Asp Gln Thr Arg Pro Asp Gln Thr Arg Pro Asp Gln Thr
    610                 615                 620
```

<210> SEQ ID NO 85
<211> LENGTH: 605
<212> TYPE: PRT
<213> ORGANISM: Brachysprira hyodysenteriae

<400> SEQUENCE: 85

```
Met Asn Asp Lys Tyr Val Ile Cys Ser Ile Thr Thr Gly Phe Thr Asp
1               5                   10                  15

Gln Leu Ile Asn Phe Ala Thr Ala Ile Tyr Ile Arg Glu Lys Tyr Lys
            20                  25                  30

Lys Asn Val Lys Leu Asp Ile Ser Trp Phe Ser Val Tyr Glu Asn Thr
        35                  40                  45

Asp Tyr Leu Gly Ile Glu Lys Arg Asn Leu Glu Val Leu Asn Ile Phe
    50                  55                  60

Asn Asp Phe Asn Phe Glu Ile Ala Thr Lys Lys Glu Ile Asp Ile Ala
65                  70                  75                  80

Leu Lys Ser Ile Phe Ile Asp Gly Arg Tyr Glu Asn Ile Asp Lys Ile
                85                  90                  95

Leu Lys Ser Asn Lys His Ile Tyr Val Gly His Thr Leu Phe Tyr Tyr
            100                 105                 110

Gly His Ile Asn Ile Ser Ser Phe Phe Asn Leu Asp Lys Tyr Phe Ile
        115                 120                 125

Asn Leu Leu Asn Glu Lys His Lys Asn Ile Leu Asn Tyr Met Ser Ser
    130                 135                 140

Phe Glu Ser Val Ala Ile His Ile Arg Arg Gly Asp Tyr Met Tyr Ala
145                 150                 155                 160

Leu Lys Ile Asp Gly Arg Lys Asn Asn Ala Ser Leu Asp Tyr Ile Tyr
                165                 170                 175

Thr Ser Ile Lys Tyr Leu Asn Asn Thr Leu Glu Asn Lys Asn Ile Lys
            180                 185                 190

Phe Tyr Ile Phe Ser Asn Asn Lys Lys Tyr Ile Lys Asn Asn Leu Ile
        195                 200                 205

Pro Ile Phe Gln Asn Asn Asn Ile Asn Phe Glu Ile Ile Glu Asp Asn
    210                 215                 220

Pro Glu Tyr Ile Asp Phe Tyr Leu Met Thr Lys Cys Lys His Ile Ile
225                 230                 235                 240

Ser Ser Leu Gly Lys Phe Ala Lys Val Ala Phe Lys Phe Ile Lys Asn
                245                 250                 255
```

Glu Asn Lys Ile Phe Ile Asp Thr Asp Asn Ile Tyr Asn Leu Lys Lys
260 265 270

Glu Tyr Phe Tyr Lys Asn Ile Cys Glu Lys Tyr Cys Asn Ile Ile Tyr
275 280 285

Glu Glu Tyr Asn Asn Ile Lys Thr Tyr Ile Ser Lys Asn Asn Met Ile
290 295 300

Tyr Ile Leu Asp Leu Ile Glu Lys Asn Asn Ile Lys Asn Ile Cys Gln
305 310 315 320

Ile Gly Leu Leu Asp Gly Leu Glu Thr His Thr Leu Leu Lys Tyr Ser
325 330 335

Ala Asp Asn Asn Asn Cys Phe Asn Leu Leu Cys Phe Glu Asn Asn Glu
340 345 350

Arg Asp Ile Val Gly Ile Glu Leu Lys Asn Leu Thr Glu Asn Glu Lys
355 360 365

Lys Leu Phe Thr Leu Tyr Ile Glu Gln Ser Pro Leu Asp Ile Asp Asn
370 375 380

Ser Phe Asn Ile Lys Asn Ile Asp Phe Ile Phe Phe Thr Lys Glu Asn
385 390 395 400

Ser Asn Pro Leu Val Phe Ile Tyr Leu Ile Tyr Leu Phe Pro Phe Met
405 410 415

Lys Glu Glu Ile Ile Ile Val Phe Asn Asp Ile Ile Ser Gly Lys Tyr
420 425 430

Tyr Ser Gly Ser Tyr Cys Ile Phe Asn Met Phe Asn Gly Glu Lys Asn
435 440 445

Gln Phe Tyr Asn Phe Asn Thr Asn Lys Tyr Asp Asn Ile Gly Tyr Ile
450 455 460

Lys Ile Lys Lys Gln Glu Leu Leu Asn Ile Ile Lys Lys Ile Ser Val
465 470 475 480

Ile Glu Tyr Asp Gly Tyr Ile Asn Lys Phe Phe Met Asn Lys Leu Ile
485 490 495

Asp Asn Arg Asn Asp Tyr Tyr Asn Tyr Phe Asp Leu Asp Met Ser Tyr
500 505 510

Ile Arg Leu Asn Asn Leu Lys Gln Tyr Met Lys Asp Lys Phe Asp Ile
515 520 525

Glu Tyr Ser Asn Tyr Ile Ile Ser Asn Ile Glu Asn Asn Ile Ile Asn
530 535 540

Tyr Glu Lys Gln Tyr Tyr Lys Asn Gln Lys Asn Asn Phe Tyr Ser Gln
545 550 555 560

Asn Gln Ile His Ile Ser Lys Ile Glu Asn Ile Ile Asp Lys His Asn
565 570 575

Lys Leu Ile Asn Ser Ile Ser Trp Trp Ile Pro Ile Lys Glu Leu Arg
580 585 590

Glu Asn Phe Lys Asn Lys Phe Ile Arg Pro Asp Gln Thr
595 600 605

<210> SEQ ID NO 86
<211> LENGTH: 628
<212> TYPE: PRT
<213> ORGANISM: Brachysprira hyodysenteriae

<400> SEQUENCE: 86

Met Asn Asp Lys Tyr Val Ile Cys Ser Ile Thr Thr Gly Phe Thr Asp
1 5 10 15

Gln Leu Ile Asn Phe Ala Thr Ala Ile Tyr Ile Arg Glu Lys Tyr Lys

```
            20                  25                  30

Lys Asn Val Lys Leu Asp Ile Ser Trp Phe Ser Val Tyr Glu Asn Thr
        35                  40                  45

Asp Tyr Leu Gly Ile Glu Lys Arg Asn Leu Glu Val Leu Asn Ile Phe
    50                  55                  60

Asn Asp Phe Asn Phe Glu Ile Ala Thr Lys Lys Glu Ile Asp Ile Ala
65                  70                  75                  80

Leu Lys Ser Ile Phe Ile Asp Gly Arg Tyr Glu Asn Ile Asp Lys Ile
                85                  90                  95

Leu Lys Ser Asn Lys His Ile Tyr Val Gly Pro Tyr Val Gly His Thr
            100                 105                 110

Leu Phe Tyr Tyr Gly His Ile Asn Ile Ser Ser Phe Phe Asn Leu Asp
        115                 120                 125

Lys Tyr Phe Ile Asn Leu Leu Asn Glu Lys His Lys Asn Ile Leu Asn
    130                 135                 140

Asp Met Ser Ser Phe Glu Ser Val Thr Ile His Ile Arg Arg Gly Asp
145                 150                 155                 160

Tyr Met Tyr Ala Leu Lys Ile Asp Gly Arg Lys Asn Asn Ala Ser Leu
                165                 170                 175

Asp Tyr Ile Tyr Thr Ser Ile Lys Tyr Leu Asn Asn Thr Leu Glu Asn
            180                 185                 190

Lys Asn Ile Lys Phe Tyr Ile Phe Ser Asn Asn Lys Lys Tyr Ile Lys
        195                 200                 205

Asn Asn Leu Ile Pro Ile Phe Gln Asn Asn Asn Ile Asn Phe Glu Ile
    210                 215                 220

Ile Glu Asp Asn Pro Glu Tyr Ile Asp Phe Tyr Leu Met Thr Lys Cys
225                 230                 235                 240

Lys His Ile Ile Ser Ser Leu Gly Lys Phe Ala Lys Val Ala Phe Lys
                245                 250                 255

Phe Ile Lys Asn Glu Asn Lys Ile Phe Ile Asp Thr Asp Asn Ile Tyr
            260                 265                 270

Asn Leu Lys Lys Glu Tyr Phe Tyr Lys Asn Ile Cys Glu Lys Tyr Cys
        275                 280                 285

Asn Ile Ile Tyr Glu Glu Tyr Asn Asn Ile Lys Thr Tyr Ile Ser Lys
    290                 295                 300

Asn Asn Met Ile Tyr Ile Leu Asp Leu Ile Glu Lys Asn Asn Ile Lys
305                 310                 315                 320

Asn Ile Cys Gln Ile Gly Leu Leu Asp Gly Leu Glu Thr His Thr Leu
                325                 330                 335

Leu Lys Tyr Ser Ala Asp Asn Asn Asn Cys Phe Asn Leu Leu Cys Phe
            340                 345                 350

Glu Asn Asn Glu Arg Asp Ile Val Gly Ile Glu Leu Lys Asn Leu Thr
        355                 360                 365

Glu Asn Glu Lys Lys Leu Phe Thr Leu Tyr Ile Glu Gln Ser Pro Leu
    370                 375                 380

Asp Ile Asp Asn Ser Phe Asn Ile Lys Asn Ile Asp Phe Ile Phe Phe
385                 390                 395                 400

Thr Lys Glu Asn Ser Asn Pro Leu Val Phe Ile Tyr Leu Ile Tyr Leu
                405                 410                 415

Phe Pro Phe Met Lys Glu Glu Ile Ile Ile Val Phe Asn Asp Ile Ile
            420                 425                 430

Ser Gly Lys Tyr Tyr Ser Gly Ser Tyr Cys Ile Phe Asn Met Phe Asn
        435                 440                 445
```

Gly Glu Lys Asn Gln Phe Tyr Asn Phe Asn Thr Asn Lys Tyr Asp Asn
450 455 460

Ile Gly Tyr Ile Lys Ile Lys Lys Gln Glu Leu Leu Asn Ile Ile Lys
465 470 475 480

Lys Ile Ser Val Ile Glu Tyr Asp Gly Tyr Ile Asn Lys Phe Phe Met
485 490 495

Asn Lys Leu Ile Asp Asn Arg Asn Asp Tyr Tyr Asn Tyr Phe Asp Leu
500 505 510

Asp Met Ser Tyr Ile Arg Leu Asn Asn Leu Lys Gln Tyr Met Lys Asp
515 520 525

Lys Phe Asp Ile Glu Tyr Ser Asn Tyr Ile Ile Ser Asn Ile Glu Asn
530 535 540

Asn Ile Ile Asn Tyr Glu Lys Gln Tyr Tyr Lys Asn Gln Lys Asn Asn
545 550 555 560

Phe Tyr Ser Gln Asn Gln Ile His Ile Ser Lys Ile Glu Asn Ile Ile
565 570 575

Asp Lys His Asn Lys Leu Ile Asn Ser Ile Ser Trp Trp Ile Pro Ile
580 585 590

Lys Lys Leu Arg Glu Asn Phe Lys Asn Lys Phe Ile Arg Pro Asp Gln
595 600 605

Thr Arg Pro Asp Gln Thr Arg Pro Asp Gln Thr Arg Pro Asp Gln Thr
610 615 620

Arg Pro Asn Met
625

<210> SEQ ID NO 87
<211> LENGTH: 639
<212> TYPE: PRT
<213> ORGANISM: Brachysprira hyodysenteriae

<400> SEQUENCE: 87

Met Asn Asp Lys Tyr Val Ile Cys Ser Ile Thr Thr Gly Phe Thr Asp
1 5 10 15

Gln Leu Ile Asn Phe Ala Thr Ala Ile Tyr Ile Arg Glu Lys Tyr Lys
20 25 30

Lys Asn Val Lys Leu Asp Ile Ser Trp Phe Ser Val Tyr Glu Asn Thr
35 40 45

Asp Tyr Leu Gly Ile Glu Lys Arg Asn Leu Glu Val Leu Asn Ile Phe
50 55 60

Asn Asp Phe Asn Phe Glu Ile Ala Thr Lys Lys Glu Ile Asp Ile Ala
65 70 75 80

Leu Lys Ser Ile Phe Ile Asp Gly Arg Tyr Glu Asn Ile Asp Lys Ile
85 90 95

Leu Lys Ser Asn Lys His Ile Tyr Val Gly Pro Tyr Val Gly His Thr
100 105 110

Leu Phe Tyr Tyr Gly His Ile Asn Ile Ser Ser Phe Phe Asn Leu Asp
115 120 125

Lys Tyr Phe Ile Asn Leu Leu Asn Glu Lys His Lys Asn Ile Leu Asn
130 135 140

Tyr Met Ser Ser Phe Glu Ser Val Ala Ile His Ile Arg Arg Gly Asp
145 150 155 160

Tyr Met Tyr Ala Leu Lys Ile Asp Gly Arg Lys Asn Asn Ala Ser Leu
165 170 175

Asp Tyr Ile Tyr Thr Ser Ile Lys Tyr Leu Asn Asn Thr Leu Glu Asn

```
            180                 185                 190

Lys Asn Ile Lys Phe Tyr Ile Phe Ser Asn Asn Lys Lys Tyr Ile Lys
        195                 200                 205

Asn Asn Leu Ile Pro Ile Phe Gln Asn Asn Asn Ile Asn Phe Glu Ile
    210                 215                 220

Ile Glu Asp Asn Pro Glu Tyr Ile Asp Phe Tyr Leu Met Thr Lys Cys
225                 230                 235                 240

Lys His Ile Ile Ser Ser Leu Gly Lys Phe Ala Lys Val Ala Phe Lys
                245                 250                 255

Phe Ile Lys Asn Glu Asn Lys Ile Phe Ile Asp Thr Asp Asn Ile Tyr
            260                 265                 270

Asn Leu Lys Lys Glu Tyr Phe Tyr Lys Asn Ile Cys Glu Lys Tyr Cys
        275                 280                 285

Asn Ile Ile Tyr Glu Glu Tyr Asn Asn Ile Lys Thr Tyr Ile Ser Lys
    290                 295                 300

Asn Asn Met Ile Tyr Ile Leu Asp Leu Ile Glu Lys Asn Asn Ile Lys
305                 310                 315                 320

Asn Ile Cys Gln Ile Gly Leu Leu Asp Gly Leu Glu Thr His Thr Leu
                325                 330                 335

Leu Lys Tyr Ser Ala Asp Asn Asn Asn Cys Phe Asn Leu Leu Cys Phe
            340                 345                 350

Glu Asn Asn Glu Arg Asp Ile Ile Gly Ile Glu Leu Lys Asn Leu Thr
        355                 360                 365

Glu Asn Glu Lys Lys Leu Phe Thr Leu Tyr Ile Glu Gln Ser Pro Leu
    370                 375                 380

Asp Ile Asp Asn Ser Phe Asn Ile Lys Asn Ile Asp Phe Ile Phe Phe
385                 390                 395                 400

Thr Lys Glu Asn Ser Asn Pro Leu Val Phe Ile Tyr Leu Ile Tyr Leu
                405                 410                 415

Phe Pro Phe Met Lys Glu Glu Ile Ile Ile Val Phe Asn Asp Ile Ile
            420                 425                 430

Ser Gly Lys Tyr Tyr Ser Gly Ser Tyr Cys Ile Phe Asn Met Phe Asn
        435                 440                 445

Gly Glu Lys Asn Gln Phe Tyr Asn Phe Asn Thr Asn Lys Tyr Asp Asn
    450                 455                 460

Ile Gly Tyr Ile Lys Ile Lys Lys Gln Glu Leu Leu Asn Ile Ile Lys
465                 470                 475                 480

Lys Ile Ser Val Ile Glu Tyr Asp Gly Tyr Ile Asn Lys Phe Phe Met
                485                 490                 495

Asn Lys Leu Ile Asp Asn Arg Asn Asp Tyr Tyr Asn Tyr Phe Asp Leu
            500                 505                 510

Asp Met Ser Tyr Ile Arg Leu Asn Asn Leu Lys Gln Tyr Met Lys Asp
        515                 520                 525

Lys Phe Asp Ile Glu Tyr Ser Asn Tyr Ile Ile Ser Asn Ile Glu Asn
    530                 535                 540

Asn Ile Ile Asn Tyr Glu Lys Gln Tyr Tyr Lys Asn Gln Lys Asn Asn
545                 550                 555                 560

Phe Tyr Ser Gln Asn Gln Ile His Ile Ser Lys Ile Glu Asn Ile Ile
                565                 570                 575

Asp Lys His Asn Lys Leu Ile Asn Ser Ile Ser Trp Trp Ile Pro Ile
            580                 585                 590

Lys Lys Leu Arg Glu Asn Phe Lys Asn Lys Phe Ile Arg Pro Asp Gln
        595                 600                 605
```

Thr Arg Pro Asp Gln Thr Arg Pro Asp Leu Ile Cys Lys Glu Tyr Ile
610 615 620

Tyr Asn Ile Leu Tyr Tyr Lys Ile Asn Lys Leu Gln Tyr Ile Asn
625 630 635

<210> SEQ ID NO 88
<211> LENGTH: 644
<212> TYPE: PRT
<213> ORGANISM: Brachysprira hyodysenteriae

<400> SEQUENCE: 88

Met Asn Asp Lys Tyr Val Ile Cys Ser Ile Thr Thr Gly Phe Thr Asp
1 5 10 15

Gln Leu Ile Asn Phe Ala Thr Ala Ile Tyr Ile Arg Glu Lys Tyr Lys
20 25 30

Lys Asn Val Lys Leu Asp Ile Ser Trp Phe Ser Val Tyr Glu Asn Thr
35 40 45

Asp Tyr Leu Gly Ile Glu Lys Arg Asn Leu Glu Val Leu Asn Ile Phe
50 55 60

Asn Asp Phe Asn Phe Glu Ile Ala Thr Lys Lys Glu Ile Asp Ile Ala
65 70 75 80

Leu Lys Ser Ile Phe Ile Asp Gly Arg Tyr Glu Asn Ile Asp Lys Ile
85 90 95

Leu Lys Ser Asn Lys His Ile Tyr Val Gly Pro Tyr Val Gly His Thr
100 105 110

Leu Phe Tyr Tyr Gly His Ile Asn Ile Ser Ser Phe Phe Asn Leu Asp
115 120 125

Lys Tyr Phe Ile Asn Leu Leu Asn Glu Lys His Lys Asn Ile Leu Asn
130 135 140

Tyr Met Ser Ser Phe Glu Ser Val Ala Ile His Ile Arg Arg Gly Asp
145 150 155 160

Tyr Met Tyr Ala Leu Lys Ile Asp Gly Arg Lys Asn Asn Ala Ser Leu
165 170 175

Asp Tyr Ile Tyr Thr Ser Ile Lys Tyr Leu Asn Asn Thr Leu Glu Asn
180 185 190

Lys Asn Ile Lys Phe Tyr Ile Phe Ser Asn Asn Lys Lys Tyr Ile Lys
195 200 205

Asn Asn Leu Ile Pro Ile Phe Gln Asn Asn Asn Ile Asn Phe Glu Ile
210 215 220

Ile Glu Asp Asn Pro Glu Tyr Ile Asp Phe Tyr Leu Met Thr Lys Cys
225 230 235 240

Lys His Ile Ile Ser Ser Leu Gly Lys Phe Ala Lys Val Ala Phe Lys
245 250 255

Phe Ile Lys Asn Glu Asn Lys Ile Phe Ile Asp Thr Asp Asn Ile Tyr
260 265 270

Asn Leu Lys Lys Glu Tyr Phe Tyr Lys Asn Ile Cys Glu Lys Tyr Cys
275 280 285

Asn Ile Ile Tyr Glu Glu Tyr Asn Asn Ile Lys Thr Tyr Ile Ser Lys
290 295 300

Asn Asn Met Ile Tyr Ile Leu Asp Leu Ile Glu Lys Asn Asn Ile Lys
305 310 315 320

Asn Ile Cys Gln Ile Gly Leu Leu Asp Gly Leu Glu Thr His Thr Leu
325 330 335

Leu Lys Tyr Ser Ala Asp Asn Asn Asn Cys Phe Asn Leu Leu Cys Phe 340                 345                 350

Glu Asn Asn Glu Arg Asp Ile Ile Gly Ile Glu Leu Lys Asn Leu Thr
        355                 360                 365

Glu Asn Glu Lys Lys Leu Phe Thr Leu Tyr Ile Glu Gln Ser Pro Leu
    370                 375                 380

Asp Ile Asp Asn Ser Phe Asn Ile Lys Asn Ile Asp Phe Ile Phe Phe
385                 390                 395                 400

Thr Lys Glu Asn Ser Asn Pro Leu Val Phe Ile Tyr Leu Ile Tyr Leu
                405                 410                 415

Phe Pro Phe Met Lys Glu Glu Ile Ile Ile Val Phe Asn Asp Ile Ile
            420                 425                 430

Ser Gly Lys Tyr Tyr Ser Gly Ser Tyr Cys Ile Phe Asn Met Phe Asn
        435                 440                 445

Gly Glu Lys Asn Gln Phe Tyr Asn Phe Asn Thr Asn Lys Tyr Asp Asn
    450                 455                 460

Ile Gly Tyr Ile Lys Ile Lys Lys Gln Glu Leu Leu Asn Ile Ile Lys
465                 470                 475                 480

Lys Ile Ser Val Ile Glu Tyr Asp Gly Tyr Ile Asn Lys Phe Phe Met
                485                 490                 495

Asn Lys Leu Ile Asp Asn Arg Asn Asp Tyr Tyr Asn Tyr Phe Asp Leu
            500                 505                 510

Asp Met Ser Tyr Ile Arg Leu Asn Asn Leu Lys Gln Tyr Met Lys Asp
        515                 520                 525

Lys Phe Asp Ile Glu Tyr Ser Asn Tyr Ile Ile Ser Asn Ile Glu Asn
    530                 535                 540

Asn Ile Ile Asn Tyr Glu Lys Gln Tyr Tyr Lys Asn Gln Lys Asn Asn
545                 550                 555                 560

Phe Tyr Ser Gln Asn Gln Ile His Ile Ser Lys Ile Glu Asn Ile Ile
                565                 570                 575

Asp Lys His Asn Lys Leu Ile Asn Ser Ile Ser Trp Trp Ile Pro Ile
            580                 585                 590

Lys Lys Leu Arg Glu Asn Phe Lys Asn Lys Phe Ile Arg Pro Asp Gln
        595                 600                 605

Thr Arg Pro Asp Gln Thr Arg Pro Asp Gln Thr Arg Pro Asp Leu Ile
    610                 615                 620

Cys Lys Glu Tyr Ile Tyr Asn Ile Leu Tyr Tyr Lys Ile Asn Lys Leu
625                 630                 635                 640

Gln Tyr Ile Asn

<210> SEQ ID NO 89
<211> LENGTH: 644
<212> TYPE: PRT
<213> ORGANISM: Brachysprira hyodysenteriae

<400> SEQUENCE: 89

Met Asn Asp Lys Tyr Val Ile Cys Ser Ile Thr Thr Gly Phe Thr Asp
1               5                   10                  15

Gln Leu Ile Asn Phe Ala Thr Ala Ile Tyr Ile Arg Glu Lys Tyr Lys
            20                  25                  30

Lys Asn Val Lys Leu Asp Ile Ser Trp Phe Ser Val Tyr Glu Asn Thr
        35                  40                  45

Asp Tyr Leu Gly Ile Glu Lys Arg Asn Leu Glu Val Leu Asn Ile Phe
    50                  55                  60

Asn Asp Phe Asn Phe Glu Ile Ala Thr Lys Lys Glu Ile Asp Ile Ala

```
65                  70                  75                  80

Leu Lys Ser Ile Phe Ile Asp Gly Arg Tyr Glu Asn Ile Asp Lys Ile
                85                  90                  95

Leu Lys Ser Asn Lys His Ile Tyr Val Gly Pro Tyr Val Gly His Thr
            100                 105                 110

Leu Phe Tyr Tyr Gly His Ile Asn Ile Ser Ser Phe Phe Asn Leu Asp
        115                 120                 125

Lys Tyr Phe Ile Asn Leu Leu Asn Glu Lys His Lys Asn Ile Leu Asn
    130                 135                 140

Asp Met Ser Ser Phe Glu Ser Val Ala Ile His Ile Arg Arg Gly Asp
145                 150                 155                 160

Tyr Met Tyr Ala Leu Lys Ile Asp Gly Arg Lys Asn Asn Ala Ser Leu
                165                 170                 175

Asp Tyr Ile Tyr Thr Ser Ile Lys Tyr Leu Asn Asn Thr Leu Glu Asn
            180                 185                 190

Lys Asn Ile Lys Phe Tyr Ile Phe Ser Asn Asn Lys Lys Tyr Ile Lys
        195                 200                 205

Asn Asn Leu Ile Pro Ile Phe Gln Asn Asn Asn Ile Asn Phe Glu Ile
    210                 215                 220

Ile Glu Asp Asn Pro Glu Tyr Ile Asp Phe Tyr Leu Met Thr Lys Cys
225                 230                 235                 240

Lys His Ile Ile Ser Ser Leu Gly Lys Phe Ala Lys Val Ala Phe Lys
                245                 250                 255

Phe Ile Lys Asn Glu Asn Lys Ile Phe Ile Asp Thr Asp Asn Ile Tyr
            260                 265                 270

Asn Leu Lys Lys Glu Tyr Phe Tyr Lys Asn Ile Cys Glu Lys Tyr Cys
        275                 280                 285

Asn Ile Ile Tyr Glu Glu Tyr Asn Asn Ile Lys Thr Tyr Ile Ser Lys
    290                 295                 300

Asn Asn Met Ile Tyr Ile Leu Asp Leu Ile Glu Lys Asn Asn Ile Lys
305                 310                 315                 320

Asn Ile Cys Gln Ile Gly Leu Leu Asp Gly Leu Glu Thr His Thr Leu
                325                 330                 335

Leu Lys Tyr Ser Ala Asp Asn Asn Asn Cys Phe Asn Leu Leu Cys Phe
            340                 345                 350

Glu Asn Asn Glu Arg Asp Ile Val Gly Ile Glu Leu Lys Asn Leu Thr
        355                 360                 365

Glu Asn Glu Lys Lys Leu Phe Thr Leu Tyr Ile Glu Gln Ser Pro Leu
    370                 375                 380

Asp Ile Asp Asn Ser Phe Asn Ile Lys Asn Ile Asp Phe Ile Phe Phe
385                 390                 395                 400

Thr Lys Glu Asn Ser Asn Pro Leu Val Phe Ile Tyr Leu Ile Tyr Leu
                405                 410                 415

Phe Pro Phe Met Lys Glu Glu Ile Ile Ile Val Phe Asn Asp Ile Ile
            420                 425                 430

Ser Gly Lys Tyr Tyr Ser Gly Ser Tyr Cys Ile Phe Asn Met Phe Asn
        435                 440                 445

Gly Glu Lys Asn Gln Phe Tyr Asn Phe Asn Thr Asn Lys Tyr Asp Asn
    450                 455                 460

Ile Gly Tyr Ile Lys Ile Lys Lys Gln Glu Leu Leu Asn Ile Ile Lys
465                 470                 475                 480

Lys Ile Ser Val Ile Glu Tyr Asp Gly Tyr Ile Asn Lys Phe Phe Met
                485                 490                 495
```

Asn Lys Leu Ile Asp Asn Arg Asn Asp Tyr Tyr Asn Tyr Phe Asp Leu
500 505 510

Asp Met Ser Tyr Ile Arg Leu Asn Asn Leu Lys Gln Tyr Met Lys Asp
515 520 525

Lys Phe Asp Ile Glu Tyr Ser Asn Tyr Ile Ile Ser Asn Ile Glu Asn
530 535 540

Asn Ile Ile Asn Tyr Glu Lys Gln Tyr Tyr Lys Asn Gln Lys Asn Asn
545 550 555 560

Phe Tyr Ser Gln Asn Gln Ile His Ile Ser Lys Ile Glu Asn Ile Ile
565 570 575

Asp Lys His Asn Lys Leu Ile Asn Ser Ile Ser Trp Trp Ile Pro Ile
580 585 590

Lys Lys Leu Arg Glu Asn Phe Lys Asn Lys Phe Ile Arg Pro Asp Gln
595 600 605

Thr Arg Pro Asp Gln Thr Arg Pro Asp Gln Thr Arg Pro Asp Leu Ile
610 615 620

Cys Lys Glu Tyr Ile Tyr Asn Ile Leu Tyr Tyr Lys Ile Asn Lys Leu
625 630 635 640

Gln Tyr Ile Asn

<210> SEQ ID NO 90
<211> LENGTH: 619
<212> TYPE: PRT
<213> ORGANISM: Brachysprira hyodysenteriae

<400> SEQUENCE: 90

Met Asn Asp Lys Tyr Val Ile Cys Ser Ile Thr Thr Gly Phe Thr Asp
1 5 10 15

Gln Leu Ile Asn Phe Ala Thr Ala Ile Tyr Ile Arg Glu Lys Tyr Lys
20 25 30

Lys Asn Val Lys Leu Asp Ile Ser Trp Phe Ser Val Tyr Glu Asn Thr
35 40 45

Asp Tyr Leu Gly Ile Glu Lys Arg Asn Leu Glu Val Leu Asn Ile Phe
50 55 60

Asn Asp Phe Asn Phe Glu Ile Ala Thr Lys Lys Glu Ile Asp Ile Ala
65 70 75 80

Leu Lys Ser Ile Phe Ile Asp Gly Arg Tyr Glu Asn Ile Asp Lys Ile
85 90 95

Leu Lys Ser Asn Lys His Ile Tyr Val Gly Pro Tyr Val Gly His Thr
100 105 110

Leu Phe Tyr Tyr Gly His Ile Asn Ile Ser Ser Phe Phe Asn Leu Asp
115 120 125

Lys Tyr Phe Ile Asn Leu Leu Asn Glu Lys His Lys Asn Ile Leu Asn
130 135 140

Asp Met Ser Ser Phe Glu Ser Val Ala Ile His Ile Arg Arg Gly Asp
145 150 155 160

Tyr Met Tyr Ala Leu Lys Ile Asp Gly Arg Lys Asn Asn Ala Ser Leu
165 170 175

Asp Tyr Ile Tyr Thr Ser Ile Lys Tyr Leu Asn Asn Thr Leu Glu Asn
180 185 190

Lys Asn Ile Lys Phe Tyr Ile Phe Ser Asn Asn Lys Lys Tyr Ile Lys
195 200 205

Asn Asn Leu Ile Pro Ile Phe Gln Asn Asn Asn Ile Asn Phe Glu Ile
210 215 220

```
Ile Glu Asp Asn Pro Glu Tyr Ile Asp Phe Tyr Leu Met Thr Lys Cys
225                 230                 235                 240

Lys His Ile Ile Ser Ser Leu Gly Lys Phe Ala Lys Val Ala Phe Lys
                245                 250                 255

Phe Ile Lys Asn Glu Asn Lys Ile Phe Ile Asp Thr Asp Asn Ile Tyr
            260                 265                 270

Asn Leu Lys Lys Glu Tyr Phe Tyr Lys Asn Ile Cys Glu Lys Tyr Cys
        275                 280                 285

Asn Ile Ile Tyr Glu Glu Tyr Asn Asn Ile Lys Thr Tyr Ile Ser Lys
    290                 295                 300

Asn Asn Met Ile Tyr Ile Leu Asp Leu Ile Glu Lys Asn Asn Ile Lys
305                 310                 315                 320

Asn Ile Cys Gln Ile Gly Leu Leu Asp Gly Leu Glu Thr His Thr Leu
                325                 330                 335

Leu Lys Tyr Ser Ala Asp Asn Asn Asn Cys Phe Asn Leu Leu Cys Phe
            340                 345                 350

Glu Asn Asn Glu Arg Asp Ile Val Gly Ile Glu Leu Lys Asn Leu Thr
        355                 360                 365

Glu Asn Glu Lys Lys Leu Phe Thr Leu Tyr Ile Glu Gln Ser Pro Leu
    370                 375                 380

Asp Ile Asp Asn Ser Phe Asn Ile Lys Asn Ile Asp Phe Ile Phe Phe
385                 390                 395                 400

Thr Lys Glu Asn Ser Asn Pro Leu Val Phe Ile Tyr Leu Ile Tyr Leu
                405                 410                 415

Phe Pro Phe Met Lys Glu Glu Ile Ile Ile Val Phe Asn Asp Ile Ile
            420                 425                 430

Ser Asp Lys Tyr Tyr Ser Gly Ser Tyr Cys Ile Phe Asn Met Phe Asn
        435                 440                 445

Gly Glu Lys Asn Gln Phe Tyr Asn Phe Asn Thr Asn Lys Tyr Asp Asn
    450                 455                 460

Ile Gly Tyr Ile Lys Ile Lys Lys Gln Glu Leu Leu Asn Ile Ile Lys
465                 470                 475                 480

Lys Ile Ser Val Ile Glu Tyr Asp Gly Tyr Ile Asn Lys Phe Phe Met
                485                 490                 495

Asn Lys Leu Ile Asp Asn Arg Asn Asp Tyr Tyr Asn Tyr Phe Asp Leu
            500                 505                 510

Asp Met Ser Tyr Ile Arg Leu Asn Asn Leu Lys Gln Tyr Met Lys Asp
        515                 520                 525

Lys Phe Asp Ile Glu Tyr Ser Asn Tyr Ile Ile Phe Asn Ile Glu Asn
    530                 535                 540

Asn Ile Ile Asn Tyr Glu Lys Gln Tyr Tyr Lys Asn Gln Lys Asn Asn
545                 550                 555                 560

Phe Tyr Ser Lys Asn Gln Ile His Ile Ser Lys Ile Glu Asn Ile Ile
                565                 570                 575

Asp Lys His Asn Lys Leu Ile Asn Ser Ile Ser Trp Trp Ile Pro Ile
            580                 585                 590

Lys Lys Leu Arg Glu Asn Phe Lys Asn Lys Phe Ile Arg Pro Asp Gln
        595                 600                 605

Thr Arg Pro Asp Gln Thr Arg Pro Asp Gln Thr
    610                 615
```

<210> SEQ ID NO 91
<211> LENGTH: 619

<212> TYPE: PRT
<213> ORGANISM: Brachysprira hyodysenteriae

<400> SEQUENCE: 91

```
Met Asn Asp Lys Tyr Val Ile Cys Ser Ile Thr Thr Gly Phe Thr Asp
1               5                   10                  15

Gln Leu Ile Asn Phe Ala Thr Ala Ile Tyr Ile Arg Glu Lys Tyr Lys
            20                  25                  30

Lys Asn Val Lys Leu Asp Ile Ser Trp Phe Ser Val Tyr Glu Asn Thr
        35                  40                  45

Asp Tyr Leu Gly Ile Glu Lys Arg Asn Leu Glu Val Leu Asn Ile Phe
    50                  55                  60

Asn Asp Phe Asn Phe Glu Ile Ala Thr Lys Lys Glu Ile Asp Ile Ala
65                  70                  75                  80

Leu Lys Ser Ile Phe Ile Asp Gly Arg Tyr Glu Asn Ile Asp Lys Ile
                85                  90                  95

Leu Lys Ser Asn Lys His Ile Tyr Val Gly Pro Tyr Val Gly His Thr
            100                 105                 110

Leu Phe Tyr Tyr Gly His Ile Asn Ile Ser Ser Phe Phe Asn Leu Asp
        115                 120                 125

Lys Tyr Phe Ile Asn Leu Leu Asn Glu Lys His Lys Asn Ile Leu Asn
    130                 135                 140

Tyr Met Ser Ser Phe Glu Ser Val Ala Ile His Ile Arg Arg Gly Asp
145                 150                 155                 160

Tyr Met Tyr Ala Leu Lys Ile Asp Gly Arg Lys Asn Asn Ala Ser Leu
                165                 170                 175

Asp Tyr Ile Tyr Thr Ser Ile Lys Tyr Leu Asn Asn Thr Leu Glu Asn
            180                 185                 190

Lys Asn Ile Lys Phe Tyr Ile Phe Ser Asn Asn Lys Lys Tyr Ile Lys
        195                 200                 205

Asn Asn Leu Ile Pro Ile Phe Gln Asn Asn Asn Ile Asn Phe Glu Ile
    210                 215                 220

Ile Glu Asp Asn Pro Glu Tyr Ile Asp Phe Tyr Leu Met Thr Lys Cys
225                 230                 235                 240

Lys His Ile Ile Ser Ser Leu Gly Lys Phe Ala Lys Val Ala Phe Lys
                245                 250                 255

Phe Ile Lys Asn Glu Asn Lys Ile Phe Ile Asp Thr Asp Asn Ile Tyr
            260                 265                 270

Asn Leu Lys Lys Glu Tyr Phe Tyr Lys Asn Ile Cys Glu Lys Tyr Cys
        275                 280                 285

Asn Ile Ile Tyr Glu Glu Tyr Asn Asn Ile Lys Thr Tyr Ile Ser Lys
    290                 295                 300

Asn Asn Met Ile Tyr Ile Leu Asp Leu Ile Glu Lys Asn Asn Ile Lys
305                 310                 315                 320

Asn Ile Cys Gln Ile Gly Leu Leu Asp Gly Leu Glu Thr His Thr Leu
                325                 330                 335

Leu Lys Tyr Ser Ala Asp Asn Asn Asn Cys Phe Asn Leu Leu Cys Phe
            340                 345                 350

Glu Asn Asn Glu Arg Asp Ile Ile Gly Ile Glu Leu Lys Asn Leu Thr
        355                 360                 365

Glu Asn Glu Lys Lys Leu Phe Thr Leu Tyr Ile Glu Gln Ser Pro Leu
    370                 375                 380

Asp Ile Asp Asn Ser Phe Asn Ile Lys Asn Ile Asp Phe Ile Phe Phe
385                 390                 395                 400
```

Thr Lys Glu Asn Ser Asn Pro Leu Val Phe Ile Tyr Leu Ile Tyr Leu
405 410 415

Phe Pro Phe Met Lys Glu Glu Ile Ile Ile Val Phe Asn Asp Ile Ile
420 425 430

Ser Gly Lys Tyr Tyr Ser Gly Ser Tyr Cys Ile Phe Asn Met Phe Asn
435 440 445

Gly Glu Lys Asn Gln Phe Tyr Asn Phe Asn Thr Asn Lys Tyr Asp Asn
450 455 460

Ile Gly Tyr Ile Lys Ile Lys Lys Gln Glu Leu Leu Asn Ile Ile Lys
465 470 475 480

Lys Ile Ser Val Ile Glu Tyr Asp Gly Tyr Ile Asn Lys Phe Phe Met
485 490 495

Asn Lys Leu Ile Asp Asn Arg Asn Asp Tyr Tyr Asn Tyr Phe Asp Leu
500 505 510

Asp Met Ser Tyr Ile Arg Leu Asn Asn Leu Lys Gln Tyr Met Lys Asp
515 520 525

Lys Phe Asp Ile Glu Tyr Ser Asn Tyr Ile Ile Ser Asn Ile Glu Asn
530 535 540

Asn Ile Ile Asn Tyr Glu Lys Gln Tyr Tyr Lys Asn Gln Lys Asn Asn
545 550 555 560

Phe Tyr Ser Gln Asn Gln Ile His Ile Ser Lys Ile Glu Asn Ile Ile
565 570 575

Asp Lys His Asn Lys Leu Ile Asn Ser Ile Ser Trp Trp Ile Pro Ile
580 585 590

Lys Lys Leu Arg Glu Asn Phe Lys Asn Lys Phe Ile Arg Pro Asp Gln
595 600 605

Thr Arg Pro Asp Gln Thr Arg Pro Asp Gln Thr
610 615

<210> SEQ ID NO 92
<211> LENGTH: 623
<212> TYPE: PRT
<213> ORGANISM: Brachysprira hyodysenteriae

<400> SEQUENCE: 92

Met Asn Asp Lys Tyr Val Ile Cys Ser Ile Thr Thr Gly Phe Thr Asp
1 5 10 15

Gln Leu Ile Asn Phe Ala Thr Ala Ile Tyr Ile Arg Glu Lys Tyr Lys
20 25 30

Lys Asn Val Lys Leu Asp Ile Ser Trp Phe Ser Val Tyr Glu Asn Thr
35 40 45

Asp Tyr Leu Gly Ile Glu Lys Arg Asn Leu Glu Val Leu Asn Ile Phe
50 55 60

Asn Asp Phe Asn Phe Glu Ile Ala Thr Lys Lys Glu Ile Asp Ile Ala
65 70 75 80

Leu Lys Ser Ile Phe Ile Asp Gly Arg Tyr Glu Asn Ile Asp Lys Ile
85 90 95

Leu Lys Ser Asn Lys His Ile Tyr Val Gly Pro Tyr Val Gly His Thr
100 105 110

Leu Phe Tyr Tyr Gly His Ile Asn Ile Ser Ser Phe Phe Asn Leu Asp
115 120 125

Lys Tyr Phe Ile Asn Leu Leu Asn Lys Lys His Lys Asn Ile Leu Asn
130 135 140

Asp Met Ser Ser Phe Glu Ser Val Ala Ile His Ile Arg Arg Gly Asp

-continued

```
145                 150                 155                 160

Tyr Met Tyr Ala Leu Lys Ile Asp Gly Arg Lys Asn Asn Ala Ser Leu
                165                 170                 175

Asp Tyr Ile Tyr Thr Ser Ile Lys Tyr Leu Asn Asn Thr Leu Glu Asn
            180                 185                 190

Lys Asn Ile Lys Phe Tyr Ile Phe Ser Asn Asn Lys Lys Tyr Ile Lys
        195                 200                 205

Asn Asn Leu Ile Pro Ile Phe Gln Asn Asn Asn Ile Asn Phe Glu Ile
    210                 215                 220

Ile Glu Asp Asn Pro Glu Tyr Ile Asp Phe Tyr Leu Met Thr Lys Cys
225                 230                 235                 240

Lys His Ile Ile Ser Ser Leu Gly Lys Phe Ala Lys Val Ala Phe Lys
                245                 250                 255

Phe Ile Lys Asn Glu Asn Lys Ile Phe Ile Asp Thr Asp Asn Ile Tyr
            260                 265                 270

Asn Leu Lys Lys Glu Tyr Phe Tyr Lys Asn Ile Cys Glu Lys Tyr Cys
        275                 280                 285

Asn Ile Ile Tyr Glu Glu Tyr Asn Asn Ile Lys Thr Tyr Ile Ser Lys
    290                 295                 300

Asn Asn Met Ile Tyr Ile Leu Asp Leu Ile Glu Lys Asn Asn Ile Lys
305                 310                 315                 320

Asn Ile Cys Gln Ile Gly Leu Leu Asp Gly Leu Glu Thr His Thr Leu
                325                 330                 335

Leu Lys Tyr Ser Ala Tyr Asn Asn Asn Cys Phe Asn Leu Leu Cys Phe
            340                 345                 350

Glu Asn Asn Glu Arg Asp Ile Val Gly Ile Glu Leu Lys Asn Leu Thr
        355                 360                 365

Glu Asn Glu Lys Lys Leu Phe Thr Leu Tyr Ile Glu Gln Ser Pro Leu
    370                 375                 380

Asp Ile Asp Asn Ser Phe Asn Ile Lys Asn Ile Asp Phe Ile Phe Phe
385                 390                 395                 400

Thr Lys Glu Asn Ser Asn Pro Leu Val Phe Ile Tyr Leu Ile Tyr Leu
                405                 410                 415

Phe Pro Phe Met Lys Glu Glu Ile Ile Ile Val Phe Asn Asp Ile Ile
            420                 425                 430

Ser Gly Lys Tyr Tyr Ser Gly Ser Tyr Cys Ile Phe Asn Met Phe Asn
        435                 440                 445

Gly Glu Lys Asn Gln Phe Tyr Asn Phe Asn Thr Asn Lys Tyr Asp Asn
    450                 455                 460

Ile Gly Tyr Ile Lys Ile Lys Lys Gln Glu Leu Leu Asn Ile Ile Lys
465                 470                 475                 480

Lys Ile Ser Val Ile Glu Tyr Asp Gly Tyr Ile Asn Lys Phe Phe Met
                485                 490                 495

Asn Lys Leu Ile Asp Asn Arg Asn Asp Tyr Tyr Asn Tyr Phe Asp Leu
            500                 505                 510

Asp Met Ser Tyr Ile Arg Leu Asn Asn Leu Lys Gln Tyr Met Lys Asp
        515                 520                 525

Lys Phe Asp Ile Glu Tyr Ser Asn Tyr Ile Ile Ser Asn Ile Glu Asn
    530                 535                 540

Asn Ile Ile Asn Tyr Glu Lys Gln Tyr Tyr Lys Asn Gln Lys Asn Asn
545                 550                 555                 560

Phe Tyr Ser Gln Asn Gln Ile His Ile Ser Lys Ile Glu Asn Ile Ile
                565                 570                 575
```

Asp Lys His Asn Lys Leu Ile Asn Ser Ile Ser Trp Trp Ile Pro Ile
580 585 590

Lys Lys Leu Arg Glu Asn Phe Lys Asn Lys Phe Ile Arg Pro Asp Gln
595 600 605

Thr Arg Pro Asp Gln Thr Arg Pro Asp Gln Thr Arg Pro Asn Met
610 615 620

<210> SEQ ID NO 93
<211> LENGTH: 633
<212> TYPE: PRT
<213> ORGANISM: Brachysprira hyodysenteriae

<400> SEQUENCE: 93

Met Asn Asp Lys Tyr Val Ile Cys Ser Ile Thr Thr Gly Phe Thr Asp
1 5 10 15

Gln Leu Ile Asn Phe Ala Thr Ala Ile Tyr Ile Arg Glu Lys Tyr Lys
20 25 30

Lys Asn Val Lys Leu Asp Ile Ser Trp Phe Ser Val Tyr Glu Asn Thr
35 40 45

Asp Tyr Leu Gly Ile Glu Lys Arg Asn Leu Glu Val Leu Asn Ile Phe
50 55 60

Asn Asp Phe Asn Phe Glu Ile Ala Thr Lys Lys Glu Ile Asp Ile Ala
65 70 75 80

Leu Lys Ser Ile Phe Ile Asp Gly Arg Tyr Glu Asn Ile Asp Lys Ile
85 90 95

Leu Lys Ser Asn Lys His Ile Tyr Val Gly Pro Tyr Val Gly His Thr
100 105 110

Leu Phe Tyr Tyr Gly His Ile Asn Ile Ser Ser Phe Phe Asn Leu Asp
115 120 125

Lys Tyr Phe Ile Asn Leu Leu Asn Glu Lys His Lys Asn Ile Leu Asn
130 135 140

Asp Met Ser Ser Phe Glu Ser Val Ala Ile His Ile Arg Arg Gly Asp
145 150 155 160

Tyr Met Tyr Ala Leu Lys Ile Asp Gly Arg Lys Asn Asn Ala Ser Leu
165 170 175

Asp Tyr Ile Tyr Thr Ser Ile Lys Tyr Leu Asn Asn Thr Leu Glu Asn
180 185 190

Lys Asn Ile Lys Phe Tyr Ile Phe Ser Asn Asn Lys Lys Tyr Ile Lys
195 200 205

Asn Asn Leu Ile Pro Ile Phe Gln Asn Asn Asn Ile Asn Phe Glu Ile
210 215 220

Ile Glu Asp Asn Pro Glu Tyr Ile Asp Phe Tyr Leu Met Thr Lys Cys
225 230 235 240

Lys His Ile Ile Ser Ser Leu Gly Lys Phe Ala Lys Val Ala Phe Lys
245 250 255

Phe Ile Lys Asn Glu Asn Lys Ile Phe Ile Asp Thr Asp Asn Ile Tyr
260 265 270

Asn Leu Lys Lys Glu Tyr Phe Tyr Lys Asn Ile Cys Glu Lys Tyr Cys
275 280 285

Asn Ile Ile Tyr Glu Glu Tyr Asn Asn Ile Lys Thr Tyr Ile Ser Lys
290 295 300

Asn Asn Met Ile Tyr Ile Leu Asp Leu Ile Glu Lys Asn Asn Ile Lys
305 310 315 320

Asn Ile Cys Gln Ile Gly Leu Leu Asp Gly Leu Glu Thr His Thr Leu 325 330 335

Leu Lys Tyr Ser Ala Asp Asn Asn Asn Cys Phe Asn Leu Leu Cys Phe
340 345 350

Glu Asn Asn Glu Arg Asp Ile Val Gly Ile Glu Leu Lys Asn Leu Thr
355 360 365

Glu Asn Glu Lys Lys Leu Phe Thr Leu Tyr Ile Glu Gln Ser Pro Leu
370 375 380

Asp Ile Asp Asn Ser Phe Asn Ile Lys Asn Ile Asp Phe Ile Phe Phe
385 390 395 400

Thr Lys Glu Asn Ser Asn Pro Leu Val Phe Ile Tyr Leu Ile Tyr Leu
405 410 415

Phe Pro Phe Met Lys Glu Glu Ile Ile Ile Val Phe Asn Asp Ile Ile
420 425 430

Ser Asp Lys Tyr Tyr Ser Gly Ser Tyr Cys Ile Phe Asn Met Phe Asn
435 440 445

Gly Glu Lys Asn Gln Phe Tyr Asn Phe Asn Thr Asn Glu Tyr Asp Asn
450 455 460

Ile Gly Tyr Ile Lys Ile Lys Lys Gln Glu Leu Leu Asn Ile Ile Lys
465 470 475 480

Lys Ile Ser Val Ile Glu Tyr Asp Gly Tyr Ile Asn Lys Phe Phe Met
485 490 495

Asn Lys Leu Ile Asp Asn Arg Asn Asp Tyr Tyr Asn Tyr Phe Asp Leu
500 505 510

Asp Met Ser Tyr Ile Arg Leu Asn Asn Leu Lys Gln Tyr Met Lys Asp
515 520 525

Lys Phe Asp Ile Glu Tyr Ser Asn Tyr Ile Ile Ser Asn Ile Glu Asn
530 535 540

Asn Ile Ile Asn Tyr Glu Lys Gln Tyr Tyr Lys Asn Gln Lys Asn Asn
545 550 555 560

Phe Tyr Ser Lys Asn Gln Ile His Ile Ser Lys Ile Glu Asn Ile Ile
565 570 575

Asp Lys His Asn Lys Leu Ile Asn Ser Ile Ser Trp Trp Ile Pro Ile
580 585 590

Lys Lys Leu Arg Glu Asn Phe Lys Asn Lys Phe Ile Arg Pro Asp Gln
595 600 605

Thr Arg Pro Asp Gln Thr Arg Pro Asp Gln Thr Arg Pro Asp Gln Thr
610 615 620

Arg Pro Asp Gln Thr Arg Pro Asn Met
625 630

<210> SEQ ID NO 94
<211> LENGTH: 623
<212> TYPE: PRT
<213> ORGANISM: Brachysprira hyodysenteriae

<400> SEQUENCE: 94

Met Asn Asp Lys Tyr Val Ile Cys Ser Ile Thr Thr Gly Phe Thr Asp
1 5 10 15

Gln Leu Ile Asn Phe Ala Thr Ala Ile Tyr Ile Arg Glu Lys Tyr Lys
20 25 30

Lys Asn Val Lys Leu Asp Ile Ser Trp Phe Ser Val Tyr Glu Asn Thr
35 40 45

Asp Tyr Leu Gly Ile Glu Lys Arg Asn Leu Glu Val Leu Asn Ile Phe
50 55 60

```
Asn Asp Phe Asn Phe Glu Ile Ala Thr Lys Lys Glu Ile Asp Ile Ala
65                  70                  75                  80

Leu Lys Ser Ile Phe Ile Asp Gly Arg Tyr Glu Asn Ile Asp Lys Ile
                85                  90                  95

Leu Lys Ser Asn Lys His Ile Tyr Val Gly Pro Tyr Val Gly His Thr
            100                 105                 110

Leu Phe Tyr Tyr Gly His Ile Asn Ile Ser Ser Phe Phe Asn Leu Asp
        115                 120                 125

Lys Tyr Phe Ile Asn Leu Leu Asn Glu Lys His Lys Asn Ile Leu Asn
    130                 135                 140

Tyr Met Ser Ser Phe Glu Ser Val Ala Ile His Ile Arg Arg Gly Asp
145                 150                 155                 160

Tyr Met Tyr Ala Leu Lys Ile Asp Gly Arg Lys Asn Asn Ala Ser Leu
                165                 170                 175

Asp Tyr Ile Tyr Thr Ser Ile Lys Tyr Leu Asn Asn Thr Leu Glu Asn
            180                 185                 190

Lys Asn Ile Lys Phe Tyr Ile Phe Ser Asn Asn Lys Lys Tyr Ile Lys
        195                 200                 205

Asn Asn Leu Ile Pro Ile Phe Gln Asn Asn Asn Ile Asn Phe Glu Ile
    210                 215                 220

Ile Glu Asp Asn Pro Glu Tyr Ile Asp Phe Tyr Leu Met Thr Lys Cys
225                 230                 235                 240

Lys His Ile Ile Ser Ser Leu Gly Lys Phe Ala Lys Val Ala Phe Lys
                245                 250                 255

Phe Ile Lys Asn Glu Asn Lys Ile Phe Ile Asp Thr Asp Asn Ile Tyr
            260                 265                 270

Asn Leu Lys Lys Glu Tyr Phe Tyr Lys Asn Ile Cys Glu Lys Tyr Cys
        275                 280                 285

Asn Ile Ile Tyr Glu Glu Tyr Asn Asn Ile Lys Thr Tyr Ile Ser Lys
    290                 295                 300

Asn Asn Met Ile Tyr Ile Leu Asp Leu Ile Glu Lys Asn Asn Ile Lys
305                 310                 315                 320

Asn Ile Cys Gln Ile Gly Leu Leu Asp Gly Leu Glu Thr His Thr Leu
                325                 330                 335

Leu Lys Tyr Ser Ala Asp Asn Asn Asn Cys Phe Asn Leu Leu Cys Phe
            340                 345                 350

Glu Asn Asn Glu Arg Asp Ile Val Gly Ile Glu Leu Lys Asn Leu Thr
        355                 360                 365

Glu Asn Glu Lys Lys Leu Phe Thr Leu Tyr Ile Glu Gln Ser Pro Leu
    370                 375                 380

Asp Ile Asp Asn Ser Phe Asn Ile Lys Asn Ile Asp Phe Ile Phe Phe
385                 390                 395                 400

Thr Lys Glu Asn Ser Asn Pro Leu Val Phe Ile Tyr Leu Ile Tyr Leu
                405                 410                 415

Phe Pro Phe Met Lys Glu Glu Ile Ile Ile Val Phe Asn Asp Ile Ile
            420                 425                 430

Ser Gly Lys Tyr Tyr Ser Gly Ser Tyr Cys Ile Phe Asn Met Phe Asn
        435                 440                 445

Gly Glu Lys Asn Gln Phe Tyr Asn Phe Asn Thr Asn Lys Tyr Asp Asn
    450                 455                 460

Ile Gly Tyr Ile Lys Ile Lys Lys Gln Glu Leu Leu Asn Ile Ile Lys
465                 470                 475                 480

Lys Ile Ser Val Ile Glu Tyr Asp Gly Tyr Ile Asn Lys Phe Phe Met
```

```
                485                 490                 495

Asn Lys Leu Ile Asp Asn Arg Asn Asp Tyr Tyr Asn Tyr Phe Asp Leu
            500                 505                 510

Asp Met Ser Tyr Ile Arg Leu Asn Asn Leu Lys Gln Tyr Met Lys Asp
        515                 520                 525

Lys Phe Asp Ile Glu Tyr Ser Asn Tyr Ile Ile Ser Asn Ile Glu Asn
    530                 535                 540

Asn Ile Ile Asn Tyr Glu Lys Gln Tyr Tyr Lys Asn Gln Lys Asn Asn
545                 550                 555                 560

Phe Tyr Ser Gln Asn Gln Ile His Ile Ser Lys Ile Glu Asn Ile Ile
                565                 570                 575

Asp Lys His Asn Lys Leu Ile Asn Ser Ile Ser Trp Trp Ile Pro Ile
            580                 585                 590

Lys Glu Leu Arg Glu Asn Phe Lys Asn Lys Phe Ile Arg Pro Asp Gln
        595                 600                 605

Thr Arg Pro Asp Gln Thr Arg Pro Asp Gln Thr Arg Pro Asn Met
    610                 615                 620


<210> SEQ ID NO 95
<211> LENGTH: 618
<212> TYPE: PRT
<213> ORGANISM: Brachysprira hyodysenteriae

<400> SEQUENCE: 95

Met Asn Asp Lys Tyr Val Ile Cys Ser Ile Thr Thr Gly Phe Thr Asp
1               5                   10                  15

Gln Leu Ile Asn Phe Ala Thr Ala Ile Tyr Ile Arg Glu Lys Tyr Lys
            20                  25                  30

Lys Asn Val Lys Leu Asp Ile Ser Trp Phe Ser Val Tyr Glu Asn Thr
        35                  40                  45

Asp Tyr Leu Gly Ile Glu Lys Arg Asn Leu Glu Val Leu Asn Ile Phe
    50                  55                  60

Asn Asp Phe Asn Phe Glu Ile Ala Thr Lys Lys Glu Ile Asp Ile Ala
65                  70                  75                  80

Leu Lys Ser Ile Phe Ile Asp Gly Arg Tyr Glu Asn Ile Asp Lys Ile
                85                  90                  95

Leu Lys Ser Asn Lys His Ile Tyr Val Gly Pro Tyr Val Gly His Thr
            100                 105                 110

Leu Phe Tyr Tyr Gly His Ile Asn Ile Ser Ser Phe Phe Asn Leu Asp
        115                 120                 125

Lys Tyr Phe Ile Asn Leu Leu Asn Glu Lys His Lys Asn Ile Leu Asn
    130                 135                 140

Tyr Met Ser Ser Phe Glu Ser Val Ala Ile His Ile Arg Arg Gly Asp
145                 150                 155                 160

Tyr Met Tyr Ala Leu Lys Ile Asp Gly Arg Lys Asn Asn Ala Ser Leu
                165                 170                 175

Asp Tyr Ile Tyr Thr Ser Ile Lys Tyr Leu Asn Asn Thr Leu Glu Asn
            180                 185                 190

Lys Asn Ile Lys Phe Tyr Ile Phe Ser Asn Asn Lys Lys Tyr Ile Lys
        195                 200                 205

Asn Asn Leu Ile Pro Ile Phe Gln Asn Asn Asn Ile Asn Phe Glu Ile
    210                 215                 220

Ile Glu Asp Asn Pro Glu Tyr Ile Asp Phe Tyr Leu Met Thr Lys Cys
225                 230                 235                 240
```

Lys His Ile Ile Ser Ser Leu Gly Lys Phe Ala Lys Val Ala Phe Lys
245 250 255

Phe Ile Lys Asn Glu Asn Lys Ile Phe Ile Asp Thr Asp Asn Ile Tyr
260 265 270

Asn Leu Lys Lys Glu Tyr Phe Tyr Lys Asn Ile Cys Glu Lys Tyr Cys
275 280 285

Asn Ile Ile Tyr Glu Glu Tyr Asn Asn Ile Lys Thr Tyr Ile Ser Lys
290 295 300

Asn Asn Met Ile Tyr Ile Leu Asp Leu Ile Glu Lys Asn Asn Ile Lys
305 310 315 320

Asn Ile Cys Gln Ile Gly Leu Leu Asp Gly Leu Glu Thr His Thr Leu
325 330 335

Leu Lys Tyr Ser Ala Asp Asn Asn Asn Cys Phe Asn Leu Leu Cys Phe
340 345 350

Glu Asn Asn Glu Arg Asp Ile Val Gly Ile Glu Leu Lys Asn Leu Thr
355 360 365

Glu Asn Glu Lys Lys Leu Phe Thr Leu Tyr Ile Glu Gln Ser Pro Leu
370 375 380

Asp Ile Asp Asn Ser Phe Asn Ile Lys Asn Ile Asp Phe Ile Phe Phe
385 390 395 400

Thr Lys Glu Asn Ser Asn Pro Leu Val Phe Ile Tyr Leu Ile Tyr Leu
405 410 415

Phe Pro Phe Met Lys Glu Glu Ile Ile Ile Val Phe Asn Asp Ile Ile
420 425 430

Ser Gly Lys Tyr Tyr Ser Gly Ser Tyr Cys Ile Phe Asn Met Phe Asn
435 440 445

Gly Glu Lys Asn Gln Phe Tyr Asn Phe Asn Thr Asn Lys Tyr Asp Asn
450 455 460

Ile Gly Tyr Ile Lys Ile Lys Lys Gln Glu Leu Leu Asn Ile Ile Lys
465 470 475 480

Lys Ile Ser Val Ile Glu Tyr Asp Gly Tyr Ile Asn Lys Phe Phe Met
485 490 495

Asn Lys Leu Ile Asp Asn Arg Asn Asp Tyr Tyr Asn Tyr Phe Asp Leu
500 505 510

Asp Met Ser Tyr Ile Arg Leu Asn Asn Leu Lys Gln Tyr Met Lys Asp
515 520 525

Lys Phe Asp Ile Glu Tyr Ser Asn Tyr Ile Ile Ser Asn Ile Glu Asn
530 535 540

Asn Ile Ile Asn Tyr Glu Lys Gln Tyr Tyr Lys Asn Gln Lys Asn Asn
545 550 555 560

Phe Tyr Ser Gln Asn Gln Ile His Ile Ser Lys Ile Glu Asn Ile Ile
565 570 575

Asp Lys His Asn Lys Leu Ile Asn Ser Ile Ser Trp Trp Ile Pro Ile
580 585 590

Lys Glu Leu Arg Glu Asn Phe Lys Asn Lys Phe Ile Arg Pro Asp Gln
595 600 605

Thr Arg Pro Asp Gln Thr Arg Pro Asn Met
610 615

<210> SEQ ID NO 96
<211> LENGTH: 395
<212> TYPE: PRT
<213> ORGANISM: Brachysprira hyodysenteriae

<400> SEQUENCE: 96

```
Met Asn Lys Cys Glu Cys Ser Gln Cys Lys Asn Arg Glu Tyr Asp Ile
1               5                   10                  15

Pro Glu Tyr Leu Val Leu Glu Asp Asp Leu Lys Ile Leu Asp Asn Glu
            20                  25                  30

Arg Pro Leu Gly Ile Ser Gly His Leu Arg Val Lys Asp Glu Ala Met
        35                  40                  45

Ser Leu Ala Glu Cys Ile Asp Ser Cys Ile Asp Phe Leu Asp Glu Leu
    50                  55                  60

Ile Ile Thr Tyr Asn Thr Ser Ser Asp Asn Thr Glu Glu Ile Leu Lys
65                  70                  75                  80

Asn Tyr Glu Lys Lys Tyr Pro Glu Lys Ile Lys Leu Phe His Tyr Lys
                85                  90                  95

Pro Asn Ile Ile Arg Tyr Asn Lys Asp Glu Tyr Asn Thr Lys Tyr Ser
            100                 105                 110

Gln Ile His Tyr Leu Asp Asn Tyr Tyr Asn Tyr Gly Leu Ser Lys Ile
        115                 120                 125

Lys Tyr Lys Tyr Tyr Val Lys Ile Asp Ala Asp Gln Ile Tyr Phe Thr
    130                 135                 140

Asp Lys Leu Leu Lys Leu Arg Glu Leu Leu Ile Leu Asp Ile Asn Gln
145                 150                 155                 160

Ile Lys Leu Ser Asn Asn Ile Asn Lys Leu Leu Leu Ile Asn Lys Ile
                165                 170                 175

Ala Trp Cys Ile Pro Ile Lys Lys Leu Arg Asn Lys Phe Arg Thr Tyr
            180                 185                 190

Cys Ile Arg Lys Tyr Phe Asn Lys Asp Lys Asn Tyr Ile Tyr Asn Gly
        195                 200                 205

Asp Glu Asn Ile Leu Ser Leu Asp Asp Phe Ile Leu Leu Ser Arg Lys
    210                 215                 220

Arg His Ser Asp Lys Asn Ile Ser Tyr Asp Leu Ala Gly Phe Asn Leu
225                 230                 235                 240

Ile Leu His Asn Asn Lys Leu Tyr Leu Asp Thr Tyr Trp Pro Met Asn
                245                 250                 255

Gly Gly Arg Phe Asp His Val Leu Tyr Gln Ala Ser Tyr Ser Asn Lys
            260                 265                 270

Tyr Phe Met Asn Glu Ile Phe Glu Val Asn Gln Thr Pro His Asn Arg
        275                 280                 285

Ile Ile Leu Gly Met Phe Trp Val His Phe Gly Asn Ile Lys His Asn
    290                 295                 300

Phe Gln Tyr Asp Asp Ser Phe Tyr Leu Leu Glu Tyr Asn Asp Ile Lys
305                 310                 315                 320

Asn Ser Lys Val Glu Asn Phe Ser His Lys Met Lys Asn Ile Asp Asn
                325                 330                 335

Asp Asp Lys Ile Glu Lys Tyr Ile Arg Asp Asn Thr Phe Ile Lys Tyr
            340                 345                 350

Phe Asp Glu Asp Lys Lys Tyr Leu Asn Asn Val Phe Tyr Asn Lys Tyr
        355                 360                 365

Leu Thr Lys Pro Leu Asp Tyr Ala Ile Lys Asn Asn Asp Glu Leu Val
    370                 375                 380

Asn Leu Tyr Gly Lys Thr Ile Ile Thr Val Lys
385                 390                 395
```

<210> SEQ ID NO 97
<211> LENGTH: 395

<212> TYPE: PRT
<213> ORGANISM: Brachysprira hyodysenteriae

<400> SEQUENCE: 97

```
Met Asn Lys Cys Glu Cys Ser Gln Cys Gln Asn Arg Glu Tyr Asp Ile
1               5                   10                  15

Ser Glu Tyr Leu Val Leu Glu Asp Asp Leu Lys Ile Leu Asp Asn Glu
            20                  25                  30

Arg Pro Leu Gly Ile Ser Gly His Leu Arg Val Lys Asp Glu Ala Met
        35                  40                  45

Ser Leu Ala Glu Cys Ile Asp Ser Cys Ile Asp Phe Leu Asp Glu Leu
    50                  55                  60

Ile Ile Thr Tyr Asn Thr Ser Ser Asp Asn Thr Glu Glu Ile Leu Lys
65                  70                  75                  80

Asn Tyr Glu Lys Lys Tyr Pro Glu Lys Ile Lys Leu Phe His Tyr Lys
                85                  90                  95

Pro Asn Ile Ile Arg Tyr Asn Lys Asp Glu Tyr Asn Thr Lys Tyr Ser
            100                 105                 110

Gln Ile His Tyr Leu Asp Asn Tyr Tyr Asn Tyr Gly Leu Ile Lys Ile
        115                 120                 125

Lys Tyr Lys Tyr Tyr Val Lys Ile Asp Ala Asp Gln Ile Tyr Phe Thr
    130                 135                 140

Asp Lys Leu Leu Lys Leu Arg Glu Leu Leu Ile Leu Asp Ile Asn Gln
145                 150                 155                 160

Ile Lys Leu Ser Asn Asn Ile Asn Lys Leu Leu Leu Ile Asn Lys Ile
                165                 170                 175

Ala Trp Cys Ile Pro Ile Lys Lys Leu Arg Asn Lys Phe Arg Thr Tyr
            180                 185                 190

Cys Ile Arg Lys Tyr Phe Asn Lys Asp Lys Asn Tyr Ile Tyr Asn Gly
        195                 200                 205

Asp Glu Asn Ile Leu Ser Leu Asp Asp Phe Ile Leu Leu Ser Arg Lys
    210                 215                 220

Arg His Ser Asp Lys Asn Ile Ser Tyr Asp Leu Ala Gly Phe Asn Leu
225                 230                 235                 240

Ile Leu His Asn Asn Lys Leu Tyr Leu Asp Thr Tyr Trp Pro Met Asn
                245                 250                 255

Gly Gly Arg Phe Asp His Val Leu Tyr Gln Ala Ser Tyr Ser Asn Lys
            260                 265                 270

Tyr Phe Met Asn Glu Ile Phe Glu Val Asn Gln Thr Pro His Asn Arg
        275                 280                 285

Ile Ile Leu Gly Met Phe Trp Val His Phe Gly Asn Ile Lys His Asn
    290                 295                 300

Phe Gln Tyr Asp Asp Ser Phe Tyr Leu Leu Glu Tyr Asn Asp Ile Lys
305                 310                 315                 320

Asn Ser Lys Val Glu Asn Phe Ser His Lys Met Lys Asn Ile Asp Asn
                325                 330                 335

Asp Asp Lys Ile Glu Lys Tyr Ile Arg Asp Asn Thr Phe Ile Lys Tyr
            340                 345                 350

Phe Asp Glu Asp Lys Lys Tyr Leu Asn Asn Val Phe Tyr Asn Lys Tyr
        355                 360                 365

Leu Thr Lys Pro Leu Asp Tyr Ala Ile Lys Asn Asn Asp Glu Leu Val
    370                 375                 380

Asn Leu Tyr Gly Lys Thr Ile Ile Thr Val Lys
385                 390                 395
```

<210> SEQ ID NO 98
<211> LENGTH: 395
<212> TYPE: PRT
<213> ORGANISM: Brachysprira hyodysenteriae

<400> SEQUENCE: 98

Met Asn Thr Cys Glu Cys Ser Gln Cys Lys Asn Arg Glu Tyr Asp Ile
1 5 10 15

Ser Glu Tyr Leu Val Leu Glu Asp Asp Leu Lys Ile Leu Asp Asn Glu
20 25 30

Arg Pro Leu Gly Ile Ser Gly His Leu Arg Val Lys Asp Glu Ala Met
35 40 45

Ser Leu Ala Glu Cys Ile Asp Ser Cys Ile Asp Phe Leu Asp Glu Leu
50 55 60

Ile Ile Thr Tyr Asn Thr Ser Ser Asp Asn Thr Glu Glu Ile Leu Lys
65 70 75 80

Asn Tyr Glu Lys Lys Tyr Pro Glu Lys Ile Lys Leu Phe His Tyr Lys
85 90 95

Pro Asn Ile Ile Arg Tyr Asn Lys Asp Glu Tyr Asn Thr Lys Tyr Ser
100 105 110

Gln Ile His Tyr Leu Asp Asn Tyr Tyr Asn Tyr Gly Leu Ile Lys Ile
115 120 125

Lys Tyr Lys Tyr Tyr Val Lys Ile Asp Ala Asp Gln Ile Tyr Phe Thr
130 135 140

Asp Lys Leu Leu Lys Leu Arg Glu Leu Leu Ile Leu Asp Ile Asn Gln
145 150 155 160

Ile Lys Leu Ser Asn Asn Ile Asn Lys Leu Leu Leu Ile Asn Lys Ile
165 170 175

Ala Trp Cys Ile Pro Ile Lys Lys Leu Arg Asn Lys Phe Arg Thr Tyr
180 185 190

Cys Ile Arg Lys Tyr Phe Asn Lys Asp Lys Asn Tyr Ile Tyr Asn Gly
195 200 205

Asp Glu Asn Ile Leu Ser Leu Asp Asp Phe Ile Leu Leu Ser Arg Lys
210 215 220

Arg His Ser Asp Lys Asn Ile Ser Tyr Asp Leu Ala Gly Phe Asn Leu
225 230 235 240

Ile Leu His Asn Asn Lys Leu Tyr Leu Asp Thr Tyr Trp Pro Met Asn
245 250 255

Gly Gly Arg Phe Asp His Val Leu Tyr Gln Ala Ser Tyr Ser Asn Lys
260 265 270

Tyr Phe Met Asn Glu Ile Phe Glu Val Asn Gln Thr Pro His Asn Arg
275 280 285

Ile Ile Leu Gly Met Phe Trp Val His Phe Gly Asn Ile Lys His Asn
290 295 300

Phe Gln Tyr Asp Asp Ser Phe Tyr Leu Leu Glu Tyr Asn Asp Ile Lys
305 310 315 320

Asn Ser Lys Val Glu Asn Phe Ser His Lys Met Lys Asn Ile Asp Asn
325 330 335

Asp Asp Lys Ile Glu Lys Tyr Ile Arg Asp Asn Thr Phe Ile Lys Tyr
340 345 350

Phe Asp Glu Asp Lys Lys Tyr Leu Asn Asn Val Phe Tyr Asn Lys Tyr
355 360 365

Leu Thr Lys Pro Leu Asp Tyr Ala Ile Lys Asn Asn Asp Glu Leu Val

```
    370                 375                 380

Asn Leu Tyr Gly Lys Thr Ile Ile Thr Val Lys
385                 390                 395


<210> SEQ ID NO 99
<211> LENGTH: 395
<212> TYPE: PRT
<213> ORGANISM: Brachysprira hyodysenteriae

<400> SEQUENCE: 99

Met Asn Lys Cys Glu Cys Ser Gln Cys Lys Asn Arg Glu Tyr Asp Ile
1               5                   10                  15

Ser Glu Tyr Leu Val Leu Glu Asp Asp Leu Lys Ile Leu Asp Asn Glu
            20                  25                  30

Arg Pro Leu Gly Ile Ser Gly His Leu Arg Val Lys Asp Glu Ala Met
        35                  40                  45

Ser Leu Ala Glu Cys Ile Asp Ser Cys Ile Asp Phe Leu Asp Glu Leu
    50                  55                  60

Ile Ile Thr Tyr Asn Thr Ser Ser Asp Asn Thr Glu Glu Ile Leu Lys
65                  70                  75                  80

Asn Tyr Glu Lys Lys Tyr Pro Glu Lys Ile Lys Leu Phe His Tyr Lys
                85                  90                  95

Pro Asn Ile Ile Arg Tyr Asn Lys Asp Glu Tyr Asn Thr Lys Tyr Ser
            100                 105                 110

Gln Ile His Tyr Leu Asp Asn Tyr Tyr Asn Tyr Gly Leu Ile Lys Ile
        115                 120                 125

Lys Tyr Lys Tyr Tyr Val Lys Ile Asp Ala Asp Gln Ile Tyr Phe Thr
    130                 135                 140

Asp Lys Leu Leu Lys Leu Arg Glu Leu Leu Ile Leu Asp Ile Asn Gln
145                 150                 155                 160

Ile Lys Leu Ser Asn Asn Ile Asn Lys Leu Leu Leu Ile Asn Lys Ile
                165                 170                 175

Ala Trp Cys Ile Pro Ile Lys Lys Leu Arg Asn Lys Phe Arg Thr Tyr
            180                 185                 190

Cys Ile Arg Lys Tyr Phe Asn Lys Asp Lys Asn Tyr Ile Tyr Asn Gly
        195                 200                 205

Asp Glu Asn Ile Leu Ser Leu Asp Asp Phe Ile Leu Leu Ser Arg Lys
    210                 215                 220

Arg His Ser Asp Lys Asn Ile Ser Tyr Asp Leu Ala Gly Phe Asn Leu
225                 230                 235                 240

Ile Leu His Asn Asn Lys Leu Tyr Leu Asp Ile Tyr Trp Pro Met Asn
                245                 250                 255

Gly Gly Arg Phe Asp His Val Leu Tyr Gln Ala Ser Tyr Ser Asn Lys
            260                 265                 270

Tyr Phe Met Asn Glu Ile Phe Glu Val Asn Gln Thr Pro His Asn Arg
        275                 280                 285

Ile Ile Leu Gly Met Phe Trp Val His Phe Gly Asn Ile Lys His Asn
    290                 295                 300

Phe Gln Tyr Asp Asp Ser Phe Tyr Leu Leu Glu Tyr Asn Asp Ile Lys
305                 310                 315                 320

Asn Ser Lys Val Glu Asn Phe Ser His Lys Met Lys Asn Ile Asp Asn
                325                 330                 335

Asp Asp Lys Ile Glu Lys Tyr Ile Arg Asp Asn Thr Phe Ile Lys Tyr
            340                 345                 350
```

Phe Asp Glu Asp Lys Lys Tyr Leu Asn Asn Val Phe Tyr Asn Lys Tyr
        355                 360                 365

Leu Thr Lys Pro Leu Asp Tyr Ala Ile Lys Asn Asn Asp Glu Leu Val
    370                 375                 380

Asn Leu Tyr Gly Lys Thr Ile Ile Thr Val Lys
385                 390                 395

<210> SEQ ID NO 100
<211> LENGTH: 287
<212> TYPE: PRT
<213> ORGANISM: Brachysprira hyodysenteriae

<400> SEQUENCE: 100

Met Lys Gly Ile Val Leu Ala Gly Gly Ser Gly Thr Arg Leu Tyr Pro
1               5                   10                  15

Met Thr Asn Val Ile Ser Lys Gln Leu Leu Pro Ile Tyr Asp Lys Pro
            20                  25                  30

Met Val Tyr Tyr Pro Leu Ser Val Leu Met Leu Ser Lys Ile Lys Asp
        35                  40                  45

Ile Leu Val Ile Ser Thr Glu Asn Asp Thr Pro Leu Phe Lys Lys Leu
    50                  55                  60

Leu Lys Asp Gly Arg Gln Trp Gly Cys Asn Ile Glu Tyr Ala Val Gln
65                  70                  75                  80

Lys Ala Pro Asn Gly Leu Ala Glu Ala Phe Ile Ile Gly Glu Ser Phe
                85                  90                  95

Ile Gly Lys Asp Asn Val Ser Met Ile Leu Gly Asp Asn Ile Phe Phe
            100                 105                 110

Gly Gln Ser Phe Ser Ser Val Leu Glu Lys Ser Ala Lys Ile Asp Asn
        115                 120                 125

Gly Ala Val Ile Phe Ala Tyr Gln Val Lys Asp Pro Glu Arg Phe Gly
    130                 135                 140

Ile Val Glu Ile Asp Lys Asp Tyr Asn Ala Leu Ser Ile Glu Glu Lys
145                 150                 155                 160

Pro Lys Asn Pro Lys Ser Asn Tyr Ala Val Thr Gly Leu Tyr Phe Tyr
                165                 170                 175

Asp Asn Asp Val Val Asn Ile Ser Lys Asn Ile Lys Pro Ser Ala Arg
            180                 185                 190

Gly Glu Leu Glu Ile Thr Asp Val Asn Lys Val Tyr Leu Glu Asn Lys
        195                 200                 205

Lys Leu Lys Val Glu Val Leu Gly Arg Gly Phe Ala Trp Leu Asp Thr
    210                 215                 220

Gly Thr Arg Asp Ser Leu Leu Gln Ala Ser Gln Phe Val Ser Ala Val
225                 230                 235                 240

Glu Asn Ile Glu Gly Met Gln Ile Ala Cys Leu Glu Glu Ile Ala Tyr
                245                 250                 255

Asn Asn Lys Trp Ile Asp Ala Ser Lys Ile Glu Glu Thr Ala Ser Lys
            260                 265                 270

Leu Lys Asn Ser Glu Tyr Gly Lys Tyr Leu Ile Asn Leu Ile Lys
        275                 280                 285

<210> SEQ ID NO 101
<211> LENGTH: 287
<212> TYPE: PRT
<213> ORGANISM: Brachysprira hyodysenteriae

<400> SEQUENCE: 101

Met Lys Gly Ile Val Leu Ala Gly Gly Ser Gly Thr Arg Leu Tyr Pro
1 5 10 15

Met Thr Asn Val Ile Ser Lys Gln Leu Leu Pro Ile Tyr Asp Lys Pro
20 25 30

Met Val Tyr Tyr Pro Leu Ser Val Leu Met Leu Ser Lys Ile Lys Asp
35 40 45

Ile Leu Val Ile Ser Thr Glu Asn Asp Thr Pro Leu Phe Lys Lys Leu
50 55 60

Leu Lys Asp Gly Ser Gln Trp Gly Cys Asn Ile Glu Tyr Ala Val Gln
65 70 75 80

Lys Ala Pro Asn Gly Leu Ala Glu Ala Phe Ile Ile Gly Glu Ser Phe
85 90 95

Ile Gly Lys Asp Asn Val Ser Met Ile Leu Gly Asp Asn Ile Phe Phe
100 105 110

Gly Gln Ser Phe Ser Ser Val Leu Glu Lys Ser Ala Lys Ile Tyr Asn
115 120 125

Gly Ala Val Ile Phe Ala Tyr Gln Val Lys Asp Pro Glu Arg Phe Gly
130 135 140

Ile Val Glu Ile Asp Lys Asp Tyr Asn Ala Leu Ser Ile Glu Glu Lys
145 150 155 160

Pro Lys Asn Pro Lys Ser Asn Tyr Ala Val Thr Gly Leu Tyr Phe Tyr
165 170 175

Asp Asn Asp Val Val Asn Ile Ser Lys Asn Ile Lys Pro Ser Ala Arg
180 185 190

Gly Glu Leu Glu Ile Thr Asp Val Asn Lys Val Tyr Leu Glu Asn Lys
195 200 205

Lys Leu Lys Val Glu Val Leu Gly Arg Gly Phe Ala Trp Leu Asp Thr
210 215 220

Gly Thr Arg Asp Ser Leu Leu Gln Ala Ser Gln Phe Val Ser Ala Val
225 230 235 240

Glu Asn Ile Glu Gly Met Gln Ile Ala Cys Leu Glu Glu Ile Ala Tyr
245 250 255

Asn Asn Lys Trp Ile Asp Ala Ser Lys Ile Glu Glu Thr Ala Ser Lys
260 265 270

Leu Lys Asn Ser Glu Tyr Gly Lys Tyr Leu Ile Asn Leu Ile Lys
275 280 285

<210> SEQ ID NO 102
<211> LENGTH: 287
<212> TYPE: PRT
<213> ORGANISM: Brachysprira hyodysenteriae

<400> SEQUENCE: 102

Met Lys Gly Ile Val Leu Ala Gly Gly Ser Gly Thr Arg Leu Tyr Pro
1 5 10 15

Met Thr Asn Val Ile Ser Lys Gln Leu Leu Pro Ile Tyr Asp Lys Pro
20 25 30

Met Val Tyr Tyr Pro Leu Ser Val Leu Met Leu Ser Lys Ile Lys Asp
35 40 45

Ile Leu Val Ile Ser Thr Glu Asn Asp Thr Pro Leu Phe Lys Lys Leu
50 55 60

Leu Lys Asp Gly Ser Gln Trp Gly Cys Asn Ile Glu Tyr Ala Val Gln
65 70 75 80

Lys Ala Pro Asn Gly Leu Ala Glu Ala Phe Ile Ile Gly Glu Ser Phe
85 90 95

```
Ile Gly Lys Asp Asn Val Ser Met Thr Leu Gly Asp Asn Ile Phe Phe
            100                 105                 110

Gly Gln Ser Phe Ser Ser Val Leu Glu Lys Ser Ala Lys Ile Asp Asn
        115                 120                 125

Gly Ala Val Ile Phe Ala Tyr Gln Val Lys Asp Pro Glu Arg Phe Gly
    130                 135                 140

Ile Val Glu Ile Asp Lys Asp Tyr Asn Ala Leu Ser Ile Glu Glu Lys
145                 150                 155                 160

Pro Lys Asn Pro Lys Ser Asn Tyr Ala Val Thr Gly Leu Tyr Phe Tyr
                165                 170                 175

Asp Asn Asp Val Val Asn Ile Ser Lys Asn Ile Lys Pro Ser Ala Arg
            180                 185                 190

Gly Glu Leu Glu Ile Thr Asp Val Asn Lys Val Tyr Leu Glu Asn Lys
        195                 200                 205

Lys Leu Lys Val Glu Val Leu Gly Arg Gly Phe Ala Trp Leu Asp Thr
    210                 215                 220

Gly Thr Arg Asp Ser Leu Leu Gln Ala Ser Gln Phe Val Ser Ala Val
225                 230                 235                 240

Glu Asn Ile Glu Gly Met Gln Ile Ala Cys Leu Glu Glu Ile Ala Tyr
                245                 250                 255

Asn Asn Lys Trp Ile Asp Ala Ser Lys Ile Glu Glu Thr Ala Ser Lys
            260                 265                 270

Leu Lys Asn Ser Glu Tyr Gly Lys Tyr Leu Ile Asn Leu Ile Lys
        275                 280                 285


<210> SEQ ID NO 103
<211> LENGTH: 287
<212> TYPE: PRT
<213> ORGANISM: Brachysprira hyodysenteriae

<400> SEQUENCE: 103

Met Lys Gly Ile Val Leu Ala Gly Gly Ser Gly Thr Arg Leu Tyr Pro
1               5                   10                  15

Met Thr Asn Val Ile Ser Lys Gln Leu Leu Pro Ile Tyr Asp Lys Pro
            20                  25                  30

Met Val Tyr Tyr Pro Leu Ser Val Leu Met Leu Ser Lys Ile Lys Asp
        35                  40                  45

Ile Leu Val Ile Ser Thr Glu Asn Asp Thr Pro Leu Phe Lys Lys Leu
    50                  55                  60

Leu Lys Asp Gly Ser Gln Trp Gly Cys Asn Ile Glu Tyr Ala Val Gln
65                  70                  75                  80

Lys Ala Pro Asn Gly Leu Ala Glu Ala Phe Ile Ile Gly Glu Ser Phe
                85                  90                  95

Ile Gly Lys Asp Asn Val Ser Met Ile Leu Gly Asp Asn Ile Phe Phe
            100                 105                 110

Gly Gln Ser Phe Ser Ser Val Leu Glu Lys Ser Ala Lys Ile Asp Asn
        115                 120                 125

Gly Ala Val Ile Phe Ala Tyr Gln Val Lys Asp Pro Glu Arg Phe Gly
    130                 135                 140

Ile Val Glu Ile Asp Lys Asp Tyr Asn Ala Leu Ser Ile Glu Glu Lys
145                 150                 155                 160

Pro Lys Asn Pro Lys Ser Asn Tyr Ala Val Thr Gly Leu Tyr Phe Tyr
                165                 170                 175

Asp Asn Asp Val Val Asn Ile Ser Lys Asn Ile Lys Pro Ser Ala Arg
```

```
            180                 185                 190

Gly Glu Leu Glu Ile Thr Asp Val Asn Lys Val Tyr Leu Glu Asn Lys
        195                 200                 205

Lys Leu Lys Val Glu Val Leu Gly Arg Gly Phe Ala Trp Leu Asp Thr
    210                 215                 220

Gly Thr Arg Asp Ser Leu Leu Gln Ala Ser Gln Phe Val Ser Ala Val
225                 230                 235                 240

Glu Asn Ile Glu Gly Met Gln Ile Ala Cys Leu Glu Glu Ile Ala Tyr
                245                 250                 255

Asn Asn Lys Trp Ile Asp Ala Ser Ile Ile Glu Glu Thr Ala Ser Lys
            260                 265                 270

Leu Lys Asn Ser Glu Tyr Gly Lys Tyr Leu Ile Asn Leu Ile Lys
        275                 280                 285


<210> SEQ ID NO 104
<211> LENGTH: 287
<212> TYPE: PRT
<213> ORGANISM: Brachysprira hyodysenteriae

<400> SEQUENCE: 104

Met Lys Gly Ile Val Leu Ala Gly Gly Ser Gly Thr Arg Leu Tyr Pro
1               5                   10                  15

Met Thr Asn Val Ile Ser Lys Gln Leu Leu Pro Ile Tyr Asp Lys Pro
            20                  25                  30

Met Val Tyr Tyr Pro Leu Ser Val Leu Met Leu Ser Lys Ile Lys Asp
        35                  40                  45

Ile Leu Val Ile Ser Thr Glu Asn Asp Thr Pro Leu Phe Lys Lys Leu
    50                  55                  60

Leu Lys Asp Gly Ser Gln Trp Gly Cys Asn Ile Glu Tyr Ala Val Gln
65                  70                  75                  80

Lys Ala Pro Asn Gly Leu Ala Glu Ala Phe Ile Ile Gly Glu Ser Phe
                85                  90                  95

Ile Gly Lys Asp Asn Val Ser Met Ile Leu Gly Asp Asn Ile Phe Phe
            100                 105                 110

Gly Gln Ser Phe Ser Ser Val Leu Glu Lys Ser Ala Lys Ile Asp Asn
        115                 120                 125

Gly Ala Val Ile Phe Ala Tyr Gln Val Lys Asp Pro Glu Arg Phe Gly
    130                 135                 140

Ile Val Glu Ile Asp Lys Asp Tyr Asn Ala Leu Ser Ile Glu Glu Lys
145                 150                 155                 160

Pro Lys Asn Pro Lys Ser Asn Tyr Ala Val Thr Gly Leu Tyr Phe Tyr
                165                 170                 175

Asp Asn Asp Val Val Asn Ile Ser Lys Asn Ile Lys Pro Ser Ala Arg
            180                 185                 190

Gly Glu Leu Glu Ile Thr Asp Val Asn Lys Val Tyr Leu Glu Asn Lys
        195                 200                 205

Lys Leu Lys Val Glu Val Leu Gly Arg Gly Phe Ala Trp Leu Asp Thr
    210                 215                 220

Gly Thr Arg Asp Ser Leu Leu Gln Ala Ser Gln Phe Val Ser Ala Val
225                 230                 235                 240

Glu Asn Ile Glu Gly Met Gln Ile Ala Cys Leu Glu Glu Ile Ala Tyr
                245                 250                 255

Asn Asn Lys Trp Ile Asp Ala Ser Lys Ile Glu Glu Thr Ala Ser Lys
            260                 265                 270
```

```
Leu Lys Asn Ser Glu Tyr Gly Lys Tyr Leu Ile Asn Leu Ile Lys
        275                 280                 285


<210> SEQ ID NO 105
<211> LENGTH: 356
<212> TYPE: PRT
<213> ORGANISM: Brachysprira hyodysenteriae

<400> SEQUENCE: 105

Met Arg Asn Phe Asn Asn Ile Leu Val Thr Gly Gly Cys Gly Phe Ile
1               5                   10                  15

Gly Thr Asn Phe Ile Arg Tyr Ile Leu Gln Lys Thr Glu Tyr Lys Gly
            20                  25                  30

Asn Ile Ile Asn Ile Asp Ala Leu Thr Tyr Ala Gly Asn Arg Glu Asn
        35                  40                  45

Leu Ile Asp Ile Glu Lys Lys Tyr Lys Asp Arg Tyr Phe Phe Glu Lys
    50                  55                  60

Val Asn Ile Cys Asp Asp Lys Lys Val Asn Glu Ile Phe Ser Gln Tyr
65                  70                  75                  80

Asn Pro Asp Cys Ile Val His Phe Ala Ala Glu Ser His Val Asp Arg
                85                  90                  95

Ser Ile Tyr Gly Pro Lys Asp Phe Leu Glu Thr Asn Ile Met Gly Thr
            100                 105                 110

Phe Ile Leu Leu Glu Ala Ala Arg Lys Leu Trp Glu Asn Asn Lys Glu
        115                 120                 125

Asn Lys Leu Phe His His Ile Ser Thr Asp Glu Val Tyr Gly Ser Leu
    130                 135                 140

Gly Glu Thr Gly Tyr Phe Tyr Glu Thr Thr Pro Tyr Asp Pro Arg Ser
145                 150                 155                 160

Pro Tyr Ser Ser Ser Lys Ala Ser Ser Asp His Ile Val Lys Ala Tyr
                165                 170                 175

Tyr His Thr Tyr Asn Leu Pro Val Thr Ile Ser Asn Cys Ser Asn Asn
            180                 185                 190

Tyr Gly Pro Tyr Gln Phe Pro Glu Lys Leu Ile Pro Leu Met Ile Ser
        195                 200                 205

Asn Ile Val Glu Glu Lys Asp Leu Pro Val Tyr Gly Asp Gly Lys Asn
    210                 215                 220

Ile Arg Asp Trp Ile Phe Val Glu Asp His Asn Asn Ala Val Ile Asp
225                 230                 235                 240

Ile Ile His Lys Gly Arg Val Gly Glu Thr Tyr Asn Ile Gly Gly Glu
                245                 250                 255

Asn Glu Ile Thr Asn Ile Asp Met Val Asn Ile Leu Cys Glu Lys Leu
            260                 265                 270

Ser Ala Lys Met Asn Lys Glu Lys Asp Tyr Tyr Lys Lys Leu Ile Lys
        275                 280                 285

Phe Val Lys Asp Arg Ser Gly His Asp Arg Arg Tyr Ala Ile Asn Cys
    290                 295                 300

Asp Lys Ile Lys Lys Glu Leu Gly Trp Glu Arg Lys Tyr Asp Phe Asn
305                 310                 315                 320

Thr Ala Ile Asp Ile Thr Ile Asp Trp Tyr Leu Asn Asn Lys Gln Trp
                325                 330                 335

Ile Asp Asn Ile Lys Ser Gly Glu Tyr Lys Lys Trp Ile Glu Leu Asn
            340                 345                 350

Tyr Ser Ser Lys
        355
```

<210> SEQ ID NO 106
<211> LENGTH: 356
<212> TYPE: PRT
<213> ORGANISM: Brachysprira hyodysenteriae

<400> SEQUENCE: 106

```
Met Arg Asn Phe Asn Asn Ile Leu Val Thr Gly Gly Cys Gly Phe Ile
1               5                   10                  15

Gly Ser Asn Phe Ile Arg Tyr Ile Leu Glu Lys Ser Asp Tyr Lys Gly
            20                  25                  30

Asn Ile Ile Asn Ile Asp Ala Leu Thr Tyr Ala Gly Asn Arg Glu Asn
        35                  40                  45

Leu Ile Asp Ile Glu Lys Lys Tyr Lys Asp Arg Tyr Phe Phe Glu Lys
    50                  55                  60

Val Asn Ile Cys Asp Asp Lys Lys Ile Asn Glu Ile Phe Ser Lys Tyr
65                  70                  75                  80

Asn Pro Asp Cys Ile Val His Phe Ala Ala Glu Ser His Val Asp Arg
                85                  90                  95

Ser Ile Tyr Gly Pro Lys Asp Phe Leu Glu Thr Asn Ile Met Gly Thr
            100                 105                 110

Phe Ile Leu Leu Glu Ala Ala Arg Lys Leu Trp Glu Asn Asn Lys Glu
        115                 120                 125

Asn Lys Leu Phe His His Ile Ser Thr Asp Glu Val Tyr Gly Ser Leu
    130                 135                 140

Gly Glu Thr Gly Tyr Phe Tyr Glu Thr Thr Pro Tyr Asp Pro Arg Ser
145                 150                 155                 160

Pro Tyr Ser Ser Ser Lys Ala Ser Ser Asp His Ile Val Lys Ala Tyr
                165                 170                 175

Tyr His Thr Tyr Asn Leu Pro Val Thr Ile Ser Asn Cys Ser Asn Asn
            180                 185                 190

Tyr Gly Pro Tyr Gln Phe Pro Glu Lys Leu Ile Pro Leu Met Ile Ser
        195                 200                 205

Asn Ile Val Glu Glu Lys Asp Leu Pro Val Tyr Gly Asp Gly Lys Asn
    210                 215                 220

Ile Arg Asp Trp Ile Phe Val Glu Asp His Asn Asn Ala Val Ile Asp
225                 230                 235                 240

Ile Ile His Lys Gly Arg Val Gly Glu Thr Tyr Asn Ile Gly Gly Glu
                245                 250                 255

Asn Glu Ile Thr Asn Ile Asp Met Val Asn Ile Leu Cys Glu Lys Leu
            260                 265                 270

Ser Ala Lys Met Asn Lys Glu Lys Asp Tyr Tyr Lys Lys Leu Ile Lys
        275                 280                 285

Phe Val Lys Asp Arg Ser Gly His Asp Arg Arg Tyr Ala Ile Asn Cys
    290                 295                 300

Asp Lys Ile Lys Lys Glu Leu Gly Trp Glu Arg Lys Tyr Asp Phe Asn
305                 310                 315                 320

Thr Ala Ile Asp Ile Thr Ile Asp Trp Tyr Leu Asn Asn Lys Gln Trp
                325                 330                 335

Ile Asp Asn Ile Lys Ser Gly Glu Tyr Lys Lys Trp Ile Glu Leu Asn
            340                 345                 350

Tyr Ser Ser Lys
        355
```

<210> SEQ ID NO 107
<211> LENGTH: 356
<212> TYPE: PRT
<213> ORGANISM: Brachysprira hyodysenteriae

<400> SEQUENCE: 107

```
Met Arg Asn Phe Asn Asn Ile Leu Val Thr Gly Gly Cys Gly Phe Ile
1               5                   10                  15

Gly Ser Asn Phe Ile Arg Tyr Ile Leu Glu Lys Ser Asp Tyr Lys Gly
            20                  25                  30

Asn Ile Ile Asn Ile Asp Ala Leu Thr Tyr Ala Gly Asn Arg Glu Asn
        35                  40                  45

Leu Ile Asp Ile Glu Lys Lys Tyr Lys Asp Arg Tyr Phe Phe Glu Lys
    50                  55                  60

Val Asn Ile Cys Asp Asp Lys Lys Ile Asn Glu Ile Phe Ser Lys Tyr
65                  70                  75                  80

Asn Pro Asp Cys Ile Val His Phe Ala Ala Glu Ser His Val Asp Arg
                85                  90                  95

Ser Ile Tyr Gly Pro Lys Asp Phe Leu Glu Thr Asn Ile Met Gly Thr
            100                 105                 110

Phe Ile Leu Leu Glu Ala Ala Arg Lys Leu Trp Glu Asn Asn Lys Glu
        115                 120                 125

Asn Lys Leu Phe His His Ile Ser Thr Asp Glu Val Tyr Gly Ser Leu
    130                 135                 140

Gly Glu Thr Gly Tyr Phe Tyr Glu Thr Thr Pro Tyr Asp Pro Arg Ser
145                 150                 155                 160

Pro Tyr Ser Ser Ser Lys Ala Ser Ser Asp His Ile Val Lys Ala Tyr
                165                 170                 175

Tyr His Thr Tyr Asn Leu Pro Val Thr Ile Ser Asn Cys Ser Asn Asn
            180                 185                 190

Tyr Gly Pro Tyr Gln Phe Pro Glu Lys Leu Ile Pro Leu Met Ile Ser
        195                 200                 205

Asn Ile Val Glu Glu Lys Asp Leu Pro Val Tyr Gly Asp Gly Lys Asn
    210                 215                 220

Ile Arg Asp Trp Ile Phe Val Glu Asp His Asn Asn Ala Val Ile Asp
225                 230                 235                 240

Ile Ile His Lys Gly Arg Val Gly Glu Thr Tyr Asn Ile Gly Gly Glu
                245                 250                 255

Asn Glu Ile Thr Asn Ile Asp Met Val Asn Ile Leu Cys Glu Lys Leu
            260                 265                 270

Ser Ala Lys Met Asn Lys Glu Lys Asp Tyr Tyr Lys Lys Leu Ile Lys
        275                 280                 285

Phe Val Lys Asp Arg Ala Gly His Asp Arg Arg Tyr Ala Ile Asn Cys
    290                 295                 300

Asp Lys Ile Lys Lys Glu Leu Gly Trp Glu Arg Lys Tyr Asp Phe Asn
305                 310                 315                 320

Thr Gly Ile Asp Ile Thr Ile Asp Trp Tyr Leu Asn Asn Lys Gln Trp
                325                 330                 335

Ile Asp Asn Ile Lys Ser Gly Glu Tyr Lys Lys Trp Ile Glu Leu Asn
            340                 345                 350

Tyr Ser Ser Lys
        355
```

<210> SEQ ID NO 108
<211> LENGTH: 356

<212> TYPE: PRT
<213> ORGANISM: Brachysprira hyodysenteriae

<400> SEQUENCE: 108

```
Met Arg Asn Phe Asn Asn Ile Leu Val Thr Gly Gly Cys Gly Phe Ile
1               5                   10                  15

Gly Ser Asn Phe Ile Arg Tyr Ile Leu Glu Lys Ser Asp Tyr Lys Gly
            20                  25                  30

Asn Ile Ile Asn Ile Asp Ala Leu Thr Tyr Ala Gly Asn Arg Glu Asn
        35                  40                  45

Leu Ile Tyr Ile Glu Lys Lys Tyr Lys Asp Arg Tyr Phe Phe Glu Lys
    50                  55                  60

Val Asn Ile Cys Asp Asp Lys Lys Ile Asn Glu Ile Phe Ser Lys Tyr
65                  70                  75                  80

Asn Pro Asp Cys Ile Val His Phe Ala Ala Glu Ser His Val Asp Arg
                85                  90                  95

Ser Ile Tyr Gly Pro Lys Asp Phe Leu Glu Thr Asn Ile Met Gly Thr
            100                 105                 110

Phe Ile Leu Leu Glu Ala Ala Arg Lys Leu Trp Glu Asn Asn Lys Glu
        115                 120                 125

Asn Lys Leu Phe His His Ile Ser Thr Asp Glu Val Tyr Gly Ser Leu
    130                 135                 140

Gly Glu Thr Gly Tyr Phe Tyr Glu Thr Thr Pro Tyr Asp Pro Arg Ser
145                 150                 155                 160

Pro Tyr Ser Ser Ser Lys Ala Ser Ser Asp His Ile Val Lys Ala Tyr
                165                 170                 175

Tyr His Thr Tyr Asn Leu Pro Val Thr Ile Ser Asn Cys Ser Asn Asn
            180                 185                 190

Tyr Gly Pro Tyr Gln Phe Pro Glu Lys Leu Ile Pro Leu Met Ile Ser
        195                 200                 205

Asn Ile Val Glu Glu Lys Asp Leu Pro Val Tyr Gly Asp Gly Lys Asn
    210                 215                 220

Ile Arg Asp Trp Ile Phe Val Glu Asp His Asn Asn Ala Val Ile Asp
225                 230                 235                 240

Ile Ile His Lys Gly Arg Val Gly Glu Thr Tyr Asn Ile Gly Gly Glu
                245                 250                 255

Asn Glu Ile Thr Asn Ile Asp Met Val Asn Ile Leu Cys Glu Lys Leu
            260                 265                 270

Ser Ala Lys Met Asn Lys Glu Lys Asp Tyr Tyr Lys Lys Leu Ile Lys
        275                 280                 285

Phe Val Lys Asp Arg Ala Gly His Asp Arg Arg Tyr Ala Ile Asn Cys
    290                 295                 300

Asp Lys Ile Lys Lys Glu Leu Gly Trp Glu Arg Lys Tyr Asp Phe Asn
305                 310                 315                 320

Thr Ala Ile Asp Ile Thr Ile Asp Trp Tyr Leu Asn Asn Lys Gln Trp
                325                 330                 335

Ile Asp Asn Ile Lys Ser Gly Glu Tyr Lys Lys Trp Ile Glu Leu Asn
            340                 345                 350

Tyr Ser Ser Lys
        355
```

<210> SEQ ID NO 109
<211> LENGTH: 192
<212> TYPE: PRT
<213> ORGANISM: Brachysprira hyodysenteriae

<400> SEQUENCE: 109

Met Pro Phe Thr Phe Lys Lys Leu Asp Ile Asn Gly Leu Phe Ile Ala
1 5 10 15

Glu Pro Arg Ile Phe Gly Asp Ser Arg Gly Tyr Phe Leu Glu Thr Tyr
20 25 30

Ser Glu Lys Asp Phe Phe Glu Ala Gly Ile Lys Glu Lys Phe Val Gln
35 40 45

Asp Asn Gln Ser Lys Ser Thr Lys Asn Val Leu Arg Gly Leu His Tyr
50 55 60

Gln Lys Lys Tyr Cys Gln Ala Lys Leu Val Arg Val Leu Glu Gly Glu
65 70 75 80

Val Phe Asp Val Ala Val Asp Leu Arg Asn Asp Ser Pro Thr Phe Gly
85 90 95

Lys Tyr Tyr Gly Val Leu Leu Thr Glu Glu Asn Lys Lys Gln Phe Phe
100 105 110

Ile Pro Lys Gly Phe Ala His Gly Phe Ile Val Leu Ser Glu Ser Ala
115 120 125

Val Phe Thr Tyr Lys Cys Ser Asp Phe Tyr His Pro Glu Glu Glu Gly
130 135 140

Gly Ile Ile Tyr Asn Asp Lys Asn Ile Asn Ile Asp Trp Thr Cys Asp
145 150 155 160

Thr Lys Asp Val Leu Val Ser Asp Lys Asp Leu Lys Leu Pro Glu Phe
165 170 175

Asp Lys Asn Lys Lys Tyr Phe Ser Leu Asp Gly Asn Trp Ile Gly Glu
180 185 190

<210> SEQ ID NO 110
<211> LENGTH: 192
<212> TYPE: PRT
<213> ORGANISM: Brachysprira hyodysenteriae

<400> SEQUENCE: 110

Met Pro Phe Thr Phe Lys Lys Leu Asp Ile Asn Gly Leu Phe Ile Ala
1 5 10 15

Glu Pro Arg Ile Phe Gly Asp Ser Arg Gly Tyr Phe Leu Glu Thr Tyr
20 25 30

Ser Glu Lys Asp Phe Phe Glu Ala Gly Ile Lys Glu Lys Phe Val Gln
35 40 45

Asp Asn Gln Ser Lys Ser Thr Lys Asn Val Leu Arg Gly Leu His Tyr
50 55 60

Gln Lys Lys Tyr Cys Gln Ala Lys Leu Val Arg Val Leu Glu Gly Lys
65 70 75 80

Val Phe Asp Val Ala Val Asp Leu Arg Asn Asp Ser Pro Thr Phe Gly
85 90 95

Lys Tyr Tyr Gly Val Leu Leu Thr Glu Glu Asn Lys Lys Gln Phe Phe
100 105 110

Ile Pro Lys Gly Phe Ala His Gly Phe Ile Val Leu Ser Glu Ser Ala
115 120 125

Val Phe Ala Tyr Lys Cys Ser Asp Phe Tyr His Pro Glu Glu Glu Gly
130 135 140

Gly Ile Ile Tyr Asn Asp Lys Asn Ile Asn Ile Asp Trp Thr Cys Asp
145 150 155 160

Thr Lys Asp Val Leu Val Ser Asp Lys Asp Leu Lys Leu Pro Glu Phe
165 170 175

Asp Lys Asn Lys Lys Tyr Phe Ser Leu Asp Gly Asn Trp Ile Gly Glu
180 185 190

<210> SEQ ID NO 111
<211> LENGTH: 192
<212> TYPE: PRT
<213> ORGANISM: Brachysprira hyodysenteriae

<400> SEQUENCE: 111

Met Pro Phe Thr Phe Lys Lys Leu Asp Ile Asn Gly Leu Phe Ile Ala
1 5 10 15

Glu Pro Arg Ile Phe Gly Asp Ser Arg Gly Tyr Phe Leu Glu Thr Tyr
20 25 30

Ser Glu Lys Asp Phe Phe Glu Ala Gly Ile Lys Glu Lys Phe Val Gln
35 40 45

Asp Asn Gln Ser Lys Ser Thr Lys Asn Val Leu Arg Gly Leu His Tyr
50 55 60

Gln Lys Lys Tyr Cys Gln Ala Lys Leu Val Arg Val Leu Glu Gly Glu
65 70 75 80

Val Phe Asp Val Ala Val Asp Leu Arg Asn Asp Ser Pro Thr Phe Gly
85 90 95

Lys Tyr Tyr Gly Val Leu Leu Thr Glu Glu Asn Lys Lys Gln Phe Phe
100 105 110

Ile Pro Lys Gly Phe Ala His Gly Phe Ile Val Leu Ser Glu Ser Ala
115 120 125

Val Phe Ala Tyr Lys Cys Ser Asp Phe Tyr His Pro Glu Glu Glu Gly
130 135 140

Gly Ile Ile Tyr Asn Asp Lys Asn Ile Asn Ile Asp Trp Thr Cys Asp
145 150 155 160

Thr Lys Asp Val Leu Val Ser Asp Lys Asp Leu Lys Leu Leu Glu Phe
165 170 175

Asp Lys Asn Lys Lys Tyr Phe Ser Leu Asp Gly Asn Trp Ile Gly Glu
180 185 190

<210> SEQ ID NO 112
<211> LENGTH: 293
<212> TYPE: PRT
<213> ORGANISM: Brachysprira hyodysenteriae

<400> SEQUENCE: 112

Met Ile Trp Val Ile Gly Lys Asn Gly Met Leu Ala Gln Asp Ile Leu
1 5 10 15

Lys Ala Phe Asn Lys Asn Asn Ile Glu Tyr Thr Ser Thr Ala Ser Asn
20 25 30

Ile Asp Ile Thr Asn Ile Asp Ile Leu Asn Asn Phe Ile Lys Asp Lys
35 40 45

Asn Ile Lys Thr Ile Ile Asn Cys Ser Ala Tyr Thr Lys Val Asp Leu
50 55 60

Ala Glu Asp Glu Lys Asp Ile Cys Tyr Lys Val Asn Gly Glu Gly Val
65 70 75 80

Lys Asn Ile Thr Glu Ile Ala Ser Asn Ile Asn Ala Asp Leu Ile His
85 90 95

Phe Ser Thr Asp Tyr Val Phe Asp Gly Glu Asn Asn Lys Pro Tyr Asn
100 105 110

Glu Glu Asp Lys Thr Asn Pro Ile Asn Ile Tyr Gly Lys Ser Lys Leu
115 120 125

```
Glu Gly Glu Lys Tyr Ala Leu Phe Tyr Asn Lys Ala Ile Val Ile Arg
    130                 135                 140

Val Ser Trp Leu Tyr Gly Ile Tyr Gly Lys Asn Phe Val Tyr Thr Met
145                 150                 155                 160

Ile Asn Leu Met Asn Ser Lys Glu Ser Ile Lys Val Val Asn Asp Gln
                165                 170                 175

Phe Gly Ser Pro Thr Tyr Thr Glu Asp Val Ala Met Val Ile Tyr Asp
            180                 185                 190

Ile Ile Lys Asn Asn Asn Phe Asp Tyr Gly Leu Tyr His Tyr Thr Asn
        195                 200                 205

Glu Gly Asn Ile Ser Trp Tyr Asp Phe Ala Lys Thr Ile Tyr Asn Lys
    210                 215                 220

Gly Lys Glu Tyr Asn Ile Ile Asn Asn Asp Cys Lys Val Asn Pro Cys
225                 230                 235                 240

Thr Thr Glu Glu Tyr Pro Thr Lys Ala Lys Arg Pro Lys Tyr Ser Val
                245                 250                 255

Leu Ser Val Glu Lys Ile Lys Arg Tyr Val Lys Ile Tyr Asn Tyr Glu
            260                 265                 270

Asp Ser Leu Asn Ser Phe Leu Thr Tyr Ile Lys Lys Ile Asn Asn Phe
        275                 280                 285

Trp Ser Leu Leu Val
    290


<210> SEQ ID NO 113
<211> LENGTH: 286
<212> TYPE: PRT
<213> ORGANISM: Brachysprira hyodysenteriae

<400> SEQUENCE: 113

Met Ile Trp Ile Ile Gly Lys Asn Gly Met Leu Ala Gln Asp Ile Leu
1               5                   10                  15

Gln Val Phe Asn Lys Asn Asn Ile Glu Tyr Thr Ser Thr Ala Ser Asn
            20                  25                  30

Ile Asp Ile Thr Asn Ile Asp Ile Leu Asn Asn Phe Ile Lys Asp Lys
        35                  40                  45

Asn Ile Lys Thr Ile Ile Asn Cys Ser Ala Tyr Thr Lys Val Asp Leu
    50                  55                  60

Ala Glu Asp Glu Lys Asp Ile Cys Tyr Lys Val Asn Gly Glu Gly Val
65                  70                  75                  80

Lys Asn Ile Thr Glu Ile Ala Ser Asn Ile Asn Ala Asp Leu Ile His
                85                  90                  95

Phe Ser Thr Asp Tyr Val Phe Asp Gly Glu Asn Asn Lys Pro Tyr Asn
            100                 105                 110

Glu Glu Asp Lys Thr Asn Pro Ile Asn Ile Tyr Gly Lys Ser Lys Leu
        115                 120                 125

Glu Gly Glu Lys Tyr Ala Leu Ser Tyr Asn Lys Ser Ile Val Ile Arg
    130                 135                 140

Val Ser Trp Leu Tyr Gly Ile Tyr Gly Lys Asn Phe Val Tyr Thr Met
145                 150                 155                 160

Ile Asn Leu Met Asn Ser Lys Glu Ser Ile Lys Val Val Asn Asp Gln
                165                 170                 175

Phe Gly Ser Pro Thr Tyr Thr Glu Asp Val Ala Met Val Ile Tyr Asp
            180                 185                 190

Ile Ile Lys Asn Asn Asn Phe Tyr Tyr Gly Leu Tyr His Tyr Thr Asn
```

```
        195                 200                 205

Glu Gly Asp Ile Ser Trp Tyr Asp Phe Ala Lys Thr Ile Tyr Asn Lys
    210                 215                 220

Gly Lys Glu Tyr Asn Ile Ile Asn Asn Asp Cys Lys Val Asn Pro Cys
225                 230                 235                 240

Thr Thr Glu Glu Tyr Pro Thr Lys Ala Lys Arg Pro Lys Tyr Ser Val
                245                 250                 255

Leu Ser Val Glu Lys Ile Lys Arg Tyr Val Lys Ile Tyr Asn Tyr Glu
            260                 265                 270

Asp Ser Leu Asn Ser Phe Phe Asn Ile Tyr Gln Lys Asn Lys
        275                 280                 285


<210> SEQ ID NO 114
<211> LENGTH: 286
<212> TYPE: PRT
<213> ORGANISM: Brachysprira hyodysenteriae

<400> SEQUENCE: 114

Met Ile Trp Ile Ile Gly Lys Asn Gly Met Leu Ala Gln Asp Ile Leu
1               5                   10                  15

Gln Val Phe Asn Lys Asn Asn Ile Glu Tyr Thr Ser Thr Ala Ser Asn
            20                  25                  30

Ile Asp Ile Thr Asn Ile Asp Ile Leu Asn Asn Phe Ile Lys Asp Lys
        35                  40                  45

Asn Ile Lys Thr Ile Ile Asn Cys Ser Ala Tyr Thr Lys Val Asp Leu
    50                  55                  60

Ala Glu Asp Glu Lys Asp Ile Cys Tyr Lys Val Asn Gly Glu Gly Val
65                  70                  75                  80

Lys Asn Ile Thr Glu Ile Ala Ser Asn Ile Asn Ala Asp Leu Ile His
                85                  90                  95

Phe Ser Thr Asp Tyr Val Phe Asp Gly Glu Asn Asn Lys Pro Tyr Asn
            100                 105                 110

Glu Glu Asp Lys Thr Asn Pro Ile Asn Ile Tyr Gly Lys Ser Lys Leu
        115                 120                 125

Glu Gly Glu Lys Tyr Ala Leu Ser Tyr Asn Lys Ser Ile Val Ile Arg
    130                 135                 140

Val Ser Trp Leu Tyr Gly Ile Tyr Gly Lys Asn Phe Val Tyr Thr Met
145                 150                 155                 160

Ile Asn Leu Met Asn Ser Lys Glu Ser Ile Lys Val Val Asn Asp Gln
                165                 170                 175

Phe Gly Ser Pro Thr Tyr Thr Glu Asp Val Ala Met Val Ile Tyr Asp
            180                 185                 190

Ile Ile Lys Asn Asn Asn Phe Asp Tyr Gly Leu Tyr His Tyr Thr Asn
        195                 200                 205

Glu Gly Asp Ile Ser Trp Tyr Asp Phe Ala Lys Thr Ile Tyr Asn Lys
    210                 215                 220

Gly Lys Glu Tyr Asn Ile Ile Asn Asn Asp Cys Lys Val Asn Pro Cys
225                 230                 235                 240

Thr Thr Glu Glu Tyr Pro Thr Lys Ala Lys Arg Pro Lys Tyr Ser Val
                245                 250                 255

Leu Ser Val Glu Lys Ile Lys Arg Tyr Val Lys Ile Tyr Asn Tyr Glu
            260                 265                 270

Asp Ser Leu Asn Ser Phe Phe Asn Ile Tyr Gln Lys Asn Lys
        275                 280                 285
```

<210> SEQ ID NO 115
<211> LENGTH: 286
<212> TYPE: PRT
<213> ORGANISM: Brachysprira hyodysenteriae

<400> SEQUENCE: 115

```
Met Ile Trp Ile Ile Gly Lys Asn Gly Met Leu Ala Gln Asp Ile Leu
1               5                   10                  15

Gln Val Phe Asn Lys Asn Asn Ile Glu Tyr Thr Ser Thr Ala Ser Asn
            20                  25                  30

Ile Asp Ile Thr Asn Ile Asp Ile Leu Asn Asn Phe Ile Lys Asp Lys
        35                  40                  45

Asn Ile Lys Thr Ile Ile Asn Cys Ser Ala Tyr Thr Lys Val Asp Leu
    50                  55                  60

Ala Glu Asp Glu Lys Asp Ile Cys Tyr Lys Val Asn Gly Glu Gly Val
65                  70                  75                  80

Lys Asn Ile Thr Glu Ile Ala Ser Asn Ile Asn Ala Asp Leu Ile His
                85                  90                  95

Phe Ser Thr Asp Tyr Val Phe Asp Gly Glu Asn Asn Lys Pro Tyr Asn
            100                 105                 110

Glu Glu Asp Lys Thr Asn Pro Ile Asn Ile Tyr Gly Lys Ser Lys Leu
        115                 120                 125

Glu Gly Glu Lys Tyr Ala Leu Phe Tyr Asn Lys Ala Ile Val Ile Arg
    130                 135                 140

Val Ser Trp Leu Tyr Gly Ile Tyr Gly Lys Asn Phe Val Tyr Thr Met
145                 150                 155                 160

Ile Asn Leu Met Asn Ser Lys Glu Ser Ile Lys Val Val Asn Asp Gln
                165                 170                 175

Phe Gly Ser Pro Thr Tyr Thr Glu Asp Val Ala Met Val Ile Tyr Asp
            180                 185                 190

Ile Ile Lys Asn Asn Asn Phe Asp Tyr Gly Leu Tyr His Tyr Thr Asn
        195                 200                 205

Glu Gly Asn Ile Ser Trp Tyr Asp Phe Ala Lys Thr Ile Tyr Asn Lys
    210                 215                 220

Gly Lys Glu Tyr Asn Ile Ile Asn Asn Asp Cys Lys Val Asn Pro Cys
225                 230                 235                 240

Thr Thr Glu Glu Tyr Pro Thr Lys Ala Lys Arg Pro Lys Tyr Ser Val
                245                 250                 255

Leu Ser Val Glu Lys Ile Lys Arg Tyr Val Lys Ile Tyr Asn Tyr Glu
            260                 265                 270

Asp Ser Leu Asn Ser Phe Phe Asn Ile Tyr Gln Lys Asn Lys
        275                 280                 285
```

<210> SEQ ID NO 116
<211> LENGTH: 286
<212> TYPE: PRT
<213> ORGANISM: Brachysprira hyodysenteriae

<400> SEQUENCE: 116

```
Met Ile Trp Val Ile Gly Lys Asn Gly Met Leu Ala Gln Asp Ile Leu
1               5                   10                  15

Lys Ala Phe Asn Lys Asn Asn Ile Glu Tyr Thr Ser Thr Ala Ser Asn
            20                  25                  30

Ile Asp Ile Thr Asn Val Asp Ile Leu Asn Asn Phe Ile Lys Asp Lys
        35                  40                  45
```

Asn Ile Lys Thr Ile Ile Asn Cys Ser Ala Tyr Thr Lys Val Asp Leu
50 55 60

Ala Glu Asp Glu Lys Asp Ile Cys Tyr Lys Val Asn Gly Glu Gly Val
65 70 75 80

Lys Asn Ile Thr Glu Ile Ala Ser Asn Ile Asn Ala Asp Leu Ile His
85 90 95

Phe Ser Thr Asp Tyr Val Phe Asp Gly Glu Asn Asn Lys Pro Tyr Asn
100 105 110

Glu Glu Asp Lys Thr Asn Pro Ile Asn Ile Tyr Gly Lys Ser Lys Leu
115 120 125

Glu Gly Glu Lys Tyr Ala Leu Phe Tyr Asn Lys Ala Ile Val Ile Arg
130 135 140

Val Ser Trp Leu Tyr Gly Ile Tyr Gly Lys Asn Phe Val Tyr Thr Met
145 150 155 160

Ile Asn Leu Met Asn Ser Lys Glu Ser Ile Lys Val Val Asn Asp Gln
165 170 175

Phe Gly Ser Pro Thr Tyr Thr Glu Asp Val Ala Met Val Ile Tyr Asp
180 185 190

Ile Ile Lys Asn Asn Asn Phe Asp Tyr Gly Leu Tyr His Tyr Thr Asn
195 200 205

Glu Gly Asn Ile Ser Trp Tyr Asp Phe Ala Lys Thr Ile Tyr Asn Lys
210 215 220

Gly Lys Glu Tyr Asn Ile Ile Asn Asn Asp Cys Lys Val Asn Pro Cys
225 230 235 240

Thr Thr Glu Glu Tyr Pro Thr Lys Ala Lys Arg Pro Lys Tyr Ser Val
245 250 255

Leu Ser Val Glu Lys Ile Lys Arg Tyr Val Lys Ile Tyr Asn Tyr Glu
260 265 270

Asp Ser Leu Asn Ser Phe Phe Asn Ile Tyr Gln Lys Asn Lys
275 280 285

<210> SEQ ID NO 117
<211> LENGTH: 286
<212> TYPE: PRT
<213> ORGANISM: Brachysprira hyodysenteriae

<400> SEQUENCE: 117

Met Ile Trp Val Ile Gly Lys Asn Gly Met Leu Ala Gln Asp Ile Leu
1 5 10 15

Lys Ala Phe Asn Lys Asn Asn Ile Glu Tyr Thr Ser Thr Ala Ser Asn
20 25 30

Ile Asp Ile Thr Asn Ile Asp Ile Leu Asn Asn Phe Ile Lys Asp Gln
35 40 45

Asn Ile Lys Thr Ile Ile Asn Cys Ser Ala Tyr Thr Lys Val Asp Leu
50 55 60

Ala Glu Asp Glu Lys Asp Ile Cys Tyr Lys Val Asn Gly Glu Gly Val
65 70 75 80

Lys Asn Ile Thr Glu Ile Ala Ser Asn Ile Asn Ala Asp Leu Ile His
85 90 95

Phe Ser Thr Asp Tyr Val Phe Asp Gly Glu Asn Asn Lys Pro Tyr Asn
100 105 110

Glu Glu Asp Lys Thr Asn Pro Ile Asn Ile Tyr Gly Lys Ser Lys Leu
115 120 125

Glu Gly Glu Lys Tyr Ala Leu Phe Tyr Asn Lys Ala Ile Val Ile Arg
130 135 140

Val Ser Trp Leu Tyr Gly Ile Tyr Gly Lys Asn Phe Val Tyr Thr Met
145 150 155 160

Ile Asn Leu Met Asn Ser Lys Glu Ser Ile Lys Val Val Asn Asp Gln
165 170 175

Phe Gly Ser Pro Thr Tyr Thr Glu Asp Val Ala Met Val Ile Tyr Asp
180 185 190

Ile Ile Lys Asn Asn Asn Phe Asp Tyr Gly Leu Tyr His Tyr Thr Asn
195 200 205

Glu Gly Asn Ile Ser Trp Tyr Asp Phe Ala Lys Thr Ile Tyr Asn Lys
210 215 220

Gly Lys Glu Tyr Asn Ile Ile Asn Asn Asp Cys Lys Val Asn Pro Cys
225 230 235 240

Thr Thr Glu Glu Tyr Pro Thr Lys Ala Lys Arg Pro Lys Tyr Ser Val
245 250 255

Leu Ser Val Glu Lys Ile Lys Arg Tyr Val Lys Ile Tyr Asn Tyr Glu
260 265 270

Asp Ser Leu Asn Ser Phe Phe Asn Ile Tyr Gln Lys Asn Lys
275 280 285

<210> SEQ ID NO 118
<211> LENGTH: 326
<212> TYPE: PRT
<213> ORGANISM: Brachysprira hyodysenteriae

<400> SEQUENCE: 118

Met Lys Arg Leu Ala Val Phe Ala Gly Tyr Asp Lys Asp Asn Ile Ile
1 5 10 15

Asp Asp Tyr Val Val Tyr Tyr Ile Lys Glu Leu Lys Lys Ile Ala Asp
20 25 30

Ile Ile Tyr Val Ser Asp Cys Asn Met Ser Asp Asn Glu Leu Lys Lys
35 40 45

Ile Asn Asn Tyr Cys Ile His Ile Ile Asn Gly Arg His Glu Glu Tyr
50 55 60

Asp Phe Gly Ser Tyr Lys Arg Gly Tyr Leu Tyr Ala Lys Glu Asn Asn
65 70 75 80

Ile Leu Gln Asn Tyr Asp Tyr Leu Ile Leu Cys Asn Asp Ser Cys Tyr
85 90 95

Gly Pro Leu Phe Asp Leu Glu Asn Ile Val Asn Lys Met Asn Asp Tyr
100 105 110

Asp Phe Gly Gly Ile Ser Ile Ser Lys Asp Leu Lys Ile Ala Asn His
115 120 125

Asn Tyr Ile Thr Ser Phe Phe Ile Tyr Ile Asn Lys Asn Ile Phe Asn
130 135 140

Lys Asp Phe Phe Asn Asp Phe Ile Tyr Asp Ile Lys Lys Glu Glu Asp
145 150 155 160

Lys Met Asp Ile Ile Lys Lys Tyr Glu Phe Gly Leu Ser Lys Leu Met
165 170 175

Leu Asp Asn Asn Ile Glu Leu Lys Gly Leu Phe Asn Asp Asn Gly Glu
180 185 190

Phe Asn Arg Pro Tyr Phe Asn Pro Leu Ala Leu Ile Glu Glu Gly Tyr
195 200 205

Pro Phe Leu Lys Lys His Val Leu Glu Lys Lys Val Thr Val Pro Leu
210 215 220

Asn Ile Asp Glu Leu Thr Asn Ile Ile Lys Ile Ile Lys Asn Asn Tyr

```
225                 230                 235                 240

Asp Ile Lys Leu Ile Val Asn His Leu Asn Arg Val Ala Asp Lys Glu
                245                 250                 255

Gln Ile Lys Tyr Leu Phe Gln Lys Tyr Lys Pro Tyr Lys Lys Thr Phe
            260                 265                 270

Ile His Glu Lys Ile Phe Ser Leu Phe Thr Arg Tyr Ser Pro Ser Gly
        275                 280                 285

Lys Tyr Gln Thr Val Tyr Lys Phe Phe Asn Phe Leu Thr Ile Ser Ile
    290                 295                 300

Asp Lys Pro Ile Lys Asp Ser Tyr Ile Glu Thr Asp Tyr Lys Asp Phe
305                 310                 315                 320

Asn Phe Leu Leu Lys Ile
                325
```

<210> SEQ ID NO 119
<211> LENGTH: 326
<212> TYPE: PRT
<213> ORGANISM: Brachysprira hyodysenteriae

<400> SEQUENCE: 119

```
Met Lys Arg Leu Ala Val Phe Ala Gly Tyr Asp Lys Asp Asn Ile Ile
1               5                   10                  15

Asp Asp Tyr Val Val Tyr Tyr Ile Lys Glu Leu Lys Lys Ile Ala Asp
            20                  25                  30

Ile Ile Tyr Val Ser Asp Cys Asn Met Ser Asp Asn Glu Leu Lys Lys
        35                  40                  45

Ile Asn Asn Tyr Cys Ile His Ile Ile Asn Gly Arg His Glu Glu Tyr
    50                  55                  60

Asp Phe Gly Ser Tyr Lys Arg Gly Tyr Leu Tyr Ala Lys Glu Asn Asn
65                  70                  75                  80

Ile Leu Gln Asn Tyr Asp Tyr Leu Ile Leu Cys Asn Asp Ser Cys Tyr
                85                  90                  95

Gly Pro Leu Phe Asp Leu Glu Asn Ile Val Asn Lys Met Asn Asp Tyr
            100                 105                 110

Asp Phe Gly Gly Ile Ser Ile Ser Lys Asp Leu Lys Ile Ala Asn His
        115                 120                 125

Asn Tyr Ile Thr Ser Phe Phe Ile Tyr Ile Asn Lys Asn Ile Phe Asn
    130                 135                 140

Lys Asp Phe Phe Asn Asp Phe Ile Tyr Asp Ile Lys Lys Glu Glu Asp
145                 150                 155                 160

Lys Met Asp Ile Ile Lys Lys Tyr Glu Phe Gly Leu Ser Lys Leu Met
                165                 170                 175

Leu Asp Asn Asn Ile Glu Leu Lys Gly Leu Phe Asn Asp Asn Gly Glu
            180                 185                 190

Phe Asn Arg Pro Tyr Phe Asn Pro Leu Ala Leu Ile Glu Glu Gly Tyr
        195                 200                 205

Pro Phe Leu Lys Lys His Val Leu Glu Lys Lys Val Thr Val Pro Leu
    210                 215                 220

Asn Ile Asp Glu Leu Thr Asn Ile Ile Lys Ile Ile Lys Asn Asn Tyr
225                 230                 235                 240

Asp Ile Lys Leu Ile Val Asn His Leu Asn Arg Val Ala Asp Lys Glu
                245                 250                 255

Gln Ile Lys Tyr Leu Phe Gln Lys Tyr Lys Pro Tyr Lys Lys Thr Phe
            260                 265                 270
```

```
Ile His Glu Lys Ile Phe Ser Leu Phe Thr Arg Tyr Ser Pro Ser Gly
        275                 280                 285

Lys Tyr Gln Thr Val Tyr Asn Phe Phe Asn Phe Leu Thr Ile Ser Ile
    290                 295                 300

Asp Lys Pro Ile Lys Asp Ser Tyr Ile Glu Thr Asp Tyr Lys Asp Phe
305                 310                 315                 320

Asn Phe Leu Leu Glu Ile
                325


<210> SEQ ID NO 120
<211> LENGTH: 326
<212> TYPE: PRT
<213> ORGANISM: Brachysprira hyodysenteriae

<400> SEQUENCE: 120

Met Lys Arg Leu Ala Val Phe Ala Gly Tyr Asp Lys Asp Asn Ile Ile
1               5                   10                  15

Asp Asp Tyr Val Val Tyr Tyr Ile Lys Glu Leu Lys Lys Ile Ala Asp
            20                  25                  30

Ile Ile Tyr Val Ser Asp Cys Asn Met Ser Asp Asn Glu Leu Lys Lys
        35                  40                  45

Ile Asn Asp Tyr Cys Ile His Ile Ile Asn Gly Arg His Glu Glu Tyr
    50                  55                  60

Asp Phe Gly Ser Tyr Lys Arg Gly Tyr Leu Tyr Ala Lys Glu Asn Asn
65                  70                  75                  80

Ile Leu Gln Asn Tyr Asp Tyr Leu Ile Leu Cys Asn Asp Ser Cys Tyr
                85                  90                  95

Gly Pro Leu Phe Asp Leu Glu Asn Ile Ile Asn Lys Met Asn Asn Tyr
            100                 105                 110

Asp Phe Gly Gly Ile Ser Ile Ser Lys Asp Leu Lys Ile Ala Asn His
        115                 120                 125

Asn Tyr Ile Thr Ser Phe Phe Ile Tyr Ile Asn Lys Asn Ile Phe Asn
    130                 135                 140

Lys Asp Phe Phe Asn Asp Phe Ile Phe Asn Ile Lys Lys Glu Glu Asp
145                 150                 155                 160

Lys Met Asp Ile Ile Lys Lys Tyr Glu Phe Gly Leu Ser Lys Leu Met
                165                 170                 175

Leu Asp Asn Asn Ile Glu Leu Lys Gly Leu Phe Asn Asp Asn Gly Glu
            180                 185                 190

Phe Asn Arg Pro Tyr Phe Asn Pro Leu Ala Leu Ile Glu Glu Gly Tyr
        195                 200                 205

Pro Phe Leu Lys Lys His Val Leu Glu Lys Lys Ile Thr Val Pro Leu
    210                 215                 220

Asn Ile Asn Glu Leu Thr Asn Ile Ile Lys Ile Ile Lys Asn Asn Tyr
225                 230                 235                 240

Asp Ile Lys Leu Ile Val Asn His Leu Asn Arg Val Ala Asp Lys Glu
                245                 250                 255

Gln Ile Lys Tyr Leu Phe Gln Lys Tyr Lys Pro Tyr Lys Lys Ile Phe
            260                 265                 270

Ile His Glu Lys Ile Phe Ser Leu Phe Thr Arg Tyr Ser Pro Ser Gly
        275                 280                 285

Lys Tyr Gln Thr Val Tyr Lys Phe Phe Asn Phe Leu Thr Ile Ser Ile
    290                 295                 300

Asp Lys Pro Ile Lys Asp Ser Tyr Ile Glu Thr Asp Tyr Lys Asp Phe
305                 310                 315                 320
```

Asn Phe Leu Leu Glu Ile
325

<210> SEQ ID NO 121
<211> LENGTH: 326
<212> TYPE: PRT
<213> ORGANISM: Brachysprira hyodysenteriae

<400> SEQUENCE: 121

Met Lys Arg Leu Ala Val Phe Ala Gly Tyr Asp Lys Asp Asn Ile Ile
1 5 10 15

Asp Asp Tyr Val Val Tyr Tyr Ile Lys Glu Leu Lys Lys Ile Ser Asp
20 25 30

Ile Ile Tyr Val Ser Asp Cys Asn Met Ser Asp Asn Glu Leu Lys Lys
35 40 45

Ile Asn Asp Tyr Cys Ile His Ile Ile Asn Gly Arg His Glu Glu Tyr
50 55 60

Asp Phe Gly Ser Tyr Lys Arg Gly Tyr Leu Tyr Ala Lys Glu Asn Asn
65 70 75 80

Ile Leu Gln Asn Tyr Asp Tyr Leu Ile Leu Cys Asn Asp Ser Cys Tyr
85 90 95

Gly Pro Leu Phe Asp Leu Glu Asn Ile Ile Asn Lys Met Asn Asp Tyr
100 105 110

Asp Phe Gly Gly Ile Ser Ile Ser Lys Asp Leu Lys Ile Ala Asn His
115 120 125

Asn Tyr Ile Thr Ser Phe Phe Ile Tyr Ile Asn Lys Asn Ile Phe Asn
130 135 140

Lys Asp Phe Phe Asn Asp Phe Ile Tyr Asp Ile Lys Lys Glu Glu Asp
145 150 155 160

Lys Met Asp Ile Ile Lys Lys Tyr Glu Phe Gly Leu Ser Lys Leu Met
165 170 175

Leu Asp Asn Asn Ile Glu Leu Lys Gly Leu Phe Asn Asp Asn Gly Glu
180 185 190

Phe Asn Arg Pro Tyr Phe Asn Pro Leu Ala Leu Ile Glu Glu Gly Tyr
195 200 205

Pro Phe Leu Lys Lys His Val Leu Glu Lys Lys Val Thr Val Pro Leu
210 215 220

Asn Ile Asp Glu Leu Thr Asn Ile Ile Lys Ile Ile Lys Asn Asn Tyr
225 230 235 240

Asp Ile Lys Leu Ile Val Asn His Leu Asn Arg Val Ala Asp Lys Glu
245 250 255

Gln Ile Lys Tyr Leu Phe Gln Lys Tyr Lys Pro Tyr Lys Lys Thr Phe
260 265 270

Ile His Glu Lys Ile Phe Ser Leu Phe Thr Arg Tyr Ser Pro Ser Gly
275 280 285

Lys Tyr Gln Thr Val Tyr Lys Phe Phe Asn Phe Leu Thr Ile Ser Ile
290 295 300

Asp Lys Pro Ile Lys Asp Ser Tyr Ile Glu Thr Asp Tyr Lys Asp Phe
305 310 315 320

Asn Phe Leu Leu Glu Ile
325

<210> SEQ ID NO 122
<211> LENGTH: 326
<212> TYPE: PRT

<213> ORGANISM: Brachysprira hyodysenteriae

<400> SEQUENCE: 122

```
Met Lys Arg Leu Ala Val Phe Ala Gly Tyr Asp Lys Asp Asn Ile Ile
1               5                   10                  15

Asp Asp Tyr Val Val Tyr Tyr Ile Lys Glu Leu Lys Lys Ile Ser Asp
            20                  25                  30

Ile Ile Tyr Val Ser Asp Cys Asn Met Ser Asp Asn Glu Leu Lys Lys
        35                  40                  45

Ile Asn Asp Tyr Cys Ile His Ile Ile Asn Gly Arg His Glu Glu Tyr
    50                  55                  60

Asp Phe Gly Ser Tyr Lys Arg Gly Tyr Leu Tyr Ala Lys Glu Asn Asn
65                  70                  75                  80

Ile Leu Gln Asn Tyr Asp Tyr Leu Ile Leu Cys Asn Asp Ser Cys Tyr
                85                  90                  95

Gly Pro Leu Phe Asp Leu Glu Asn Ile Ile Asn Lys Met Asn Asp Tyr
            100                 105                 110

Asp Phe Gly Gly Ile Ser Ile Ser Lys Asp Leu Lys Ile Ala Asn His
        115                 120                 125

Asn Tyr Ile Thr Ser Phe Phe Ile Tyr Ile Asn Lys Asn Ile Phe Asn
    130                 135                 140

Lys Asp Phe Phe Asn Asp Phe Ile Tyr Asp Ile Lys Lys Glu Glu Asp
145                 150                 155                 160

Lys Met Asp Ile Ile Lys Lys Tyr Glu Phe Gly Leu Ser Lys Leu Met
                165                 170                 175

Leu Asp Asn Asn Ile Glu Leu Lys Gly Leu Phe Asn Asp Asn Gly Glu
            180                 185                 190

Phe Asn Arg Pro Tyr Phe Asn Pro Leu Ala Leu Ile Glu Glu Gly Tyr
        195                 200                 205

Pro Phe Leu Lys Lys His Val Leu Glu Lys Lys Val Thr Val Pro Leu
    210                 215                 220

Asn Ile Asp Glu Leu Thr Asn Ile Ile Lys Ile Ile Lys Asn Asn Tyr
225                 230                 235                 240

Asp Ile Lys Leu Ile Val Asn His Leu Asn Arg Val Ala Asp Lys Glu
                245                 250                 255

Gln Ile Lys Tyr Leu Phe Gln Lys Tyr Lys Pro Tyr Lys Lys Thr Phe
            260                 265                 270

Ile His Glu Lys Ile Phe Ser Leu Phe Thr Arg Tyr Ser Pro Ser Gly
        275                 280                 285

Lys Tyr Gln Thr Val Tyr Asn Phe Phe Asn Phe Leu Thr Ile Ser Ile
    290                 295                 300

Asp Lys Pro Ile Lys Asp Ser Tyr Ile Glu Thr Asp Tyr Lys Asp Phe
305                 310                 315                 320

Asn Phe Leu Leu Glu Ile
                325
```

<210> SEQ ID NO 123
<211> LENGTH: 326
<212> TYPE: PRT
<213> ORGANISM: Brachysprira hyodysenteriae

<400> SEQUENCE: 123

```
Met Lys Arg Leu Ala Val Phe Ala Gly Tyr Asp Lys Asp Asn Ile Ile
1               5                   10                  15

Asp Asp Tyr Val Val Tyr Tyr Ile Lys Glu Leu Lys Lys Ile Ser Asp
```

-continued

```
            20                  25                  30

Ile Ile Tyr Val Ser Asp Cys Asn Met Ser Asp Asn Glu Leu Lys Lys
        35                  40                  45

Ile Asn Asp Tyr Cys Ile His Ile Ile Asn Gly Arg His Glu Glu Tyr
    50                  55                  60

Asp Phe Gly Ser Tyr Lys Arg Gly Tyr Leu Tyr Ala Lys Glu Asn Asn
65                  70                  75                  80

Ile Leu Gln Asn Tyr Asp Tyr Leu Ile Leu Cys Asn Asp Ser Cys Tyr
                85                  90                  95

Gly Pro Leu Phe Asp Leu Glu Asn Ile Ile Asn Lys Met Asn Asp Tyr
            100                 105                 110

Asp Phe Gly Gly Ile Ser Ile Ser Lys Asp Leu Lys Ile Ala Asn His
        115                 120                 125

Asn Tyr Ile Thr Ser Phe Phe Ile Tyr Ile Asn Lys Asn Ile Phe Asn
    130                 135                 140

Lys Asp Phe Phe Asn Asn Phe Ile Tyr Asp Ile Lys Lys Glu Glu Asp
145                 150                 155                 160

Lys Met Asp Ile Ile Lys Lys Tyr Glu Phe Gly Leu Ser Lys Leu Met
                165                 170                 175

Leu Asp Asn Asn Ile Glu Leu Lys Gly Leu Phe Asn Asp Asn Gly Glu
            180                 185                 190

Phe Asn Arg Pro Tyr Phe Asn Pro Leu Ala Leu Ile Glu Glu Gly Tyr
        195                 200                 205

Pro Phe Leu Lys Lys His Val Leu Glu Lys Lys Val Thr Val Pro Leu
    210                 215                 220

Asn Ile Asp Glu Leu Thr Asn Ile Ile Lys Ile Ile Lys Asn Asn Tyr
225                 230                 235                 240

Asp Ile Lys Leu Ile Val Asn His Leu Asn Arg Val Ala Asp Lys Glu
                245                 250                 255

Gln Ile Lys Tyr Leu Phe Gln Lys Tyr Lys Pro Tyr Lys Lys Thr Phe
            260                 265                 270

Ile His Glu Lys Ile Phe Ser Leu Phe Thr Arg Tyr Ser Pro Ser Gly
        275                 280                 285

Lys Tyr Gln Thr Val Tyr Asn Phe Phe Asn Phe Leu Thr Ile Ser Ile
    290                 295                 300

Asp Lys Pro Ile Lys Asp Ser Tyr Ile Glu Thr Asp Tyr Lys Asp Phe
305                 310                 315                 320

Asn Phe Leu Leu Glu Ile
                325
```

IMMUNOGENIC AND VACCINE COMPOSITIONS AGAINST SWINE DYSENTERY

FIELD OF THE INVENTION

The present invention belongs to the field of diseases caused by intestinal spirochaetes. Particularly, the invention relates to novel immunogenic and vaccine compositions for swine dysentery. More particularly, the invention relates to novel immunogenic and vaccine compositions for the prevention and/or treatment of infections caused by *Brachyspira hyodysenteriae.*

BACKGROUND OF THE INVENTION

*Brachyspira* spp. are anaerobic intestinal spirochaetes that can be isolated from pigs, and other mammals, including birds and humans. In pigs, seven *Brachyspira* spp. have been described, i.e. *Brachyspira hyodysenteriae, Brachyspira pilosicoli, Brachyspira intermedia, Brachyspira murdochii, Brachyspira innocens, Brachyspira suanatina* and *Brachyspira hampsonii. B. hyodysenteriae* is especially relevant in pigs as it causes swine dysentery and hence considerable economic losses to the pig industry. Furthermore, reduced susceptibility of *B. hyodysenteriae* to antimicrobials is of increasing concern. The epidemiology of *B. hyodysenteriae* infections is only partially understood, but different methods for detection, identification and typing have supported recent improvements in knowledge and understanding.

*B. hyodysenteriae* (previously known as *Serpulina* or *Treponema hyodysenteriae*) is the etiologic agent of swine dysentery (SD), a severe, infectious disease characterized by mucohemorrhagic diarrhea and marked inflammation limited to the large intestine (cecum and/or colon). *B. hyodysenteriae* is the specie with the highest incidence in pig farms with a high economic impact on affected farms worldwide.

Different approaches have been used to control SD, varying from the prophylactic use of antimicrobial agents, to complete destocking of infected herds and prevention of re-entry of infected carrier pigs. All these options are expensive and, if they are to be fully effective, they require the use of tedious diagnostic tests to monitor progress.

Since an immunological response is induced following colonization with *B. hyodysenteriae*, pigs recovered from SD are protected from re-infection. Despite of this fact, attempts to develop vaccines to control the disease had very limited success, either because they have provided inadequate protection on a herd basis, or they have been too costly and difficult to produce on a large scale for a feasible commercial use (WO2017/118581).

Vaccines based on inactivated *B. hyodysenteriae* isolates were reported to have limited success, but the main disadvantage of the inactivated vaccines is that they do not provide protection against different strains/serotypes (Olson et al., American Journal of Veterinary Research, 1994, 67-71; Diego et al., Vaccine, 1995, 663-667).

Autogenous preparations, also known as "autogenous vaccines" or "autovaccines" are vaccines prepared from the cultures of the microorganisms isolated from the animal's own tissues or secretions in presence of the infection. These autogenous preparations have also been used to develop vaccines against SD. However, this approach is costly and time consuming and it has shown that confers protection exclusively against the same strain of *B. hyodysenteriae* that causes clinical signs of the infected pigs.

Other examples of inactivated based *B. hyodysenteriae* vaccines are: (i) those disclosed in the patent family belonging to the PCT Publication No. WO2014/207202 filed by Aquilon CyL and Universidad de León. The Applicants disclose a universal vaccine against swine dysentery comprising specific bacteria from at least two genetically diverse strains of *B. hyodysenteriae*, and (ii) those disclosed in the patent family belonging to the PCT Publication No. WO2019/081583 filed by Aquilon CyL, where it is disclosed a single strain dysentery vaccine comprising a particular *B. hyodysenteriae* bacteria. Despite these attempts to develop vaccines to control SD, they all had very limited success, because they have provided inadequate protection on a herd basis, particularly to provide cross-protection against heterologous *B. hyodysenteriae* strains, and they have been too costly and difficult to produce to make them commercially viable.

Regarding the use of attenuated vaccines different approaches have also been disclosed, mostly based on *B. hyodysenteriae* mutants which are defective in one or more virulence factors or hemolysins associated genes.

An example of attenuated vaccine is described in the patent document WO2017/118581, filed by the Universiteit Gent. This document discloses a strain of *B. hyodysenteriae* that is useful as live attenuated vaccine.

Recombinant subunit vaccines have also been described. However, none of them have achieved significant protection.

Despite such efforts, there is no commercial vaccine available to protect swine against different strains of *B. hyodysenteriae.*

Therefore, there remains a need for novel, safe and effective vaccines against *B. hyodysenteriae* infections in swine, and particularly vaccines that confer heterologous protection against different *B. hyodysenteriae* strains.

SUMMARY OF THE INVENTION

The authors of the present invention have found that *B. hyodysenteriae* strains can be classified into four different groups (S0, S1, S2 and S3) based on the structure of a gene cluster located on a plasmid of about 36 kb (pBH) and comprising, among others, genes from the rfbBADC operon. The inventors have also shown that vaccines comprising inactivated *B. hyodysenteriae* strains pertaining to the S1 and/or S2 group are effective in treating and/or preventing infections caused by *B. hyodysenteriae*, even if the infection was caused by a heterologous strain. Additionally, multivalent vaccines comprising strains pertaining to the S1 and S2 groups have higher efficacy than autogenous vaccines, and are also able to confer cross-protection against heterologous *B. hyodysenteriae* strains.

Therefore, the authors of the present invention have surprisingly found a novel gene cluster located on the plasmid pBH which is associated with obtaining effective protection against SD, particularly for conferring cross-protection between heterologous *B. hyodysenteriae* strains.

Therefore, in a first aspect, the invention relates to an immunogenic or vaccine composition comprising an isolated inactivated bacterium from the species *Brachyspira hyodysenteriae*, wherein said bacterium comprises the gene on the locus BHWA1_02689 (fucT) of the *B. hyodysenteriae* plasmid pBHWA1 identified by the GenBank accession number NC_012226.1 or a variant of said gene of any strain of *B. hyodysenteriae.*

In a second aspect, the invention relates to a method for producing an immunogenic or vaccine composition comprising an isolated bacterium from the species *Brachyspira hyodysenteriae*, wherein the method comprises the steps of:

(a) determining if the bacterium from the species *Brachyspira hyodysenteriae* comprises the gene on the locus BHWA1_02689 (fucT) of the *B. hyodysenteriae* plasmid pBHWA1 identified by the GenBank accession number NC_012226.1 or a variant of said gene of any strain of *B. hyodysenteriae*, or the product of said gene or variant, (b) selecting the bacterium from the species *Brachyspira hyodysenteriae* if said bacterium comprises the fucT gene or a variant of said gene of any strain of *B. hyodysenteriae* or the product of said gene or variant, (c) inactivating the bacterium selected in step (b) and (d) formulating the bacterium inactivated in step (c) in an immunogenic or vaccine composition.

In another aspect, the invention relates to an immunogenic or vaccine composition obtainable by the method of the second aspect.

In another aspect, the invention relates to a method for selecting a bacterium from the species *Brachyspira hyodysenteriae* useful for manufacturing a vaccine against swine dysentery comprising determining the presence or absence of the gene on the locus BHWA1_02689 (fucT) of the *B. hyodysenteriae* plasmid pBHWA1 identified by the GenBank accession number NC_012226.1 or a variant of said gene of any strain of *B. hyodysenteriae* and/or of the product of said gene or variant, wherein if the bacterium comprises said gene or variant or the product of said gene or variant, the bacterium is selected for manufacturing a vaccine against swine dysentery.

In another aspect, the invention relates to the immunogenic or vaccine composition of the first aspect for use as a medicament.

In another aspect, the invention relates to the immunogenic composition of the first aspect for use in inducing an immune response against a bacterium from the species *Brachyspira hyodysenteriae.*

In another aspect, the invention relates to the vaccine composition of the first aspect for use in the protection against an infection caused by a bacterium from the species *Brachyspira hyodysenteriae.*

DETAILED DESCRIPTION OF THE INVENTION

Immunogenic or Vaccine Composition

Figure 1:
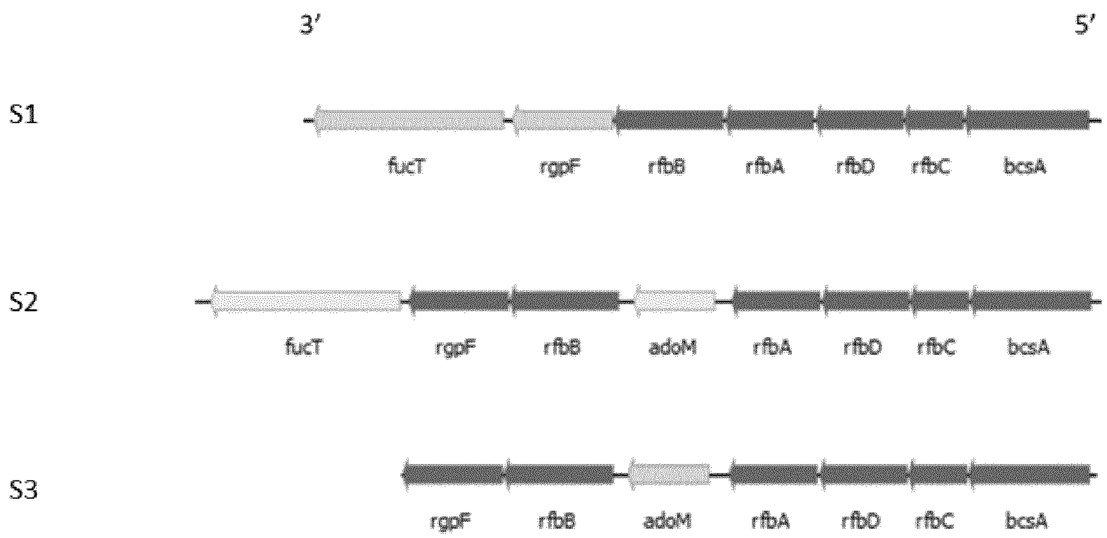
FIG. 1. Genomic structures of the gene cluster comprising the rfbBADC operon and the different genetic structures found (S1 to S3). The different genes are identified.

In a first aspect, the invention relates to an immunogenic or vaccine composition comprising an isolated inactivated bacterium from the species *Brachyspira hyodysenteriae*, wherein said bacterium comprises the gene on the locus BHWA1_02689 (fucT gene) of the *B. hyodysenteriae* plasmid pBHWA1 identified by the GenBank accession number NC_012226.1 or a variant of said gene of any strain of *B. hyodysenteriae.*

Throughout the present description and in the claims, the expressions in singular preceded by the articles "a" or "the" are understood to also include, in a broad manner, the reference to the plural, unless the context clearly indicates the contrary.

The term "immunogenic composition", as used herein, refers to a composition that elicits an immune response in a subject that has been exposed to said composition. An immune response may induce antibodies and/or cell-mediated immune responses against a specific immunogen. Thus, an immune response in particular means but is not limited to the development in a subset of a cellular and/or antibody-mediated immune response to the composition or vaccine of the invention. Immunogenic compositions can be prepared, for instance, as injectable pharmaceutic form such as liquid solutions, suspensions, emulsions, and freeze-dried compositions. The immunogenic composition comprises components with antigenic properties, such as immunogenic polypeptides, lipoligosaccharides, glycoconjugates, whole killed bacterium, supernatants of microorganism cultures, including bacteria, protozoa and viruses. A molecule is "antigenic" when it is capable of specifically interacting with an antigen recognition molecule of the immune system, such as an immunoglobulin (antibody) or T cell antigen receptor.

The term "antigen" refers to a component against which a subject can initiate an immune response, e.g. humoral and/or cellular immune response. Depending on the intended function of the composition, one or more antigens may be included.

The term "vaccine composition", as used herein, refers to a composition that establishes or improves immunity to a particular disease by inducing an adaptive immune response including an immunological memory. A vaccine typically contains an agent that resembles a disease-causing microorganism or a part thereof (e.g. a polypeptide). Vaccines can be prophylactic or therapeutic. The term "vaccine composition", as also used herein, refers to an immunogenic composition of the invention complemented by pharmaceutically acceptable excipients and/or carriers, that when administered to a subject, elicits, or is able to elicit directly or indirectly, an immune response in the host or subject. Particularly, the vaccines of the present invention elicit an immunological response in the host or subject of a cellular or antibody-mediated type upon administration to the subject that it is protective. The vaccine may be a "combination vaccine". The term "combination vaccine" means that the vaccine contains various antigens in a single preparation. The vaccine composition of the invention can be also administered in combination with other vaccine compositions.

The term "bacterium from the species *Brachyspira hyodysenteriae*", as used herein, refers to a spirochete bacterium of a species identified in the NCBI database with the Taxonomy ID: 159. The species *Brachyspira hyodysenteriae* was previously named *Serpulina hyodysenteriae* and *Treponema hyodysenteriae*. The expression "the bacterium" or "a bacterium" should be understood to include also reference to the plural.

The term "strain", as used herein, refers to variants of a bacterial *B. hyodysenteriae* species that can be distinguished by one or more characteristics, such as ribosomal RNA sequence variation, DNA polymorphisms, serological typing, or toxin production, from other variants within that species.

The term "reference strain", as used herein, refers to a specific strain that is widely used within the scientific community or adopted by formally recognized institutions, particularly the *B. hyodysenteriae* reference strain is the *B. hyodysenteriae* strain WA1.

The term "reference sequence", as used herein, refers to a nucleotide or amino acid sequence from the *Brachyspira* spp. reference strain, particularly from *B. hyodysenteriae* strain WA1, to which a particular nucleotide or amino acid sequence can be compared to when identifying the sequence identity between said particular sequence and the reference sequence. The reference sequence can be a nucleotide sequence from any part of the genome, including extrachromosomal elements, or a sequence of a protein encoded in any part of the genome, including extrachromosomal elements. The reference sequence of strain WA1 is identified by the accession number NC_012225.1 in the GenBank database.

The term "plasmid pBH", as used herein, refers to the circular plasmid of about 36 kilobase (kb) present in some *B. hyodysenteriae* strains which comprises an rfbBADC operon. This operon presents a gene arrangement unique to *B. hyodysenteriae*, and it is predicted to be involved in lipooligosaccharide (LOS) biosynthesis. In the particular case of the *B. hyodysenteriae* reference strain WA1 the plasmid pBH is known as pBHWA1 and has 35,940 base pairs. The plasmid of the WA1 reference strain is identified by the accession number NC_012226.1 in the GenBank database. The genes rfbA, rfbB, rfbC, rfbD form an operon on the plasmid pBH of 36 kb in the order rfbBADC in the *B. hyodysenteriae* reference strain WA1 (taxonomy ID 565034 in the NCBI Taxonomy Browser). This operon rfbBADC groups the genes related to the lipooligosaccharide synthesis, and also groups 4 of the 6 rfb genes present in the plasmid. The term plasmid pBH, however, is not restricted to this particular plasmid, but it refers to any plasmid from any *B. hyodysenteriae* strain of about 36 kb comprising the operon rfbBADC.

The term "sequence identity" means that sequences are identical (i.e., on a nucleotide-by-nucleotide basis for nucleic acids or amino acid-by-amino acid basis for polypeptides) over a window of comparison. The percentage of sequence identity is calculated by comparing two optimally aligned sequences over the comparison window, determining the number of positions at which the identical nucleotides or amino acids occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The term "substantially identical" means that two nucleotide or amino acid sequences share at least 60% sequence identity, at least 70%, at least 75%, at least 80%, at least 85%, at least 90%, at least 95%, at least 96%, at least 97%, at least 98, or at least 99% sequence identity over a region of at least 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 nucleotides or amino acids. In a particular embodiment, "substantially identical" means that two nucleotide or amino acid sequences share at least 60% sequence identity, at least 70%, at least 75%, at least 80%, at least 85%, at least 90%, at least 95%, at least 96%, at least 97%, at least 98, or at least 99% sequence identity over the whole length of one of the sequences, or over the whole length of both sequences.

As used herein, the term "isolated" means that the bacterium has been removed from its natural and original environment. The term "isolated" does not necessarily reflect the extent to which the bacterium has been purified.

As used herein, the term "inactivated" refers to a dead/killed or inactivated cell of a microorganism, in this case a bacterium from the species *B. hyodysenteriae*, which is no longer capable growth on a plate having medium specific for said microorganism, and it also encompasses lysates, fractions or extracts of the microorganism. The inactivation of a microorganism refers to any process by which a viable cell is converted to a non-viable cell. The terms "viable", "alive" or "viability", as used herein, refer to the ability of a cell to maintain itself or recover its potentialities and survive until they are able to divide to generate a bacterial progeny. Thus, a cell that is viable or alive indicates that the cell is able to survive and divide; conversely, a cell that is non-viable indicates that the cell is not able to survive and divide. It will be appreciated that non-viable cells include dead/killed cells.

Viability can be determined by a number of assays that are conventional in the art. These include cytolysis or membrane leakage assays, such as the lactate dehydrogenase assay, the propidium iodide assay, the trypan blue assay and the 7-aminoactinomycin D assay, as well as genomic and proteomic assays that test the activation of stress pathways using DNA microarrays and protein chips. Viability can also be determined by checking the absence of cells after their culture in an appropriate culture medium. Therefore, an inactivated *B. hyodysenteriae* is different to an attenuated or live attenuated *B. hyodysenteriae*, wherein the cells are alive and viable.

The bacterium from the species *B. hyodysenteriae* can be inactivated by any suitable means used for inactivating microorganisms and known by the skilled person, either by physical or chemical methods among others, for example, formaldehyde inactivation, microwave inactivation, pressure inactivation, acid inactivation, base inactivation, alcohol inactivation, peroxide inactivation, irradiation and thermal inactivation. In a particular embodiment, the bacterium from the species *B. hyodysenteriae* is inactivated by formaldehyde. In a particular embodiment, formaldehyde inactivation is performed by incubating the bacteria with formaldehyde at 0.01%-1.0% (v/v), for example at 0.05%-0.8% (v/v), at 0.1%-0.5% (v/v), at 0.2% (v/v). In a particular embodiment, formaldehyde inactivation is performed by incubating the bacteria with formaldehyde during 6 hours to 7 days, for example during 8 hours to 5 days, during 10 hours to 2 days, during 12 hours to 36 hours, during 24 hours. In a particular embodiment, formaldehyde inactivation is performed by incubating the bacteria with formaldehyde at 25° C. to 40° C., at 28° C. to 39° C., at 30° C. to 38° C., at 35° C. to 37° C., at 37° C. In a more particular embodiment, formaldehyde inactivation is performed by incubating the bacteria with formaldehyde at 0.2% (v/v) during 24 hours at 37° C.

The term "fucT", "fucT gene" or "gene on the locus BHWA1_02689 of the *B. hyodysenteriae* plasmid identified by the GenBank accession number NC_012226.1" refers to a gene that encodes the protein alpha-1,2-fucosyltransferase and that can be found on the plasmid pBH of about 36 kb of *B. hyodysenteriae*. In a particular embodiment, the gene fucT refers to the gene of the WA1 reference strain of *B. hyodysenteriae*. The fucT gene of the WA1 reference strain of *B. hyodysenteriae* can be found on the locus BHWA1_02689, and has a sequence corresponding to positions 26872 to 28743 in the sequence of the plasmid pBHWA1 identified in the GenBank database by the accession number NC_012226.1 (4 Apr. 2020). The fucT gene of the strain of *B. hyodysenteriae* WA1 has the sequence of SEQ ID NO: 5.

In another particular embodiment, the bacterium from the species *B. hyodysenteriae* comprises a variant of the fucT gene of any strain of *B. hyodysenteriae*.

The term "variant", as used herein, applies to genes of *B. hyodysenteriae*, refers to variants of said genes that appear in other strains of *B. hyodysenteriae* or to artificial variants of said genes, that is, variants that cannot be naturally found in *B. hyodysenteriae*. Variants of the same gene in different strains of the same species or artificial variants may have insertions, deletions or substitutions of one or more base pairs. Variants of the same gene in different strains or artificial variants will have a certain degree of sequence identity, for example, at least 60%, at least 65%, at least 70%, at least 75%, at least 80%, at least 85%, at least 90%, at least 95%, at least 98%, at least 99% or higher sequence identity. The degree of identity between two polynucleotides may be determined using computer algorithms and methods which are widely known to those skilled in the art. The identity between two polynucleotides is preferentially determined using BLASTP algorithm [BLASTManual, Altschul, S. et al., NCBI NLM NIH Bethesda, Md. 20894, Altschul, S., et al., J. Mol. Biol. 215: 403-410 (1990)]. In a preferred embodiment, the sequence identity is determined throughout the whole length of the sequence of the gene from the WA1 reference strain of *B. hyodysenteriae*, or throughout the whole length of the variant or of both.

In a particular embodiment, the variant of the fucT gene has at least 60%, at least 65%, at least 70%, at least 75%, at least 80%, at least 85%, at least 90%, at least 95%, at least 96%, at least 97%, at least 98%, at least 99% or higher sequence identity with the fucT gene.

In a particular embodiment, the variant of the fucT gene comprises or consist of the sequence selected from the group consisting of SEQ ID NO: 17-31.

Strain B-7493 comprises the variant of the fucT gene of SEQ ID NO: 18.

Strain B-7500 comprises the variant of the fucT gene of SEQ ID NO: 30.

Strains B-7482 and B-7484 comprise the variant of the fucT gene of SEQ ID NO: 25.

Strain B-7494 comprises the variant of the fucT gene of SEQ ID NO: 29.

Strain B-8397 comprises the variant of the fucT gene of SEQ ID NO: 22.

In a particular embodiment, the variant of the fucT gene maintains the same function of the fucT gene when the variant replaces the fucT gene on locus BHWA1_02689 from the WA1 reference strain.

In a particular embodiment, the variant of the gene on the locus BHWA1_02689 from the WA1 reference strain that maintains the same function encodes a protein which is an alpha-1,2-fucosyltransferase.

As shown in examples 2-5, the administration of an immunogenic or vaccine composition comprising an isolated and inactivated *B. hyodysenteriae* bacterium comprising a variant of the fucT gene is able to reduce the clinical signs of swine dysentery when administered to pigs that are subsequently infected with *B. hyodysenteriae*. Particularly, immunogenic or vaccine compositions comprising an isolated and inactivated *B. hyodysenteriae* bacterium comprising a variant of the fucT gene reduce the diarrhea score, intestinal lesion score and average daily weight loss and increase survival rate in the vaccinated pigs infected with *B. hyodysenteriae*. Therefore, in a particular embodiment, the administration of an immunogenic or vaccine composition comprising an isolated and inactivated *B. hyodysenteriae* bacterium comprising a variant of the fucT gene induces at least 50%, at least 60%, at least 70%, at least 80%, at least 90%, at least 95%, at least 98%, at least 99%, at least 100% or higher of the reduction in the clinical signs of swine dysentery, particularly diarrhea score, intestinal lesion score and/or average daily weight loss, and/or results in a survival rate of at least 50%, at least 60%, at least 70%, at least 80%, at least 90%, at least 95%, at least 98%, at least 99%, at least 100% or higher, than the immunogenic or vaccine composition comprising an isolated and inactivated *B. hyodysenteriae* bacterium comprising a variant of the fucT gene of sequence SEQ ID NO: 18, 30, 25, 29 and 22.

The term "diarrhea score" refers to a parameter that measures the degree of diarrhea. The diarrhea score can be determined by methods know by the skilled person, for example, the methods described by Burrough E R et al., J Vet Diagn Invest. 2012, 24(6): 1025-34 and by Hansen C F et al., Br J Nutr. 2011, 106(10): 1506-13. In a particular embodiment, the diarrhea score is determined with the following scoring system:

normal stool (no diarrhea): 0 points
pasty stool (consistency of cement, mild diarrhea): 1 point
liquid stool with fecal content (moderate diarrhea): 2 points
watery stool (severe diarrhea, does not look like stool): 3 points
presence of mucus: 0.5 points
presence of blood: 0.5 points In a particular embodiment, the vaccine composition of the invention or the vaccine composition obtained by the first method of the invention induces a reduction in the diarrhea score after 1 to 200 days post-vaccination, for example after 2 to 190 days post-vaccination, after 3 to 180 days post-vaccination, after 4 to 170 days post-vaccination, after 5 to 150 days post-vaccination, after 6 to 130 days post-vaccination, after 7 to 100 days post-vaccination, after 10 to 75 days post-vaccination, after 12 to 50 days post-vaccination, after 15 to 25 days post-vaccination, after 20 days post-vaccination, in subjects suffering from an infection by a bacterium from the species *B. hyodysenteriae*. The term "reduction in the diarrhea score" refers to any reduction compared with non-vaccinated control subjects, for example, a reduction of at least 5%, at least 10%, at least 20%, at least 30%, at least 40%, at least 50%, at least 60%, at least 70%, at least 80%, at least 90%, at least 95%, at least 100% or higher.

The term "intestinal lesion score" refers to a parameter that measures the degree of lesion in the intestine of a subject. In a particular embodiment, the intestinal lesion score is determined with the following scoring system:

absence of lesion: 0 points
mild enteritis, lesions in specific areas, normal or pasty content: 1 point
moderate enteritis, extensive lesions, diarrheal content: 2 points
severe enteritis, severely damaged or atrophic intestine, watery/blood stools, fibrin: 3 points
very severe enteritis, totally atrophic intestine, completely ulcerated mucosa: 4 points.

In another particular embodiment, the intestinal lesion score is determined with the following scoring system:

absence of lesion: 0 points
mild enteritis, lesions in specific areas, normal or pasty content: 1 point
moderate enteritis, extensive lesions, diarrheal content: 2 points
severe enteritis, severely damaged or atrophic intestine, watery/blood stools, fibrin: 3 points.

In a particular embodiment, the vaccine composition of the invention or the vaccine composition obtained by the first method of the invention induces a reduction in the intestinal lesion score after 1 to 200 days post-vaccination, for example after 2 to 190 days post-vaccination, after 3 to 180 days post-vaccination, after 4 to 170 days post-vaccination, after 5 to 150 days post-vaccination, after 6 to 130 days post-vaccination, after 7 to 100 days post-vaccination, after 10 to 75 days post-vaccination, after 12 to 50 days post-vaccination, after 15 to 25 days post-vaccination, after 20 days post-vaccination, in subjects suffering from an infection by a bacterium from the species *Brachyspira hyodysenteriae*. The term "reduction in the intestinal lesion score" refers to any reduction compared with non-vaccinated control subjects, for example, a reduction of at least 5%, at least 10%, at least 20%, at least 30%, at least 40%, at least 50%, at least 60%, at least 70%, at least 80%, at least 90%, at least 95%, at least 100% or higher.

The term "daily weight loss", as used herein, refers to the average weight the subject loss per day during a period of time after being infected with a bacterium of the species *B. hyodysenteriae*. In a particular embodiment, the vaccine composition of the invention or the vaccine composition obtained by the first method of the invention induces a reduction in the daily weight loss after 1 to 200 days post-vaccination, for example after 2 to 190 days post-vaccination, after 3 to 180 days post-vaccination, after 4 to 170 days post-vaccination, after 5 to 150 days post-vaccination, after 6 to 130 days post-vaccination, after 7 to 100 days post-vaccination, after 10 to 75 days post-vaccination, after 12 to 50 days post-vaccination, after 15 to 25 days post-vaccination, after 20 days post-vaccination, in subjects suffering from an infection by a bacterium from the species *Brachyspira hyodysenteriae*. The term "reduction in the daily weight loss" refers to any reduction compared with non-vaccinated control subjects, for example, a reduction of at least 5%, at least 10%, at least 20%, at least 30%, at least 40%, at least 50%, at least 60%, at least 70%, at least 80%, at least 90%, at least 95%, at least 100% or higher.

The term "survival rate", as used herein, refers to the percentage of subjects diagnosed with a disease, such as a subject with an infection by a bacterium of the species *Brachyspira hyodysenteriae*, that are alive after a certain period of time. In a particular embodiment, the vaccine composition of the invention or the vaccine composition obtained by the first method of the invention induces an increase in the survival rate after 1 to 200 days post-vaccination, for example after 2 to 190 days post-vaccination, after 3 to 180 days post-vaccination, after 4 to 170 days post-vaccination, after 5 to 150 days post-vaccination, after 6 to 130 days post-vaccination, after 7 to 100 days post-vaccination, after 10 to 75 days post-vaccination, after 12 to 50 days post-vaccination, after 15 to 25 days post-vaccination, after 20 days post-vaccination, in subjects suffering from an infection by a bacterium from the species *Brachyspira hyodysenteriae*. The term "increased in the survival rate" refers to any increased compared with non-vaccinated control subjects, for example, an increase of at least 5%, at least 10%, at least 20%, at least 30%, at least 40%, at least 50%, at least 60%, at least 70%, at least 80%, at least 90%, at least 95%, at least 100% or higher.

In a particular embodiment of the immunogenic or vaccine composition of the invention, the fucT gene or the variant thereof is comprised in a gene cluster, and the bacterium is a S1 or a S2 bacterium, wherein the gene cluster of the S1 bacterium comprises the following genes: the gene on the locus BHWA1_02695 (bcsA) of the *B. hyodysenteriae* plasmid pBHWA1 identified by the GenBank accession number NC_012226.1 or a variant of said gene of any strain of *B. hyodysenteriae*, the rfbC gene, the rfbD gene, the rfbA gene, the rfbB gene, the gene on the locus BHWA1_02690 (rgpF) of the *B. hyodysenteriae* plasmid pBHWA1 identified by the GenBank accession number NC_012226.1 or a variant of said gene of any strain of *B. hyodysenteriae* and the fucT gene or a variant of said gene of any strain and the gene cluster of the S2 bacterium comprises the following genes: the gene on the locus BHWA1_02695 (bcsA) of the *B. hyodysenteriae* plasmid pBHWA1 identified by the GenBank accession number NC_012226.1 or a variant of said gene of any strain of *B. hyodysenteriae*, the rfbC gene, the rfbD gene, the rfbA gene, a gene having the sequence of SEQ ID NO: 8 (adoM) or a variant of said gene of any strain of *B. hyodysenteriae*, the rfbB gene, the gene on the locus BHWA1_02690 (rgpF) of the *B. hyodysenteriae* plasmid pBHWA1 identified by the GenBank accession number NC_012226.1 or a variant of said gene of any strain of *B. hyodysenteriae* and the fucT gene or a variant of said gene of any strain of *B. hyodysenteriae*.

The term "gene cluster" as used herein, refers to a set of closely linked genes that encode functionally-related products and that usually grouped together in the genome. In the context of the composition of the invention, the gene cluster refers to a cluster comprising the rfbBADC operon and other related genes.

The term "operon", as used herein, refers to a genetic unit that controls gene expression in prokaryotes. An operon typically comprises one or more genes that encode one or more polypeptide(s) or RNA(s) and the adjacent regulatory region (or regions) that controls the transcription of the genes. The regulatory region typically comprises a promoter and an operator. The coding region of a prokaryotic gene is historically termed a "cistron." Operons that contain multiple cistrons are termed "polycistronic." The genes in a polycistronic operon are typically related in function and are typically co-transcribed as a single unit and expressed in a coordinated manner.

The term "rfb operon" or "rfbAD operon" or "rfbBADC" operon, as used herein, refers to an operon that groups several genes related to the lipooligosaccharide synthesis, including 4 of the 6 rfb genes present in the plasmid pBH of *B. hyodysenteriae*. The term "rfb genes" refers to 6 genes, named rfbA, rfbB, rfbC, rfbD, rfbE and rfbF. The rfb operon of *B. hyodysenteriae* includes the genes rfbA, rfbB, rfbC and rfbD and is described by Bellgard et al., PLoS ONE 2009, 4(3) e4641.

The gene cluster comprising the rfb operon of *B. hyodysenteriae* also comprises the genes bcsA, rgpF and optionally adoM and fucT. The structure of the gene cluster is what differentiates S1, S2, S3 and S0 *B. hyodysenteriae* bacteria as explained before.

Therefore, in a particular embodiment, the gene cluster comprising the rfb operon of *B. hyodysenteriae* comprises or consist of the genes bcsA, rfbC, rfbD, rfbA, rfbB, rgpF and fucT (gene cluster from S1 bacteria). In a more particular embodiment, the gene cluster comprising the rfb operon comprises or consists of, from the 5' to the 3' end, the genes bcsA, rfbC, rfbD, rfbA, rfbB, rgpF and fucT.

In another particular embodiment, the gene cluster comprising the rfb operon of *B. hyodysenteriae* comprises or consists of the genes bcsA, rfbC, rfbD, rfbA, adoM, rfbB, rgpF and fucT (gene cluster from S2 bacteria). In a more particular embodiment, the gene cluster comprising the rfb operon comprises or consists of, from the 5' to the 3' end, the genes bcsA, rfbC, rfbD, rfbA, adoM, rfbB, rgpF and fucT.

In another particular embodiment, the gene cluster comprising the rfb operon of *B. hyodysenteriae* comprises or consists of the genes bcsA, rfbC, rfbD, rfbA, adoM, rfbB and rgpF and does not comprise the gene fucT (gene cluster from S3 bacteria). In a more particular embodiment, the gene cluster comprising the rfb operon comprises or consists of, from the 5' to the 3' end, the genes bcsA, rfbC, rfbD, rfbA, AdoM, rfbB and rgpF.

The term "S1 bacterium", as used herein, refers to a strain or a bacterium from the species *B. hyodysenteriae* comprising a gene cluster comprising or consisting of the genes bcsA, rfbC, rfbD, rfbA, rfbB, rgpF and fucT, or variants of said genes of any strain of *B. hyodysenteriae*. In a particular embodiment, the S1 bacterium comprises a gene cluster comprising or consisting of, from the 5' to the 3' end, the genes bcsA, rfbC, rfbD, rfbA, rfbB, rgpF and fucT. In a more particular embodiment, the S1 bacterium does not comprise the gene adoM.

The term "S2 bacterium", as used herein, refers to a strain or a bacterium from the species *B. hyodysenteriae* comprising a gene cluster comprising or consisting of the genes bcsA, rfbC, rfbD, rfbA, adoM, rfbB, rgpF and fucT. In a particular embodiment, the S2 bacterium comprises a gene cluster comprising or consisting of, from the 5' to the 3' end, the genes bcsA, rfbC, rfbD, rfbA, adoM, rfbB, rgpF and fucT.

The term "S3 bacterium", as used herein, refers to a strain or a bacterium from the species *B. hyodysenteriae* comprising a gene cluster comprising or consisting of the genes bcsA, rfbC, rfbD, rfbA, adoM, rfbB and rgpF. In a particular embodiment, the S3 bacterium comprises a gene cluster comprising or consisting of, from the 5' to the 3' end, the genes bcsA, rfbC, rfbD, rfbA, adoM, rfbB and rgpF. In a more particular embodiment, the S3 bacterium does not comprise the gene fucT.

In a particular embodiment, the S1, S2 and S3 bacterium comprises the gene cluster in the plasmid pBH.

In a particular embodiment, the S1 and S2 bacterium comprises the gene cluster comprising the fucT gene in the plasmid pBH.

The term "S0 bacterium", as used herein, refers to a strain or a bacterium from the species *B. hyodysenteriae* that does not comprise the plasmid pBH. In a particular embodiment, the S0 bacterium does not comprise an rfb operon. In a more particular embodiment, the S0 bacterium does not comprise any of the genes bcsA, rfbC, rfbD, rfbA, rfbB, rgpF, fucT and adoM.

In a particular embodiment, the immunogenic or vaccine composition comprises a S1 bacterium, and the S1 bacterium comprises gene cluster comprising or consisting of, from the 5' to the 3' end, the genes bcsA, rfbC, rfbD, rfbA, rfbB, rgpF and fucT.

In another particular embodiment, the immunogenic or vaccine composition comprises a S2 bacterium, and the S2 bacterium comprises a gene cluster comprising or consisting of, from the 5' to the 3' end, the genes bcsA, rfbC, rfbD, rfbA, adoM, rfbB, rgpF and fucT.

The term "rfbA" refers to a gene that encodes the protein glucose-1-phosphate thymidylyltransferase and that can be found on the plasmid pBH of *B. hyodysenteriae*. The rfbA gene can be from a bacterium from any strain of *B. hyodysenteriae*. In a particular embodiment, the rfbA gene refers to the gene of the WA1 reference strain of *B. hyodysenteriae*. The rfbA gene of the WA1 reference strain of *B. hyodysenteriae* can be found on the locus BHWA1_02692, and has a sequence corresponding to positions 30900 to 31763 in the sequence of the plasmid pBHWA1 identified in the GenBank database by the accession number NC_012226.1 (4 Apr. 2020). The rfbA gene of the reference strain of *B. hyodysenteriae* WA1 has the sequence of SEQ ID NO: 1.

In a particular embodiment, the rfbA gene is the gene of the reference strain WA1 of *B. hyodysenteriae* WA1 or a variant of said gene of any strain of *B. hyodysenteriae.*

In a particular embodiment, the variant of the rfbA gene from the WA1 reference strain has at least 60%, at least 65%, at least 70%, at least 75%, at least 80%, at least 85%, at least 90%, at least 95%, at least, 96%, at least 97%, at least 98%, at least 99% or higher sequence identity with the rfbA gene from the WA1 reference strain.

In a particular embodiment, the variant of the rfbA gene from the WA1 reference strain comprises or consist of a sequence selected from the group consisting of SEQ ID NO: 32-44.

- Strain B-7482 comprises the variant of the rfbA gene of SEQ ID NO: 32.
- Strains B-7484 and B-8397 comprise the variant of the rfbA gene of SEQ ID NO: 34.
- Strain B-7494 comprises the variant of the rfbA gene of SEQ ID NO: 44.
- Strain B-7500 comprises the variant of the rfbA gene of SEQ ID NO: 39.
- Strain B-8295 comprises the variant of the rfbA gene of SEQ ID NO: 41.
- Strain B-7493 comprises the variant of the rfbA gene of SEQ ID NO: 42.

In a particular embodiment, the variant of the rfbA gene from the WA1 reference strain maintains the same function of the rfbA gene from the WA1 reference strain. In a particular embodiment, the expression "maintains the same function" means that the variant is capable of performing the same function as the rfbA gene of the WA1 reference strain when forming part of the rfb operon instead of the rfbA gene of the *B. hyodysenteriae* reference strain WA1 and together with the rest of the genes of the operon. In a more particular embodiment, the variant maintains the function of the rfbA gene when it is found in a gene cluster comprising or consisting of

- the genes bcsA, rfbC, rfbD, rfbA, rfbB, rgpF and fucT, more particularly, from the 5' to the 3' end, the genes bcsA, rfbC, rfbD, rfbA, rfbB, rgpF and fucT (gene cluster from S1 bacterium),
- the genes bcsA, rfbC, rfbD, rfbA, adoM, rfbB, rgpF and fucT, more particularly, from the 5' to the 3' end, the genes bcsA, rfbC, rfbD, rfbA, adoM, rfbB, rgpF and fucT (gene cluster from S2 bacterium);
- the genes bcsA, rfbC rfbD, rfbA, adoM, rfbB and rbpF, wherein the operon does not comprise the gene fucT; more particularly, from the 5' to the 3' end, the genes bcsA, rfbC, rfbD, rfbA, AdoM, rfbB and rgpF (gene cluster from S3 bacterium).

In a particular embodiment, the administration of an immunogenic or vaccine composition comprising an isolated and inactivated *B. hyodysenteriae* bacterium comprising a variant of the rfbA gene induces at least 50%, at least 60%, at least 70%, at least 80%, at least 90%, at least 95%, at least 98%, at least 99%, at least 100% or higher of the reduction in the clinical signs of swine dysentery, particularly diarrhea score, intestinal lesion score and/or average daily weight loss, and/or results in a survival rate of at least 50%, at least 60%, at least 70%, at least 80%, at least 90%, at least 95%, at least 98%, at least 99%, at least 100% or higher, than the immunogenic or vaccine composition comprising an isolated and inactivated *B. hyodysenteriae* bacterium comprising a variant of rfbA comprising or consisting of the sequence of SEQ ID NO: 32, 34, 44, 39, 41 and 42.

In a particular embodiment, the variant of the rfbA gene from the WA1 reference strain encodes a protein which is a glucose-1-phosphate thymidylyltransferase.

The term "rfbB" refers to a gene that encodes the protein dTDP-glucose 4,6-dehydratase and that can be found on the plasmid pBH of *B. hyodysenteriae*. The rfbB gene can be from a bacterium from any strain of *B. hyodysenteriae*. In a particular embodiment, the gene rfbB refers to the gene of the WA1 reference strain of *B. hyodysenteriae*. The gene rfbB of the WA1 reference strain of *B. hyodysenteriae* can be found on the locus BHWA1_02691, and has a sequence corresponding to positions 29816 to 30886 in the sequence of the plasmid pBHWA1 identified in the GenBank database by the accession number NC_012226.1 (4 Apr. 2020). The rfbB gene of the reference strain of *B. hyodysenteriae* WA1 has the sequence of SEQ ID NO: 2.

In a particular embodiment, the rfbB gene is the gene of the WA1 reference strain of *B. hyodysenteriae* or a variant of said gene of any strain of *B. hyodysenteriae.*

In a particular embodiment, the variant of the rfbB gene from the WA1 reference strain has at least 60%, at least 65%, at least 70%, at least 75%, at least 80%, at least 85%, at least 90%, at least 95%, at least 96%, at least 97%, at least 98%, at least 99% or higher sequence identity with the rfbB gene from the WA1 reference strain.

In a particular embodiment, the variant of the rfbB gene from the WA1 reference strain comprises or consist of a sequence selected from the group consisting of SEQ ID NO: 45-54.

- Strain B-7482 comprises a variant of the rfbB gene of sequence SEQ ID NO: 45.
- Strain B-7493 comprises a variant of the rfbB gene of sequence SEQ ID NO: 46.
- Strain B-7500 comprises a variant of the rfbB gene of sequence SEQ ID NO: 49.
- Strain B-8295 comprises a variant of the rfbB gene of sequence SEQ ID NO: 52.
- Strains B-7484, B-7494 and B-8397 comprise a variant of the rfbB gene of sequence SEQ ID NO: 53.

In a particular embodiment, the variant of the rfbB gene from the reference WA1 strain maintains the same function of the rfbB gene from the WA1 strain. In a particular embodiment, the variant is capable of performing the same function as the rfbB gene of the WA1 reference strain when forming part of the rfb operon instead of the rfbB gene of the *B. hyodysenteriae* reference strain WA1 and together with the rest of the genes of the operon. In a more particular embodiment, the variant maintains the function of the rfbB gene when it is found in a gene cluster comprising or consisting of the genes previously indicated for the gene cluster comprising the rfb operon from S1, S2 or S3 bacterium.

In a particular embodiment, the administration of an immunogenic or vaccine composition comprising an isolated and inactivated *B. hyodysenteriae* bacterium comprising a variant of the rfbB gene induces at least 50%, at least 60%, at least 70%, at least 80%, at least 90%, at least 95%, at least 98%, at least 99%, at least 100% or higher of the reduction in the clinical signs of swine dysentery, particularly diarrhea score, intestinal lesion score and/or average daily weight loss, and/or results in a survival rate of at least 50%, at least 60%, at least 70%, at least 80%, at least 90%, at least 95%, at least 98%, at least 99%, at least 100% or higher, than the immunogenic or vaccine composition comprising an isolated and inactivated *B. hyodysenteriae* bacterium comprising a variant of rfbB comprising or consisting of the sequence of SEQ ID NO: 45, 46, 49, 52 and 53.

In a particular embodiment, the variant of the rfbB gene from the WA1 reference strain encodes a protein which is a dTDP-glucose 4,6-dehydratase.

The term "rfbC" refers to a gene that encodes the protein dTDP-4-dehydrorhamnose 3,5-epimerase and that can be found on the plasmid pBH of *B. hyodysenteriae*. The rfbC gene can be from a bacterium from any strain of *B. hyodysenteriae*. In a particular embodiment, the gene rfbC refers to the gene of the WA1 reference strain of *B. hyodysenteriae*. The gene rfbC of the WA1 reference strain of *B. hyodysenteriae* can be found on the locus BHWA1_02694, and has a sequence corresponding to positions 32648 to 33226 in the sequence of the plasmid pBHWA1 identified in the GenBank database by the accession number NC_012226.1 (4 Apr. 2020). The rfbC gene of the reference strain of *B. hyodysenteriae* WA1 has the sequence of SEQ ID NO: 3.

In a particular embodiment, the rfbC gene is the gene of the WA1 reference strain of *B. hyodysenteriae* or a variant of said gene of any strain of *B. hyodysenteriae.*

In a particular embodiment, the variant of the rfbC gene from the WA1 reference strain has at least 60%, at least 65%, at least 70%, at least 75%, at least 80%, at least 85%, at least 90%, at least 95%, at least 96%, at least 97%, at least 98%, at least 99% or higher sequence identity with the rfbC gene from the WA1 reference strain.

In a particular embodiment, the variant of the rfbC gene from the WA1 reference strain comprises or consist of a sequence selected from the group consisting of SEQ ID NO: 55-61.

Strains B-7482, B-7500, B-7484, B-7494 and B-8397 comprise the rfbC gene of sequence SEQ ID NO: 3.

Strain B-8295 comprises a variant of the rfbC gene of sequence SEQ ID NO: 61.

Strain B-7493 comprises a variant of the rfbC gene of sequence SEQ ID NO: 57.

In a particular embodiment, the variant of the rfbC gene from the WA1 reference strain that maintains the same function encodes a protein which is a dTDP-4-dehydrorhamnose 3,5-epimerase.

In a particular embodiment, the variant of the rfbC gene from the WA1 reference strain maintains the same function of the rfbC gene from the WA1 reference strain. In a particular embodiment, the variant is capable of performing the same function as the rfbC gene of the WA1 reference strain when forming part of the rfb operon instead of the rfbC gene of the *B. hyodysenteriae* reference strain WA1 and together with the rest of the genes of the operon. In a more particular embodiment, the variant maintains the function of the rfbC gene when it is found in a gene cluster comprising or consisting of the genes previously indicated for the gene cluster comprising the rfb operon from S1, S2 or S3 bacterium.

In a particular embodiment, the administration of an immunogenic or vaccine composition comprising an isolated and inactivated *B. hyodysenteriae* bacterium comprising a variant of the rfbC gene induces at least 50%, at least 60%, at least 70%, at least 80%, at least 90%, at least 95%, at least 98%, at least 99%, at least 100% or higher of the reduction in the clinical signs of swine dysentery, particularly diarrhea score, intestinal lesion score and/or average daily weight loss, and/or results in a survival rate of at least 50%, at least 60%, at least 70%, at least 80%, at least 90%, at least 95%, at least 98%, at least 99%, at least 100% or higher, than the immunogenic or vaccine composition comprising an isolated and inactivated *B. hyodysenteriae* bacterium comprising the rfbC gene of sequence SEQ ID NO: 3 or a variant of rfbC comprising or consisting of the sequence of SEQ ID NO: 61 and 57.

The term "rfbD" refers to a gene that encodes the protein dTDP-4-dehydrorhamnose reductase and that can be found on the plasmid pBH of *B. hyodysenteriae*. The rfbD gene can be from a bacterium from any strain of *B. hyodysenteriae*. In a particular embodiment, the gene rfbD refers to the gene of the WA1 reference strain of *B. hyodysenteriae*. The gene rfbD of the WA1 reference strain of *B. hyodysenteriae* can be found on the locus BHWA1_02693, and has a sequence corresponding to positions 31782 to 32642 in the sequence of the plasmid pBHWA1 identified in the GenBank database by the accession number NC_012226.1 (4 Apr. 2020). The rfbD gene of the strain of *B. hyodysenteriae* WA1 has the sequence of SEQ ID NO: 4.

In a particular embodiment, the rfbD gene is the gene of the WA1 reference strain of *B. hyodysenteriae* or a variant of said gene of any strain of *B. hyodysenteriae.*

In a particular embodiment, the variant of the rfbD gene from the WA1 reference strain has at least 60%, at least 65%, at least 70%, at least 75%, at least 80%, at least 85%, at least 90%, at least 95%, at least 96%, at least 97%, at least 98%, at least 99% or higher sequence identity with the rfbD gene from the WA1 reference strain.

In a particular embodiment, the variant of the rfbD gene from the WA1 reference strain comprises or consist of a sequence selected from the group consisting of SEQ ID NO: 62-68.

Strains B-7482 and B-8295 comprise the rfbD gene of sequence SEQ ID NO: 4.

Strains B-7500, B-7484, B-7494 and B-8397 comprise a variant of the rfbD gene of sequence SEQ ID NO: 62.

Strain B-7493 comprises a variant of the rfbD gene of sequence SEQ ID NO: 68.

In a particular embodiment, the variant of the rfbD gene from the WA1 reference strain that maintains the same function encodes a protein which is a dTDP-4-dehydrorhamnose 3,5-epimerase.

In a particular embodiment, the variant of the rfbD gene from the WA1 reference strain maintains the same function of the rfbD gene from the WA1 reference strain. In a particular embodiment, the variant is capable of performing the same function as the rfbD gene of the WA1 reference strain when forming part of the rfb operon instead of the rfbD gene of the *B. hyodysenteriae* reference strain WA1 and together with the rest of the genes of the operon. In a more particular embodiment, the variant maintains the function of the rfbD gene when it is found in a gene cluster comprising or consisting of the genes previously indicated for the gene cluster comprising the rfb operon from S1, S2 or S3 bacterium.

In a particular embodiment, the administration of an immunogenic or vaccine composition comprising an isolated and inactivated *B. hyodysenteriae* bacterium comprising a variant of the rfbD gene induces at least 50%, at least 60%, at least 70%, at least 80%, at least 90%, at least 95%, at least 98%, at least 99%, at least 100% or higher of the reduction in the clinical signs of swine dysentery, particularly diarrhea score, intestinal lesion score and/or average daily weight loss, and/or results in a survival rate of at least 50%, at least 60%, at least 70%, at least 80%, at least 90%, at least 95%, at least 98%, at least 99%, at least 100% or higher, than the immunogenic or vaccine composition comprising an isolated and inactivated *B. hyodysenteriae* bacterium comprising the rfbD gene of sequence SEQ ID NO: 4 or a variant of rfbD comprising or consisting of the sequence of SEQ ID NO: 62 and 68.

The term "rgpF" or "gene on the locus BHWA1_02690 of the *B. hyodysenteriae* plasmid identified by the GenBank accession number NC_012226.1" refers to a gene that encodes the lipopolysaccharide biosynthesis protein-like protein and that can be found on the plasmid pBH of *B. hyodysenteriae*. The rgpF gene can be from a bacterium from any strain of *B. hyodysenteriae*. In a particular embodiment, the rgpF gene refers to the gene of the WA1 reference strain of *B. hyodysenteriae*. The rgpF gene of the WA1 reference strain of *B. hyodysenteriae* can be found on the locus BHWA1_02690, and has a sequence corresponding to positions 28827 to 29807 in the sequence of the plasmid pBHWA1 identified in the GenBank database by the accession number NC_012226.1 (4 Apr. 2020). The rgpF gene of the reference strain of *B. hyodysenteriae* WA1 has the sequence of SEQ ID NO: 6.

In a particular embodiment, the rgpF gene is a variant of said gene of any strain of *B. hyodysenteriae*.

In a particular embodiment, the variant of the rgpF gene has at least 60%, at least 65%, at least 70%, at least 75%, at least 80%, at least 85%, at least 90%, at least 95%, at least 96%, at least 97%, at least 98%, at least 99% or higher sequence identity with the rgpF gene.

In a particular embodiment, the variant of the gene rgpF comprises or consist of a sequence selected from the group consisting of SEQ ID NO: 69-76.

Strains B-7482, B-8295, B-7484, B-7494 and B-8397 comprise a variant of the rgpF gene of sequence SEQ ID NO: 71.

Strain B-7493 comprises a variant of the rgpF gene of sequence SEQ ID NO: 74.

Strain B-7500 comprises a variant of the rgpF gene of sequence SEQ ID NO: 75.

In a particular embodiment, the variant of rgpF maintains the same function of the gene rgpF. In a particular embodiment, the variant is capable of performing the same function as the gene rgpF when forming part of the gene cluster comprising the rfb operon instead of the gene of the *B. hyodysenteriae* reference strain WA1 located on locus BHWA1_02690 and together with the rest of the genes of the gene cluster. In a more particular embodiment, the variant maintains the function of the gene rgpF when it is found in a gene cluster comprising or consisting of the genes previously indicated for a gene cluster comprising the rfb operon from S1, S2 or S3 bacterium.

In a particular embodiment, the administration of an immunogenic or vaccine composition comprising an isolated and inactivated *B. hyodysenteriae* bacterium comprising a variant of the rgpF gene induces at least 50%, at least 60%, at least 70%, at least 80%, at least 90%, at least 95%, at least 98%, at least 99%, at least 100% or higher of the reduction in the clinical signs of swine dysentery, particularly diarrhea score, intestinal lesion score and/or average daily weight loss, and/or results in a survival rate of at least 50%, at least 60%, at least 70%, at least 80%, at least 90%, at least 95%, at least 98%, at least 99%, at least 100% or higher, than the immunogenic or vaccine composition comprising an isolated and inactivated *B. hyodysenteriae* bacterium comprising a variant of rgpF comprising or consisting of the sequence of SEQ ID NO: 71, 74 and 75.

In a particular embodiment, the variant of the rgpF gene that maintains the same function as the rgpF gene encodes a lipopolysaccharide biosynthesis protein-like protein.

The term "bcsA" or "gene on the locus BHWA1_02695 of the *B. hyodysenteriae* plasmid identified by the GenBank accession number NC_012226.1" refers to a gene that encodes a glycosyltransferase family 2 protein and that can be found on the plasmid pBH of *B. hyodysenteriae*. The bcsA gene can be from a bacterium from any strain of *B. hyodysenteriae*. In a particular embodiment, the bcsA gene refers to the gene of the WA1 reference strain of *B. hyodysenteriae*. The bcsA gene of the WA1 reference strain of *B. hyodysenteriae* can be found on the locus BHWA1_02695 of the plasmid of WA1 reference strain of *B. hyodysenteriae*, and has a sequence corresponding to positions 33234 to 34421 in the sequence of the plasmid pBHWA1 identified in the GenBank database by the accession number NC_012226.1 (4 Apr. 2020). The bcsA gene can be from a bacterium from any strain of *B. hyodysenteriae*. In a particular embodiment, the gene bcsA refers to the gene of the WA1 reference strain of *B. hyodysenteriae*. The bcsA gene of the reference strain of *B. hyodysenteriae* WA1 has the sequence of SEQ ID NO: 7.

In a particular embodiment, the gene cluster comprises a variant of the bcsA gene of any strain of *B. hyodysenteriae*.

In a particular embodiment, the variant of the bcsA gene has at least 60%, at least 65%, at least 70%, at least 75%, at least 80%, at least 85%, at least 90%, at least 95%, at least 96%, at least 97%, at least 98%, at least 99% or higher sequence identity with the bcsA gene.

In a particular embodiment, the variant of the bcsA gene comprises or consist of a sequence selected from the group consisting of SEQ ID NO: 77-81.

Strain B-7500 comprises a variant of the bcsA gene of sequence SEQ ID NO: 77.

Strain B-7484 comprises a variant of the bcsA gene of sequence SEQ ID NO: 81.

Strains B-7482, B-7493, B-8295, B-7494 and B-8397 comprise the bcsA gene of sequence SEQ ID NO: 7.

In a particular embodiment, the variant of the bcsA gene maintains the same function of the gene bcsA. In a particular embodiment, the variant is capable of performing the same function as the gene bcsA when forming part of the gene cluster instead of the gene of the *B. hyodysenteriae* reference strain WA1 on the locus BHWA1_02695 and together with the rest of the genes of the gene cluster. In a more particular embodiment, the variant maintains the function of the gene on the locus BHWA1_02695 when it is found in gene cluster comprising or consisting of the genes previously indicated for the gene cluster comprising the rfb operon from S1, S2 or S3 bacterium.

In a particular embodiment, the variant of the bcsA gene that maintains the same function as the bcsA gene encodes a glycosyltransferase family 2 protein.

In a particular embodiment, the administration of an immunogenic or vaccine composition comprising an isolated and inactivated *B. hyodysenteriae* bacterium comprising a variant of the bcsA gene induces at least 50%, at least 60%, at least 70%, at least 80%, at least 90%, at least 95%, at least 98%, at least 99%, at least 100% or higher of the reduction in the clinical signs of swine dysentery, particularly diarrhea score, intestinal lesion score and/or average daily weight loss, and/or results in a survival rate of at least 50%, at least 60%, at least 70%, at least 80%, at least 90%, at least 95%, at least 98%, at least 99%, at least 100% or higher, than the immunogenic or vaccine composition comprising an isolated and inactivated *B. hyodysenteriae* bacterium comprising the bcsA gene of sequence SEQ ID NO: 7 or a variant of bcsA comprising or consisting of the sequence of SEQ ID NO: 77 or 81.

The term "gene having the sequence of SEQ ID NO: 8" or "adoM" refers to a gene that encodes a methyltransferase domain-containing protein. The adoM gene can be from a bacterium from any strain of *B. hyodysenteriae.*

In a particular embodiment, the gene cluster comprises a variant of the adoM gene of any strain of *B. hyodysenteriae.*

In a particular embodiment, the variant of the adoM gene has at least 60%, at least 65%, at least 70%, at least 75%, at least 80%, at least 85%, at least 90%, at least 95%, at least 96%, at least 97%, at least 98%, at least 99% or higher sequence identity with the sequence of the adoM gene.

In a particular embodiment, the variant of the adoM gene comprises or consist of the sequence of SEQ ID NO: 82.

Strains B-7484, B-7494 and B-8397 comprise the adoM gene of sequence SEQ ID NO: 8.

In a particular embodiment, the variant of the adoM gene maintains the same function of the gene adoM. In a particular embodiment, the variant is capable of performing the same function as the gene adoM when forming part of the gene cluster instead of the gene adoM of SEQ ID NO:8 and together with the rest of the genes of the gene cluster. In a more particular embodiment, the variant maintains the function of the adoM gene when it is found in gene cluster comprising or consisting of the genes previously indicated for the gene cluster comprising the rfb operon from S2 or S3 bacterium.

In a particular embodiment, the administration of an immunogenic or vaccine composition comprising an isolated and inactivated *B. hyodysenteriae* bacterium comprising a variant of the adoM gene induces at least 50%, at least 60%, at least 70%, at least 80%, at least 90%, at least 95%, at least 98%, at least 99%, at least 100% or higher of the reduction in the clinical signs of swine dysentery, particularly diarrhea score, intestinal lesion score and/or average daily weight loss, and/or results in a survival rate of at least 50%, at least 60%, at least 70%, at least 80%, at least 90%, at least 95%, at least 98%, at least 99%, at least 100% or higher, than the immunogenic or vaccine composition comprising an isolated and inactivated *B. hyodysenteriae* bacterium comprising a the adoM gene of sequence SEQ ID NO: 8.

In a particular embodiment, the variant of the adoM gene encodes a methyltransferase domain-containing protein.

In a particular embodiment, the S1 bacterium is a bacterium from a strain selected from the group consisting of B-7493, B-7500, B-8295, and B-7482.

The strain B-7500 corresponds to a strain of *B. hyodysenteriae* deposited by HIPRA SCIENTIFIC S.L.U. (Avda. La Selva, 135-17160, Amer, Girona, Spain) in the Leibniz-Institut DSMZ-Deutsche Sammlung von Mikroorganismen und Zellkulturen GmbH (Inhoffenstr. 7 B, D-38124 Braunschweig, Germany) under accession number DSM 33602 on Jul. 29, 2020.

The strain B-8295 corresponds to a strain of *B. hyodysenteriae* deposited by HIPRA SCIENTIFIC S.L.U. (Avda. La Selva, 135-17160, Amer, Girona, Spain) in the Leibniz-Institut DSMZ-Deutsche Sammlung von Mikroorganismen und Zellkulturen GmbH (Inhoffenstr. 7 B, D-38124 Braunschweig, Germany) under accession number DSM 33603 on Jul. 29, 2020.

In a particular embodiment, the S2 bacterium is a bacterium from a strain selected from the group consisting of B-7484, B-7494, and B-8397.

The strain B-8397 corresponds to a strain of *B. hyodysenteriae* deposited by HIPRA SCIENTIFIC S.L.U. (Avda. La Selva, 135-17160, Amer, Girona, Spain) in the Leibniz-Institut DSMZ-Deutsche Sammlung von Mikroorganismen und Zellkulturen GmbH (Inhoffenstr. 7 B, D-38124 Braunschweig, Germany) under accession number DSM 33604 on Jul. 29, 2020.

In a particular embodiment, the immunogenic or vaccine composition comprises or consists of at least two strains of a S1 bacterium. In a particular embodiment, the two strains are selected from the group consisting of B-7493, B-7500, B-8295 and B-7482. In a more particular embodiment, the two strains are B-7500 and B-8295.

In another particular embodiment, the immunogenic or vaccine composition comprises at least two strains of a S2 bacterium. In a particular embodiment, the two strains are selected from the group consisting of B-8397, B-7484, and B-7494. In a more particular embodiment, the two strains are B-8397 and B-7484.

In another particular embodiment, the immunogenic or vaccine composition comprises at least two strains of a S1 bacterium and at least one strain of a S2 bacterium.

In a more particular embodiment, the immunogenic or vaccine composition comprises or consists of S1 strains B-7500 and B-8295 and S2 strain B-8397.

In another particular embodiment, the immunogenic or vaccine composition comprises at least one strain of a S1 bacterium and at least two strains of a S2 bacterium.

In another particular embodiment, the immunogenic or vaccine composition comprises or consists of at least two strains of a S1 bacterium and at least two strains of a S2 bacterium. In a more particular embodiment, the immunogenic or vaccine composition comprises or consists of the S1 strains B-7500 and B-8295 and the S2 strains B-8397 and B-7484.

In another particular embodiment, the immunogenic or vaccine composition comprises or consists of at least three strains of a S1 bacterium and at least two strains of a S2 bacterium. In a more particular embodiment, the immunogenic or vaccine composition comprises or consists of the S1 strains B-7500, B-8295 and B-7482 and the S2 strains B-8397 and B-7484.

In a particular embodiment the immunogenic or vaccine composition comprises or consists of:

the strain B-7500, deposited by in the Leibniz-Institut DSMZ-Deutsche Sammlung von Mikroorganismen und Zellkulturen GmbH under accession number DSM 33602, the strain B-8295, deposited in the Leibniz-Institut DSMZ-Deutsche Sammlung von Mikroorganismen und Zellkulturen GmbH under accession number DSM 33603 and the strain B-8397, deposited in the Leibniz-Institut DSMZ-Deutsche Sammlung von Mikroorganismen und Zellkulturen GmbH under accession number DSM 33604.

In a particular embodiment, the immunogenic or vaccine composition of the invention further comprises a veterinary acceptable excipient.

The term "veterinary acceptable" means that the component can be administered to a subject along with the immunogenic or vaccine composition of the invention without causing any undesirable biological effect or interacting in a deleterious manner with any of the other components of the composition. It is usually approved by a regulatory agency of a state or federal government or is included in the Eur. Ph. or the U.S. Pharmacopoeia or other generally recognized pharmacopoeia, including those that apply for use in animals, and more particularly in swine.

The term "excipient" refers to a vehicle, or diluent that is administered with the active ingredient and includes solvents, dispersion media, coatings, stabilizing agents, diluents, preservatives, antibacterial and antifungal agents, isotonic agents, adsorption-delaying agents, and the like. Such pharmaceutical excipients can be sterile liquids, such as water and oils, including those of petroleum, animal, vegetable or synthetic origin, such as peanut oil, soybean oil, mineral oil, sesame oil and similar. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21st Edition, 2005; or "Handbook of Pharmaceutical Excipients", Rowe C. R.; Paul J. S.; Marian E. Q., sixth Edition.

Suitable veterinary acceptable vehicles include, for example, water, salt solutions, alcohol, vegetable oils, polyethylene glycols, gelatin, lactose, amylose, magnesium stearate, talc, surfactants, silicic acid, viscous paraffin, perfume oil, monoglycerides and diglycerides of fatty acids.

In a particular embodiment, the immunogenic or vaccine composition further comprises an adjuvant. The term "adjuvant", as used herein, refers to a substance which, when added to an immunogenic agent, non-specifically enhances or potentiates an immune response to the agent in a recipient host upon exposure to the mixture. Illustrative non-limitative examples of adjuvants that can be included in the immunogenic or vaccine composition of the invention include adjuvants formed by aluminum salts (alum), such as aluminum hydroxide, aluminum phosphate, aluminum sulfate, etc., formulations of oil-in-water or water-in-oil emulsions such as complete Freund's Adjuvant (CFA) as well as the incomplete Freund's Adjuvant (IFA); mineral gels; block copolymers, Avridine™, SEAM62, adjuvants formed by components of the bacterial cell wall such as adjuvants including liposaccharides (e.g., lipid A or Monophosphoryl Lipid A (MPLA), trehalose dimycolate (TDM), and components of the cell wall skeleton (CWS), heat shock proteins or the derivatives thereof, adjuvants derived from ADP-ribosylating bacterial toxins, which include diphtheria toxin (DT), pertussis toxin (PT), cholera toxin (CT), *Escherichia coli* heat-labile toxins (LT1 and LT2), *Pseudomonas* Endotoxin A and exotoxin, *Bacillus cereus* exoenzyme B, *Bacillus sphaericus* toxin, *Clostridium botulinum* toxins C2 and C3, *Clostridium limosum* exoenzyme as well as the toxins of *Clostridium perfringens, Clostridium spiriforma* and *Clostridium difficile, Staphylococcus aureus*, EDIM and mutants of mutant toxins such as CRM-197, non-toxic mutants of diphtheria toxin; saponins such as ISCOMs (immunostimulating complexes), chemokines, quimiokines and cytokines such as interleukins (IL-1 1L-2, IL-4, IL-5, IL-6, IL-7, IL-8, IL-12, etc), interferons (such as the interferon gamma) macrophage colony stimulating factor (M-CSF), tumor necrosis factor (TNF), defensins 1 or 2, RANTES, MIPI-alpha, and MEP-2, muramyl peptides such as N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-s-n-glycero-3-hydroxyphosphoryloxy)-ethylamine (MTP-PE), etc.; adjuvants or immunostimulants derived from the family of CpG molecules, CpG dinucleotides and synthetic oligonucleotides which comprise CpG motifs, *C. limosum* exoenzyme and synthetic adjuvants such as PCPP, the cholera toxin, *Salmonella* toxin, alum and the like, aluminum hydroxide, N-acetyl-muramyl-L-threonyl-D-isoglutamine (thr-MDP), N-acetyl-nor-muramyl-L-alanyl-D-isoglutamine, MTP-PE and RIBI, containing three components extracted from bacteria, monophosphoryl lipid A, trehalose dimycolate and cell wall skeleton (MPL+TDM+CWS) in a squalene emulsion at 2% Tween 80. Other examples of adjuvants include DDA (dimethyl dioctadecyl ammonium bromide) and Quil-A. In a particular embodiment the adjuvant is an oily adjuvant of manide oleate and mineral oil. In another embodiment, the adjuvant is a water-in-oil emulsion. In a particular embodiment, the adjuvant is an aluminum containing adjuvant, such as aluminum hydroxide, Montanide IMS1313, diethylaminoethyl (DEAE) or a combination thereof.

The immunogenic composition or vaccine composition can be formulated or administered by any means known to one skilled in the art, such as by the parental route, such as intramuscular, subcutaneous, intradermal, transdermal or intravenous route or by the mucosal route, such as oral, ocular or intranasal route. Preferably, the immunogenic or vaccine composition is formulated for parenteral route, and more preferably for intramuscular route.

The immunogenic or vaccine composition can be formulated in unit dosage form, suitable for individual administration of precise dosages. In pulse doses, a bolus administration of the immunogenic or vaccine composition of the invention is provided, followed by a time-period wherein no composition is administered to the subject, followed by a second bolus administration. An immunologically or therapeutically effective amount of the immunogenic or vaccine composition can be administered in a single dose, or in multiple doses, for example daily, during a course of treatment. In specific, non-limiting examples, pulse doses of the immunogenic or vaccine composition are administered during the course of a day, during the course of a week, or during the course of a month. In a particular embodiment, two doses are administered, being the first dose and the second dose separated by a period of at least 1, at least 2, at least 3, at least 4, at least 5, at least 6, 7, at least 10, at least 15, at least 20, at least 21, at least 25, at least 30, at least 60, at least 90 days or more, preferably at least 21 days.

Amounts effective for therapeutic or prophylactic use can depend on the age, weight, general state of the subject, and other clinical factors. Thus, the final determination of the appropriate treatment or protocol regimen will be made by the attending clinician and/or veterinarian.

Method for Producing the Immunogenic or Vaccine Composition and Obtained Immunogenic or Vaccine Composition In another aspect, the invention relates to a method for producing an immunogenic or vaccine composition comprising an isolated bacterium from the species *Brachyspira hyodysenteriae*, hereinafter first method of the invention, wherein the method comprises the steps of:

(a) determining if the bacterium from the species *Brachyspira hyodysenteriae* comprises the gene on the locus BHWA1_02689 (fucT) of the *B. hyodysenteriae* plasmid pBHWA1 identified by the GenBank accession number NC_012226.1 or a variant of said gene of any strain of *B. hyodysenteriae*, or the product of said gene or variant (b) selecting the bacterium from the species *Brachyspira hyodysenteriae* if said bacterium comprises the fucT gene or a variant of said gene of any strain of *B. hyodysenteriae* or the product of said gene or variant, (c) inactivating the bacterium selected in step (b) and (d) formulating the bacterium inactivated in step (c) in an immunogenic or vaccine composition.

The terms "immunogenic or vaccine composition", "inactivated bacterium", "*Brachyspira hyodysenteriae*", "fucT" and "variant" have been previously defined in connection with the immunogenic or vaccine composition of the invention. All the particular and preferred embodiments of regarding these terms also apply to the first method of the invention.

The first step of the first method of the invention comprises determining if the bacterium from the species *B. hyodysenteriae* comprises the gene fucT or a variant of said gene or the product of said gene or variant.

The presence or absence of a gene can be determined by any method known by the skilled person suitable for detecting nucleic acids, for example, methods based on hybridization, such as Northern blot analysis and in situ hybridization (ISH) (including fluorescence in situ hybridization (FISH), chromogenic in situ hybridization (CISH) or silver in situ hybridization (SISH)), standard polymerase chain reaction (PCR), multiplex and/or singleplex real time RT-PCR, assays using nucleic acid arrays, Sanger sequencing, next generation sequencing (NGS), etc.

The term "gene product" as used herein, refers to both the transcriptional product of the gene (mRNA) or to the translation product of the gene (protein encoded by the gene). Therefore, the gene product can be detected by determining the presence of the mRNA of the gene or of the protein encoded by said gene.

The presence of a messenger RNA can be determined by methods well known in the art. For example, the nucleic acid contained in the blood sample is first extracted according to standard methods, for example using lytic enzymes or chemical solutions or extracted by nucleic-acid-binding resins following the manufacturer's instructions. The extracted mRNA is then detected by hybridization (e.g., Northern blot analysis or by oligonucleotide microarrays after converting the mRNA into a labelled cDNA) and/or amplification (e.g., RT-PCR). Quantitative or semi-quantitative RT-PCR is preferred. Real-time quantitative or semi-quantitative RT-PCR is particularly advantageous. Preferably, primer pairs can be designed in order to overlap an intron, to distinguish cDNA amplification from putative genomic contamination. Suitable primers may be easily designed by the skilled person. Other methods of amplification include ligase chain reaction (LCR), transcription-mediated amplification (TMA), strand displacement amplification (SDA) and nucleic acid sequence based amplification (NASBA). Preferably, the quantity of mRNA is measured by quantitative or semi-quantitative RT-PCR or by real-time quantitative or semi-quantitative RT-PCR. Other methods for determining the presence of a messenger RNA include next generation sequencing (NGS).

The presence of a protein can be determined by any method known in the art suitable for the determination and quantification of a protein in a sample. By way of a non-limiting illustration, the presence of a protein can be determined by means of a technique which comprises the use of antibodies with the capacity for binding specifically to the assayed protein (or to fragments thereof containing the antigenic determinants), or alternatively by means of a technique which does not comprise the use of antibodies such as, for example, by techniques based on mass spectroscopy. The antibodies can be monoclonal, polyclonal or fragment thereof, Fv, Fab, Fab' and F(ab')2, scFv, diabodies, triabodies, tetrabodies and humanized antibodies. Similarly, the antibodies may be labelled. Illustrative, but non-exclusive, examples of markers that can be herein used include radioactive isotopes, enzymes, fluorophores, chemiluminescent reagents, enzyme cofactors or substrates, enzyme inhibitors, particles, or dyes. There is a wide variety of known tests that can be used according to the present invention, such as combined application of non-labelled antibodies (primary antibodies) and labelled antibodies (secondary antibodies), Western blot or immunoblot, ELISA (enzyme-linked immunosorbent assay), RIA (radioimmunoassay), competitive EIA (enzyme immunoassay), DAS-ELISA (double antibody sandwich ELISA), two-dimensional gel electrophoresis, capillary electrophoresis, immunocytochemical and immunohistochemical techniques, immunoturbidimetry, immunofluorescence, techniques based on the use of biochips or protein microarrays including specific antibodies or assays based on the colloidal precipitation in formats such as reagent strips and assays based on antibody-linked quantum dots. Other forms of detecting proteins include, for instance, affinity chromatography techniques or ligand-binding assays.

The protein encoded by the fucT gene is an alpha-1,2-fucosyltransferase. In a particular embodiment, said protein is the alpha-1,2-fucosyltransferase from the WA1 reference strain of *B. hyodysenteriae* or a variant of said protein from any strain of *B. hyodysenteriae*. The alpha-1,2-fucosyltransferase from the WA1 reference strain of *B. hyodysenteriae* is the protein identified by the accession number A0A3B6VCF4 in the Uniprot (entry version 6, 17 Jun. 2020; Sequence version 1, 5 Dec. 2018). In a particular embodiment, the protein encoded by the gene fucT has the sequence of SEQ ID NO: 9. In a particular embodiment, the protein encoded by the fucT gene variant is a protein having at least 60%, at least 65%, at least 70%, at least 75%, at least 80%, at least 85%, at least 90%, at least 95%, at least 96%, at least 97%, at least 98%, at least 99% or higher sequence identity with the protein of SEQ ID NO: 9. In a particular embodiment, the protein encoded by the fucT gene variant comprises or consists of a sequence selected from the group consisting of SEQ ID NO: 83-95.

The second step of the first method of the invention comprises selecting the bacterium from the species *B. hyodysenteriae* if said bacterium comprises the fucT gene or a variant of said gene of any strain of *B. hyodysenteriae* or the product of said gene or variant.

The third step of the first method of the invention comprises inactivating the bacterium selected in step (b). The term "inactivated bacterium" has been previously defined, and methods for inactivating bacteria have been described, including for example, formaldehyde inactivation, microwave inactivation, pressure inactivation, acid inactivation, base inactivation, alcohol inactivation, peroxide inactivation, irradiation, and thermal inactivation. In a particular embodiment, the bacterium is inactivated by formaldehyde. In a particular embodiment, formaldehyde inactivation is performed by incubating the bacteria with formaldehyde at 0.01%-1.0% (v/v), for example at 0.05%-0.8% (v/v), at 0.1%-0.5% (v/v), at 0.2% (v/v). In a particular embodiment, formaldehyde inactivation is performed by incubating the bacteria with formaldehyde during 6 hours to 7 days, for example during 8 hours to 5 days, during 10 hours to 2 days, during 12 hours to 36 hours, during 24 hours. In a particular embodiment, formaldehyde inactivation is performed by incubating the bacteria with formaldehyde at 25° C. to 40° C., at 28° C. to 39° C., at 30° C. to 38° C., at 35° C. to 37° C., at 37° C. In a more particular embodiment, formaldehyde inactivation is performed by incubating the bacteria with formaldehyde at 0.2% (v/v) during 24 hours at 37° C.

The fourth step of the first method of the invention comprises formulating the inactivated bacterium or bacteria in an immunogenic or vaccine composition. The term "formulating" as used herein, means that the bacterium is mixed with one or more components suitable for administration of the bacterium to a subject, in particular to a pig. In a particular embodiment, formulating the bacterium in an immunogenic or vaccine composition comprises adding a veterinary acceptable excipient as previously defined.

In a particular embodiment, formulating the bacterium in an immunogenic or vaccine composition comprises adding an adjuvant to the bacterium. The term "adjuvant" has been previously defined in connection with the immunogenic or vaccine composition of the invention. In particular embodiment the adjuvant is an aluminum containing adjuvant, such as aluminum hydroxide, Montanide IMS1313, diethylaminoethyl (DEAE) or a combination thereof.

In a particular embodiment, the first method of the invention further comprises

- determining if the bacterium is a S1 bacterium, wherein the fucT gene or the variant of said gene is comprised in a gene cluster, and wherein the gene cluster of the S1 bacterium comprises the following genes: the gene on the locus BHWA1_02695 (bcsA) of the *B. hyodysenteriae* plasmid pBHWA1 identified by the GenBank accession number NC_012226.1 or a variant of said gene of any strain of *B. hyodysenteriae*, the rfbC gene, the rfbD gene, the rfbA gene, the rfbB gene, the gene on the locus BHWA1_02690 (rgpF) of the *B. hyodysenteriae* plasmid pBHWA1 identified by the GenBank accession number NC_012226.1 or a variant of said gene of any strain of *B. hyodysenteriae* and the fucT gene or a variant of said gene of any strain of *B. hyodysenteriae* and/or
- determining if the bacterium is a S2 bacterium, wherein the fucT gene or the variant of said gene is comprised in a gene cluster, and wherein the gene cluster of the S2 bacterium comprises the following genes: the gene on the locus BHWA1_02695 (bcsA) of the *B. hyodysenteriae* plasmid pBHWA1 identified by the GenBank accession number NC_012226.1 or a variant of said gene of any strain of *B. hyodysenteriae*, the rfbC gene, the rfbD gene, the rfbA gene, a gene having the sequence of SEQ ID NO: 8 (adoM) or a variant of said gene of any strain of *B. hyodysenteriae*, the rfbB gene, the gene on the locus BHWA1_02690 (rgpF) of the *B. hyodysenteriae* plasmid pBHWA1 identified by the GenBank accession number NC_012226.1 or a variant of said gene of any strain of *B. hyodysenteriae* and the fucT gene or a variant of said gene of any strain of *B. hyodysenteriae*.

The step of determining if a bacterium is a S1 or a S2 bacterium can be performed, as previously defined, by determining if the bacterium comprises the indicated genes of the gene cluster of S1 or S2 *B. hyodysenteriae* bacteria or the products of said genes.

The terms "S1 bacterium", "S2 bacterium", "gene cluster", "bcsA", "rfbC", "rfbD", "rfbA", "rfbB", "rgpF", "AdoM", "fucT", and "variant" have been previously defined in connection with the immunogenic or vaccine composition of the invention. All the particular and preferred embodiments of regarding these terms also apply to the first method of the invention.

In a particular embodiment, the protein encoded by the gene bcsA is a glycosyltransferase family 2 protein encoded by the gene bcsA from the WA1 reference strain of *B. hyodysenteriae* or a variant of said protein from any strain of *B. hyodysenteriae*. In a particular embodiment, said protein is the protein identified by the accession number WP_044555473.1 in the GenBank Database (29 Apr. 2020). In a particular embodiment, the protein encoded by the gene bcsA has the sequence of SEQ ID NO: 10.

In a particular embodiment, the protein encoded by the bcsA gene variant is a protein having at least 60%, at least 65%, at least 70%, at least 75%, at least 80%, at least 85%, at least 90%, at least 95%, at least 96%, at least 97%, at least 98%, at least 99% or higher sequence identity with the protein of SEQ ID NO: 10. In a particular embodiment, the protein encoded by the bcsA gene variant comprises or consists of a sequence selected from the group consisting of SEQ ID NO: 96-99.

The protein encoded by the gene rfbA is a glucose-1-phosphate thymidylyltransferase. In a particular embodiment, said protein is the glucose-1-phosphate thymidylyltransferase from the WA1 reference strain of *B. hyodysenteriae* or a variant of said protein from any strain of *B. hyodysenteriae*. The glucose-1-phosphate thymidylyltransferase from the WA1 reference strain of *B. hyodysenteriae* is the protein identified by the accession number A0A3B6VFJ0_BRAHW in the Uniprot (entry version 5, 11 Dec. 2019; Sequence version 1, 5 Dec. 2018). In a particular embodiment, the protein encoded by the gene rfbA has the sequence of SEQ ID NO: 11.

In a particular embodiment, the protein encoded by the rfbA gene variant is a protein having at least 60%, at least 65%, at least 70%, at least 75%, at least 80%, at least 85%, at least 90%, at least 95%, at least 96%, at least 97%, at least 98%, at least 99% or higher sequence identity with the protein of SEQ ID NO: 11. In a particular embodiment, the protein encoded by the rfbA gene variant comprises or consists of a sequence selected from the group consisting of SEQ ID NO: 100-104.

The protein encoded by the gene rfbB is a dTDP-glucose 4,6-dehydratase. In a particular embodiment, said protein is the dTDP-glucose 4,6-dehydratase from the WA1 reference strain of *B. hyodysenteriae* or a variant of said protein from any strain of *B. hyodysenteriae*. The dTDP-glucose 4,6-dehydratase from the WA1 reference strain of *B. hyodysenteriae* is the protein identified by the accession number A0A3B6VCL3_BRAHW in the Uniprot (entry version 6, 11 Dec. 2019; Sequence version 1, 5 Dec. 2018). In a particular embodiment, the protein encoded by the gene rfbB has the sequence of SEQ ID NO: 12.

In a particular embodiment, the protein encoded by the rfbB gene variant is a protein having at least 60%, at least 65%, at least 70%, at least 75%, at least 80%, at least 85%, at least 90%, at least 95%, at least 96%, at least 97%, at least 98%, at least 99% or higher sequence identity with the protein of SEQ ID NO: 12. In a particular embodiment, the protein encoded by the rfbB gene comprises or consists of a sequence selected from the group consisting of SEQ ID NO: 105-108.

The protein encoded by the gene rfbC is a dTDP-4-dehydrorhamnose 3,5-epimerase. In a particular embodiment, said protein is the dTDP-4-dehydrorhamnose 3,5-epimerase from the WA1 reference strain of *B. hyodysenteriae* or a variant of said protein from any strain of *B. hyodysenteriae*. The dTDP-4-dehydrorhamnose 3,5-epimerase from the WA1 reference strain of *B. hyodysenteriae* is the protein identified by the accession number A0A3B6VCK2_BRAHW in the Uniprot (entry version 8, 17 Jun. 2020; Sequence version 1, 5 Dec. 2018). In a particular embodiment, the protein encoded by the gene rfbC has the sequence of SEQ ID NO: 13.

In a particular embodiment, the protein encoded by the rfbC gene variant is a protein having at least 60%, at least 65%, at least 70%, at least 75%, at least 80%, at least 85%, at least 90%, at least 95%, at least 96%, at least 97%, at least 98%, at least 99% or higher sequence identity with the protein of SEQ ID NO: 13. In a particular embodiment, the protein encoded by the rfbC gene comprises or consists of a sequence selected from the group consisting of SEQ ID NO: 109-111.

The protein encoded by the gene rfbD is a dTDP-4-dehydrorhamnose reductase. In a particular embodiment, said protein is the dTDP-4-dehydrorhamnose reductase from the WA1 reference strain of *B. hyodysenteriae* or a variant of said protein from any strain of *B. hyodysenteriae*. The dTDP-4-dehydrorhamnose reductase from the WA1 reference strain of *B. hyodysenteriae* is the protein identified by the accession number A0A3B6VIP7_BRAHW in the Uniprot (entry version 5, 11 Dec. 2019; Sequence version 1, 5 Dec. 2018). In a particular embodiment, the protein encoded by the gene rfbD has the sequence of SEQ ID NO: 14.

In a particular embodiment, the protein encoded by the rfbD gene variant is a protein having at least 60%, at least 65%, at least 70%, at least 75%, at least 80%, at least 85%, at least 90%, at least 95%, at least 96%, at least 97%, at least 98%, at least 99% or higher sequence identity with the protein of SEQ ID NO: 14. In a particular embodiment, the protein encoded by the rfbD gene comprises or consists of a sequence selected from the group consisting of SEQ ID NO: 112-117.

The protein encoded by the gene rgpF is a lipopolysaccharide biosynthesis protein-like protein. In a particular embodiment, said protein is the lipopolysaccharide biosynthesis protein-like protein from the WA1 reference strain of *B. hyodysenteriae* or a variant of said protein from any strain of *B. hyodysenteriae*. The lipopolysaccharide biosynthesis protein-like protein from the WA1 reference strain of *B. hyodysenteriae* is the protein identified by the accession number 0A3B6VGX0_BRAHW in the Uniprot (entry version 5, 11 Dec. 2019; Sequence version 1, 5 Dec. 2018). In a particular embodiment, the protein encoded by the gene rgpF has the sequence of SEQ ID NO: 15.

In a particular embodiment, the protein encoded by the rgpF gene variant is a protein having at least 60%, at least 65%, at least 70%, at least 75%, at least 80%, at least 85%, at least 90%, at least 95%, at least 96%, at least 97%, at least 98%, at least 99% or higher sequence identity with the protein of SEQ ID NO: 15. In a particular embodiment, the protein encoded by the rgpF gene comprises or consists of a sequence selected from the group consisting of SEQ ID NO: 118-123.

The protein encoded by the gene adoM is a methyltransferase domain-containing protein. In a particular embodiment, the protein encoded by the gene adoM has the sequence of SEQ ID NO: 16 or a variant of said protein from any strain of *B. hyodysenteriae*.

In a particular embodiment, the protein encoded by the adoM variant is a protein having at least 60%, at least 65%, at least 70%, at least 75%, at least 80%, at least 85%, at least 90%, at least 95%, at least 96%, at least 97%, at least 98%, at least 99% or higher sequence identity with the protein of SEQ ID NO: 16.

In a more particular embodiment, the first method of the invention further comprises

- determining if the gene cluster of the S1 bacterium comprises, from the 5' to the 3' end, the following genes: bcsA or a variant of said gene of any strain of *B. hyodysenteriae*, rfbC, rfbD, rfbA, rfbB, rgpF or a variant of said gene of any strain of *B. hyodysenteriae* and fucT or a variant of said gene of any strain of *B. hyodysenteriae;*
  and/or
- determining if the gene cluster of the S2 bacterium comprises, from the 5' to the 3' end, the following genes: bcsA or a variant of said gene of any strain of *B. hyodysenteriae*, rfbC, rfbD, rfbA, adoM or a variant of said gene of any strain of *B. hyodysenteriae*, rfbB, rgpF or a variant of said gene of any strain of *B. hyodysenteriae* and fucT or a variant of said gene of any strain of *B. hyodysenteriae*.

In a particular embodiment, at least two strains of a S1 bacterium are selected. In a particular embodiment, the two strains are selected from the group consisting of B-7493, B-7500, B-8295 and B-7482. In a more particular embodiment, the two strains are B-7500 and B-8295.

In another particular embodiment, at least two strains of a S2 bacterium are selected. In a particular embodiment, the two strains are selected from the group consisting of B-8397, B-7484, and B-7494. In a more particular embodiment, the two strains are B-8397 and B-7484.

In another particular embodiment, at least two strains of a S1 bacterium and at least one strain of a S2 bacterium are selected. In a more particular embodiment, S1 strains B-7500 and B-8295 and S2 strain B-8397 are selected.

In another particular embodiment, at least one strain of a S1 bacterium and at least two strains of a S2 bacterium are selected.

In another particular embodiment, at least two strains of a S1 bacterium and at least two strains of a S2 bacterium are selected. In a more particular embodiment, S1 strains B-7500 and B-8295 and S2 strains B-8397 and B-7484 are selected.

In another particular embodiment, at least three strains of a S1 bacterium and at least two strains of a S2 bacterium are selected. In a more particular embodiment, S1 strains B-7500, B-8295 and B-7482 and S2 strains B-8397 and B-7484 are selected.

In another aspect, the invention relates to an immunogenic or vaccine composition obtainable by, obtained by or directly obtained by the first method of the invention. In a particular embodiment, the immunogenic or vaccine composition obtained by the first method of the invention is the immunogenic or vaccine composition previously defined in the first aspect of the invention.

Methods for Selecting a Bacterium from the Species *B. hyodysenteriae*

As shown in Examples 2 and 3, vaccines against swine dysentery comprising inactivated S1 or S2 *B. hyodysenteriae* bacteria are capable of reducing the clinical signs of the disease. Both types of bacteria comprise a gene cluster comprising the fucT gene, which is absent in S0 and S3 bacteria. Therefore, the presence or absence of fucT gene or of its gene product could be used for selecting a bacterium useful for producing a vaccine against swine dysentery.

Therefore, in another aspect, the invention relates to a method for selecting an isolated bacterium from the species *Brachyspira hyodysenteriae* useful for manufacturing a vaccine against swine dysentery, hereinafter second method of the invention, comprising determining the presence or absence of the gene on the locus BHWA1_02689 (fucT) of the *B. hyodysenteriae* plasmid pBHWA1 identified by the GenBank accession number NC_012226.1 or a variant of said gene of any strain of *B. hyodysenteriae* and/or of the product of said gene or variant, wherein if the bacterium comprises said gene or variant or the product of said gene or variant, the bacterium is selected for manufacturing a vaccine against swine dysentery.

The terms "vaccine", "*Brachyspira hyodysenteriae*", "fucT" and "variant" have been previously defined in connection with the immunogenic or vaccine composition of the invention. All the particular and preferred embodiments of the first aspect of the invention regarding these terms also apply to the second method of the invention.

The term "swine dysentery", as used herein, refers to an infectious disease caused by *Brachyspira hyodysenteriae* and that affects swine, characterized by mucohemorrhagic diarrhea and marked inflammation limited to the large intestine (cecum and/or colon). All ages of swine may have SD although it seldom is apparent in piglets less than three weeks old. The disease occurs more frequently during the growing/finishing periods. As used herein the term "disease caused by *Brachyspira hyodysenteriae*" in particular relates to dysentery caused by *B. hyodysenteriae*, more particular to swine dysentery. The term "clinical signs caused by *Brachyspira hyodysenteriae*" in particular relates to any clinical sign selected from mucus and/or blood in feces (dysentery), diarrhoea, weight loss, lesions in the large intestine, spirochaete (*Brachyspira hyodysenteriae*) in the large intestine.

The second method of the invention comprises determining the presence or absence of the fucT gene or of a variant of said gene of any strain of *B. hyodysenteriae* or of the product of said gene or variant. The presence or absence of the fucT gene can be determined by any suitable method for detecting the presence of nucleic acids previously described.

The term "gene product" has been previously defined.

In a particular embodiment of the second method of the invention, the bacterium from the species *B. hyodysenteriae* is a wild-type bacterium, that is, a bacterium having a genome that has not been artificially modified.

In a particular embodiment, the second method of the invention further comprises:

(a) determining if the bacterium from the species *Brachyspira hyodysenteriae* comprises the following genes or the products of the following genes: the gene on the locus BHWA1_02695 (bcsA) of the *B. hyodysenteriae* plasmid pBHWA1 identified by the GenBank accession number NC_012226.1 or a variant of said gene of any strain of *B. hyodysenteriae*, the rfbC gene, the rfbD gene, the rfbA gene, the rfbB gene, the gene on the locus BHWA1_02690 (rgpF) of the *B. hyodysenteriae* plasmid pBHWA1 identified by the GenBank accession number NC_012226.1 or a variant of said gene of any strain of *B. hyodysenteriae* and the fucT gene or a variant of said gene of any strain of *B. hyodysenteriae,*
wherein if the bacterium comprises said genes or the products of said genes the bacterium is selected for manufacturing a vaccine against swine dysentery,
and/or (b) determining if the bacterium from the species *B. hyodysenteriae* comprises the following genes or the products of the following genes: the gene on the locus BHWA1_02695 (bcsA) of the *B. hyodysenteriae* plasmid pBHWA1 identified by the GenBank accession number NC_012226.1 or a variant of said gene of any strain of *B. hyodysenteriae*, the rfbC gene, the rfbD gene, the rfbA gene, a gene having the sequence of SEQ ID NO: 8 (adoM) or a variant of said gene of any strain of *B. hyodysenteriae*, the rfbB gene, the gene on the locus BHWA1_02690 (rgpF) of the *B. hyodysenteriae* plasmid pBHWA1 identified by the GenBank accession number NC_012226.1 or a variant of said gene of any strain of *B. hyodysenteriae* and the fucT gene or a variant of said gene of any strain of *B. hyodysenteriae,*
wherein if the bacterium comprises said genes or the products of said genes the bacterium is selected for manufacturing a vaccine against swine dysentery.

The term "gene product" has been previously defined, as well as methods for determining the presence or absence of the product of a gene.

Medical Uses

In another aspect, the invention relates to the immunogenic or vaccine composition of the invention or to the immunogenic or vaccine composition obtained by the first method of the invention for use as a medicament.

Alternatively, the invention relates to the use of the immunogenic or vaccine composition of the invention or of the immunogenic or vaccine composition obtained by the first method of the invention for the manufacture of a medicament.

In another aspect, the invention relates to the immunogenic composition of the invention or to the immunogenic composition obtained by the first method of the invention for use in inducing an immune response against a bacterium from the species *Brachyspira hyodysenteriae.*

Alternatively, the invention relates to use of the immunogenic composition of the invention or of the immunogenic composition obtained by the first method of the invention for the manufacture of a medicament for inducing an immune response against a bacterium from the species *Brachyspira hyodysenteriae.*

Alternatively, the invention relates to a method for inducing an immune response against a bacterium from the species *Brachyspira hyodysenteriae* comprising administering to a subject an immunologically or therapeutically effective amount of the immunogenic composition of the invention or of the immunogenic composition obtained by the first method of the invention.

In another aspect, the invention relates to the vaccine composition of the invention or to the vaccine composition obtained by the first method of the invention for use in the protection against an infection caused by a bacterium from the species *Brachyspira hyodysenteriae.*

Alternatively, the invention relates to the use of the vaccine composition of the invention or of the vaccine composition obtained by the first method of the invention for the manufacture of a medicament for the protection against an infection caused by a bacterium from the species *Brachyspira hyodysenteriae*.

Alternatively, the invention relates to a method for preventing an infection caused by a bacterium from the species *Brachyspira hyodysenteriae* in a subject comprising administering to a subject an immunologically or therapeutically effective amount of the vaccine composition of the invention or of the vaccine composition obtained by the first method of the invention.

In another aspect, the invention relates to the vaccine composition of the invention or the vaccine composition obtained by the first method of the invention for use in the treatment and/or prevention of swine dysentery.

Alternatively, the invention relates to the use of the vaccine composition of the invention or of the vaccine composition obtained by the first method of the invention for the manufacture of a medicament for the prevention and/or treatment of swine dysentery.

Alternatively, the invention relates to a method for treating and/or preventing swine dysentery comprising administering to a subject an immunologically or therapeutically effective amount of vaccine composition of the invention or of the vaccine composition obtained by the first method of the invention.

In a particular embodiment of the medical uses of the invention, the vaccine composition of the invention or the vaccine composition obtained by the first method of the invention induces a reduction in the clinical signs of the infection by a bacterium from the species *Brachyspira hyodysenteriae*. In a more particular embodiment, said clinical signs are diarrhea score, intestinal lesion score and/or average daily weight loss. The term "reduction of the clinical signs of a disease caused by *Brachyspira hyodysenteriae*" or "reduction of symptoms associated with *Brachyspira hyodysenteriae* infection", respectively, means, but is not limited to, reducing the number of infected subjects in a group, reducing or eliminating the number of subjects exhibiting clinical symptoms of infection, or reducing the severity of any clinical symptoms that are present in the subjects, in comparison to wild-type infection. For example, it should refer to any reduction of pathogen load, pathogen shedding, reduction in pathogen transmission, or reduction of any clinical sign of *Brachyspira hyodysenteriae* infection, in particular selected from mucus and/or blood in feces (dysentery), diarrhea, weight loss, lesions in the large intestine, spirochaete (*Brachyspira hyodysenteriae*) in the large intestine. Preferably, these clinical signs are reduced in subjects receiving the immunogenic composition of the invention by at least 10% in comparison to subjects not receiving the composition and may become infected. More preferably, clinical signs are reduced in subjects receiving the composition of the present invention by at least 20%, preferably by at least 30%, preferably by at least 40%, preferably by at least 50%, preferably by at least 60%, preferably by at least 70%, preferably by at least 80%, preferably by at least 90%, preferably by at least 95%, preferably by at least 99% or even more preferably by at least 100% of the clinical signs, particularly, diarrhea score, intestinal lesion score and average daily weight loss in comparison to subjects not receiving the composition of the invention.

In a particular embodiment of the medical uses of the invention, the vaccine composition of the invention or the vaccine composition obtained by the first method of the invention prevents or delays the onset of the clinical signs of the infection by a bacterium from the species *Brachyspira hyodysenteriae*.

In a particular embodiment of the medical uses of the invention, the vaccine composition of the invention or the vaccine composition obtained by the first method of the invention induces an increase in the survival rate in subjects suffering from an infection by a bacterium from the species *Brachyspira hyodysenteriae*. The term "survival rate" and "increased survival rate" has been previously defined.

The term "subject" or "host", as used herein, refers to the target individuals in need thereof to whom the immunogenic composition or vaccine of the invention are administered, among others humans, mammals, livestock, or any other animal species susceptible to be vaccinated with the composition of the invention. Preferably, the mammal is a porcine specie, more preferably is swine or pig. As used herein, the term "pig" or "swine" is intended for porcine species including, among others, pigs, boars, sows, gilts and piglets of any age or in any phase of their production cycle; it is also intended for sows and gilts, and more particularly for piglets. A gilt is a female pig approximately under the age of 1 year. The term refers to a pig who has not farrowed or given birth to a litter or progeny. Once a pig has had a litter or progeny and is past approximately her first year, the pig is known as sow.

The term "treatment", as used herein, refers to any type of therapy, which is aimed at terminating, preventing, ameliorating or reducing the susceptibility to a clinical condition or existing disease as described herein, including complete curing of a disease as well as amelioration or alleviation of said disease. In a preferred embodiment, the term treatment relates to prophylactic treatment (i.e. a therapy to reduce the susceptibility to a clinical condition), of a disorder or a condition as defined herein. Thus, "treatment," "treating," and their equivalent terms refer to obtaining a desired pharmacologic or physiologic effect, covering any treatment of a pathological condition or disorder in a mammal, including a swine. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or, at least, clinical signs associated therewith, so that the host no longer suffers from the disorder or its clinical signs, such as causing regression of the disorder or its clinical signs, for example, by restoring or repairing a lost, missing or defective function, or stimulating an inefficient process, or (4) relieving, alleviating, or ameliorating the disorder, or clinical signs associated therewith, where ameliorating is used in a broad sense to refer to at least a reduction in the magnitude of a parameter, such as inflammation, pain, immune deficiency, reduction of the pathogen load, the pathogen shedding, or reduction in pathogen transmission.

The term "prevention" or "reduction" or "preventing" or "reducing", respectively, as used herein, means, but is not limited to a process of prophylaxis in which a subject is exposed to the immunogenic or vaccine composition of the invention prior to the induction or onset of the disease process, and wherein said immunogenic or vaccine composition, when administered to said pig, elicits or is able to elicit an immune response in said pig against *B. hyodysenteriae*. Altogether, such treatment results in reduction of the clinical signs of swine dysentery or of clinical signs associated with swine dysentery, respectively or reduction of bacteria titer. More specifically, the term "prevention" or "preventing", as used herein, means generally a process of prophylaxis in which a pig is exposed to the immunogenic or vaccine composition of the present invention prior to the induction or onset of swine dysentery.

Herein, "reduction of clinical signs associated with swine dysentery" means, but is not limited to, reducing the number of infected subjects in a group, reducing or eliminating the number of subjects exhibiting clinical signs of infection, or reducing the severity of any clinical signs that are present in the subjects, in comparison to wild-type infection. For example, it should refer to any reduction of bacteria titer, reduction in bacteria transmission, or reduction of any clinical sign of swine dysentery. Preferably these clinical signs are reduced in subjects receiving the composition of the present invention by at least 10 percent in comparison to subjects not receiving the composition and may become infected. More preferably, clinical signs are reduced in subjects receiving the composition of the present invention by at least 20 percent, preferably by at least 30 percent, more preferably by at least 40 percent, and even more preferably by at least 50 percent in comparison to subjects not receiving the composition and may become infected. The clinical signs, as mentioned herein, can be selected from the group consisting of diarrhea, intestinal lesion and bacteria titer in the colon.

In a particular embodiment, the administration of the immunogenic or vaccine composition of the invention or of the immunogenic or vaccine composition obtained by the method of the invention is able to reduce and/or prevent the clinical signs of swine dysentery when administered to pigs that are subsequently infected with *B. hyodysenteriae* when compared to pigs that do not receive the immunogenic or vaccine composition of the invention or the immunogenic or vaccine composition obtained by the method of the invention. Particularly, said immunogenic or vaccine compositions reduce the diarrhea score, intestinal lesion score and daily weight loss and increases the survival rate in the vaccinated pigs infected with *B. hyodysenteriae*. In a more particular embodiment, the administration of said immunogenic or vaccine composition induces at least 10%, at least 20%, at least 30%, at least 40%, at least 50%, at least 60%, at least 70%, at least 80%, at least 90%, at least 95%, at least 98%, at least 99%, at least 100% or higher reduction in the clinical signs of swine dysentery, particularly diarrhea score, intestinal lesion and daily weight loss, and induces an increase in the survival rate of at least 10%, at least 20%, at least 30%, at least 40%, at least 50%, at least 60%, at least 70%, at least 80%, at least 90%, at least 95%, at least 98%, at least 99%, at least 100% or higher when administered to pigs that are subsequently infected with *B. hyodysenteriae* when compared to pigs that do not receive the immunogenic or vaccine composition of the invention or the immunogenic or vaccine composition obtained by the method of the invention.

The terms "diarrhea score", "intestinal lesion score", "daily weight loss" and "survival rate" have been previously defined.

The term "immunologically effective amount" or "therapeutically effective amount", as used herein, relates to the sufficient amount of the composition of the invention to provide the desired effect, i.e. to achieve an appreciable prevention, cure, delay, reduction of severity or amelioration of one or more clinical signs derived from the disease, and will generally be determined by, among other causes, the characteristics of the agent itself (the *B. hyodysenteriae* bacteria) and the therapeutic effect to be achieved. As used herein "immunologically effective amount" or "therapeutically effective amount" also means an amount sufficient to reduce any clinical signs as previously defined by at least 10%, preferably by at least 20%, preferably by at least 30%, preferably by at least 40%, preferably by at least 50%, preferably by at least 60%, preferably by at least 70%, preferably by at least 80%, preferably by at least 90%, preferably by at least 95%, preferably by at least 99%, and more preferably by at least 100% compared to a non-vaccinated control group. It will also depend on the subject to be treated, the severity of the disease suffered by said subject, the chosen dosage form, etc. For this reason, the doses that may be mentioned in this invention must be considered only as guides for the person skilled in the art, who must adjust the doses depending on the aforementioned variables. In an embodiment, the effective amount produces the amelioration of one or more clinical signs of the disease that is being treated. Even though individual needs vary, determination of optimal ranges for immunologically or therapeutically effective amounts of the compounds according to the invention belongs to the common experience of those experts in the art. In general, the dosage needed to provide an effective treatment or prevention, which can be adjusted by one expert in the art, will vary depending on age, health, fitness, sex, diet, weight, degree of alteration of the receptor, frequency of treatment, nature and condition of the injury, nature and extent of impairment or illness, medical condition of the subject, route of administration, pharmacological considerations such as activity, efficacy, pharmacokinetic and toxicology profile of the particular compound used, if using a system drug delivery, and if the compound is administered as part of a combination of drugs.

In a particular embodiment, the immunogenic or vaccine composition comprises or consists of at least two strains of a S1 bacterium. In a particular embodiment, the two strains are selected from the group consisting of B-7493, B-7500, B-8295 and B-7482. In a more particular embodiment, the two strains are B-7500 and B-8295.

In another particular embodiment, the immunogenic or vaccine composition comprises at least two strains of a S2 bacterium. In a particular embodiment, the two strains are selected from the group consisting of B-8397, B-7484, and B-7494. In a more particular embodiment, the two strains are B-8397 and B-7484.

In another particular embodiment, the immunogenic or vaccine composition comprises at least two strains of a S1 bacterium and at least one strain of a S2 bacterium. In a more particular embodiment, the immunogenic or vaccine composition comprises or consists of S1 strains B-7500 and B-8295 and S2 strain B-8397.

In another particular embodiment, the immunogenic or vaccine composition comprises at least one strain of a S1 bacterium and at least two strains of a S2 bacterium.

In another particular embodiment, the immunogenic or vaccine composition comprises or consists of at least two strains of a S1 bacterium and at least two strains of a S2 bacterium. In a more particular embodiment, the immunogenic or vaccine composition comprises or consists of the S1 strains B-7500 and B-8295 and the S2 strains B-8397 and B-7484.

In another particular embodiment, the immunogenic or vaccine composition comprises or consists of at least three strains of a S1 bacterium and at least two strains of a S2 bacterium. In a more particular embodiment, the immunogenic or vaccine composition comprises or consists of the S1 strains B-7500, B-8295 and B-7482 and the S2 strains B-8397 and B-7484.

The term "cross-protection" implies terminating, preventing, ameliorating or reducing the susceptibility of a *B. hyodysenteriae* infections or clinical signs of swine dysentery caused by at least one *B. hyodysenteriae* strain that is different from the strains that are present in the immunogenic or vaccine composition.

The term "heterologous strain", as used herein, refers to a strain that is different from the strains that are comprised in the immunogenic or vaccine composition.

In a particular embodiment, the immunogenic composition induces an immune response against a strain of *B. hyodysenteriae* different from the strain that is comprised in the immunogenic composition or, alternatively the immunogenic composition is able to confer cross-protection against a strain of *B. hyodysenteriae* different from the strain of *B. hyodysenteriae* that is comprised in the immunogenic composition.

In a particular embodiment, the vaccine composition induces protection against a strain of *B. hyodysenteriae* different from the strain comprised in the vaccine or, alternatively the vaccine composition induces cross-protection against a strain of *B. hyodysenteriae* different from the strain of *B. hyodysenteriae* that is comprised in the vaccine composition.

In a particular embodiment of the medical uses of the invention, the vaccine composition of the invention or the vaccine composition obtained by the first method of the invention induces a reduction in the clinical signs of the infection by a strain of bacterium from the species *Brachyspira hyodysenteriae* different from the strain that is comprised in the vaccine composition when compared to subjects that do not receive the vaccine composition. In a more particular embodiment, said clinical signs are diarrhea score, intestinal lesion score and/or average daily weight loss. In a particular embodiment, the reduction is of at least 5%, at least 10%, at least 20%, at least 30%, at least 40%, at least 50%, at least 60%, at least 70%, at least 80%, at least 90%, at least 95% or 100% of the clinical signs, particularly, diarrhea score, intestinal lesion score and average daily weight loss, when compared to subjects that do not receive the vaccine composition of the invention.

In a particular embodiment of the medical uses of the invention, the vaccine composition of the invention or the vaccine composition obtained by the first method of the invention prevents or delays the onset of the clinical signs of the infection by a strain of bacterium from the species *Brachyspira hyodysenteriae* different from the strain comprised in the vaccine composition.

In a particular embodiment of the medical uses of the invention, the vaccine composition of the invention or the vaccine composition obtained by the first method of the invention induces an increase in the survival rate in subjects suffering from an infection by a strain of a bacterium from the species *Brachyspira hyodysenteriae* different from the strain comprised in the vaccine composition. In a particular embodiment, the vaccine composition of the invention or the vaccine composition obtained by the first method of the invention induces an increase in the survival rate after 1 to 200 days post-vaccination, for example after 2 to 190 days post-vaccination, after 3 to 180 days post-vaccination, after 4 to 170 days post-vaccination, after 5 to 150 days post-vaccination, after 6 to 130 days post-vaccination, after 7 to 100 days post-vaccination, after 10 to 75 days post-vaccination, after 12 to 50 days post-vaccination, after 20 days post-vaccination in subjects suffering from an infection by a bacterium from the species *Brachyspira hyodysenteriae*. The term "increased in the survival rate" refers to any increased compared with non-vaccinated control subjects, for example, an increase of at least 5%, at least 10%, at least 20%, at least 30%, at least 40%, at least 50%, at least 60%, at least 70%, at least 80%, at least 90%, at least 95%, at least 100% or higher.

In a particular embodiment, the immunogenic or vaccine composition is administered by intramuscular, subcutaneous, intradermal, transdermal, intravenous, oral, ocular or intranasal route. In a particular embodiment, the immunogenic or vaccine composition is administered by intramuscular, subcutaneous, intradermal, transdermal or intravenous route. In a particular embodiment, the immunogenic or vaccine composition is administered by intramuscular route.

In a particular embodiment, the immunogenic or vaccine composition comprises an immunologically or therapeutically effective amount of an isolated and inactivated *B. hyodysenteriae* strain.

In a particular embodiment, the immunogenic or vaccine composition is administered at a dose of at least $10^8$, at least $10^9$, at least $10^{10}$, at last $10^{11}$ bacteria of each strain/dose.

In a particular embodiment, two or more doses of the immunogenic or vaccine composition are administered, preferably two doses, being the doses separated by least 1, at least 2, at least 3, at least 4, at least 5, at least 6, at least 7, at least 10, at least 14, at least 20, at least 21, at least 25, at least 30, at least 60, at least 90 days or more, preferably at least 14 or at least 21 days.

EXAMPLES

Example 1: Determination of the Genomic Structure of *Brachyspira hyodysenteriae* Isolates Based on the 36 kb Plasmid (pBH 36 kb)

The objective of this study was to analyze *Brachyspira hyodysenteriae* (Bhyo) isolates from different geographical origin by determining the architecture of a gene cluster comprising the genes of the operon rfbAD (also known as rfbBADC) located at the plasmid pBH of 36 kb in reference to the standard WA1 *Brachyspira hyodysenteriae* isolate.

The genes rfbA, rfbB, rfbC, rfbD are located forming an operon in the plasmid pBH of 36 kb in the *B. hyodysenteriae* strain WA1 (GenBank No. NC_012226.1). This operon rfbBADC groups the genes related to the lipooligosaccharide synthesis, grouping 4 of the 6 genes rfb present in the plasmid.

Materials and Methods 49 isolated Bhyo strains from different geographical origins isolated from pigs with confirmed clinical cases of swine dysentery caused by *B. hyodysenteriae* were used in this study. The 49 strains included isolates from Argentina (3), Australia (3), Belgium (4), Canada (1), Germany (4), Japan (5), Portugal (1), Spain (17), Sweden (5), United Kingdom (1), and USA (5).

The DNA of the different isolates was obtained by SDS lysis. *B. hyodysenteriae* strain cultures of 15 ml were centrifuged at 4000 g for 10 minutes and resuspended in 0.5 ml of 10 mM Tris pH 8, 0.5M NaCl and 10 mM EDTA. Subsequently, 10 μL of 20% SDS were added and the lysate was deproteinized twice with a volume of Phenol-Chloroform. The DNA was then precipitated by adding two volumes of absolute ethanol. DNA was recovered both by simple decantation and by sedimentation at 13000 g for 5 minutes. Once washed with 70% ethanol and dried, the DNAs were finally dissolved in 50-100 μL of 10 mM Tris and 1 mM EDTA.

The DNA samples obtained were used as starting material to perform ultrasequencing in an Illumina Myseq.

For mass sequencing (Shotgun) and direct from the extracted DNAs, the Nextera kit (Paired ends, Illumina) was used, which produces fragments of 400-600 bases. During sequencing, an Illumina MySeq apparatus with a 2×150 base reading chip was used, which determines the sequence of this number of bases for each end of said fragments. In typical sequencing, the sequence of 1-4 million fragments is determined. The first analysis of the sequences obtained was performed by aligning them with the reference sequence of the 36 kb plasmid pBH of the WA1 reference strain. For this, the Bowtie2 (Langmead et al., *Nature Methods* 2012, 357-359), SamTools (Li et al., *Bioinformatics,* 2008, 2078-2079) and VarScan (Koboldt et al., *Genome Research,* 2012, 568-576) programs were used. De novo assembly was performed on the sequences of the isolates that had said plasmid to establish the arrangement of genes in the plasmid skeleton. Assembling "de novo" of the fragments obtained is not a trivial task. There are several bioinformatic packages, and most of them use algorithms based on graph theory (Bruijin's graphs). In this case, the genomes of the different isolates have been assembled using the Velvet (Zerbino et al., *Genome Research,* 2009, 821-829) and SPAdes (Bankevich et al., *Journal of Computational biology,* 2012, 455-477) programs. The identification of ORFs on the obtained contigs was performed using the Glimmer program (NCBI). Multiple alignments of the polypeptide sequences were performed using the ClustalX v2.1 program.

Once the sequences for all the isolated Bhyo strains were obtained, the presence or absence of the 36 kb plasmid pBH in all sequenced isolates was studied. This was done by aligning all the sequences obtained with that of the cdsM operon, which contains the replication and metabolism genes of the plasmid. The presence of the cdsM operon was used as the criteria for determining the presence of the pBH plasmid in each isolate. After assessing the presence or absence of the 36 kb pBH plasmid in the different Bhyo isolates, the gene distribution of the cluster containing the operon rfbAD was studied for each strain. To do so, the 36 kb pBH plasmid sequences were aligned with those of the rfbAD operon and the adjacent genes of the 36 kb pBH plasmid of the Bhyo reference strain WA1.

Once the presence of the rfbAD genes was confirmed, the architecture of the gene cluster containing said operon together with the adjacent genes was determined in all the isolates carrying the 36 kb plasmid pBH. For this, a "de novo" assembly was performed with the results of the ultrasequencing and annotated to identify the presence or the absence of the different genes of this operon and the adjacent genes. After the annotation, the architecture of the cluster for all the samples analyzed was determined. The analysis of the gene distribution surprisingly suggested the existence of three different structures of the gene cluster containing the operon rfbAD of the 36 kb plasmid pBH among the isolates (FIG. 1). A first gene cluster structure, designated as structure 1 (S1), includes the isolates that have an identical structure to the plasmid 36 kb pBH of the reference Bhyo WA1 strain. A second gene cluster structure, designated as structure 2 (S2), includes isolates that have the insertion of the adoM gene between the genes rfbA and rfbB. A third gene cluster structure, designated as structure 3 (S3), incudes isolates that have the insertion of the adoM gene between the genes rfbA and rfbB but lack the gene fucT (homologous to the gene BHWA1_02689 characterized in the 36 kb plasmid pBH of reference strain WA1, GenBank No. NC_012226.1), which codes for an α-1,2-fucosyltransferase. It was also found that some Bhyo isolates did not have the 36 kb plasmid pBH, thus not comprising the identified genetic cluster as the other groups (S1, S2 and S3).

The following table shows the allocation of the different Bhyo strains based on the structure of the gene cluster comprising the rfbAD operon.

TABLE 1

Distribution of the 49 Bhyo isolates analyzed by the genomic structure of the gene cluster comprising the rfbAD operon.

| Family | No. Isolates | Cluster of genes in pBH of 36 kb (5' to 3') |
|---|---|---|
| S1 | 27 | bcsA, rfbC, rfbD, rfbA, rfbB, rgpF, fucT |
| S2 | 4 | bcsA, rfbC, rfbD, rfbA, adoM, rfbB, rgpF, fucT |
| S3 | 11 | bcsA, rfbC, rfbD, rfbA, adoM, rfbB, rfpF |
| S0 | 7 | No plasmid of 36 kb |

This study confirms the presence of a 36 kb pBH plasmid in most isolates of Bhyo obtained from different geographical origins and coming from clinical cases of swine dysentery. A different genomic structure based on the gene cluster comprising the rfbAD operon was found for the Bhyo isolates allowing its classification in four groups (S1 to S3 and S0).

Example 2: Efficacy Study of Different Monovalent Experimental Vaccines Against an Experimental Infection of *B. hyodysenteriae* Strain B-7493

A total of 50 pigs between 5 and 6 weeks of age were chosen for this study. The animals were randomly assigned into 5 groups of 10 pigs each one (Groups A to E). On Day 0 pigs received a first dose of an experimental vaccine according to the group assignment. Three weeks later (Day 21) pigs received a second dose of the vaccine. Vaccines were administered at the neck by intramuscular route at 2 mL for each administration.

Group A received a vaccine comprising $3.33\times10^9$ total bacteria (BT) per dose of the inactivated *B. hyodysenteriae* strain B-7493, USA isolate. This USA isolate showed a genomic arrangement consistent with the gene cluster structure S1 (as determined in Example 1). This vaccine was formulated with the same strain as the one used for the experimental infection, thus it is a homologous vaccine. The vaccine was also formulated at 50% v/v with a commercial adjuvant, Montanide IMS 1313.

Group B received a vaccine comprising $3.33\times10^9$ total bacteria (BT) per dose of the inactivated *B. hyodysenteriae* strain B-7500, Spanish isolate. This Spanish isolate showed a genomic arrangement consistent with the gene cluster structure S1 (as determined in Example 1). The vaccine was formulated at 50% v/v with the commercial adjuvant Montanide IMS 1313.

Group C received a vaccine comprising $3.33\times10^9$ total bacteria (BT) per dose of inactivated *B. hyodysenteriae* strain B-7843, USA isolate. This USA isolate showed a genomic arrangement consistent with the gene cluster structure S3 (as determined in Example 1). The vaccine was formulated at 50% v/v with the commercial adjuvant Montanide IMS 1313.

Group D corresponded to the positive control group, which received a mock vaccine comprising PBS without antigen and 50% v/v of the same Montanide IMS 1313 adjuvant (mock-vaccinated-challenged group).

Group E corresponded to the negative control group which received a mock vaccine comprising PBS without antigen and 50% v/v of the same Montanide IMS 1313 adjuvant. This group did not receive the experimental infection. Therefore, this group served as strict negative control group (mock-vaccinated-non-challenged group).

All *B. hyodysenteriae* strains used for preparing the experimental vaccines were inactivated with formaldehyde before administering the vaccine to the animals.

At Day 42, pigs were experimentally infected (challenged) with a fresh culture of *B. hyodysenteriae* strain B-7493, which is an American isolate with a gene cluster structure S1. The challenge consisted of orally administering 3 doses at 3 consecutive days of 100 mL/dose of a culture of *B. hyodysenteriae* strain B-7493 at a titer of $1\times10^9$ spirochetes/dose per animal by an esophageal cannula. The negative control group (Group E) did not receive the experimental infection.

To assess the efficacy of the vaccines after the experimental infection, it was evaluated the appearance of mucohemorrhagic diarrhea and the intestinal lesion score in all groups as main efficacy parameters. The appearance of mucohemorrhagic diarrhea was considered as the main clinical sign of swine dysentery.

Diarrhea was monitored on a daily basis from day 1 to day 20 post-infection. Subsequently, a weighted diarrhea score was calculated.

Diarrhea score was evaluated according to the following table:

TABLE 2

| Diarrhea score |
|---|
| — Normal stool (no diarrhea) |
| 1 pasty stool (consistency of cement, mild diarrhea) |
| 2 liquid stool with fecal content (moderate diarrhea) |
| 3 watery stool (severe diarrhea, does not look like stool) |

If presence of mucus is detected it was added 0.5 points to the diarrhea score, and another 0.5 points for the presence of blood. Thus, the diarrhea score ranged from 0 to 4.

Then, the mean for the different groups was calculated.

Another parameter assessed to determine the efficacy of the vaccines was the intestinal lesion score. Animals were euthanized on day 64 of the study and assessed for large intestine intestinal lesions. The score was calculated according to the following table:

TABLE 3

| Intestinal lesion score |
|---|
| 0 Absence of lesion |
| 1 Mild enteritis, lesions in specific areas, normal or pasty content |
| 2 Moderate enteritis, extensive lesions, diarrheal content |
| 3 Severe enteritis, severely damaged or atrophic intestine, watery/blood stools, fibrin |

The mean of the intestinal lesion score per group was calculated.

Figure 2:
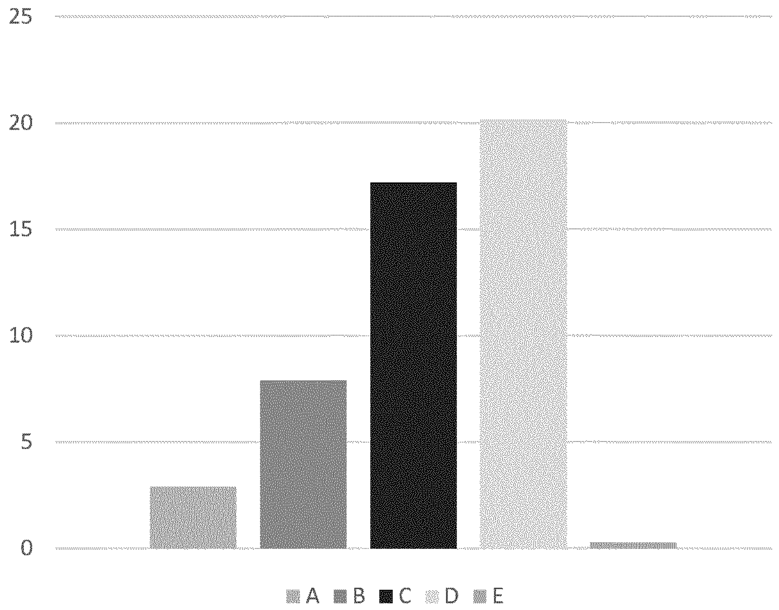
FIG. 2. Mean diarrhea score of pigs from day 1 to 20 after the experimental infection, groups A to E. Group A corresponds to pigs vaccinated with inactivated strain B-7493 (gene cluster structure S1); Group B corresponds to pigs vaccinated with inactivated strain B-7500 (gene cluster structure S1); Group C corresponds to pigs vaccinated with inactivated strain B-7843 (gene cluster structure S3); Group D corresponds to pigs vaccinated with a mock vaccine; Group E corresponds to negative control group, mock vaccinated-no challenged group. The diarrhea score is represented on the y-axis.
Figure 3:
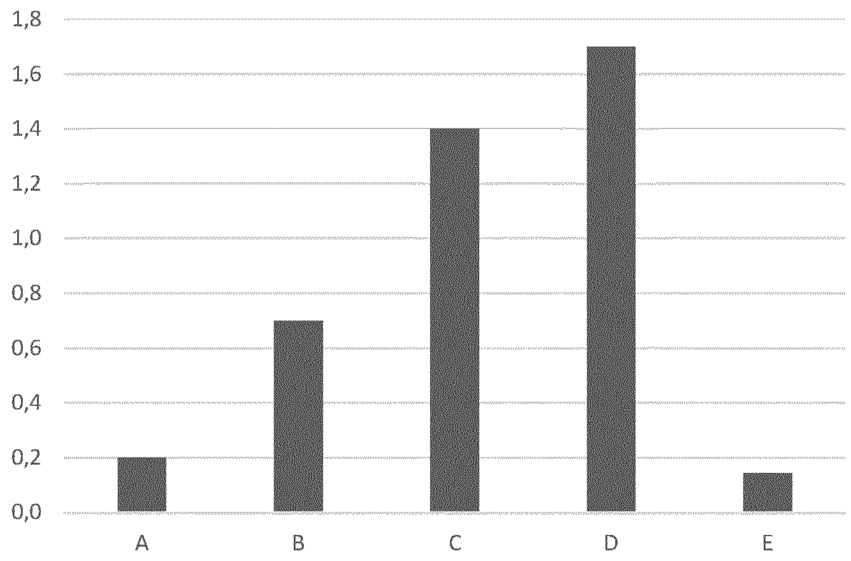
FIG. 3. Mean intestinal lesion score of pigs after the experimental infection, groups A to E. Group A corresponds to pigs vaccinated with inactivated strain B-7493 (gene cluster structure S1); Group B corresponds to pigs vaccinated with inactivated strain B-7500 (gene cluster structure S1); Group C corresponds to pigs vaccinated with inactivated strain B-7843 (gene cluster structure S3); Group D corresponds to pigs vaccinated with a mock vaccine; Group E corresponds to negative control group, mock vaccinated—no challenged group. The intestinal lesion score is represented on the y-axis.

In Groups A and B, a clear reduction of diarrhea and intestinal lesions was observed (FIGS. 2 and 3). Significant efficacy of the vaccines with *B. hyodysenteriae* strains having the genomic structure S1 was observed. Even if the Bhyo strain is heterologous to the challenge strain (as in Group B). In contrast, the vaccine comprising a *B. hyodysenteriae* strain having the genomic structure S3 (Group C), did not show protection against the experimental infection as this group performed similar to the positive control group (mock-vaccinated-challenged group).

To sum up, after experimental infection with the inoculum of the *B. hyodysenteriae* B-7493 strain, it is observed that vaccines with inactivated *B. hyodysenteriae* strains having the genomic structure S1 significantly reduced the clinical parameters associated to swine dysentery as the diarrhea and intestinal lesion scores. It is further demonstrated that strains having the genomic structure S1 are able to confer cross-protection against heterologous Bhyo strains.

Example 3: Efficacy Study of Experimental Vaccines Against Experimental Infection of *B. hyodysenteriae* Strain B-7484

A total of 57 pigs between 5 and 6 weeks of age were chosen for this study. The animals were randomly assigned into 6 groups (Groups A to F) of 10 pigs each one, except for Group F in which only 7 animals were allotted. On Day 0, pigs received a first dose of an experimental vaccine according to the group assignment. Three weeks later (Day 21), pigs received a second dose of the vaccine. Vaccines were administered at the neck by intramuscular route at 2 mL for each administration.

Group A received a vaccine comprising $8\times10^9$ total bacteria (BT) per dose of the inactivated *B. hyodysenteriae* strain B-7500, Spanish isolate. This Spanish isolate showed a genomic arrangement consistent with the gene cluster structure S1 (as determined in Example 1). The vaccine was formulated at 50% v/v with a commercial adjuvant Montanide IMS 1313.

Group B received a vaccine comprising $8\times10^9$ total bacteria (BT) per dose of the inactivated *B. hyodysenteriae* strain B-7484, Spanish isolate. This Spanish isolate showed a genomic arrangement consistent with the gene cluster structure S2 (as determined in Example 1). This vaccine was formulated with the same strain as the one used for the experimental infection, thus it is a homologous vaccine. The vaccine was also formulated at 50% v/v with the commercial adjuvant Montanide IMS 1313.

Group C received a vaccine comprising $8\times10^9$ total bacteria (BT) per dose of the inactivated *B. hyodysenteriae* strain B-7494, Spanish isolate. This Spanish isolate showed a genomic arrangement consistent with the gene cluster structure S2 (as determined in Example 1). The vaccine was formulated at 50% v/v with the commercial adjuvant Montanide IMS 1313.

Group D received a vaccine comprising $8\times10^9$ total bacteria (BT) per dose of inactivated *B. hyodysenteriae* strain B-7843, USA isolate. This USA isolate showed a genomic arrangement consistent with the gene cluster structure S3 (as determined in Example 1). The vaccine was formulated at 50% v/v with the commercial adjuvant Montanide IMS 1313.

Group E corresponded to the positive control group, which received a mock vaccine comprising PBS without antigen and 50% v/v of the same adjuvant Montanide IMS 1313 (mock-vaccinated-challenged group).

Group F corresponded to the negative control group which received a mock vaccine comprising PBS without antigen and 50% v/v of the same Montanide IMS 1313 adjuvant. This group did not receive the experimental infection. Therefore, the group F worked as strict negative control group (mock-vaccinated-non challenged group).

All *B. hyodysenteriae* strains used for preparing the experimental vaccines were inactivated with formaldehyde before administering the vaccine to the animals.

At Day 41, pigs were experimentally infected (challenged) with a fresh culture of the very virulent *B. hyodysenteriae* strain B-7484, which is a Spanish isolate with a gene cluster structure S2. The challenge consisted of orally administering 2 doses at 2 consecutive days of 100 mL/dose of the culture of *B. hyodysenteriae* strain B-7484 at a titer of $1\times10^9$ spirochetes/dose per animal by an esophageal cannula. The negative control group (Group F) did not receive the experimental infection.

To assess the efficacy of the vaccines after the experimental infection, it was evaluated the appearance of mucohemorrhagic diarrhea. The appearance of mucohemorrhagic diarrhea was considered as the main clinical sign of swine dysentery. Diarrhea was monitored on a daily basis from day 1 to day 10 post-infection. Then, a weighted diarrhea score was obtained as detailed in Example 2.

Figure 4:
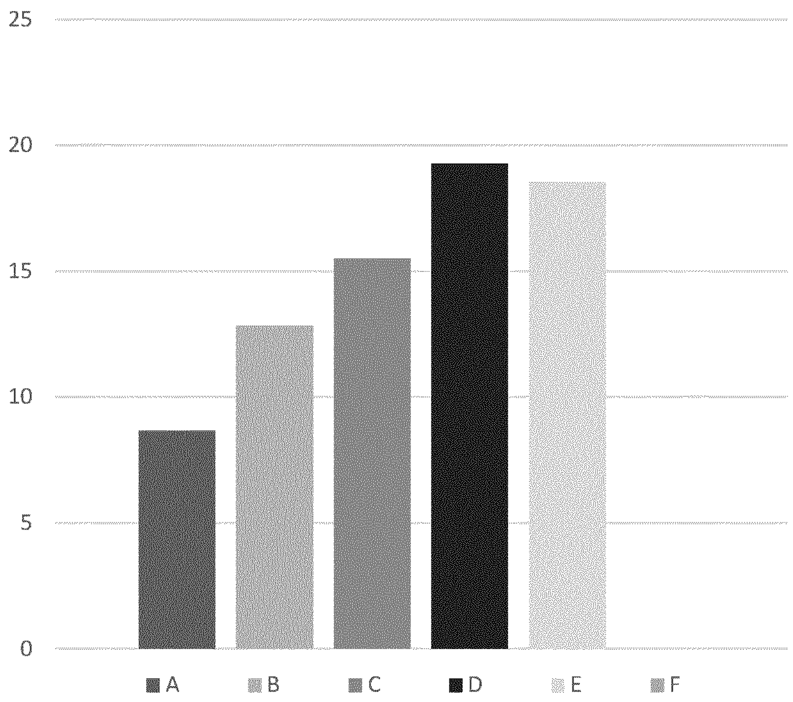
FIG. 4: Mean diarrhea score of pigs from day 1 to 10 after the experimental infection, groups A to F. Group A corresponds to pigs vaccinated with inactivated strain B-7500 (gene cluster structure S1); Group B corresponds to pigs vaccinated with inactivated strain B-7484 (gene cluster structure S2); Group C corresponds to pigs vaccinated with inactivated strain B-7494 (gene cluster structure S2); Group D corresponds to pigs vaccinated with inactivated strain B-7843 (gene cluster structure S3); Group E corresponds to pigs vaccinated with a mock vaccine; Group F corresponds to negative control group, mock-vaccinated-no infected group. The diarrhea score is represented on the y-axis.

The results show a reduction on the diarrhea score in Groups A, B and C (FIG. 4). Thus, there is efficacy of vaccines comprising inactivated Bhyo strains having the genomic structure S1 or S2. Surprisingly, cross-protection is also observed, as efficacy was obtained even if the vaccine strain was heterologous to the challenge strain (Groups A and C).

Vaccines comprising inactivated Bhyo strains having the genomic structure S1 (Group A) resulted in higher efficacy compared to the homologous vaccine strain (Group B). On the contrary, the vaccine comprising a *B. hyodysenteriae* strain having the genomic structure S3 (Group D), did not confer protection against the experimental infection as this group performed similar to the positive control group (mock-vaccinated-challenged).

Example 4: Efficacy Study of Experimental Multivalent Vaccines Against Experimental Infection of *B. hyodysenteriae* Strain B-7484

A total of 66 pigs between 4 and 5 weeks of age were chosen for this study. The animals were randomly assigned into 6 groups of 11 pigs each one (A to E). On Day 0, pigs received a first dose of an experimental vaccine according to the group assignment. Three weeks later (Day 21) pigs received a second dose of the vaccine. Vaccines were administered at the neck by intramuscular route at 2 mL for each administration.

Group A received a vaccine comprising $1\times10^{10}$ total bacteria (BT) per dose of the inactivated *B. hyodysenteriae* strain B-7500, Spanish isolate and $1\times10^{10}$ BT per dose of the inactivated *B. hyodysenteriae* strain B-8295, Argentinian isolate. Both, the Spanish isolate and the Argentinian isolate showed a genomic arrangement consistent with the gene cluster structure S1 (as determined in Example 1). The vaccine was formulated at 2% (w/v) with DEAE-Dextran, and 30% (w/v) with Aluminum hydroxide gel as adjuvant.

Group B received a vaccine comprising $1\times10^{10}$ total bacteria (BT) per dose of the inactivated *B. hyodysenteriae* strain B-7500, which is a Spanish isolate, $1\times10^{10}$ BT per dose of the inactivated *B. hyodysenteriae* strain B-8295, which is an Argentinian isolate and $1\times10^{10}$ BT per dose of the inactivated *B. hyodysenteriae* strain B-8397, which is a German isolate. Both, the Spanish isolate and the Argentinian isolate showed a genomic arrangement consistent with the gene cluster structure S1 (as determined in Example 1); and the German isolate B-8397 holds a genomic arrangement consistent with the gene cluster structure S2 (as determined in Example 1). The vaccine was formulated at 2% (w/v) with DEAE-Dextran, and 30% (w/v) with Aluminum hydroxide gel as adjuvant.

Group C received a vaccine comprising $1\times10^{10}$ total bacteria (BT) per dose of the inactivated *B. hyodysenteriae* strain B-7500, $1\times10^{10}$ BT per dose of the inactivated *B. hyodysenteriae* strain B-8295, $1\times10^{10}$ BT per dose of the inactivated *B. hyodysenteriae* strain B-8397, and $1\times10^{10}$ BT per dose of the inactivated *B. hyodysenteriae* strain B-7484. This last isolate B-7484 corresponds to a Spanish isolate having a genomic arrangement consistent with the gene cluster structure S2 (as determined in Example 1). The vaccine was formulated at 2% (w/v) with DEAE-Dextran, and 30% (w/v) with Aluminum hydroxide gel as adjuvant.

Group D received a vaccine comprising $1\times10^{10}$ total bacteria (BT) per dose of the inactivated *B. hyodysenteriae* strain B-7500, $1\times10^{10}$ BT per dose of the inactivated *B. hyodysenteriae* strain B-8295, $1\times10^{10}$ BT per dose of the inactivated *B. hyodysenteriae* strain B-8397, $6.69\times10^9$ BT per dose of the inactivated *B. hyodysenteriae* strain B-7484, and $1\times10^{10}$ BT per dose of the inactivated *B. hyodysenteriae* strain B-7482. This last isolate B-7482 corresponds to a Spanish isolate having a genomic arrangement consistent with the gene cluster structure S1 (as determined in Example 1). The vaccine was formulated at 2% (w/v) with DEAE-Dextran, and 30% (w/v) with Aluminum hydroxide gel as adjuvant.

Group E corresponded to the control group which received a mock vaccine comprising PBS without antigen and formulated at 2% (w/w) of DEAE-Dextran, and 30% (w/v) of Aluminum hydroxide gel (mock-vaccinated-challenged group).

All *B. hyodysenteriae* strains used for preparing the experimental vaccines were inactivated with formaldehyde before administering the vaccine to the animals.

At Day 36, pigs were experimentally infected (challenged) with a fresh culture of the very virulent *B. hyodysenteriae* strain B-7484, which is a Spanish isolate with a gene cluster structure consistent with S2. The challenge consisted of orally administering 3 doses at 3 consecutive days of 100 mL/dose of the culture of *B. hyodysenteriae* strain B-7484 at a titer about $3\times10^{10}$ alive spirochetes/dose per animal by an esophageal cannula.

To assess the efficacy of the vaccines after the experimental infection, different parameters were evaluated: (i) pig survival, it was monitored on daily basis from day 1 to day 20 post-infection, (ii) average daily weight gain from day 1 to day 23 post-infection was also calculated, and (iii) intestinal lesion score, animals were euthanized on day 58 of the study and the intestinal lesion score was obtained. The score was calculated based on the following table. Then, the mean intestinal lesion score for the different groups was calculated.

TABLE 4

| Score to assess the intestinal lesion score |
|---|
| 0 Absence of lesion |
| 1 Mild enteritis, lesions in specific areas, normal or pasty content |

TABLE 4-continued

| Score to assess the intestinal lesion score |
|---|
| 2 Moderate enteritis, extensive lesions, diarrheal content |
| 3 Severe enteritis, severely damaged or atrophic intestine, watery/blood stools, fibrin |
| 4 Very severe enteritis, totally atrophic intestine, completely ulcerated mucosa |

Figure 5:
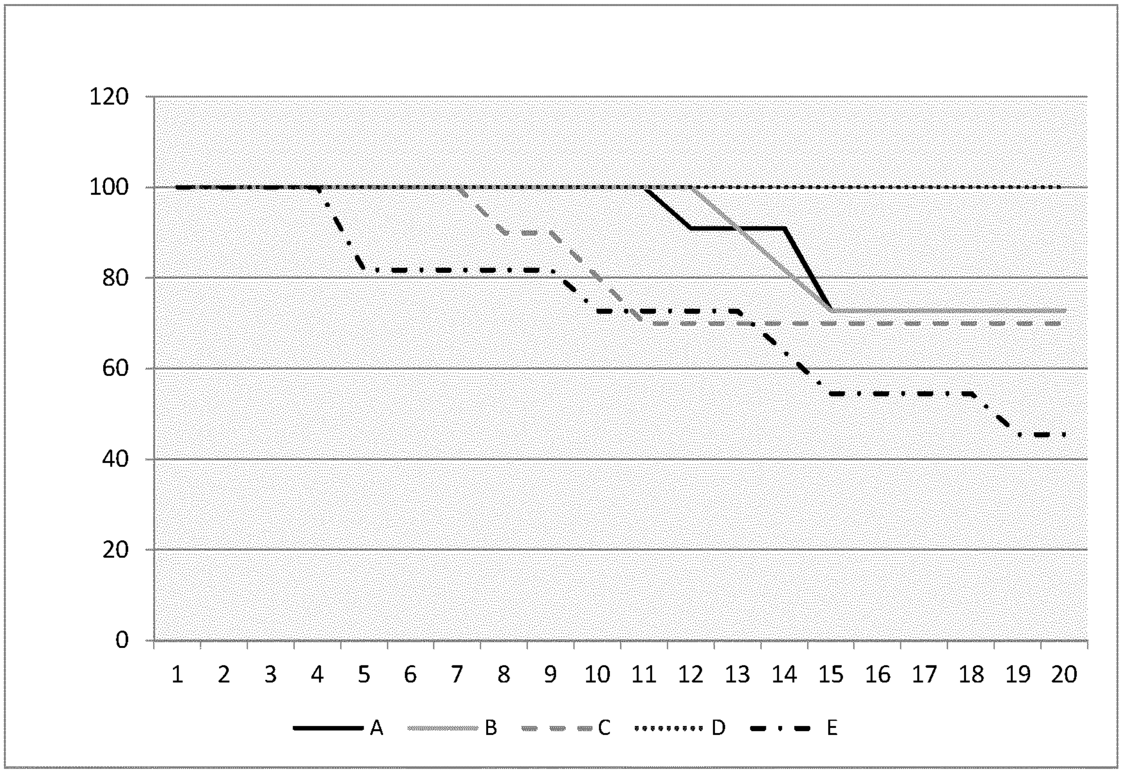
FIG. 5. Survival percentage of pigs from day 1 to 20 after the experimental infection (Days 36 to 56 of the study), groups A to E. Group A corresponds to pigs vaccinated with inactivated strains B-7500 and B-8295 (both with gene cluster structure S1); Group B corresponds to pigs vaccinated with inactivated strains B-7500, B-8295, and B-8397 (gene cluster structure S2); Group C corresponds to pigs vaccinated with inactivated strains B-7500, B-8295, B-8397, and B-7484 (gene cluster structure S2); Group D corresponds to pigs vaccinated with inactivated strains B-7500, B-8295, B-8397, B-7484, and B-7482 (gene cluster structure S1); Group E corresponds to pigs vaccinated with a mock vaccine. The percentage of pig survival is represented on the y-axis. Days after experimental infection are represented on the x-axis.
Figure 6:
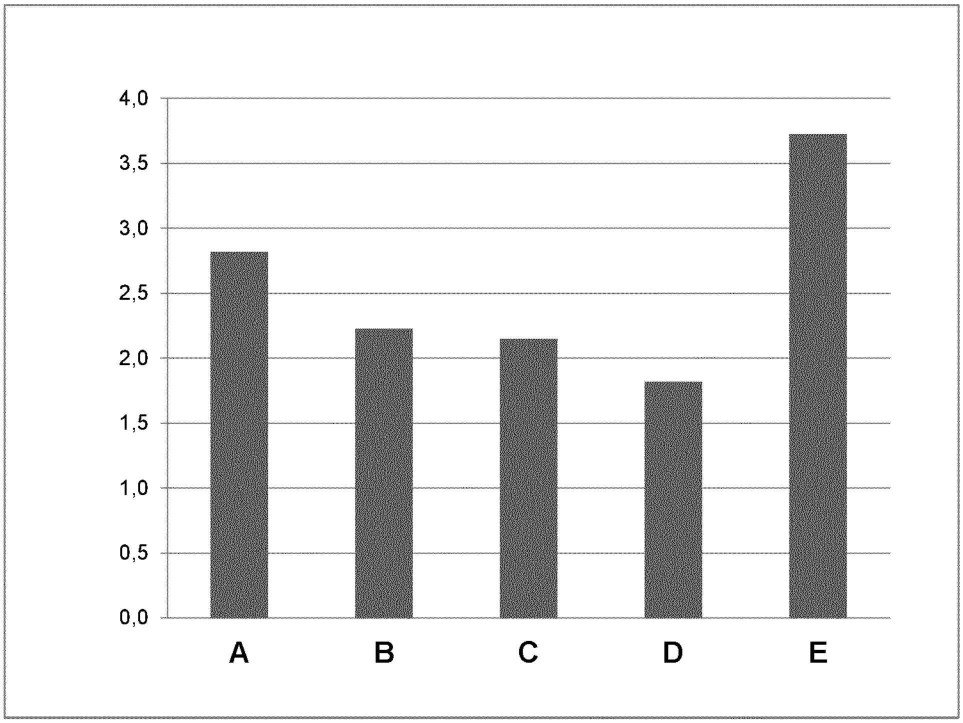
FIG. 6. Mean intestinal lesion score of pigs, euthanized after receiving the experimental infection at day 58, groups A to E. Group A corresponds to pigs vaccinated with inactivated strains B-7500 and B-8295 (both with gene cluster structure S1); Group B corresponds to pigs vaccinated with inactivated strains B-7500, B-8295, and B-8397 (gene cluster structure S2); Group C corresponds to pigs vaccinated with inactivated strains B-7500, B-8295, B-8397, and B-7484 (gene cluster structure S2); Group D corresponds to pigs vaccinated with inactivated strains B-7500, B-8295, B-8397, B-7484, and B-7482 (gene cluster structure S1); Group E corresponds to pigs vaccinated with a mock vaccine. The intestinal lesion score is represented on the y-axis.

Pig survival and intestinal lesion score results are shown in FIGS. 5 to 6. The results reveal that multivalent Bhyo experimental vaccines administered to all groups (A to D) are effective, they all show efficacy against swine dysentery. Particularly, all vaccinated groups present higher survival rate and reduced intestinal lesion scores when compared to control group E.

Average daily weight gain results are shown in Table 5. For this specific parameter, the results demonstrate that animals vaccinated with multivalent experimental vaccines comprising Bhyo isolates having different genomic arrangement (Groups B to D) increased the average daily weight gain over the study and got a superior final weight gain after 23 days post infection when compared to control group E. In Group A (animals vaccinated with an experimental vaccine comprising two isolates having the same genomic arrangement consistent with the gene cluster S1, it was observed that some animals increased their weight over the study, however the mean did not result in an increase of the average daily weight gain. Nevertheless, Group A performed better in terms of average daily weight gain when compared to the control group (Group E). Overall, and taking into account that this group had also a high percentage of survival rate and a reduced intestinal lesion score when compared to control group E, indicates that the vaccine of Group A also protects pigs affected from swine dysentery from weight loss.

TABLE 5

Mean of the Average daily weight gain and total weight gain in kilograms until day 23 after the experimental infection (day 58 of the study), groups A to E.

| Group | Average Daily Weight Gain (Kg) | Weight gain (Kg) |
|---|---|---|
| Group A | −0.03 | −0.80 |
| Group B | 0.14 | 3.2 |
| Group C | 0.11 | 2.5 |
| Group D | 0.06 | 1.6 |
| Group E | −0.09 | −2.1 |

Furthermore, it was surprisingly observed that multivalent vaccines comprising a combination of Bhyo strains having the 36 kb plasmid pBH with the genomic arrangement consistent with the gene cluster structure S1 and S2 (Groups B to D) had higher efficacy and improved protection than vaccines comprising Bhyo strains having just one genomic arrangement, in particular comprising isolates having the genomic arrangement consistent with the gene cluster S1 (Group A). Animals in Groups B to D showed an increased survival rate, higher average daily weight gain and a reduced intestinal lesion score than animals in Group A. This higher efficacy and better protection was shown even when the strain used for the experimental infection is not present in the vaccine composition (Group B).

Overall the results indicate that a vaccine comprising *B. hyodysenteriae* strains having the genomic arrangement consistent with the gene cluster structure S1 and/or S2 are effective against swine dysentery and that cross-protection against *B. hyodysenteriae* infections from heterologous strains is attained.

Example 5: Efficacy Study of Experimental Trivalent Vaccine Against Experimental Infection with Different Heterologous *B. hyodysenteriae* Strains A total of 66 pigs between 4 and 5 weeks of age were chosen for this study. The animals were randomly assigned into 6 groups of 11 pigs each one (A to F). On Day 0, pigs received a first dose of an experimental vaccine according to the group assignment. Two weeks later (Day 14) pigs received a second dose of the vaccine. Vaccines were administered at the neck by intramuscular route at 2 mL for each administration.

- Groups A, C and E received a vaccine comprising $1.5\times10^{10}$ total bacteria (BT) per dose of the inactivated *B. hyodysenteriae* strain B-7500, which is a Spanish isolate having a genomic arrangement consistent with the gene cluster structure S1 (as determined in Example 1), $1.5\times10^{10}$ BT per dose of the inactivated *B. hyodysenteriae* strain B-8295, which is an Argentinian isolate having a genomic arrangement consistent with the gene cluster structure S1 (as determined in Example 1), and $1.5\times10^{10}$ BT per dose of the inactivated *B. hyodysenteriae* strain B-8397, which is a German isolate having a genomic arrangement consistent with the gene cluster structure S2 (as determined in Example 1). The vaccine was formulated at 2% (w/v) with DEAE-Dextran, and 30% (w/v) with Aluminum hydroxide gel as adjuvant.
- Group B, D and F corresponded to control groups which received a mock vaccine comprising PBS formulated at 2% (w/v) with DEAE-Dextran, and 30% (w/v) with Aluminum hydroxide gel as adjuvant. Each group acted as the control group for the vaccinated Groups A, C and E, respectively.

All *B. hyodysenteriae* strains used for preparing the experimental vaccines were inactivated with formaldehyde before administering the vaccine to the animals.

At Day 36, pigs were experimentally infected (challenged) with a fresh culture of different heterologous *B. hyodysenteriae* strains. Groups A and B were experimentally infected with a fresh culture of the *B. hyodysenteriae* strain B-7493, which is a USA isolate having a genomic arrangement consistent with the gene cluster structure S1 (as determined in Example 1). Groups C and D were experimentally infected with a fresh culture of the *B. hyodysenteriae* strain B-7482, which is a Spanish isolate having a genomic arrangement consistent with the gene cluster structure S1 (as determined in Example 1). Groups E and F were experimentally infected with a fresh culture of the *B. hyodysenteriae* strain B-7484, which is a Spanish isolate having a genomic arrangement consistent with the gene cluster structure S2 (as determined in Example 1).

The challenge consisted of orally administering 2 doses at 2 consecutive days of 100 mL/dose of the fresh culture of *B. hyodysenteriae* strain at a titer between $1.4\times10^{10}$ and $3.6\times10^{10}$ spirochetes/dose per animal by an esophageal cannula.

To assess the efficacy of the vaccines after the experimental infection different parameters were evaluated: (i) pig survival, it was monitored on daily basis from day 1 to day 20 post-infection, and (ii) intestinal lesion score, animals were euthanized on day 57 of the study and the intestinal lesion score was assessed. The score was calculated as described in Example 4.

Figure 7:
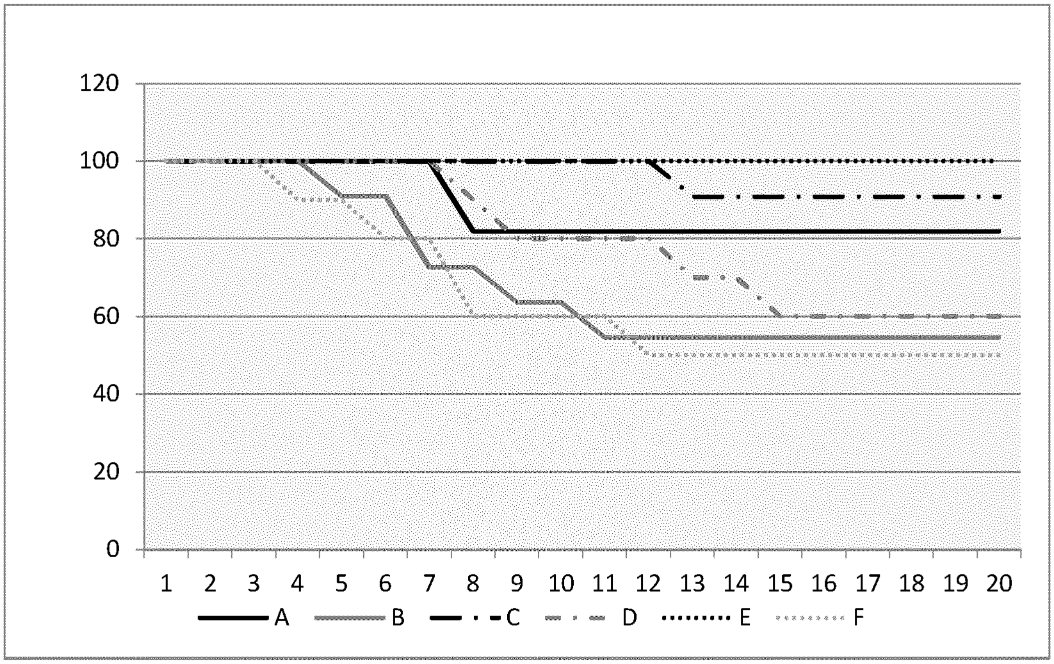
FIG. 7. Survival percentage of pigs from day 1 to 20 after the experimental infection (Days 36 to 56 of the study), groups A to F. Groups A, C and E correspond to pigs vaccinated with a vaccine comprising inactivated strains B-7500 (gene cluster structure S1), B-8295 (gene cluster structure S1), and B-8397 (gene cluster structure S2); Groups B, D and F correspond to pigs vaccinated with a mock vaccine. Groups A and B were experimentally infected with the strain B-7493; Groups C and D were experimentally infected with the strain B-7482; Groups E and F were experimentally infected with the strain B-7484. The percentage of pig survival is represented on the y-axis. Days after experimental infection are represented on the x-axis.
Figure 8:
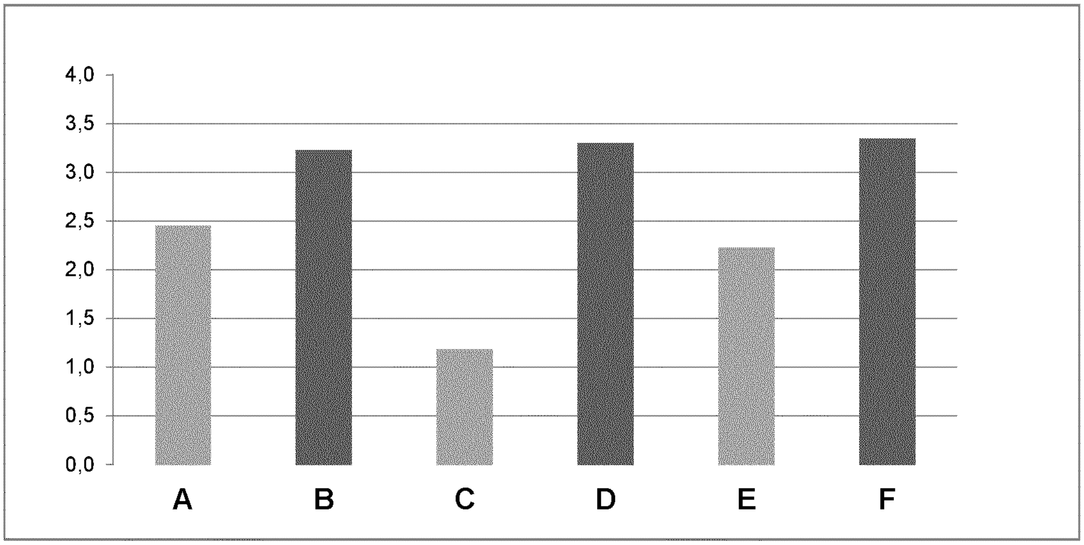
FIG. 8. Mean intestinal lesion score of pigs, euthanized after receiving the experimental infection at day 57, groups A to F. Groups A, C and E correspond to pigs vaccinated with a vaccine comprising inactivated strains B-7500 (gene cluster structure S1), B-8295 (gene cluster structure S1), and B-8397 (gene cluster structure S2); Groups B, D and F correspond to pigs vaccinated with a mock vaccine. Groups A and B were experimentally infected with the strain B-7493; Groups C and D were experimentally infected with the strain B-7482; Groups E and F were experimentally infected with the strain B-7484. The intestinal lesion score is represented on the y-axis.

Results are shown in FIGS. 7 and 8.

The results clearly show that all vaccinated groups had higher survival rate, more than 80% survival at day 20 post-infection, and also showed a reduced intestinal lesion score when compared to the control groups. This results surprisingly demonstrate not only protection against swine dysentery but also the cross-protection traits of the experimental trivalent vaccine, as the vaccine is efficacious even with heterologous strains of different geographical origins. Therefore, the results confirm, again, that a vaccine comprising inactivated *B. hyodysenteriae* strains having the genomic cluster structure S1 and/or S2 are highly effective against swine dysentery and in obtaining cross-protection against *B. hyodysenteriae* infections, even if the infections are caused by heterologous strains and of different geographic origins.

The invention claimed is:

1. An immunogenic or vaccine composition comprising an isolated and inactivated bacterium from the species *Brachyspira hyodysenteriae*, wherein said bacterium comprises the gene on the locus BHWA1_02689 (fucT) of the *B. hyodysenteriae* plasmid pBHWA1 identified by the GenBank accession number NC_012226.1 (4 Apr. 2020), wherein said gene has the sequence of SEQ ID NO: 5, or a variant of said gene of any strain of *B. hyodysenteriae*, wherein the variant of the fucT gene has at least 60% sequence identity with the sequence of SEQ ID NO: 5.

2. The immunogenic or vaccine composition according to claim 1, wherein the variant of the fucT gene has at least 80% sequence identity with the sequence of SEQ ID NO: 5.

3. The immunogenic or vaccine composition according to claim 2, wherein the variant of the fucT gene comprises a sequence selected from the group consisting of SEQ ID NO: 17-31.

4. The immunogenic or vaccine composition according to claim 1, wherein the fucT gene or the variant of said gene is comprised in a gene cluster, and wherein the bacterium is a S1 or a S2 bacterium, wherein the gene cluster of the S1 bacterium comprises the following genes: the gene on the locus BHWA1_02695 (bcsA) of the *B. hyodysenteriae* plasmid pBHWA1 identified by the GenBank accession number NC_012226.1 (4 Apr. 2020), wherein said gene has the sequence of SEQ ID NO: 7, or a variant of said gene of any strain of *B. hyodysenteriae*, wherein said variant has at least 60% sequence identity with the sequence of SEQ ID NO: 7, the rfbC gene, the rfbD gene, the rfbA gene, the rfbB gene, the gene on the locus BHWA1_02690 (rgpF) of the *B. hyodysenteriae* plasmid pBHWA1 identified by the GenBank accession number NC_012226.1 (4 Apr. 2020), wherein said gene has the sequence of SEQ ID NO: 6, or a variant of said gene of any strain of *B. hyodysenteriae*, wherein said variant has at least 60% sequence identity with the sequence of SEQ ID NO: 6, and the fucT gene or the variant of said gene of any strain and the gene cluster of the S2 bacterium comprises the following genes: the gene on the locus BHWA1_02695 (bcsA) of the *B. hyodysenteriae* plasmid pBHWA1 identified by the GenBank accession number NC_012226.1 (4 Apr. 2020), wherein said gene has the sequence of SEQ ID NO: 7, or a variant of said gene of any strain of *B. hyodysenteriae*, wherein said variant has at least 60% sequence identity with the sequence of SEQ ID NO: 7, the rfbC gene, the rfbD gene, the rfbA gene, a gene having the sequence of SEQ ID NO: 8 (adoM) or a variant of said gene of any strain of *B. hyodysenteriae*, wherein said variant has at least 60% sequence identity with the sequence of SEQ ID NO: 8, the rfbB gene, the gene on the locus BHWA1_02690 (rgpF) of the *B. hyodysenteriae* plasmid pBHWA1 identified by the GenBank accession number NC_012226.1 (4 Apr. 2020), wherein said gene has the sequence of SEQ ID NO: 6, or a variant of said gene of any strain of *B. hyodysenteriae*, wherein said variant has at least 60% sequence identity with the sequence of SEQ ID NO: 6, and the fucT gene or the variant of said gene of any strain of *B. hyodysenteriae.*

5. The immunogenic or vaccine composition according to claim 4, wherein the variant of the rgpF gene has at least 60% sequence identity with the sequence of SEQ ID NO: 6, and/or, the variant of the bcsA gene has at least 60% sequence identity with the sequence of SEQ ID NO: 7, and/or the variant of the adoM gene has at least 60% sequence identity with the sequence of SEQ ID NO: 8.

6. The immunogenic or vaccine composition according to claim 5, wherein the variant of the rgpF gene comprises a sequence selected from the group consisting of SEQ ID NO: 69-76 and/or the variant of the bcsA gene comprises a sequence selected from the group consisting of SEQ ID NO: 77-81 and/or the variant of the adoM gene comprises the sequence of SEQ ID NO: 82.

7. The immunogenic or vaccine composition according to claim 4, wherein the gene cluster of the S1 bacterium comprises, from the 5' to the 3' end, the following genes: bcsA or the variant of said gene of any strain of *B. hyodysenteriae*, rfbC, rfbD, rfbA, rfbB, rgpF or the variant of said gene of any strain of *B. hyodysenteriae* and fucT or the variant of said gene of any strain of *B. hyodysenteriae;* and the gene cluster of the S2 bacterium comprises, from the 5' to the 3' end, the following genes: bcsA or the variant of said gene of any strain of *B. hyodysenteriae*, rfbC, rfbD, rfbA, adoM or the variant of said gene of any strain of *B. hyodysenteriae*, rfbB, rgpF or the variant of said gene of any strain of *B. hyodysenteriae* and fucT or the variant of said gene of any strain of *B. hyodysenteriae.*

8. The immunogenic or vaccine composition according to claim 4, wherein the composition comprises at least two strains of a S1 bacterium.

9. The immunogenic or vaccine composition according to claim 4, wherein the composition comprises at least two strains of a S2 bacterium.

10. The immunogenic or vaccine composition according to claim 1, further comprising an adjuvant.

11. The immunogenic or vaccine composition according to claim 10, wherein the adjuvant is an aluminum containing adjuvant, diethylaminoethyl (DEAE) or a combination thereof.

12. The immunogenic or vaccine composition according to claim 1, wherein the bacterium has been inactivated by formaldehyde.

13. A method for producing an immunogenic or vaccine composition comprising an isolated bacterium from the species *Brachyspira hyodysenteriae*, wherein the method comprises the steps of:

(a) determining if the bacterium from the species *Brachyspira hyodysenteriae* comprises the gene on the locus BHWA1_02689 (fucT) of the *B. hyodysenteriae* plasmid pBHWA1 identified by the GenBank accession number NC_012226.1 (4 Apr. 2020), wherein said gene has the sequence of SEQ ID NO: 5, or a variant of said gene of any strain of *B. hyodysenteriae*, wherein said variant has at least 60% sequence identity with the sequence of SEQ ID NO: 5, or the product of said gene or variant, (b) selecting the bacterium from the species *Brachyspira hyodysenteriae* if said bacterium comprises the fucT gene or the variant of said gene of any strain of *B. hyodysenteriae* or the product of said gene or variant, (c) inactivating the bacterium selected in step (b) and (d) formulating the bacterium inactivated in step (c) in an immunogenic or vaccine composition.

14. An immunogenic or vaccine composition obtainable by the method according to claim 13.

15. A method for selecting a bacterium from the species *Brachyspira hyodysenteriae* useful for manufacturing a vaccine against swine dysentery comprising determining the presence or absence of the gene on the locus BHWA1_02689 (fucT) of the *B. hyodysenteriae* plasmid pBHWA1 identified by the GenBank accession number NC_012226.1 (4 Apr. 2020), wherein said gene has the sequence of SEQ ID NO: 5, or a variant of said gene of any strain of *B. hyodysenteriae*, wherein said variant has at least 60% sequence identity with the sequence of SEQ ID NO: 5, and/or of the product of said gene or variant, wherein if the bacterium comprises said gene or variant or the product of said gene or variant, the bacterium is selected for manufacturing a vaccine against swine dysentery.

16. A method for inducing an immune response against a bacterium from the species *Brachyspira hyodysenteriae* comprising administering to a subject an immunologically or therapeutically effective amount of the immunogenic composition according to claim 1.

17. A method for preventing an infection caused by a bacterium from the species *Brachyspira hyodysenteriae* in a subject comprising administering to a subject an immunologically or therapeutically effective amount of the vaccine composition according to claim 1.

18. The method according to claim 17, wherein the vaccine induces protection against a strain of *B. hyodysenteriae* different from the strain that is comprised in the vaccine.

* * * * *